US007119183B2

(12) United States Patent
Seed et al.

(10) Patent No.: US 7,119,183 B2
(45) Date of Patent: Oct. 10, 2006

(54) RAPID IMMUNOSELECTION CLONING METHOD

(75) Inventors: Brian Seed, Boston, MA (US); Alejandro Aruffo, Belle Mead, NJ (US); David Camerini, Charlottesville, VA (US)

(73) Assignee: The General Hospital Corporation, Charlestown, MA (US)

( * ) Notice: Subject to any disclaimer, the term of this patent is extended or adjusted under 35 U.S.C. 154(b) by 71 days.

(21) Appl. No.: 09/836,544

(22) Filed: Apr. 17, 2001

(65) Prior Publication Data

US 2004/0072283 A1 Apr. 15, 2004

Related U.S. Application Data

(60) Division of application No. 07/983,647, filed on Dec. 1, 1992, now Pat. No. 6,218,525, which is a continuation-in-part of application No. 07/553,759, filed on Jul. 13, 1990, now abandoned, which is a continuation-in-part of application No. 07/498,809, filed on Mar. 23, 1990, now abandoned, which is a continuation-in-part of application No. 07/379,076, filed on Jul. 13, 1989, now abandoned, which is a continuation-in-part of application No. 07/160,416, filed on Feb. 25, 1988, now abandoned.

(51) Int. Cl.
*C07H 21/04* (2006.01)

(52) U.S. Cl. .................................... 536/23.1; 536/23.5

(58) Field of Classification Search ............... 536/23.1, 536/23.5

See application file for complete search history.

(56) References Cited

U.S. PATENT DOCUMENTS

| | | | | |
|---|---|---|---|---|
| 5,506,126 A | 4/1996 | Seed et al. | | |
| 5,830,731 A | 11/1998 | Seed et al. | | |
| 5,849,898 A | 12/1998 | Seed et al. | | |
| 6,111,093 A | 8/2000 | Seed et al. | | |
| 6,218,525 B1 | 4/2001 | Seed et al. | | |
| 6,607,879 B1 * | 8/2003 | Cocks et al. | .................... | 435/6 |
| 6,812,339 B1 * | 11/2004 | Venter et al. | ............ | 536/24.31 |
| 2004/0077003 A1 * | 4/2004 | Cocks et al. | ................... | 435/6 |

OTHER PUBLICATIONS

Aruffo and Seed (1987) *EMBO J.* 6:3313-3316.
Aruffo and Seed (1987) *Proc. Natl. Acad. Sci.* 84:8573-8577.
Gerald, et al. (1986) *J. Gen. Virol.* 67:2695-2703.
Huynh, et al. (1985) "DNA Cloning vol. 1, A Practical Approach" Glover, D.M. (ed.), IRL Press, Oxford, pp. 49-78.
Johnson, et al. (1986) *Nature* 323:74-76.
Oshima, et al. (1987) *Proc. Natl. Acad. Sci. USA* 84:685-689.
Seed (1987) *Nature* 329:840-842.
Seed, et al. (1987) *Proc. Natl. Acad. Sci. USA* 84:3365-3369.
Shaw, et al. (1986) *Nature* 323:262-264.
Simmons, et al. (1988) *Nature* 331:624-627.
Sleckman, et al. (1988) *Nature* 328:351-353.
Stuve, et al. (1987) *J. Virol* 61(2):326-335.
Yang, et al. (1986) *Cell* 47:3-10.
Allen and Seed (1988) *Nuc. Acids Res.* 16:11824.
Bowen et al. (1989) *J. Cell. Biol.* 109:421-427.
Hotta et al. (1988) *Cancer Res.* 48:2955.
Seigelman and Weissman (1989) *Proc. Natl. Acad. Sci. USA* 86:5562-5566.
Tandon et al. (1989) *J. Biol. Chem.* 264:7570-7575.
Tedder et al. (1989) *J. Cell. Biol.* 170:123-133.
Allen et al. (1989) "Isolation and Expression of Functional High-Affinity Fc Receptor Complementary DNAs," *Science* 243:378-381.
Allen et al. (1988) "Nucleotide Sequence of Three cDNAs for the Human High Affinity Fc Receptor (FcRI)," *Nuc. Acids Res.* 16(24):11824.
Bigler et al. (1988) "A Modulating Disulfide-Linked T Cell Activation Antigen," *J. Immunol.* 141:21-28.
Camerini et al. (Nov. 1991) "The Cell Activation Antigen CD27 is a Member of the Nerve Growth Factor/Tumor Necrosis Factor Receptor Gene Family," *J. Immunol.* 147:3165-3169.
Dalchau et al. (1980) "Monoclonal Antibody to a Human Brain-Granulocyte-T Lymphocyte Antigen Probably Homologous to the W 3/13 Antigen of the Rat," *Eur. J. Immunol.* 10:745-749.
Grob et al. (1985) "Characterization of the Human Melanoma Nerve Growth Factor Receptor," *J. Biol. Chem.* 260(13):8044-8049.
Hansen et al. (1980) "Monoclonal Antibodies Identifying a Novel T-Cell Antigen and la Antigens of Human Lymphocytes," *Immunogenetics* 10:247-260.
Johnson et al. (1986) "Expression and Structure of the Human NGF Receptor," *Cell* 47:545-554.
Kanof et al. (1987) "Induction of CD4 Suppressor T Cells with Anti-Leu-8 Antibody," *J. Immunol.* 139:49-54.
Ledbetter et al. (1985) "Antibodies to Tp44 Augment and Sustain Proliferative Responses of Activated T Cells," *J. Immunol.* 135(4):2311-2336.

(Continued)

*Primary Examiner*—Christina Chan
*Assistant Examiner*—Marianne DiBrino
(74) *Attorney, Agent, or Firm*—Greenlee, Winner and Sullivan, P.C.

(57) ABSTRACT

A simple and highly efficient method for cloning cDNAs including CD27 (SEQ ID NO:28) from mammalian expression libraries based on transient expression in mammalian host cells has been discovered. Novel expression vectors allowing highly efficient construction of mammalian cDNA libraries are disclosed. The cloning method of the invention which has been used to clone genes for cell surface antigens of human lymphocytes, has general application in gene cloning. Cell surface antigens cloned according to the present invention have been purified, and the nucleotide and amino acid sequences determined. These antigens have diagnostic and therapeutic utility in immune-mediated infections in mammals, including humans.

1 Claim, 32 Drawing Sheets

OTHER PUBLICATIONS

Ledbetter et al. (1986) "Antibody Binding to CD5 (Tp67) and Tp44 T-Cell Surface Molecules: Effects on Cyclic Nucleotides, Cytoplasmic Free Calcium, and cAMP-Mediated Suppression," *J. Immunol.* 137:3299-3305.

Martin et al. (1986) "A 44 Kilodalton Cell Surface Homodimer Regulates Interleukin 2 Production by Activated Human T Lymphocytes," *J. Immunol.* 136(9):3282-3287.

Pezzutto et al. (1987) "Amplification of Human B Cell Activation by a Monoclonal Antibody to the B Cell-Specific Antigen Cd22, Bp 130/140," *J. Immunol.* 138:98-103.

Pezzutto et al. (1988) "Role of the CD22 Human B Cell Antigen in B Cell Triggering by Anti-Immunoglobulin," *J. Immunol.* 140:1791-1795.

Poletti et al. (1988) "Double Labeling Immunohistologic and Flow Cytometric Analysis of Human B Cells with Particular Reference to Leu-8 Expression," *Human Pathology* 19(9):1001-1007.

Rajasekariah et al. (1987) "A Genomic Clone Encoding the T6 (cd1) Antigen," In; Leucocyte Typing III, Oxford University Press, vol. T1.3, pp. 74-76.

Schwartz-Albiez et al. (1988) "The B Cell-Associated CD37 Antigen (gp40-52) Structure and Subcellular Expression of an Extensively Glycosylated Glycoprotein," *J. Immunol.* 140:905-914.

Seed et al. (1987) "Molecular Cloning of the CD2 Antigen, The T-Cell Erythrocyte Receptor, by a rapid Immunoselection Procedure," *Proc. Natl. Acad. Sci. USA* 84:3365-3369.

Siegelman et al. (Jul. 1989) "Human Homologue of Mouse Lymph Node Homing Receptor: Evolutionary Conservation at Tandem Cell Interaction Domains," *Proc. Natl. Acad. Sci. USA* 86:5562-5566.

Smith et al. (1987) "Blocking of HIV-1 Infectivity by a Soluble, Secreted Form of the CD4 Antigen," *Science* 238:1704-1706.

Stamenkovic et al. (Mar. 1989) "A Lymphocyte Molecule Implicated in Lymph Node Homing is a Member of the Cartilage Link Protein Family," *Cell* 56:1057-1062.

Stamenkovic et al. (May 1989) "A B-Lymphocyte Activation Molecule Related to the Nerve Growth Factor Receptor and Induced by Cytokines in Carcinomas," *EMBO J.* 8(5):1403-1410.

Stefanova et al. (1989) "Reactivity of the Non-Linear/NK Panel Antibodies with Purified Antigens CD45, CD43, CD44, and CD18, and Three 'Novel' Antigens MEM-43, MEM-53, and MEM-102," In: *Leukocyte Typing IV*, Knapp, B. ed., pp. 678-679.

Stengelin et al. (1988) "Isolation of cDNAs for Two Distinct Human Fc Receptors by Ligand Affinity Cloning," *EMBO J.* 7(4):1053-1959.

Stuve et al. (1987) "Structure and Expression of the Herpes Simplex Virus Type 2 Glycoprotein gB Gene," *J. Virol.* 61(2):326-335.

Sutherland et al. (1984) "Isolation and Characterization of a Human T Lymphocyte-Associated Glycoprotein (gp40)," *J. Immunol.* 133(1):327-333.

Tandon et al. (May 1989) "Identification of Glycoprotein IV (CD36) as a Primary Receptor for Platelet-Collagen Adhesion," *J. Biol. Chem.* 264(13):7576-7583.

Tandon et al. (1989) "Isolation and Characterization pf Platelet Glycoprotein IV (CD36)," *J. Biol. Chem.* 264(13):7570-7575.

Tomassini et al. (1986) "Isolation of a Receptor Protein Involved in Attachment of Human Rhinoviruses," *J. Virol.* 58(2):290-295.

Treiger et al. (1986) "A Secreted Form of the Human Interleukin 2 Receptor Encoded by an "Anchor Minus" cDNA," *J. Immunol.* 136(11):4099-4105.

Van Lier et al. (1988) "Anti-CD 27 Monoclonal Antibodies Identify Two Functionally Distict Sub Populations Within the CD4+ Cell Subset," *Eur. J. Immunol.* 18:811-816.

* cited by examiner

```
   1 GGCGTAATCT GCTGCTTGCA AACAAAAAAA CCACCGCTAC CAGCGGTGGT
  51 TTGTTTGCCG GATCAAGAGC TACCAACTCT TTTTCCGAAG GAACTGGCTT
 101 CAGCAGAGCG CAGATACCAA ATACTGTCCT TCTAGTGTAG CCGTAGTTAG
 151 GCCACCACTT CAAGAACTCT GTAGCACCGC CTACATACCT CGCTCTGCTA
 201 ATCCTGTTAC CAGTGGCTGC TGCCAGTGGC GATAAGTCGT GTCTTACCGG
 251 GTTGGACTCA AGACGATAGT TACCGGATAA GGCGCAGCGG TCGGGCTGAA
 301 CGGGGGGTTC GTGCACACAG CCCAGCTTGG AGCGAACGAC CTACACCGAA
 351 CTGAGATACC TACAGCGTGA GCTATGAGAA AGCGCCACGC TTCCCGAAGG
 401 GAGAAAGGCG GACAGGTATC CGGTAAGCGG CAGGGTCGGA ACAGGAGAGC
 451 GCACGAGGGA GCTTCCAGGG GGAAACGCCT GGTATCTTTA TAGTCCTGTC
 501 GGGTTTCGCC ACCTCTGACT TGAGCGTCGA TTTTTGTGAT GCTCGTCAGG
 551 GGGGCGGAGC CTATGGAAAA ACGCCAGCAA CGCCGAATTA CCGCGGTCTT
 601 TCTCAACGTA ACACTTTACA GCGGCGCGTC ATTTGATATG ATGCGCCCCG
 651 CTTCCCGATA AGGGAGCAGG CCAGTAAAAG CATTACCCGT GGTGGGGTTC
 701 CCGAGCGGCC AAAGGGAGCA GACTCTAAAT CTGCCGTCAT CGACTTCGAA
 751 GGTTCGAATC CTTCCCCCAC CACCATCACT TTCAAAAGTC CGAAAGAATC
 801 TGCTCCCTGC TTGTGTGTTG GAGGTCGCTG AGTAGTGCGC GAGTAAAATT
 851 TAAGCTACAA CAAGGCAAGG CTTGACCGAC AATTGCATGA AGAATCTGCT
 901 TAGGGTTAGG CGTTTTGCGC TGCTTCGCGA TGTACGGGCC AGATATACGC
 951 GTTGACATTG ATTATTGACT AGTTATTAAT AGTAATCAAT TACGGGGTCA
1001 TTAGTTCATA GCCCATATAT GGAGTTCCGC GTTACATAAC TTACGGTAAA
1051 TGGCCCGCCT GGCTGACCGC CCAACGACCC CCGCCCATTG ACGTCAATAA
1101 TGACGTATGT TCCCATAGTA ACGCCAATAG GGACTTTCCA TTGACGTCAA
1151 TGGGTGGACT ATTTACGGTA AACTGCCCAC TTGGCAGTAC ATCAAGTGTA
1201 TCATATGCCA AGTACGCCCC CTATTGACGT CAATGACGGT AAATGGCCCG
1251 CCTGGCATTA TGCCCAGTAC ATGACCTTAT GGGACTTTCC TACTTGGCAG
1301 TACATCTACG TATTAGTCAT CGCTATTACC ATGGTGATGC GGTTTTGGCA
1351 GTACATCAAT GGGCGTGGAT AGCGGTTTGA CTCACGGGGA TTTCCAAGTC
1401 TCCACCCCAT TGACGTCAAT GGGAGTTTGT TTTGGCACCA AAATCAACGG
1451 GACTTTCCAA AATGTCGTAA CAACTCCGCC CCATTGACGC AAATGGGCGG
1501 AATTCCTGGG CGGGACTGGG GAGTGGCGAG CCCTCAGATG CTGCATATAA
1551 GCAGCTGCTT TTTGCCTGTA CTGGGTCTCT CTGGTTAGAC CAGATCTGAG
1601 CCTGGGAGCT CTCTGGCTAA CTAGAGAACC CACTGCTTAA GCCTCAATAA
1651 AGCTTCTAGA GATCCCTCGA CCTCGAGGGA TCTTCCATAC CTACCAGTTC
```

FIG. 1A

```
1701  TGCGCCTGCA GGTCGCGGCC GCGACTCTAG AGGATCTTTG TGAAGGAACC
1751  TTACTTCTGT GGTGTGACAT AATTGGACAA ACTACCTACA GAGATTTAAA
1801  GCTCTAAGGT AAATATAAAA TTTTTAAGTG TATAATGTGT TAAACTACTG
1851  ATTCTAATTG TTTGTGTATT TTAGATTCCA ACCTATGGAA CTGATGAATG
1901  GGAGCAGTGG TGGAATGCCT TTAATGAGGA AAACCTGTTT TGCTCAGAAG
1951  AAATGCCATC TAGTGATGAT GAGGCTACTG CTGACTCTCA ACATTCTACT
2001  CCTCCAAAAA AGAAGAGAAA GGTAGAAGAC CCCAAGGACT TTCCTTCAGA
2051  ATTGCTAAGT TTTTTGAGTC ATGCTGTGTT TAGTAATAGA ACTCTTGCTT
2101  GCTTTGCTAT TTACACCACA AAGGAAAAAG CTGCACTGCT ATACAAGAAA
2151  ATTATGGAAA AATATTCTGT AACCTTTATA AGTAGGCATA ACAGTTATAA
2201  TCATAACATA CTGTTTTTTC TTACTCCACA CAGGCATAGA GTGTCTGCTA
2251  TTAATAACTA TGCTCAAAAA TTGTGTACCT TTAGCTTTTT AATTTGTAAA
2301  GGGGTTAATA AGGAATATTT GATGTATAGT GCCTTGACTA GAGATCATAA
2351  TCAGCCATAC CACATTTGTA GAGGTTTTAC TTGCTTTAAA AAACCTCCCA
2401  CACCTCCCCC TGAACCTGAA ACATAAAATG AATGCAATTG TTGTTGTTAA
2451  CTTGTTTATT GCAGCTTATA ATGGTTACAA ATAAAGCAAT AGCATCACAA
2501  ATTTCACAAA TAAAGCATTT TTTTCACTGC ATTCTAGTTG TGGTTTGTCC
2551  AAACTCATCA ATGTATCTTA TCATGTCTGG ATCCTGTGGA ATGTGTGTCA
2601  GTTAGGGTGT GGAAAGTCCC CAGGCTCCCC AGCAGGCAGA AGTATGCAAA
2651  GCATGCATCT CAATTAGTCA GCAACCAGGT GTGGAAAGTC CCCAGGCTCC
2701  CCAGCAGGCA GAAGTATGCA AAGCATGCAT CTCAATTAGT CAGCAACCAT
2751  AGTCCCGCCC CTAACTCCGC CCATCCCGCC CCTAACTCCG CCCAGTTCCG
2801  CCCATTCTCC GCCCCATGGC TGACTAATTT TTTTTATTTA TGCAGAGGCC
2851  GAGGCCGCCT CGGCCTCTGA GCTATTCCAG AAGTAGTGAG GAGGCTTTTT
2901  TGGAGGCCTA GGCTTTTGCA AAAAGCTAAT TC
```

FIG. 1B

```
     CCTAAGATGAGCTTTCCATGTAAATTTGTAGCCAGCTTCCTTCTGATTTTCAATGTTTCT   (60)
             MetSerPheProCysLysPheValAlaSerPheLeuLeuIlePheAsnValSer

     TCCAAAGGTGCAGTCTCCAAAGAGATTACGAATGCCTTGGAAACCTGGGGTGCCTTGGGT   (120)
     SerLysGlyAlaValSerLysGluIleThrAsnAlaLeuGluThrTrpGlyAlaLeuGly
        1
     CAGGACATCAACTTGGACATTCCTAGTTTTCAAATGAGTGATGATATTGACGATATAAAA   (180)
 20  GlnAspIleAsnLeuAspIleProSerPheGlnMetSerAspAspIleAspAspIleLys

     TGGGAAAAAACTTCAGACAAGAAAAAGATTGCACAATTCAGAAAAGAGAAAGAGACTTTC   (240)
 40  TrpGluLysThrSerAspLysLysLysIleAlaGlnPheArgLysGluLysGluThrPhe

     AAGGAAAAAGATACATATAAGCTATTTAAAAATGGAACTCTGAAAATTAAGCATCTGAAG   (300)
 60  LysGluLysAspThrTyrLysLeuPheLysAsnGlyThrLeuLysIleLysHisLeuLys
                                     ---CHO---
     ACCGATGATCAGGATATCTACAAGGTATCAATATATGATACAAAAGGAAAAAATGTGTTG   (360)
 80  ThrAspAspGlnAspIleTyrLysValSerIleTyrAspThrLysGlyLysAsnValLeu

     GAAAAAATATTTGATTTGAAGATTCAAGAGAGGGTCTCAAAACCAAAGATCTCCTGGACT   (420)
100  GluLysIlePheAspLeuLysIleGlnGluArgValSerLysProLysIleSerTrpThr

     TGTATCAACACAACCCTGACCTGTGAGGTAATGAATGGAACTGACCCCGAATTAAACCTG   (480)
120  CysIleAsnThrThrLeuThrCysGluValMetAsnGlyThrAspProGluLeuAsnLeu
        ---CHO---                          ---CHO---
     TATCAAGATGGGAAACATCTAAAACTTTCTCAGAGGGTCATCACACACAAGTGGACCACC   (540)
140  TyrGlnAspGlyLysHisLeuLysLeuSerGlnArgValIleThrHisLysTrpThrThr

     AGCCTGAGTGCAAAATTCAAGTGCACAGCAGGGAACAAAGTCAGCAAGGAATCCAGTGTC   (600)
160  SerLeuSerAlaLysPheLysCysThrAlaGlyAsnLysValSerLysGluSerSerVal

     GAGCCTGTCAGCTGTCCAGAGAAAGGTCTGGACATCTATCTCATCATTGGCATATGTGGA   (660)
180  GluProValSerCysProGluLysGlyLeuAspIleTyrLeuIleIleGlyIleCysGly
                                                --------------------
     GGAGGCAGCCTCTTGATGGTCTTTGTGGCACTGCTCGTTTTCTATATCACCAAAAGGAAA   (720)
200  GlyGlySerLeuLeuMetValPheValAlaLeuLeuValPheTyrIleThrLysArgLys
     ----------TM---------------------------------
     AAACAGAGGAGTCGGAGAAATGATGAGGAGCTGGAGACAAGAGCCCACAGAGTAGCTACT   (780)
220  LysGlnArgSerArgArgAsnAspGluGluLeuGluThrArgAlaHisArgValAlaThr

     GAAGAAAGGGGCCGGAAGCCCCAACAAATTCCAGCTTCAACCCCTCAGAATCCAGCAACT   (840)
240  GluGluArgGlyArgLysProGlnGlnIleProAlaSerThrProGlnAsnProAlaThr

     TCCCAACATCCTCCTCCACCACCTGGTCATCGTTCCCAGGCACCTAGTCATCGTCCCCCG   (900)
260  SerGlnHisProProProProProGlyHisArgSerGlnAlaProSerHisArgProPro

     CCTCCTGGACACCGTGTTCAGCACCAGCCTCAGAAGAGGCCTCCTGCTCCGTCGGGCACA   (960)
280  ProProGlyHisArgValGlnHisGlnProGlnLysArgProProAlaProSerGlyThr
```

FIG. 2A

```
    CAAGTTCACCAGCAGAAAGGCCCGCCCCTCCCCAGACCTCGAGTTCAGCCAAAACCTCCC    (1020)
300 GLNVALHISGLNGLNLYSGLYPROPROLEUPROARGPROARGVALGLNPROLYSPROPRO

    CATGGGGCAGCAGAAAACTCATTGTCCCCTTCCTCTAATTAAAAAAGATAGAAACTGTCT    (1080)
320 HISGLYALAALAGLUASNSERLEUSERPROSERSERASNEND

    TTTTCAATAAAAAGCACTGTGGATTTCTGCCCTCCTGATGTGCATATCCGTACTTCCATG    (1140)

    AGGTGTTTTCTGTGTGCAGAACATTGTCACCTCCTGAGGCTGTGGGCCACAGCCACCTCT    (1200)

    GCATCTTCGAACTCAGCCATGTGGTCAACATCTGGAGTTTTTGGTCTCCTCAGAGAGCTC    (1260)

    CATCACACCAGTAAGGAGAAGCAATATAAGTGTGATTGCAAGAATGGTAGAGGACCGAGC    (1320)

    ACAGAAATCTTAGAGATTTCTTGTCCCCTCTCAGGTCATGTGTAGATGCGATAAATCAAG    (1380)

    TGATTGGTGTGCCTGGGTCTCACTACAAGCAGCCTATCTGCTTAAGAGACTCTGGAGTTT    (1440)

    CTTATGTGCCCTGGTGGACACTTGCCCACCATCCTGTGAGTAAAAGTGAAATAAAAGCTT    (1500)

    TGAC  (1504)
```

FIG. 2B

```
  1 GCCCGACGAGCCATGGTTGCTGGGAGCGACGCCGGGCGGGCCCTGGGGGTCCTCAGCGTGGTCTGCCTGCTGCACTGCTTTGGTTTCATC 90
  1               MetValAlaGlySerAspAlaGlyArgAlaLeuGlyValLeuSerValValCysLeuLeuHisCysPheGlyPheIle 26

 91 AGCTGTTTTTCCCAACAAATATATGGTGTTGTGTATGGGAATGTAACTTTCCATGTACCAAGCAATGTGCCTTTAAAAGAGGTCCTATGG 180
 27 SerCysPheSerGlnGlnIleTyrGlyValValTyrGlyAsnValThrPheHisValProSerAsnValProLeuLysGluValLeuTrp 56
                                    ---CHO---

181 AAAAAACAAAAGGATAAAGTTGCAGAACTGGAAAATTCTGAATTCAGAGCTTTCTCATCTTTTAAAAATAGGGTTTATTTAGACACTGTG 270
 57 LysLysGlnLysAspLysValAlaGluLeuGluAsnSerGluPheArgAlaPheSerSerPheLysAsnArgValTyrLeuAspThrVal 86

271 TCAGGTAGCCTCACTATCTACAACTTAACATCATCAGATGAAGATGAGTATGAAATGGAATCGCCAAATATTACTGATACCATGAAGTTC 360
 87 SerGlySerLeuThrIleTyrAsnLeuThrSerSerAspGluAspGluTyrGluMetGluSerProAsnIleThrAspThrMetLysPhe 116
               ---CHO---                                          ---CHO---

361 TTTCTTTATGTGCTTGAGTCTCTTCCATCTCCCACACTAACTTGTGCATTGACTAATGGAAGCATTGAAGTCCAATGCATGATACCAGAG 450
117 PheLeuTyrValLeuGluSerLeuProSerProThrLeuThrCysAlaLeuThrAsnGlySerIleGluValGlnCysMetIleProGlu 146
                                                    ---CHO---

451 CATTACAACAGCCATCGAGGACTTATAATGTACTCATGGGATTGTCCTATGGAGCAATGTAAACGTAACTCAACCAGTATATATTTTAAG 540
147 HisTyrAsnSerHisArgGlyLeuIleMetTyrSerTrpAspCysProMetGluGlnCysLysArgAsnSerThrSerIleTyrPheLys 176
                                                                  ---CHO---

541 ATGGAAAATGATCTTCCACAAAAAATACAGTGTACTCTTAGCAATCCATTATTTAATACAACATCATCAATCATTTTGACAACCTGTATC 630
177 MetGluAsnAspLeuProGlnLysIleGlnCysThrLeuSerAsnProLeuPheAsnThrThrSerSerIleIleLeuThrThrCysIle 206
                                                    ---CHO---

631 CCAAGCAGCGGTCATTCAAGACACAGATATGCACTTATACCCATACCATTAGCAGTAATTACAACATGTATTGTCCTGTATATGAATGTT 720
207 ProSerSerGlyHisSerArgHisArgTyrAlaLeuIleProIleProLeuAlaValIleThrThrCysIleValLeuTyrMetAsnVal 236
                                ==============================================================

721 CTTTAATTGAGAAGACAATTTCTTCATTTTTAGGTATTCTGAAATGTGACAGAAAACCAGACAGAACCAACTCCAATTGATTGGTAACAG 810
237 LeuEnd
    ===
811 AAGATGAAGACAACAGCATAACTAAATTATTTTAAAAACTAAAAAGCCATCTGATTTCTCATTT 874
```

FIG. 4A

1 GGCGTAATCT GCTGCTTGCA AACAAAAAAA CCACCGCTAC CAGCGGTGGT
51 TTGTTTGCCG GATCAAGAGC TACCAACTCT TTTTCCGAAG GTAACTGGCT
101 TCAGCAGAGC GCAGATACCA AATACTGTCC TTCTAGTGTA GCCGTAGTTA
151 GGCCACCACT TCAAGAACTC TGTAGCACCG CCTACATACC TCGCTCTGCT
201 AATCCTGTTA CCAGTGGCTG CTGCCAGTGG CGATAAGTCG TGTCTTACCG
251 GGTTGGACTC AAGACGATAG TTACCGGATA AGGCGCAGCG GTCGGGCTGA
301 ACGGGGGGTT CGTGCACACA GCCCAGCTTG GAGCGAACGA CCTACACCGA
351 ACTGAGATAC CTACAGCGTG AGCATTGAGA AAGCGCCACG CTTCCCGAAG
401 GGAGAAAGGC GGACAGGTAT CCGGTAAGCG GCAGGGTCGG AACAGGAGAG
451 CGCACGAGGG AGCTTCCAGG GGGAAACGCC TGGTATCTTT ATAGTCCTGT
501 CGGGTTTCGC CACCTCTGAC TTGAGCGTCG ATTTTTGTGA TGCTCGTCAG
551 GGGGGCGGAG CCTATGGAAA AACGCCAGCA ACGCAAGCTA GCTTCTAGCT
601 AGAAATTGTA AACGTTAATA TTTTGTTAAA ATTCGCGTTA AATTTTTGTT
651 AAATCAGCTC ATTTTTTAAC CAATAGGCCG AAATCGGCAA AATCCCTTAT
701 AAATCAAAAG AATAGCCCGA GATAGGGTTG AGTGTTGTTC CAGTTTGGAA
751 CAAGAGTCCA CTATTAAAGA ACGTGGACTC CAACGTCAAA GGGCGAAAAA
801 CCGTCTATCA GGGCGATGGC CGCCCACTAC GTGAACCATC ACCCAAATCA
851 AGTTTTTTGG GGTCGAGGTG CCGTAAAGCA CTAAATCGGA ACCCTAAAGG
901 GAGCCCCCGA TTTAGAGCTT GACGGGGAAA GCCGGCGAAC GTGGCGAGAA
951 AGGAAGGGAA GAAAGCGAAA GGAGCGGGCG CTAGGGCGCT GGCAAGTGTA
1001 GCGGTCACGC TGCGCGTAAC CACCACACCC GCCGCGCTTA ATGCGCCGCT
1051 ACAGGGCGCG TACTATGGTT GCTTTGACGA GCACGTATAA CGTGCTTTCC

FIG. 6A

```
1101  TCGTTGGAAT CAGAGCGGGA GCTAAACAGG AGGCCGATTA AAGGGATTTT
1151  AGACAGGAAC GGTACGCCAG CTGGATCACC GCGGTCTTTC TCAACGTAAC
1201  ACTTTACAGC GGCGCGTCAT TTGATATGAT GCGCCCCGCT TCCCGATAAG
1251  GGAGCAGGCC AGTAAAAGCA TTACCCGTGG TGGGGTTCCC GAGCGGCCAA
1301  AGGGAGCAGA CTCTAAATCT GCCGTCATCG ACTTCGAAGG TTCGAATCCT
1351  TCCCCCACCA CCATCACTTT CAAAAGTCCG AAAGAATCTG CTCCCTGCTT
1401  GTGTGTTGGA GGTCGCTGAG TAGTGCGCGA GTAAAATTTA AGCTACAACA
1451  AGGCAAGGCT TGACCGACAA TTGCATGAAG AATCTGCTTA GGGTTAGGCG
1501  TTTTGCGCTG CTTCGCGATG TACGGGCCAG ATATACGCGT TGACATTGAT
1551  TATTGACTAG TTATTAATAG TAATCAATTA CGGGGTCATT AGTTCATAGC
1601  CCATATATGG AGTTCCGCGT TACATAACTT ACGGTAAATG GCCCGCCTGG
1651  CTGACCGCCC AACGACCCCC GCCCATTGAC GTCAATAATG ACGTATGTTC
1701  CCATAGTAAC GCCAATAGGG ACTTTCCATT GACGTCAATG GGTGGACTAT
1751  TTACGGTAAA CTGCCCACTT GGCAGTACAT CAAGTGTATC ATATGCCAAG
1801  TACGCCCCCT ATTGACGTCA ATGACGGTAA ATGGCCCGCC TGGCATTATG
1851  CCCAGTACAT GACCTTATGG GACTTTCCTA CTTGGCAGTA CATCTACGTA
1901  TTAGTCATCG CTATTACCAT GGTGATGCGG TTTTGGCAGT ACATCAATGG
1951  GCGTGGATAG CGGTTTGACT CACGGGGATT TCCAAGTCTC CACCCCATTG
2001  ACGTCAATGG GAGTTTGTTT TGGCACCAAA ATCAACGGGA CTTTCCAAAA
2051  TGTCGTAACA ACTCCGCCCC ATTGACGCAA ATGGGCGGAA TTCCTGGGCG
2101  GGACTGGGGA GTGGCGAGCC CTCAGATGCT GCATATAAGC AGCTGCTTTT
2151  TGCCTGTACT GGGTCTCTCT GGTTAGACCA GATCTGAGCC TGGGAGCTCT
2201  CTGGCTAACT AGAGAACCCA CTGCTTAAGC CTCAATAAAG CTTCTAGAGA
2251  TCCCTCGACC TCGAGATCCA TTGTGCTGGC GCGGATTCTT TATCACTGAT
```

FIG. 6B

```
2301 AAGTTGGTGG ACATATTATG TTTATCAGTG ATAAAGTGTC AAGCATGACA
2351 AAGTTGCAGC CGAATACAGT GATCCGTGCC GCCCTAGACC TGTTGAACGA
2401 GGTCGGCGTA GACGGTCTGA CGACACGCAA ACTGGCGGAA CGGTTGGGGG
2451 TTCAGCAGCC GGCGCTTTAC TGGCACTTCA GGAACAAGCG GGCGCTGCTC
2501 GACGCACTGG CCGAAGCCAT GCTGGCGGAG AATCATAGCA CTTCGGTGCC
2551 GAGAGCCGAC GACGACTGGC GCTCATTTCT GACTGGGAAT GCCCGCAGCT
2601 TCAGGCAGGC GCTGCTCGCC TACCGCCAGC ACAATGGATC TCGAGGGATC
2651 TTCCATACCT ACCAGTTCTG CGCCTGCAGG TCGCGGCCGC GACTCTAGAG
2701 GATCTTTGTG AAGGAACCTT ACTTCTGTGG TGTGACATAA TTGGACAAAC
2751 TACCTACAGA GATTTAAAGC TCTAAGGTAA ATATAAAATT TTTAAGTGTA
2801 TAATGTGTTA AACTACTGAT TCTAATTGTT TGTGTATTTT AGATTCCAAC
2851 CTATGGAACT GATGAATGGG AGCAGTGGTG GAATGCCTTT AATGAGGAAA
2901 ACCTGTTTTG CTCAGAAGAA ATGCCATCTA GTGATGATGA GGCTACTGCT
2951 GACTCTCAAC ATTCTACTCC TCCAAAAAAG AAGAGAAAGG TAGAAGACCC
3001 CAAGGACTTT CCTTCAGAAT TGCTAAGTTT TTTGAGTCAT GCTGTGTTTA
3051 GTAATAGAAC TCTTGCTTGC TTTGCTATTT ACACCACAAA GGAAAAAGCT
3101 GCACTGCTAT ACAAGAAAAT TATGGAAAAA TATTCTGTAA CCTTTATAAG
3151 TAGGCATAAC AGTTATAATC ATAACATACT GTTTTTTCTT ACTCCACACA
3201 GGCATAGAGT GTCTGCTATT AATAACTATG CTCAAAAATT GTGTACCTTT
3251 AGCTTTTTAA TTTGTAAAGG GGTTAATAAG GAATATTTGA TGTATAGTGC
3301 CTTGACTAGA GATCATAATC AGCCATACCA CATTTGTAGA GGTTTTACTT
3351 GCTTTAAAAA ACCTCCCACA CCTCCCCCTG AACCTGAAAC ATAAAATGAA
3401 TGCAATTGTT GTTGTTAACT TGTTTATTGC AGCTTATAAT GGTTACAAAT
3451 AAAGCAATAG CATCACAAAT TTCACAAATA AAGCATTTTT TTCACTGCAT
```

FIG. 6C

```
3501  TCTAGTTGTG GTTTGTCCAA ACTCATCAAT GTATCTTATC ATGTCTGGAT
3551  CCTGTGGAAT GTGTGTCAGT TAGGGTGTGG AAAGTCCCCA GGCTCCCCAG
3601  CAGGCAGAAG TATGCAAAGC ATGCATCTCA ATTAGTCAGC AACCAGGTGT
3651  GGAAAGTCCC CAGGCTCCCC AGCAGGCAGA AGTATGCAAA GCATGCATCT
3701  CAATTAGTCA GCAACCATAG TCCCGCCCCT AACTCCGCCC ATCCCGCCCC
3751  TAACTCCGCC CAGTTCCGCC CATTCTCCGC CCCATGGCTG ACTAATTTTT
3801  TTTATTTATG CAGAGGCCGA GGCCGCCTCG GCCTCTGAGC TATTCCAGAA
3851  GTAGTGAGGA GGCTTTTTTG GAGGCCTAGG CTTTTGCAAA AAGCTAATTC
```

FIG. 6D

```
AGACTCTCAGGCCTTGGCAGGTGCGTCTTTCAGTTCCCCTCACACTTCGGGTTCCTCGGG   (60)

GAGGAGGGGCTGGAACCCTAGCCCATCGTCAGGACAAAGATGCTCAGGCTGCTCTTGGCT   (120)
                                      MetLeuArgLeuLeuLeuAla
                                      -18
CTCAACTTATTCCCTTCAATTCAAGTAACAGGAAACAAGATTTTGGTGAAGCAGTCGCCC   (180)
LeuAsnLeuPheProSerIleGlnValThrGlyAsnLysIleLeuValLysGlnSerPro
                                      +1
ATGCTTGTAGCGTACGACAATGCGGTCAACCTTAGCTGCAAGTATTCCTACAATCTCTTC   (240)
MetLeuValAlaTyrAspAsnAlaValAsnLeuSerCysLysTyrSerTyrAsnLeuPhe
                              ---CHO---
TCAAGGGAGTTCCGGGCATCCCTTCACAAAGGACTGGATAGTGCTGTGGAAGTCTGTGTT   (300)
SerArgGluPheArgAlaSerLeuHisLysGlyLeuAspSerAlaValGluValCysVal

GTATATGGGAATTACTCCCAGCAGCTTCAGGTTTACTCAAAAACGGGGTTCAACTGTGAT   (360)
ValTyrGlyAsnTyrSerGlnGlnLeuGlnValTyrSerLysThrGlyPheAsnCysAsp
      ---CHO---
GGGAAATTGGGCAATGAATCAGTGACATTCTACCTCCAGAATTTGTATGTTAACCAAACA   (420)
GlyLysLeuGlyAsnGluSerValThrPheTyrLeuGlnAsnLeuTyrValAsnGlnThr
        ---CHO---                                   ---CHO---
GATATTTACTTCTGCAAAATTGAAGTTATGTATCCTCCTCCTTACCTAGACAATGAGAAG   (480)
AspIleTyrPheCysLysIleGluValMetTyrProProProTyrLeuAspAsnGluLys

AGCAATGGAACCATTATCCATGTGAAAGGGAAACACCTTTGTCCAAGTCCCCTATTTCCC   (540)
SerAsnGlyThrIleIleHisValLysGlyLysHisLeuCysProSerProLeuPhePro
  ---CHO---
GGACCTTCTAAGCCCTTTTGGGTGCTGGTGGTGGTTGGTGGAGTCCTGGCTTGCTATAGC   (600)
GlyProSerLysProPheTrpValLeuValValValGlyGlyValLeuAlaCysTyrSer
                  ----------------------------------TM-------
TTGCTAGTAACAGTGGCCTTTATTATTTTCTGGGTGAGGAGTAAGAGGAGCAGGCTCCTG   (660)
LeuLeuValThrValAlaPheIleIlePheTrpValArgSerLysArgSerArgLeuLeu
-----------------------------------------
CACAGTGACTACATGAACATGACTCCCCGCCGCCCCGGGCCCACCCGCAAGCATTACCAG   (720)
HisSerAspTyrMetAsnMetThrProArgArgProGlyProThrArgLysHisTyrGln

CCCTATGCCCCACCACGCGACTTCGCAGCCTATCGCTCCTGACACGGACGCCTATCCAGA   (780)
ProTyrAlaProProArgAspPheAlaAlaTyrArgSerEnd
                                      202
AGCCAGCCGGCTGGCAGCCCCCATCTGCTCAATATCACTGCTCTGGATAGGAAATGACCG   (840)

CCATCTCCAGCCGGCCACCTCAGCCCCTGTTGGGCCACCAATGCCAATTTTTCTCGAGTG   (900)

ACTAGACCAAATATCAAGATCATTTTGAGACTCTGAAATGAAGTAAAAGAGATTTCCTGT   (960)

GACAGGCCAAGTCTTACAGTGCCATGGCCCACATTCCAACTTACCATGTACTTAGTGACT   (1020)

TGACTGAGAAGTTAGGGTAGAAAACAAAAAGGGAGTGGATTCTGGGAGCCTCTTCCCTTT   (1080)
```

FIG. 7A

CTCACTCACCTGCACATCTCAGTCAAGCAAAGTGTGGTATCCACAGACATTTTAGTTGCA (1140)
GAAGAAAGGCTAGGAAATCATTCCTTTTGGTTAAATGGGTGTTTAATCTTTTGGTTAGTG (1200)
GGTTAAACGGGGTAAGTTAGAGTAGGGGGAGGGATAGGAAGACATATTTAAAAACCATTA (1260)
AAACACTGTCTCCCACTCATGAAATGAGCCACGTAGTTCCTATTTAATGCTGTTTTCCTT (1320)
TAGTTTAGAAATACATAGACATTGTCTTTTATGAATTCTGATCATATTTAGTCATTTTGA (1380)
CCAAATGAGGGATTTGGTCAAATGAGGGATTCCCTCAAAGCAATATCAGGTAAACCAAGT (1440)
TGCTTTCCTCACTCCCTGTCATGAGACTTCAGTGTTAATGTTCACAATATACTTTCGAAA (1500)
GAATAAAATAGTTC (1514)

FIG. 7B

```
TAGACCCAGAGAGGCTCAGCTGCACTCGCCCGGCTGGGAGAGCTGGGTGTGGGGAACATG   (60)
                                                          MET
GCCGGGCCTCCGAGGCTCCTGCTGCTGCCCCTGCTTCTGGCGCTGGCTCGCGGCCTGCCT   (120)
ALAGLYPROPROARGLEULEULEULEUPROLEULEULEUALALEUALAARGGLYLEUPRO
GGGGCCCTGGCTGCCCAAGGTAAGAGCTTCCCAGGCTCTCCATGGCCACAGCTCCGGAGC   (180)
GLYALALEUALAALAGLN /
TCTCCCTGCCCCATGAGCTCAGAGCCCCCAGTCTGAGCCACAGCACAGCCCCCAGGAAGC   (240)
GGGTGGGGTGCTGAGCGGCCTCCAGTGTCTGAGGACTCATTTAACAGAAGGAAAAAGGGT   (300)
GGACCCGGTGGGGAGTGGCCGGGGCTGTCCAGGCAGGGCCGCTGCTTTGGGAGGAAGAAG   (360)
CCCACAGTCTCGGAACACGAGGACAGCACCTCCCCCAACACCACAGCCGGTGCCCAGATC   (420)
TGCTCCATGCCCCGTAAGGCACCGTGTCTTTGGCGACATGTCAGCCCTGGGCTGTCTCAG   (480)
GGCCCCACCATCCCCACCACTGTCCCCTGCAGGGAGGACATTCTCTGTCCTTCTGGCCAG   (540)
                                /
ACTGATGGTGACAGCCCAGGTCCTCCCAGAGGTGCAGCAGTCTCCCCACTGCACGACTGT   (600)
                             GLUVALGLNGLNSERPROHISCYSTHRTHRVA
CCCCGTGGGAGCCTCCGTCAACATCACCTGCTCCACCAGCGGGGGCCTGCGTGGGATCTA   (660)
LPROVALGLYALASERVALASNILETHRCYSSERTHRSERGLYGLYLEUARGGLYILETY
                 ---CHO---
CCTGAGGCAGCTCGGGCCACAGCCCCAAGACATCATTTACTACGAGGACGGGGTGGTGCC   (720)
RLEUARGGLNLEUGLYPROGLNPROGLNASPILEILETYRTYRGLUASPGLYVALVALPR
CACTACGGACAGACGGTTCCGGGGCCGCATCGACTTCTCAGGGTCCCAGGACAACCTGAC   (780)
OTHRTHRASPARGARGPHEARGGLYARGILEASPPHESERGLYSERGLNASPASNLEUTH
                                                     ---CHO--
TATCACCATGCACCGCCTGCAGCTGTCGGACACTGGCACCTACACCTGCCAGGCCATCAC   (840)
RILETHRMETHISARGLEUGLNLEUSERASPTHRGLYTHRTYRTHRCYSGLNALAILETH
-
GGAGGTCAATGTCTACGGCTCCGGCACCCTGGTCCTGGTGACAGAGGAACAGTCCCAAGG   (900)
RGLUVALASNVALTYRGLYSERGLYTHRLEUVALLEUVALTHRGLUGLUGLNSERGLNGL
ATGGCACAGATGCTCGGACGCCCCACCAAGGGCCTCTGCCCTCCCTGCCCCACCGACAGG   (960)
YTRPHISARGCYSSERASPALAPROPROARGALASERALALEUPROALAPROPROTHRGL
CTCCGCCCTCCCTGACCCGCAGACAGCCTCTGCCCTCCCTGACCCGCCAGCAGCCTCTGC   (1020)
YSERALALEUPROASPPROGLNTHRALASERALALEUPROASPPROPROALAALASERAL
CCTCCCTGCGGCCCTGGCGGTGATCTCCTTCCTCCTCGGGCTGGGCCTGGGGGTGGCGTG   (1080)
ALEUPROALAALALEUALAVALILESERPHELEULEUGLYLEUGLYLEUGLYVALALACY
------------------------------TM----------------*
```

FIG. 8A

TGTGCTGGCGAGGACACAGATAAAGAAACTGTGCTCGTGGCGGGATAAGAATTCGGCGGC (1140)
sValLeuAlaArgThrGlnIleLysLysLeuCysSerTrpArgAspLysAsnSerAlaAl

ATGTGTGGTGTACGAGGACATGTCGCACAGCCGCTGCAACACGCTGTCCTCCCCCAACCA (1200)
aCysValValTyrGluAspMetSerHisSerArgCysAsnThrLeuSerSerProAsnGl

GTACCAGTGACCCAGTGGGCCCCTGCACGTCCCGCCTGTGGTCCCCCCAGCACCTTCCCT (1260)
nTyrGlnEnd

GCCCCACCATGCCCCCCACCCTGCCACACCCCTCACCCTGCTGTCCTCCCACGGCTGCAG (1320)

CAGAGTTTGAAGGGCCCAGCCGTGCCCAGCTCCAAGCAGACACACAGGCAGTGGCCAGGC (1380)

CCCACGGTGCTTCTCAGTGGACAATGATGCCTCCTCCGGGAAGCCTTCCCTGCCCAGCCC (1440)

ACGCCGCCACCGGGAGGAAGCCTGACTGTCCTTTGGCTGCATCTCCCGACCATGGCCAAG (1500)

GAGGGCTTTTCTGTGGGATGGGCCTGGCACGCGGCCCTCTCCTGTCAGTGCCGGCCCACC (1560)

CACCAGCAGGCCCCCAACCCCCAGGCAGCCCGGCAGAGGACGGGAGGAGACCAGTCCCCC (1620)

ACCCAGCCGTACCAGAAATAAAGGCTTCTGTGCTTCAAAAAAAAA (1665)

FIG. 8B

```
     CCCAAATGTCTCAGAATGTATGTCCCAGAAACCTGTGGCTGCTTCAACCATTGACAGTTT  (60)
         METSERGLNASNVALCYSPROARGASNLEUTRPLEULEUGLNPROLEUTHRVALL
         -29
     TGCTGCTGCTGGCTTCTGCAGACAGTCAAGCTGCAGCTCCCCCAAAGGCTGTGCTGAAAC  (120)
     EULEULEULEUALASERALAASPSERGLNALAALAALAPROPROLYSALAVALLEULYSL
                                   -1 +1
     TTGAGCCCCCGTGGATCAACGTGCTCCAGGAGGACTCTGTGACTCTGACATGCCAGGGGG  (180)
10   EUGLUPROPROTRPILEASNVALLEUGLNGLUASPSERVALTHRLEUTHRCYSGLNGLYA
                                                        *
     CTCGCAGCCCTGAGAGCGACTCCATTCAGTGGTTCCACAATGGGAATCTCATTCCCACCC  (240)
30   LAARGSERPROGLUSERASPSERILEGLNTRPPHEHISASNGLYASNLEUILEPROTHRH

     ACACGCAGCCCAGCTACAGGTTCAAGGCCAACAACAATGACAGCGGGGAGTACACGTGCC  (300)
50   ISTHRGLNPROSERTYRARGPHELYSALAASNASNASNASPSERGLYGLUTYRTHRCYSG
                                         ---CHO---             *
     AGACTGGCCAGACCAGCCTCAGCGACCCTGTGCATCTGACTGTGCTTTCCGAATGGCTGG  (360)
70   LNTHRGLYGLNTHRSERLEUSERASPPROVALHISLEUTHRVALLEUSERGLUTRPLEUV

     TGCTCCAGACCCCTCACCTGGAGTTCCAGGAGGGAGAAACCATCATGCTGAGGTGCCACA  (420)
90   ALLEUGLNTHRPROHISLEUGLUPHEGLNGLUGLYGLUTHRILEMETLEUARGCYSHISS
                                                          *
     GCTGGAAGGACAAGCCTCTGGTCAAGGTCACATTCTTCCAGAATGGAAAATCCCAGAAAT  (480)
110  ERTRPLYSASPLYSPROLEUVALLYSVALTHRPHEPHEGLNASNGLYLYSSERGLNLYSP

     TCTCCCGTTTGGATCCCACCTTCTCCATCCCACAAGCAAACCACAGTCACAGTGGTGATT  (540)
130  HESERARGLEUASPPROTHRPHESERILEPROGLNALAASNHISSERHISSERGLYASPT
                                            ---CHO---
     ACCACTGCACAGGAAACATAGGCTACACGCTGTTCTCATCCAAGCCTGTGACCATCACTG  (600)
150  YRHISCYSTHRGLYASNILEGLYTYRTHRLEUPHESERSERLYSPROVALTHRILETHRV
           *
     TCCAAGTGCCCAGCATGGGCAGCTCTTCACCAATGGGGATCATTGTGGCTGTGGTCATTG  (660)
170  ALGLNVALPROSERMETGLYSERSERSERPROMETGLYILEILEVALALAVALVALILEA
                                      -------------------------
     CGACTGCTGTAGCAGCCATTGTTGCTGCTGTAGTGGCCTTGATCTACTGCAGGAAAAAGC  (720)
190  LATHRALAVALALAALAILEVALALAALAVALVALALALEUILETYRCYSARGLYSLYSA
     ----------TM------------------------------------*-
     GGATTTCAGCCAATTCCACTGATCCTGTGAAGGCTGCCCAATTTGAGCCACCTGGACGTC  (780)
210  RGILESERALAASNSERTHRASPPROVALLYSALAALAGLNPHEGLUPROPROGLYARGG

     AAATGATTGCCATCAGAAAGAGACAACTTGAAGAAACCAACAATGACTATGAAACAGCTG  (840)
230  LNMETILEALAILEARGLYSARGGLNLEUGLUGLUTHRASNASNASPTYRGLUTHRALAA

     ACGGCGGCTACATGACTCTGAACCCCAGGGCACCTACTGACGATGATAAAAACATCTACC  (900)
250  SPGLYGLYTYRMETTHRLEUASNPROARGALAPROTHRASPASPASPLYSASNILETYRL
```

FIG. 9-A

TGACTCTTCCTCCCAACGACCATGTCAACAGTAATAACTAAAGAGTAACGTTATGCCATG (960)
270 EUTHRLEUPROPROASNASPHISVALASNSERASNASNEND
282
TGGTCATACTCTCAGCTTGCTGAGTGGATGACAAAAAGAGGGGAATTGTTAAAGGAAAAT (1020)
TTAAATGGAGACTGGAAAAATCCTGAGCAAACAAAACCACCTGGCCCTTAGAAATAGCTT (1080)
TAACTTTGCTTAAACTACAAACACAAGCAAAACTTCACGGGGTCATACTACATACAAGCA (1140)
TAAGCAAAACTTAACTTGGATCATTTCTGGTAAATGCTTATGTTAGAAATAAGACAACCC (1200)
CAGCCAATCACAAGCAGCCTACTAACATATAATTAGGTGACTAGGGACTTTCTAAGAAGA (1260)
TACCTACCCCCAAAAAACAATTATGTAATTGAAAACCAACCGATTGCCTTTATTTTGCTT (1320)
CCACATTTTCCCAATAAATACTTGCCTGTGACATTTTGCCACTGGAACACTAAACTTCAT (1380)
GAATTGCGCCTCAGATTTTTCCTTTAACATCTTTTTTTTTTTTTGACAGAGTCTCAATCTG (1440)
TTACCCAGGCTGGAGTGCAGTGGTGCTATCTTGGCTCACTGCAAACCCGCCTCCCAGGTT (1500)
TAAGCGATTCTCATGCCTCAGCCTCCCAGTAGCTGGGATTAGAGGCATGTGCCATCATAC (1560)
CCAGCTAATTTTTGTATTTTTATTTTTTTTTTTAGTAGAGACAGGGTTTCGCAATGTT (1620)
GGCCAGGCCGATCTCGAACTTCTGGCCTCTAGCGATCTGCCCGCCTCGGCCTCCCAAAGT (1680)
GCTGGGATGACCAGCATCAGCCCCAATGTCCAGCCTCTTTAACATCTTCTTTCCTATGCC (1740)
CTCTCTGTGGATCCCTACTGCTGGTTTCTGCCTTCTCCATGCTGAGAACAAAATCACCTA (1800)
TTCACTGCTTATGCAGTCGGAAGCTCCAGAAGAACAAAGAGCCCAATTACCAGAACCACA (1860)
TTAAGTCTCCATTGTTTTGCCTTGGGATTTGAGAAGAGAATTAGAGAGGTGAGGATCTGG (1920)
TATTTCCTGGACTAAATTCCCCTTGGGGAAGACGAAGGGATGCTGCAGTTCCAAAAGAGA (1980)
AGGACTCTTCCAGAGTCATCTACCTGAGTCCCAAAGCTCCCTGTCCTGAAAGCCACAGAC (2040)
AATATGGTCCCAAATGACTGACTGCACCTTCTGTGCCTCAGCCGTTCTTGACATCAAGAA (2100)
TCTTCTGTTCCACATCCACACAGCCAATACAATTAGTCAAACCACTGTTATTAACAGATG (2160)
TAGCAACATGAGAAACGCTTATGTTACAGGTTACATGAGAGCAATCATGTAAGTCTATAT (2220)
GACTTCAGAAATGTTAAAATAGACTAACCTCTAACAACAAATTAAAAGTGATTGTTTCAA (2280)
GGTGAAAAAA (2290)

FIG. 9-B

```
  1 AAAGACAAACTGCACCCACTGAACTCCGCAGCTAGCATCCAAATCAGCCCTTGAGATTTGAGGCCTTGGAGACTCAGGAGTTTTGAGAGC

 91 AAAATCACAACACCCAGAAATTCAGTAAATGGGACTTTCCCGGCAGAGCCAATGAAAGGCCCTATTGCTATGCAATCTGGTCCAAAACCA
  1    MetThrThrProArgAsnSerValAsnGlyThrPheProAlaGluProMetLysGlyProIleAlaMetGlnSerGlyProLysPro
                               ---CHO---

181 CTCTTCAGGAGGATGTCTTCACTGGTGGGCCCCACGCAAAGCTTCTTCATGAGGGAATCTAAGACTTTGGGGGCTGTCCAGATTATGAAT
 30 LeuPheArgArgMetSerSerLeuValGlyProThrGlnSerPhePheMetArgGluSerLysThrLeuGlyAlaValGlnIleMetAsn
                                                                       ===========================

271 GGGCTCTTCCACATTGCCCTGGGGGGTCTTCTGATGATCCCAGCAGGGATCTATGCACCCATCTGTGTGACTGTGTGGTACCCTCTCTGG
 60 GlyLeuPheHisIleAlaLeuGlyGlyLeuLeuMetIleProAlaGlyIleTyrAlaProIleCysValThrValTrpTyrProLeuTrp
    ==========================================================================================

361 GGAGGCATTATGTATATTATTTCCGGATCACTCCTGGCAGCAACGGAGAAAAACTCCAGGAAGTGTTTGGTCAAAGGAAAAATGATAATG
 90 GlyGlyIleMetTyrIleIleSerGlySerLeuLeuAlaAlaThrGluLysAsnSerArgLysCysLeuValLysGlyLysMetIleMet
    ==========================================                                       =========

451 AATTCATTGAGCCTCTTTGCTGCCATTTCTGGAATGATTCTTTCAATCATGGACATACTTAATATTAAAATTTCCCATTTTTTAAAAATG
120 AsnSerLeuSerLeuPheAlaAlaIleSerGlyMetIleLeuSerIleMetAspIleLeuAsnIleLysIleSerHisPheLeuLysMet
    ==================================================================

541 GAGAGTCTGAATTTTATTAGAGCTCACACACCATATATTAACATATACAACTGTGAACCAGCTAATCCCTCTGAGAAAAACTCCCCATCT
150 GluSerLeuAsnPheIleArgAlaHisThrProTyrIleAsnIleTyrAsnCysGluProAlaAsnProSerGluLysAsnSerProSer

631 ACCCAATACTGTTACAGCATACAATCTCTGTTCTTGGGCATTTTGTCAGTGATGCTGATCTTTGCCTTCTTCCAGGAACTTGTAATAGCT
180 ThrGlnTyrCysTyrSerIleGlnSerLeuPheLeuGlyIleLeuSerValMetLeuIlePheAlaPhePheGlnGluLeuValIleAla
             ===============================================================
```

FIG. 10A-1

```
 721 GGCATCGTTGAGAATGAATGGAAAAGAACGTGCTCCAGACCCAAATCTAACATAGTTCTCCTGTCAGCAGAAGAAAAAAAAGAACAGACT
 210 GlyIleValGluAsnGluTrpLysArgThrCysSerArgProLysSerAsnIleValLeuLeuSerAlaGluGluLysLysGluGlnThr

 811 ATTGAAATAAAAGAAGAAGTGGTTGGGCTAACTGAAACATCTTCCCAACCAAAGAATGAAGAAGACATTGAAATTATTCCAATCCAAGAA
 240 IleGluIleLysGluGluValValGlyLeuThrGluThrSerSerGlnProLysAsnGluGluAspIleGluIleIleProIleGlnGlu

 901 GAGGAAGAAGAAGAAACAGAGACGAACTTTCCAGAACCTCCCCAAGATCAGGAATCCTCACCAATAGAAAATGACAGCTCTCCTTAAGTG
 270 GluGluGluGluGluThrGluThrAsnPheProGluProProGlnAspGlnGluSerSerProIleGluAsnAspSerSerProEnd 297
                                                                                ---CHO---

 991 ATTTCTTCTGTTTTCTGTTTCCTTTTTTAAACATTAGTGTTCATAGCTTCCAAGAGACATGCTGACTTTCATTTCTTGAGGTACTCTGCA
                                                      *

1081 CATACGCACCACATCTCTATCTGGCCTTTGCATGGAGTGACCATAGCTCCTTCTCTCTTACATTGAATGTAGAGAATGTAGCCATTGTAG

1171 CAGCTTGTGTTGTCACGCTTCTTCTTTTGAGCAACTTTCTTACACTGAAGAAAGGCAGAATGAGTGCTTCAGAATGTGATTTCCTACTAA

1261 CCTGTTCCTTGGATAGGCTTTTTAGTATAGTATTTTTTTTTGTCATTTTCTCCATCAGCAACCAGGGAGACTGCACCTGATGGAAAAGAT

1351 ATATGACTGCTTCATGACATTCCTAAACTATCTTTTTTTTATTCCACATCTACGTTTTTGGTGGAGTCCCTTTTTATCATCCTTAAAACA

1441 ATGATGCAAAAGGGCTTTAGAGCACAATGGATCT 1474
```

FIG. 10A-2

```
1    CTCAGCCTCGCTATGGCTCCCAGCAGCCCCCGGCCCGCGCTGCCCGCACTCCTGGTCCTGCTCGGGGCTCTGTTCCCA
                    MetAlaProSerSerProArgProAlaLeuProAlaLeuLeuValLeuLeuGlyAlaLeuPhePro
                   (-25)
     GGACCTGGCAATGCCCAGACATCTGTGTCCCCCTCAAAAGTC
     GlyProGlyAsnAlaGlnThrSerValSerProSerLysVal
         (+1)                          (+11)
121  ATCCTGCCCCGGGGAGGCTCCGTGCTGGTGACATGCAGCACCTCCTGTGACCAGCCCAAGTTGTTGGGCATAGAGACC
     IleLeuProArgGlyGlySerValLeuValThrCysSerThrSerCysAspGlnProLysLeuLeuGlyIleGluThr

     CCGTTGCCTAAAAAGGAGTTGCTCCTGCCTGGGAACAACCGG
     ProLeuProLysLysGluLeuLeuLeuProGlyAsnAsnArg
                                       (+61)
241  AAGGTGTATGAACTGAGCAATGTGCAAGAAGATAGCCAACCAATGTGCTATTCAAACTGCCCTGATGGGCAGTCAACA
     LysValTyrGluLeuSerAsnValGlnGluAspSerGlnProMetCysTyrSerAsnCysProAspGlyGlnSerThr

     GCTAAAACCTTCCTCACCGTGTACTGGACTCCAGAACGGGTG
     AlaLysThrPheLeuThrValTyrTrpThrProGluArgVal
                                       (+91)
361  GAACTGGCACCCCTCCCCTCTTGGCAGCCAGTGGGCAAGAACCTTACCCTACGCTGCCAGGTGGAGGGTGGGGCACCC
     GluLeuAlaProLeuProSerTrpGlnProValGlyLysAsnLeuThrLeuArgCysGlnValGluGlyGlyAlaPro
                                         ---CHO---
     CGGGCCAACCTCACCGTGGTGCTGCTCCGTGGGGAGAAGGAG
     ArgAlaAsnLeuThrValValLeuLeuArgGlyGluLysGlu
                               ---------(+131)
481  CTGAAACGGGAGCCAGCTGTGGGGGAGCCCGCTGAGGTCACGACCACGGTGCTGGTGAGGAGAGATCACCATGGAGCC
     LeuLysArgGluProAlaValGlyGluProAlaGluValThrThrThrValLeuValArgArgAspHisHisGlyAla

     AATTTCTCGTGCCGCACTGAACTGGACCTGCGGCCCCAAGGG
     AsnPheSerCysArgThrGluLeuAspLeuArgProGlnGly
     ---CHO---                        (+171)
601  CTGGAGCTGTTTGAGAACACCTCGGCCCCCTACCAGCTCCAGACCTTTGTCCTGCCAGCGACTCCCCCACAACTTGTC
     LeuGluLeuPheGluAsnThrSerAlaProTyrGlnLeuGlnThrPheValLeuProAlaThrProProGlnLeuVal
                   ---CHO---
     AGCCCCCGGGTCCTAGAGGTGGACACGCAGGGGACCGTGGTC
     SerProArgValLeuGluValAspThrGlnGlyThrValVal
                                      (+211)
```

FIG. 11-A

```
721   TGTTCCCTGGACGGGCTGTTCCCAGTCTCGGAGGCCCAGGTCCACCTGGCACTGGGGGACCAGAGGTTGAACCCCACA
      CysSerLeuAspGlyLeuPheProValSerGluAlaGlnValHisLeuAlaLeuGlyAspGlnArgLeuAsnProThr

      GTCACCTATGGCAACGACTCCTTCTCGGCCAAGGCCTCAGTC
      ValThrTyrGlyAsnAspSerPheSerAlaLysAlaSerVal
                ---CHO---                  (+251)
841   AGTGTGACCGCAGAGGACGAGGGCACCCAGCGGCTGACGTGTGCAGTAATACTGGGGAACCAGAGCCAGGAGACACTG
      SerValThrAlaGluAspGluGlyThrGlnArgLeuThrCysAlaValIleLeuGlyAsnGlnSerGlnGluThrLeu
                                                                  ---CHO---
      CAGACAGTGACCATCTACAGCTTTCCGGCGCCCAACGTGATT
      GlnThrValThrIleTyrSerPheProAlaProAsnValIle
                                           (+291)
961   CTGACGAAGCCAGAGGTCTCAGAAGGGACCGAGGTGACAGTGAAGTGTGAGGCCCACCCTAGAGCCAAGGTGACGCTG
      LeuThrLysProGluValSerGluGlyThrGluValThrValLysCysGluAlaHisProArgAlaLysValThrLeu

      AATGGGGTTCCAGCCCAGCCACTGGGCCCGAGGGCCCAGCTC
      AsnGlyValProAlaGlnProLeuGlyProArgAlaGlnLeu
                                           (+331)
1081  CTGCTGAAGGCCACCCCAGAGGACAACGGGCGCAGCTTCTCCTGCTCTGCAACCCTGGAGGTGGCCGGCCAGCTTATA
      LeuLeuLysAlaThrProGluAspAsnGlyArgSerPheSerCysSerAlaThrLeuGluValAlaGlyGlnLeuIle

      CACAAGAACCAGACCCGGGAGCTTCGTGTCCTGTATGGCCCC
      HisLysAsnGlnThrArgGluLeuArgValLeuTyrGlyPro
          ---CHO---                        (+371)
1201  CGACTGGACGAGAGGGATTGTCCGGGAAACTGGACGTGGCCAGAAAATTCCCAGCAGACTCCAATGTGCCAGGCTTGG
      ArgLeuAspGluArgAspCysProGlyAsnTrpThrTrpProGluAsnSerGlnGlnThrProMetCysGlnAlaTrp
                                  ---CHO---
      GGGAACCCATTGCCCGAGCTCAAGTGTCTAAAGGATGGCACT
      GlyAsnProLeuProGluLeuLysCysLeuLysAspGlyThr
                                           (+411)
1321  TTCCCACTGCCCATCGGGGAATCAGTGACTGTCACTCGAGATCTTGAGGGCACCTACCTCTGTCGGGCCAGGAGCACT
      PheProLeuProIleGlyGluSerValThrValThrArgAspLeuGluGlyThrTyrLeuCysArgAlaArgSerThr

      CAAGGGGAGGTCACCCGCGAGGTGACCGTGAATGTGCTCTCC
      GlnGlyGluValThrArgGluValThrValAsnValLeuSer
                                           (+451)
```

FIG. 11-B

```
1441 CCCCGGTATGAGATTGTCATCATCACTGTGGTAGCAGCCGCAGTCATAATGGGCACTGCAGGCCTCAGCACGTACCTC
     ProArgTyrGluIleValIleIleThrValValAlaAlaAlaValIleMetGlyThrAlaGlyLeuSerThrTyrLeu
                 -----------------------------------TM----------------------------------
     TATAACCGCCAGCGGAAGATCAAGAAATACAGACTACAACAG
     TyrAsnArgGlnArgLysIleLysLysTyrArgLeuGlnGln
     ---                                   (+491)
1561 GCCCAAAAAGGGACCCCCATGAAACCGAACACACAAGCCACGCCTCCCTGAACCTATCCCGGGACAGGGCCTCTTCCT
     AlaGlnLysGlyThrProMetLysProAsnThrGlnAlaThrProPro
                                                (+507)
     CGGCCTTCCCATATTGGTGGCAGTGGTGCCACACTGAACAGA

1681 GTGGAAGACATATGCCATGCAGCTACACCTACCGGCCCTGGGACGCCGGAGGACAGGGCATTGTCCTCAGTCAGATAC
1801 GGCCACGCATCTGATCTGTAGTCACATGACTAAGCCAAGAGGAAGG
      AACAGCATTTGGGGCCATGGTACCTGCACACCTAAAACACTA
```

FIG. 11-C

```
   1  ..GGAGAGTC TGACCACCAT GCCACCTCCT CGCCTCCTCT TCTTCCTCCT
  51  CTTCCTCACC CCCATGGAAG TCAGGCCCGA GGAACCTCTA GTGGTGAAGG
 101  TGGAAGAGGG AGATAACGCT GTGCTGCAGT GCCTCAAGGG GACCTCAGAT
 151  GGCCCCACTC AGCAGCTGAC CTGGTCTCGG GAGTCCCCGC TTAAACCCTT
 201  CTTAAAACTC AGCCTGGGGC TGCCAGGCCT GGGAATCCAC ATGAGGCCCC
 251  TGGcCATCTG GCTTTTCATC TTCAACGTCT CTCAACAGAT GGGGGGCTTC
 301  TACCTGTGCC AGCCGGGGCC CCCCTCTGAG AAGGCCTGGC AGCCTGGCTG
 351  GACAGTCAAT GTGGAGGGCA GCGGGGAGCT GTTCCGGTGG AATGTTTCGG
 401  ACCTAGGTGG CCTGGGCTGT GGCCTGAAGA ACAGGTCCTC AGAGGGCCCC
 451  AGCTCCCCTT CCGGGAAGCT CATGAGCCCC AAGCTGTATG TGTGGGCCAA
 501  AGACCGCCCT GAGATCTGGG AGGGAGAGCC TCCGTGTGTC CCACCGAGGG
 551  ACAGCCTGAA CCAGAGCCTC AGCCAGGACC TCACCATGGC CCCTGGCTCC
 601  ACACTCTGGC TGTCCTGTGG GGTACCCCCT GACTCTGTGT CCAGGGGCCC
 651  CCTCTCCTGG ACCCATGTGC ACCCCAAGGG GCCTAAGTCA TTGCTGAGCC
 701  TAGAGCTGAA GGACGATCGC CCGGCCAGAG ATATGTGGGT AATGGAGACG
 751  GGTCTGTTGT TGCCCCGGGC CACAGCTCAA GACGCTGGAA AGTATTATTG
 801  TCACCGTGGC AACCTGACCA TGTCATTCCA CCTGGAGATC ACTGCTCGGC
 851  CAGTACTATG GCACTGGCTG CTGAGGACTG GTGGCTGGAA GGTCTCAGCT
 901  GTCACTTTGG CTTATCTGAT CTTCTGCCTG TGTTCCCTTG TGGGCATTCT
 951  TCATCTTCAA AGAGCCCTGG TCCTGAGGAG GAAAAGAAAG CGAATGACTG
1001  ACCCCACCAG GAGATTCTTC AAAGTGACGC CTCCCCCAGG AAGCGGGCCC
1051  CAGAACCAGT ACGGGAACGT GCTGTCTCTC CCCACACCCA CCTCAGGCCT
1101  CGGACGCGCC CAGCGTTGGG CCGCAGGCCT GGGGGGCACT GCCCCGTCTT
1151  ATGGAAACCC GAGCAGCGAC GTCCAGGCGG ATGGAGCCTT GGGGTCCCGG
```

FIG. 12-A

```
1201 AGCCGCCGGG AGTGGGCCCA GAAGAAGAGG AAGGGGAGGG CTATGAGGAA
1251 CCTGACAGTG AGGAGGACTC CGAGTTCTAT GAGAACGACT CCAACCTTGG
1301 GCAGGACCAG CTCTCCCAGG ATGGCAGCGG CTACGAGAAC CCTGAGGATG
1351 AGCCCCTGGG TCCTGAGGAT GAAGACTCCT TCTCCAACGC TGAGTCTTAT
1401 GAGAACGAGG ATGAAGAGCT GACCCAGCCG GTCGCCAGGA CAATGGACTT
1451 CCTGAGCCCT CATGGGTCAG CCTGGGACCC CAGCCGGGAA GCAACCTCCC
1501 TGGGGTCCCA GTCCTATGAG GATATGAGAG GAATCCTGTA TGCAGCCCCC
1551 CAGCTCCGCT CCATTCGGGG CCAGCCTGGA CCCAATCATG AGGAAGATGC
1601 AGACTCTTAT GAGAACATGG ATAATCCCGA TGGGCCAGAC CCAGCCTGGG
1651 GAGGAGGGGG CCGCATGGGC ACCTGGAGCA CCAGGTGATC CTCAGGTGGC
1701 CAGCCTGGAT CTCCTCAAGT CCCCAAGATT CACACCTGAC TCTGAAATCT
1751 GAAGACCTCG AGCAGATGAT GCCAACCTCT GGAGCAATGT TGCTTAGGAT
1801 GTGTGCATGT GTGTAAGTGT GTGTGTGTGT GTGTGTGTGT GTGTGTGTGT
1851 ATACATGCCA GTGACACTTC CAGTCCCCTT TGTATTCCTT AAATAAACTC
1901 AATGAGCTCT TCCAAAAAAA AAAA
```

FIG. 12-B

```
1    ACAAAGACAA ACTGCACCCA CTGAACTCCG CAGCTAGCAT CCAAATCAGC
51   CCTTGAGATT TGAGGCCTTG GAGACTCAGG AGTTTTGAGA GCAAAATGAC
101  AACACCCAGA AATTCAGTAA ATGGGACTTT CCCGGCAGAG CCAATGAAAG
151  GCCCTATTGC TATGCAATCT GGTCCAAAAC CACTCTTCAG GAGGATGTCT
201  TCACTGGTGG GCCCCACGCA AAGCTTCTTC ATGAGGGAAT CTAAGACTTT
251  GGGGGCTGTC CAGATTATGA ATGGGCTCTT CCACATTGCC CTGGGGGGTC
301  TTCTGATGAT CCCAGCAGGG ATCTATGCAC CCATCTGTGT GACTGTGTGG
351  TACCCTCTCT GGGGAGGCAT TATGTATATT ATTTCCGGAT CACTCCTGGC
401  AGCAACGGAG AAAAACTCCA GGAAGTGTTT GGTCAAAGGA AAAATGATAA
451  TGAATTCATT GAGCCTCTTT GCTGCCATTT CTGGAATGAT TCTTTCAATC
501  ATGGACATAC TTAATATTAA AATTTCCCAT TTTTTAAAAA TGGAGAGTCT
551  GAATTTTATT AGAGCTCACA CACCATATAT TAACATATAC AACTGTGAAC
601  CAGCTAATCC CTCTGAGAAA AACTCCCCAT CTACCCAATA CTGTTACAGC
651  ATACAATCTC TGTTCTTGGG CATTTTGTCA GTGATGCTGA TCTTTGCCTT
701  CTTCCAGGAA CTTGTAATAG CTGGCATCGT TGAGAATGAA TGGAAAAGAA
751  CGTGCTCCAG ACCCAAATCT AACATAGTTC TCCTGTCAGC ACAAGAAAAA
801  AAAGAACAGA CTATTGAAAT AAAAGAAGAA GTGGTTGGGC TAACTGAAAC
851  ATCTTCCCAA CCAAAGAATG AAGAAGACAT TGAAATTATT CCAATCCAAG
901  AAGAGGAAGA AGAAGAAACA GAGACGAACT TTCCAGAACC TCCCCAAGAT
951  CAGGAATCCT CACCAATAGA AAATGACAGC TCTCCTTAAG TGATTTCTTC
1001 TGTTTTCTGT TTCCTTTTTT AAACATTAGT GTTCATAGCT TCCAAGAGAC
1051 ATGCTGACTT TCATTTCTTG AGGTACTCTG CACATACGCA CCACATCTCT
```

FIG. 13-A

```
1101  ATCTGGCCTT TGCATGGAGT GACCATAGCT CCTTCTCTCT TACATTGAAT
1151  GTAGAGAATG TAGCCATTGT AGCAGCTTGT GTTGTCACGC TTCTTCTTTT
1201  GAGCAACTTT CTTACACTGA AGAAAGGCAG AATGAGTGCT TCAGAATGTG
1251  ATTTCCTACT AACCTGTTCC TTGGATAGGC TTTTTAGTAT AGTATTTTTT
1301  TTTGTCATTT TCTCCATCAG CAACCAGGGA GACTGCACCT GATGGAAAAG
1351  ATATATGACT GCTTCATGAC ATTCCTAAAC TATCTTTTTT TTATTCCACA
1401  TCTACGTTTT TGGTGGAGTC CCTTTTTATC ATCCTTAAAA CAATGATGCA
1451  AAAGGGCTTT AGAGCACAAT GGATCT
```

FIG. 13-B

```
1     CCCAAATGTC TCAGAATGTA TGTCCCAGAA ACCTGTGGCT GCTTCAACCA
51    TTGACAGTTT TGCTGCTGCT GGCTTCTGCA GACAGTCAAG CTGCAGCTCC
101   CCCAAAGGCT GTGCTGAAAC TTGAGCCCCC GTGGATCAAC GTGCTCCAGG
151   AGGACTCTGT GACTCTGACA TGCCAGGGGG CTCGCAGCCC TGAGAGCGAC
201   TCCATTCAGT GGTTCCACAA TGGGAATCTC ATTCCCACCC ACACGCAGCC
251   CAGCTACAGG TTCAAGGCCA ACAACAATGA CAGCGGGGAG TACACGTGCC
301   AGACTGGCCA GACCAGCCTC AGCGACCCTG TGCATCTGAC TGTGCTTTCC
351   GAATGGCTGG TGCTCCAGAC CCCTCACCTG GAGTTCCAGG AGGGAGAAAC
401   CATCATGCTG AGGTGCCACA GCTGGAAGGA CAAGCCTCTG GTCAAGGTCA
451   CATTCTTCCA GAATGGAAAA TCCCAGAAAT TCTCCCGTTT GGATCCCACC
501   TTCTCCATCC CACAAGCAAA CCACAGTCAC AGTGGTGATT ACCACTGCAC
551   AGGAAACATA GGCTACACGC TGTTCTCATC CAAGCCTGTG ACCATCACTG
601   TCCAAGTGCC CAGCATGGGC AGCTCTTCAC CAATGGGGAT CATTGTGGCT
651   GTGGTCATTG CGACTGCTGT AGCAGCCATT GTTGCTGCTG TAGTGGCCTT
701   GATCTACTGC AGGAAAAAGC GGATTTCAGC CAATTCCACT GATCCTGTGA
751   AGGCTGCCCA ATTTGAGCCA CCTGGACGTC AAATGATTGC CATCAGAAAG
801   AGACAACTTG AAGAAACCAA CAATGACTAT GAAACAGCTG ACGGCGGCTA
851   CATGACTCTG AACCCCAGGG CACCTACTGA CGATGATAAA AACATCTACC
901   TGACTCTTCC TCCCAACGAC CATGTCAACA GTAATAACTA AAGAGTAACG
951   TTATGCCATG TGGTCATACT CTCAGCTTGC TGAGTGGATG ACAAAAAGAG
1001  GGGAATTGTT AAAGGAAAAT TTAAATGGAG ACTGGAAAAA TCCTGAGCAA
1051  ACAAAACCAC CTGGCCCTTA GAAATAGCTT TAACTTTGCT TAAACTACAA
1101  ACACAAGCAA AACTTCACGG GGTCATACTA CATACAAGCA TAAGCAAAAC
1151  TTAACTTGGA TCATTTCTGG TAAATGCTTA TGTTAGAAAT AAGACAACCC
1201  CAGCCAATCA CAAGCAGCCT ACTAACATAT AATTAGGTGA CTAGGGACTT
1251  TCTAAGAAGA TACCTACCCC CAAAAAACAA TTATGTAATT GAAAACCAAC
1301  CGATTGCCTT TATTTTGCTT CCACATTTTC CCAATAAATA CTTGCCTGTG
1351  ACATTTTGCC ACTGGAACAC TAAACTTCAT GAATTGCGCC TCAGATTTTT
1401  CCTTTAACAT CTTTTTTTTT TTTGACAGAG TCTCAATCTG TTACCCAGGC
1451  TGGAGTGCAG TGGTGCTATC TTGGCTCACT GCAAACCCGC CTCCCAGGTT
1501  TAAGCGATTC TCATGCCTCA GCCTCCCAGT AGCTGGGATT AGAGGCATGT
1551  GCCATCATAC CCAGCTAATT TTTGTATTTT TTATTTTTTT TTTTTAGTAG
1601  AGACAGGGTT TCGCAATGTT GGCCAGGCCG ATCTCGAACT TCTGGCCTCT
1651  AGCGATCTGC CCGCCTCGGC CTCCCAAAGT GCTGGGATCA CCAGCATCAG
```

FIG. 14-A

```
1701 CCCCAATGTC CAGCCTCTTT AACATCTTCT TTCCTATGCC CTCTCTGTGG
1751 ATCCCTACTG CTGGTTTCTG CCTTCTCCAT GCTGAGAACA AAATCACCTA
1801 TTCACTGCTT ATGCAGTCGG AAGCTCCAGA AGAACAAAGA GCCCAATTAC
1851 CAGAACCACA TTAAGTCTCC ATTGTTTTGC CTTGGGATTT GAGAAGAGAA
1901 TTAGAGAGGT GAGGATCTGG TATTTCCTGG ACTAAATTCC CCTTGGGGAA
1951 GACGAAGGGA TGCTGCAGTT CCAAAAGAGA AGGACTCTTC CAGAGTCATC
2001 TACCTGAGTC CCAAAGCTCC CTGTCCTGAA AGCCACAGAC AATATGGTCC
2051 CAAATGACTG ACTGCACCTT CTGTGCCTCA GCCGTTCTTG ACATCAAGAA
2101 TCTTCTGTTC CACATCCACA CAGCCAATAC AATTAGTCAA ACCACTGTTA
2151 TTAACAGATG TAGCAACATG AGAAACGCTT ATGTTACAGG TTACATGAGA
2201 GCAATCATGT AAGTCTATAT GACTTCAGAA ATGTTAAAAT AGACTAACCT
2251 CTAACAACAA ATTAAAAGTG ATTGTTTCAA GGTGAAAAAA
```

FIG. 14-B

```
1    GCTGTGACTG CTGTGCTCTG GGCGCCACTC GCTCCAGGGA GTGATGGGAA
51   TCCTGTCATT CTTACCTGTC CTTGCCACTG AGAGTGACTG GGCTGACTGC
101  AAGTCCCCCC AGCCTTGGGG TCATATGCTT CTGTGGACAG CTGTGCTATC
151  CCTGGCTCCT GTTGCTGGGA CACCTGCAGC TCCCCCAAAG GCTGTGCTGA
201  AACTCGAGCC CCAGTGGATC AACGTGCTCC AGGAGGACTC TGTGACTCTG
251  ACATGCCGGG GGACTCACAG CCCTGAGAGC GACTCCATTC AGTGGTTCCA
301  CAATGGGAAT CTCATTCCCA CCCACACGCA GCCCAGCTAC AGGTTCAAGG
351  CCAACAACAA TGACAGCGGG GAGTACACGT GCCAGACTGG CCAGACCAGC
401  CTCAGCGACC CTGTGCATCT GACTGTGCTT TCTGGTCAGT GGAGGAAGGC
451  CCCAGGGTGG ACCTGGGAGG GCCAGGACGG ATGAAATCTG CTTTCAGGCA
501  GAGGTTTGCA GGAAAGGGGG GTGGCCTGCT TACTGGGAAG TATCGCTGTG
551  AGTTGCCTCA GCACATATCA GTGGTTGTTT TTGCCTCAGT TCTGATTGAA
601  CAGAAGAAGG TTTCAAGGCC AAAAACAGGC AGCCAAGTGT GAGAGAAGCA
651  GAAGGAAATC CCTACTGCAT AAAACCCATT TCCATTTTAA TGGCAGAATT
701  GAAAAGCACA GACCACAACT GAATCCTAGC CCTGGAAATG ACTCACTATA
751  CAACATGATG AATTCATTTA ACCCTTGAGT TTCCATTTCT TCACCTGCTC
801  CGTGGGGCAC TAACGCCTCC CTCAGAGGCT TCTGGTGAGA ATCAGTGTTT
851  CCCTGCCCCC GCCCCGCCCT CCATGCCCCT TCTCCACGTT CTCACTGTGC
901  TAGGTGCTCT TCTCTGTCTT TCTCTTCCAC CAGCCTGTGG GAAACCTGAG
951  ATGAAAGTCG TGTCTTACCC ATCTTTGTAT TTCCAGCATC TGAAACTGGG
1001 CAGAGCTTAA TAAATATTTT GCTGGAGAGG TTGATGATCT TACAAAGCTC
1051 CCATTGAAAG GTGGCTCTCT GTAAAGCAAA GTTACAATGA GATTGTGATG
1101 AACATTGTCC TTGTGGCTTT TCACTTAGTC CCCTCCCTTC ACCTGAAGAG
1151 CAAATTTTCC TCAAAAGTAC ACAGCAAACG AATGACCCAC TGGTGACACT
1201 GTTGCCTTTA GACCCTGCTG GAAAGAAGCT CCACATTTAT TAACATTCCC
1251 GAAGTAAATT TATCAGGTAG CATTCATCAG GTAACATTTG TTGCACATTC
1301 ATGACTTTTC TACTGTCCAC AAAGGCATAT GTCCTTATCA TATGCGGACT
1351 CCTCGGTCAC ACTGGATTCT TCCTTCCCTC CTCGACATGG AAGAGATGGC
1401 ATCTTAGGGT CTCTTGTGTT CTTCCTGCAG AGGCCTGTCG GGCAGGAAAA
1451 GGCTGCAGCT GCCTTCCTGG GAGAAGGAGG AGATGAGTGT ATCCTGAACA
1501 CCTATTATGT GCTAGGGGCT ATTGTAGATA CATGACACTA TCATGCTCAT
1551 TTTCACGAAT GAGGAAACTG AGGCTCAGAA GACTTAAATT ATTTGCCCAA
1601 GAGTTATAAA TGACAGAGCC AGCATTAGAG TCCAGGACTG TCTGATTTCA
1651 GACCTAAGCT GTTCCCTCTG CACATCGTGT CCCACCAGTA AGGAAGATCT
```

FIG. 15-A

```
1701 GGGTCTCAGA GCTGAGCCAA GACCTCCCGG GTCCTCTGCG GTTTTTTGTG
1751 TCTTTCAGAG TGGCTGGTGC TCCAGACCCC TCACCTGGAG TTCCAGGAGG
1801 GAGAAACCAT CGTGCTGAGG TGCCACAGCT GGAAGGACAA GCCTCTGGTC
1851 AAGGTCACAT TCTTCCAGAA TGGAAAATCC AAGAAATTTT CCCGTTCGGA
1901 TCCCAACTTC TCCATCCCAC AAGCAAACCA CAGTCACAGT GGTGATTACC
1951 ACTGCACAGG AAACATAGGC TACACGCTGT ACTCATCCAA GCCTGTGACC
2001 ATCACTGTCC AAGCTCCCAG CTCTTCACCG ATGGGGATCA TTGTGGCTGT
2051 GGTCACTGGG ATTGCTGTAG CGGCCATTGT TGCTGCTGTA GTGGCCTTGA
2101 TCTACTGCAG GAAAAAGCGG ATTTCAGGTT TGTAGCTCCT CCCGGTCCCT
2151 TTTGTTATCA GTTTCCACTT T
```

FIG. 15-B

```
  1  GCCTCGCTCG GGCGCCCAGT GGTCCTGCCG CCTGGTCTCA CCTCGCCATG
 51  GTTCGTCTGC CTCTGCAGTG CGTCCTCTGG GGCTGCTTGC TGACCGCTGT
101  CCATCCAGAA CCACCCACTG CATGCAGAGA AAAACAGTAC CTAATAAACA
151  GTCAGTGCTG TTCTTTGTGC CAGCCAGGAC AGAAACTGGT GAGTGACTGC
201  ACAGAGTTCA CTGAAACGGA ATGCCTTCCT TGCGGTGAAA GCGAATTCCT
251  AGACACCTGG AACAGAGAGA CACACTGCCA CCAGCACAAA TACTGCGACC
301  CCAACCTAGG GCTTCGGGTC CAGCAGAAGG GCACCTCAGA AACAGACACC
351  ATCTGCACCT GTGAAGAAGG CTGGCACTGT ACGAGTGAGG CCTGTGAGAG
401  CTGTGTCCTG CACCGCTCAT GCTCGCCCGG CTTTGGGGTC AAGCAGATTG
451  CTACAGGGGT TTCTGATACC ATCTGCGAGC CCTGCCCAGT CGGCTTCTTC
501  TCCAATGTGT CATCTGCTTT CGAAAAATGT CACCCTTGGA CAAGCTGTGA
551  GACCAAAGAC CTGGTTGTGC AACAGGCAGGC ACAAACAAGA CTGATGTTGT
601  CTGTGGTCCC CAGGATCGGC TGAGAGCCCT GGTGGTGATC CCCATCATCT
651  TCGGGATCCT GTTTGCCATC CTCTTGGTGC TGGTCTTTAT CAAAAAGGTG
701  GCCAAGAAGC CAACCAATAA GGCCCCCCAC CCCAAGCAGG AACCCCAGGA
751  GATCAATTTT CCCGACGATC TTCCTGGCTC CAACACTGCT GCTCCAGTGC
801  AGGAGACTTT ACATGGATGC CAACCGGTCA CCCAGGAGGA TGGCAAAGAG
851  AGTCGCATCT CAGTGCAGGA GAGACAGTGA GGCTGCACCC ACCCAGGAGT
901  GTGGCCACGT GGGCAAACAG GCAGTTGGCC AGAGAGCCTG GTGCTGCTGC
951  TGCAGGGGTG CAGGCAGAAG CGGGGAGCTA TGCCCAGTCA GTGCCAGCCC
     CTC
```

FIG. 16

RAPID IMMUNOSELECTION CLONING METHOD

This application is a divisional of U.S. patent application Ser. No. 07/983,647, filed Dec. 1, 1992; now U.S. Pat. No. 6,218,525 which is a continuation-in-part of U.S. patent application Ser. No. 07/553,759, filed Jul. 13, 1990 now abandoned; which is a continuation-in-in-part of U.S. patent application Ser. No. 07/498,809 filed Mar. 23, 1990 (abandoned); which is a continuation-in-part of U.S. patent application Ser. No. 07/379,076, filed Jul. 13, 1989 (abandoned); which is a continuation-in-part of U.S. patent application Ser. No. 07/160,416, filed Feb. 25, 1988 (abandoned). Each of these predecessor applications and all references cited herein are incorporated by reference in their entirety.

BACKGROUND

A basic tool in the field of recombinant genetics is the conversion of poly(A)$^+$ mRNA to double-stranded (ds) cDNA, which then can be inserted into a cloning vector and expressed in an appropriate host cell. Molecular cloning methods for ds cDNA have been reviewed, for example, by Williams, "The Preparation and Screening of a cDNA Clone Bank," in Williamson, ed., *Genetic Engineering*, Vol. 1, p. 2, Academic Press, New York (1981); Maniatis, "Recombinant DNA", in Prescott, ed., *Cell Biology, Academic Press, New York (*1980); and Efstratiadis et al., "Cloning of Double-Stranded DNA," in Stelo et al., *Genetic Engineering*, Vol. 1, p. 15, Plenum Press, New York (1979).

A substantial number of variables affect the successful cloning of a particular gene and cDNA cloning strategy thus must be chosen with care. A method common to many cDNA cloning strategies involves the construction of a "cDNA library" which is a collection of cDNA clones derived from the total poly(A)$^+$ mRNA derived from a cell of the organism of interest.

A mammalian cell may contain up to 30,000 different mRNA sequences, and the number of clones required to obtain low-abundance mRNAs, for example, may be much greater. Methods of constructing genomic eukaryotic DNA libraries in different expression vectors, including bacteriophage lambda, cosmids, and viral vectors, are known. Some commonly used methods are described, for example, in Maniatis et al., *Molecular Cloning: A Laboratory Manual*, Cold Spring Harbor Laboratory, publisher, Cold Spring Harbor, N.Y. (1982).

Once a genomic cDNA library has been constructed, it is necessary to isolate from the thousands of host cells the cell containing the particular human gene of interest. Many different methods of isolating target genes from cDNA libraries have been or utilized, with varying success. These include, for example, the use of nucleic acid probes, which are labeled mRNA fragments having nucleic acid sequences complementary to the DNA sequence of the target gene. When this method is applied to cDNA clones of abundant mRNAs in transformed bacterial hosts, colonies hybridizing strongly to the probe are likely to contain the target DNA sequences. The identity of the clone then may be proven, for example, by in situ hybridization/selection (Goldberg et al., *Methods Enzymol.,* 68:206 (1979)) hybrid-arrested translation (Paterson et al., *Proceedings of the National Academy of Sciences,* 74:4370 (1977)), or direct DNA sequencing (Maxam and Gilbert, *Proceedings of the National Academy of Sciences,* 74:560 (1977); Maat and Smith, *Nucleic Acids Res.,* 5:4537 (1978)).

Such methods, however, have major drawbacks when the object is to clone mRNAs of relatively low abundance from cDNA libraries. For example, using direct in situ colony hybridization, it is very difficult to detect clones containing cDNA complementary to mRNA species present in the initial library population at less than one part in 200. As a result, various methods for enriching mRNA in the total population (e.g. size fractionation, use of synthetic oligodeoxynucleotides, differential hybridization, or immunopurification) have been developed and are often used when low abundance mRNAs are cloned. Such methods are described, for example, in Maniatis et al., *Molecular Cloning: A Laboratory Manual*, supra.

Many functional eukaryotic proteins initially exist in the form of precursor molecules which contain leader or signal sequences at their N-terminal ends. These leader sequences bind to the cell membrane and draw the remainder of the protein through the lipid bilayer, after which the signal sequence is cleaved from the protein by a signal peptidase enzyme. The protein thus functions only after secretion from the cells (for example, insulin, serum albumin, antibodies, and digestive tract enzymes), or after the proteins have been anchored to the outer surface of a cell membrane (for example, histocompatibility antigens).

The cell surface antigens characteristic of mammalian T lymphocytes are additional examples of proteins that anchor to the cell surface. In mammals, certain cells derived from bone marrow mature into lymphocytes, which are present in the lymphoid organs, including the thymus, spleen, lymph nodes, and lymphoid aggregates, and also circulate actively through the blood and lymph systems. Mature lymphocyte cells may be divided into two populations: thymus-dependent (T) lymphocytes and thymus-independent (B) lymphocytes. T lymphocytes migrate to the interior of the thymus, where they undergo differentiative proliferation. During their differentiation process, they express characteristic cell surface membrane alloantigens, including Thy-1, TLA, gv-1, Ly-1, Ly-2, Ly-3, and Ly-5. As they mature, T lymphocytes lose the TLA antigens and some of the Thy-1 antigens, and gain histocompatibility antigens, acquiring the membrane conformation typical of the recirculating T lymphocytes. This is described, for example, by Mota, "Activity of Immune Cells," in Bier et al., eds., *Fundamentals of Immunology,* 2d Ed., Springer-Verlag, Berlin, pp. 35–62 (1986).

T lymphocytes are involved indirectly in the formation of antibodies and their activities thus have required complex analysis of cell function, rather than simple antibody titer measurement. Partly due to this, their importance in development of immunologic competence was not recognized until relatively recently. Mature T lymphocytes synthesize and express an unique pattern of surface glycoprotein antigens which serve as markers for identification of different T lymphocyte subpopulations, including T helper cells, T suppressor cells, and T cytotoxic cells. Each of these subpopulations plays a very important role in regulating the immune system. (Mota, supra).

In humans, the functional and phenotypic heterogeneity of T lymphocytes is well accepted. Two major subpopulations are known: effector T cells mediating cellular immunity; and regulator T cells containing helper and suppressor T lymphocytes. These two subpopulations have been defined with heteroantisera, autoantibodies, and monoclonal antibodies directed at cell surface antigens. For example, earlier in their development, human lymphoid cells in the thymus express an antigen designated T11 which reacts strongly to a monoclonal antibody designated Cluster of Differentiation 2 (CD2), and react slightly with monoclonal antibody CD5 to cell surface antigen T1. During maturation, these cells lose T11 (CD2) and acquire three new antigens defined by monoclonal antibodies CD4, CD8, and CD1. With further maturation, the thymocytes cease to express cell surface antigens reactive with monoclonal antibody CD1, express the T3 antigen reactive with monoclonal antibody CD3, and then segregate into two subpopulations which express either T4 (CD4) or T8 (CD8) antigen. Immunologic competence is acquired at this stage, but is not completely developed until thymic lymphocytes migrate outside the thymus. (Mota, supra.) In contrast with the majority of thymocytes, circulating T lymphocytes express the T1 (CD5) and T3 (CD3) antigens. The T4 (CD4) antigen is present on approximately 55–65% of peripheral T lymphocytes, whereas the T8 (CD8) antigen is expressed on 20–30%. These two subpopulations correspond to helper and to suppressor and cytotoxic T cells, respectively.

In addition to providing a convenient means of distinguishing T lymphocyte subpopulations, these cell surface antigens are important for mature T cell activation and effector function. T cell activation involves a complex series of cell surface interactions between the T cell and the target cell or stimulator cell in addition to binding of the T cell receptor to its specific antigen.

For example, CD2, the human T cell erythrocyte receptor, allows thymocytes and T-lymphocytes to adhere to target cells (e.g., erythrocytes) and to thymic epithelium. This occurs via a specific molecular ligand for CD2, designated LFA-3, in humans, which is a widely distributed surface antigen. This phenomenon has long been employed to detect, assay and purify human cells producing antibodies to sheep erythrocytes and serves as the basis for the E-rosette test, first described by Zaalberg, *Nature* 202:1231 (1964). CD2/LFA-3 interactions also have been shown to mediate cytolytic target conjugation (Shaw et al., *Nature* 323:262–264 (1986), and the mixed lymphocyte reaction (Martin et al., *J. Immunol.* 131:180–185 (1983). Anti-CD2 monoclonal antibodies can directly activate peripheral T-lymphocytes via an antigen-independent pathway (Meuer et al., *Cell* 36:897–906 (1984)), indicating an even wider immunoregulatory role for CD2.

Recognition that T lymphocytes are the main effectors of cell-mediated immunity and also are involved as helper or suppressor cells in modulating the immune response has resulted in a significant contribution to the increasing practical application of clinical immunology to medicine. The scope of this application includes defense against infections, prevention of diseases by immunization, organ transplantation, blood banking, and treatment of deficiencies of the immune system and a variety of disorders that are mediated by immunologic mechanisms. Moreover, immunologic techniques frequently are used in the clinical laboratory, as in the measurement of hormones and drugs. Clinical immunology is described, for example, in Weir, ed., *Handbook of Experimental Immunology in Four Volumes: Volume 4: Applications of Immunological Methods in Biomedical Sciences,* 4th Ed., Blackwell Scientific Publications, Oxford (1986); Boguslaski et al., eds., *Clinical Immunochemistry: Principles of Methods and Applications*, Little, Brown & Co., Boston (1984); Holborow et al., eds., *Immunology in Medicine: A Comprehensive Guide to Clinical Immunology,* 2d Ed., Grune & Stratton, London (1983); and Petersdorf et al., eds., *Harrison's Principles of Internal Medicine,* 10th ed., McGraw-Hill, New York, publisher, pp. 344–391 (1983). Clearly, a more thorough understanding of the proteins which mediate the immune system would be of significant value in clinical immunology.

Use of mammalian expression libraries to isolate cDNAs encoding mammalian proteins such as those described above would offer several advantages. For example, the protein expressed in a mammalian host cell should be functional and should undergo any normal posttranslational modification. A protein ordinarily transported through the intracellular membrane system to the cell surface should undergo the complete transport process. A mammalian expression system also would allow the study of intracellular transport mechanisms and of the mechanism that insert and anchor cell surface proteins to membranes.

One common mammalian host cell, called a "COS" cell, is formed by infecting monkey kidney cells with a mutant viral vector, designated simian virus strain 40 (SV40), which has functional early and late genes, but lacks a functional origin of replication. In COS cells, any foreign DNA cloned on a vector containing the SV40 origin of replication will replicate because SV40 T antigen is present in COS cells. The foreign DNA will replicate transiently, independently of the cellular DNA.

With the exception of some recent lymphokine cDNAs isolated by expression in COS cells (Wong, G. G., et al., *Science* 228:810–815 (1985); Lee, F. et al., *Proceedings of the National Academy of Sciences, USA* 83:2061–2065 (1986); Yokota, T., et al., *Proceedings of the National Academy of Sciences, USA* 83:5894–5898 (1986); Yang, Y., et al., *Cell* 47:3–10 (1986)), however, few cDNAs in general are isolated from mammalian expression libraries. There appear to be two principal reasons for this: First, the existing technology (Okayama, H. et al., *Mol. Cell. Biol.* 2:161–170 (1982)) for construction of large plasmid libraries is difficult to master, and library size rarely approaches that accessible by phage cloning techniques. (Huynh, T. et al., *In: DNA Cloning Vol. I, A Practical Approach*, Glover, D. M. (ed.), IRL Press, Oxford (1985), pp. 49–78). Second, the existing vectors are, with one exception (Wong, G. G., et al., *Science* 228:810–815 (1985)), poorly adapted for high level expression, particularly in COS cells. The reported successes with lymphokine cDNAs do not imply a general fitness of the methods used, since these cDNAs are particularly easy to isolate from expression libraries. Lymphokine bioassays are very sensitive ((Wong, G. G., et al., *Science* 228:810–815 (1985); Lee, F. et al., *Proceedings of the National Academy of Sciences, USA* 83:2061–2065 (1986); Yokota, T. et al., *Proceedings of the National Academy of Sciences, USA* 83:5894–5898 (1986); Yang, Y. et al., *Cell* 47:3–10 (1986)) and the mRNAs are typically both abundant and short (Wong, G. G. et al., *Science* 228:810–815 (1985); Lee, F., et al., *Proceedings of the National Academy of Sciences, USA* 83:2061–2065 (1986); Yokota, T., et al., *Proceedings of the National Academy of Sciences, USA* 83:5894–5898 (1986); Yang, Y., et al., *Cell* 47:3–10 (1986)).

Thus, expression in mammalian hosts previously has been most frequently employed solely as a means of verifying the identity of the protein encoded by a gene isolated by more traditional cloning methods. For example, Stuve et al., *J. Virol.* 61 (2):327–335 (1987), cloned the gene for glycoprotein gB2 of herpes simplex type II strain 333 by plaque hybridization of M13-based recombinant phage vectors used to transform competent *E. coli* JM101. The identity of the protein encoded by the clone thus isolated was verified by transfection of mammalian COS and Chinese hamster ovary (CHO) cells. Expression was demonstrated by immunofluorescence and radioimmunoprecipitation.

Oshima et al. used plaque hybridization to screen a phage lambda gt11 cDNA library for the gene encoding human placental beta-glucuronidase. Oshima et al., *Proceedings of the National Academy of Sciences, U.S.A.* 84:685–689 (1987). The identity of isolated cDNA clones was verified by immunoprecipitation of the protein expressed by COS-7 cells transfected with cloned inserts using the SV40 late promoter.

Transient expression in mammalian cells has been employed as a means of confirming the identity of genes previously isolated by other screening methods. Gerald et al., *Journal of General Virology* 67:2695–2703 (1986). Mackenzie, *Journal of Biological Chemistry* 261:14112–14117 (1986); Seif et al., *Gene* 43:1111–1121 (1986); Orkin et al., *Molecular and Cellular Biology* 5 (4):762–767 (1985). These methods often are inefficient and tedious and require multiple rounds of screening to identify full-length or overlapping clones. Prior screening methods based upon expression of fusion proteins are inefficient and require large quantities of monoclonal antibodies. Such drawbacks are compounded by use of inefficient expression vectors, which result in protein expression levels that are inadequate to enable efficient selection.

SUMMARY OF THE INVENTION

The present invention relates to a powerful new method for cloning cDNA encoding cell surface antigens, to a method of constructing cDNA libraries, to high efficiency expression vectors particularly suited for high level expression in eukaryotic host cells, and to the isolated nucleotide sequences and their encoded products.

The highly efficient cloning technique of the present invention is based upon transient expression of antigen in eukaryotic cells and physical selection of cells expressing the antigen by adhesion to an antibody-coated substrate, such as a culture dish. The methods of the present invention are useful for the isolation and molecular cloning of any protein which can be expressed and transported to the cell surface membrane of a eukaryotic cell.

The method for cloning cDNA encoding a cell surface antigen of the present invention comprises preparing a cDNA library; introducing this cDNA library into eukaryotic mammalian cells, preferably tissue culture cells; culturing these cells under conditions allowing expression of the cell surface antigen; exposing the cells to a first antibody or antibodies directed against the cell surface antigen, thereby allowing the formation of a cell surface antigen-first antibody complex; subsequently exposing the cells to a substrate coated with a second antibody directed against the first antibody, thereby causing cells expressing the cell surface antigen to adhere to the substrate via the formation of a cell surface antigen-first antibody-second antibody complex; and separating adherent from non-adherent cells.

By means of the cloning method of the present invention, isolation and molecular cloning of genes encoding such cell surface antigens as the following have been accomplished: the CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8 antigens. The nucleotide sequences of genes cloned by the method of the present invention have been determined and the amino acid sequences of the encoded proteins have been identified. A cloned gene, such as that encoding CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8, is also the subject of the present invention.

Once the gene encoding an antigen has been cloned according to the method of the present invention, that gene can be expressed in a prokaryotic or a eukaryotic host cell to produce the encoded protein or portion thereof in substantially pure form such as it does not exist in nature. Another aspect of the present invention relates to substantially pure cell surface antigens, particularly: CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8 antigens and their functional analogues and equivalents. The primary amino acid sequences of the CD1a, CD1b, CD2, CD7, CD14, CD16, CD19, CD20, CD22, CD27, CD28, CDw32a, CDw32b, CD33, CD34, CD40, CD44, CD53, ICAM, LFA-3, FcRIa, FcRIb, TLiSa and Leu8 antigens have been determined. The invention thus also relates to the amino acid sequences of those antigens and their functional equivalents and to the nucleotide sequences encoding those antigens.

This invention also relates to high efficiency cDNA expression vectors which allow the generation of very large mammalian expression libraries and yield large amounts of protein in mammalian host cells, resulting in efficient selection. In a particular embodiment of this invention, a cDNA expression vector comprises a suppressor tRNA gene; an SV40 origin; a synthetic transcription unit, comprising a chimeric promoter composed of human cytomegalovirus AD169 immediate early enhancer sequence fused to the HIV LTR −60 to +80 sequences, inserted between the suppressor tRNA gene and the SV40 origin; a polylinker comprising two BstXI sites separated by a replaceable DNA sequence and flanked by XbaI sites; and an SV40 small t antigen splice and early region polyadenylation signals.

A further aspect of the present invention comprises a synthetic transcription unit for use in a cDNA expression vector, comprising a chimeric promoter composed of human cytomegalovirus AD169 immediate early enhancer sequences fused to HIV LTR −60 to +80 sequences. The small size and particular arrangement of the sequences of the cDNA expression vector of the present invention allow highly efficient replication in host mammalian tissue culture cells, such as COS cells. Moreover, this vector employs a polylinker containing two inverted BstXI sites separated by a short replaceable DNA segment, which allows the use of very efficient oligonucleotide-based cDNA insertion strategy.

In another aspect, the present invention comprises a vector comprising two identical BstXI sites in inverted orientation each with respect to the other, which BstXI sites are separated by a short replaceable DNA fragment. Another aspect of the invention is a polylinker as described above.

A further aspect of the invention relates to an oligonucleotide-based cDNA insertion method, comprising ligating synthetic DNA oligonucleotides to the cDNA segment desired to be inserted into a vector, the synthetic DNA oligonucleotides giving the same terminal sequences as those of the short replaceable DNA fragment of the polylinker of the invention, and inserting the resulting cDNA segment plus synthetic DNA oligonucleotide terminal sequences into the polylinker of the vector, from which the short replaceable DNA fragment previously has been removed.

In preparing cDNA libraries according to the present invention, it has been discovered that many tumors are heavily infiltrated by macrophages and lymphocytes, and thus may be employed as a source of macrophage or lymphocyte transcripts to good effect, instead of tumor cell lines commonly used. In another aspect, then, the present invention relates to the use of tumor cells, particularly human tumor cells, to prepare cDNA libraries for use according to the methods of the present invention.

Another advantage of the powerful selection system of the present invention is that directional insertion of the cDNA is not necessary. The method of the present invention results in library construction efficiencies which are on a par with those described for phage vectors such as lambda gt10 and lambda gt11, with the additional advantage that clones generated according to the methods of the present invention are easier to manipulate.

The immunoselection technique of the present invention allows efficient use of antibodies, which may be monoclonal or polyclonal, in relatively small absolute amounts. The method of the present invention also is quite rapid. Generally, three or fewer cycles of immunoselection, and rescue are required to isolate a target cDNA clone. Thus, the method of the present invention also results in the efficient use of labor and materials when cloning genes encoding cell surface antigens. As described above, this method has been employed to successfully clone genes encoding cell surface antigens associated with mammalian T lymphocytes (e.g. antigens CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8).

The purified genes and proteins of the present invention are useful for immunodiagnostic and immunotherapeutic applications, including the diagnosis and treatment of immune-mediated diseases, infections, and disorders in animals, including humans. They can also be used to identify, isolate and purify other antibodies and antigens. Such diagnostic and therapeutic uses comprise yet another aspect of the present invention. Moreover, the substantially pure proteins of the present invention may be prepared as medicaments or pharmaceutical compositions for therapeutic administration. The present invention further relates to such medicaments and compositions.

BRIEF DESCRIPTION OF THE DRAWINGS

FIGS. 1A–1B. Nucleotide sequence of expression vector piH3 (SEQ ID NO:1)

Nucleotides 1–589 are derived from pMB1 origin (pBR322 ori); nucleotides 590–597 are derived from the SacII linker (ACCGCGT); nucleotides 598–799 are derived from the synthetic tyrosine suppressor tRNA gene (supF gene); nucleotides 800–947 are derived from a remnant of the ASV LTR fragment (PvuII to Mlu1); nucleotides 948–1500 are derived from the human cytomegalovirus AD169 enhancer; nucleotides 1501–1650 are derived from HIV TATA and tat-responsive elements; nucleotides 1651–1716 are derived from the piLNXAN polylinker (HindIII to Xba); nucleotides 1717–2569 are derived from pSV to splice and poly-Adenylation signals; nucleotides 2570–2917 are derived from the SV40 origin of replication (PvuII to (HindIII); and nucleotides 2918–2922 are derived from piVX, remnant of R1 site from polylinker.

FIGS. 2A–2B. Nucleotide sequence of the CD2cDNA insert (SEQ ID NO:2)

Nucleotide numbering is given in parentheses at right, amino acid numbering, left. Locations of the potential sites for addition of asparagine-linked carbohydrate (CHO) are shown, as well as the predicted transmembrane (TM) sequence. The amino acid sequence is numbered from the projected cleavage site of the secretory signal sequence. See also SEQ ID NO:3 for the amino acid sequence.

Figure 3:
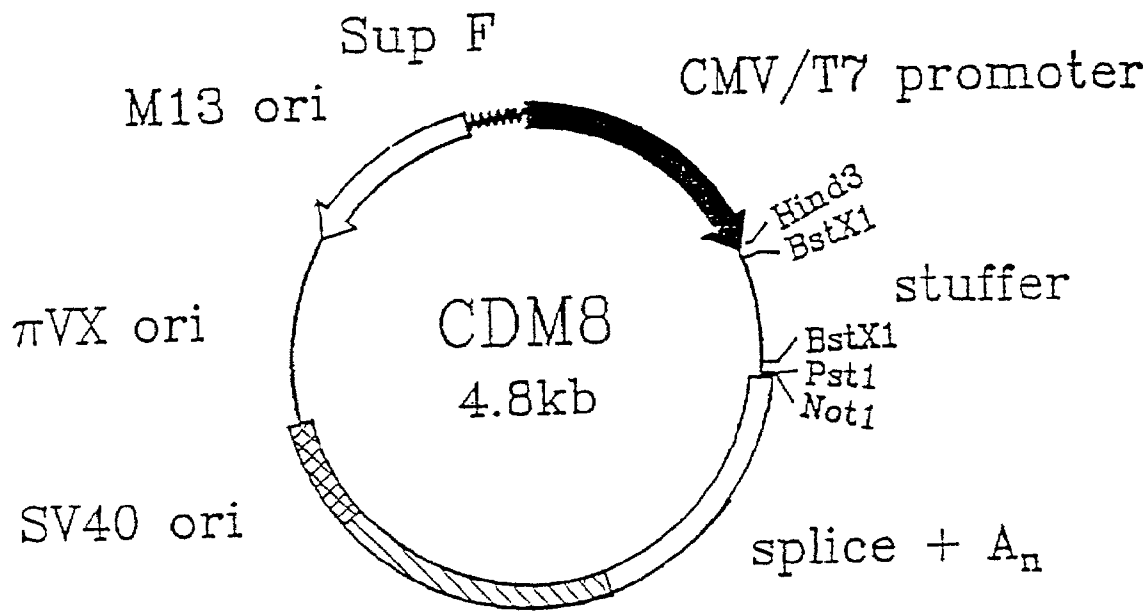

FIG. 3. Restriction map of the CDM8 expression vector

The CDM8 vector includes a deleted version of a mutant polyoma virus early region selected for high efficiency expression in both murine and monkey cells. Substantially all of the human immunodeficiency promoter region has been replaced with the cognate sequences of the human cytomegalovirus immediate early promoter, and by inclusion of a bacteriophage T7 promoter between the eukaryotic promoter and the site of cDNA insertion. Arrows indicate the direction of transcription.

Figure 4B:
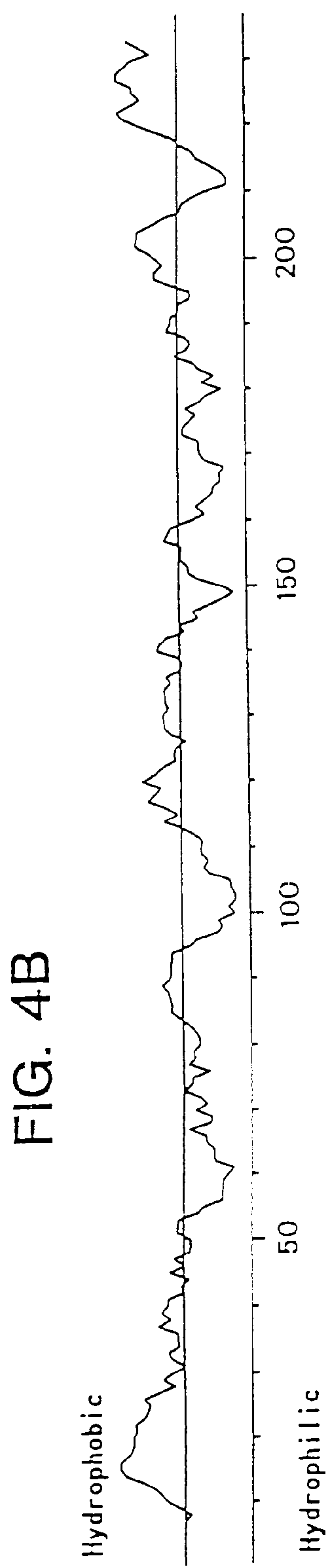

FIGS. 4A–4B. Nucleotide sequence and corresponding amino acid sequence of the LFA-3 antigen (SEQ ID NO:4 and SEQ ID NO:5)

WOP cells transfected with a clone encoding the LFA-3 antigen were detected by indirect immunofluorescence, amplified and sequenced. FIG. 4A shows the 874 base pair insert containing an open reading frame of 237 residues originating at a methionine codon, and terminating in a series of hydrophobic residues. Hydrophobic and hydrophilic regions within this open reading frame are shown in FIG. 4B.

Figure 5:
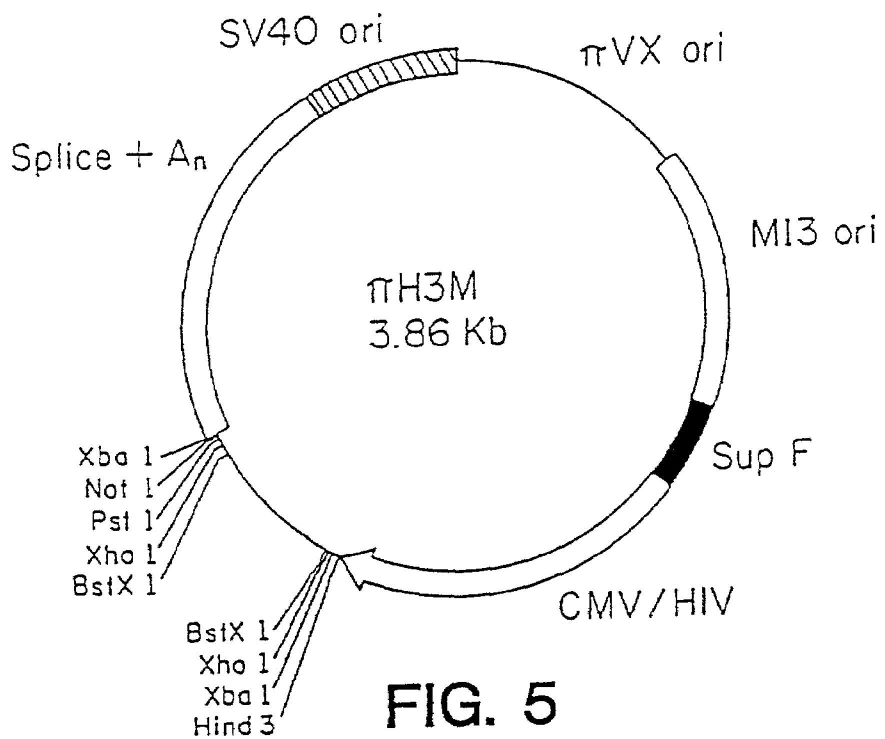

FIG. 5. Restriction Map of the piH3M vector

The direction of transcription is indicated by an arrow. Restriction endonuclease sites flanking the BstXI cloning sites are shown.

FIGS. 6A–6D. Nucleotide sequence of the piH3M vector (SEQ ID NO:6)

There are 7 segments. Residues 1–587 are from the pBR322 origin of replication, 588–1182 from the M13 origin, 1183–1384 from the supF gene, 1385–2238 are from the chimeric cytomegalovirus/human immunodeficiency virus promoter, 2239–2647 are from the replaceable fragment, 2648–3547 from plasmid pSV2 (splice and polyadenylation signals), and 3548–3900 from the SV40 virus origin.

FIGS. 7A–7B. Nucleotide sequence of the CD28 cDNA (SEQ ID NO:7)

Nucleotide numbering is given in parentheses at right, amino acid numbering, center and left. Location of the potential sites for addition of asparagine-linked carbohydrate (CHO) are shown, as well as the predicted transmembrane (TM) sequence. The amino acid sequence is numbered from the projected cleavage site of the secretory signal sequence. see also SEQ ID NO:8 for the CD28 amino acid sequence.

FIGS. 8A–8B. Nucleotide sequence of the CD7 cDNA insert (SEQ ID NO:9)

Nucleotide numbering is given in parentheses at right. Splice donor and acceptor sites indicated by (/). The location of the potential sites for addition of asparagine-linked carbohydrate (CHO) are shown, the potential fatty acid esterification site is denoted (*), and the predicted transmembrane domain (TM) is underlined. See also SEQ ID NO:39 for the CD7 amino acid sequence. Nucleotide sequences potentially involved in hairpin formation are denoted by (.). The presumed polyadenylation signal is underlined.

FIGS. 9A–9B. Nucleotide sequence of the CDw32 cDNA (SEQ ID NO:10)

Nucleotide number is given in the parenthesis at right, amino acid numbering, center and left. Locations of the potential sites for addition of asparagine-linked carbohydrate (CHO) are shown, as well as the predicted transmembrane (TM) sequence. The amino acid sequence is numbered from the projected cleavage site of the secretory signal sequence. Cysteine residues are underscored with asterisks. See also SEQ ID NO:40 for the CDw32 amino acid sequence.

FIGS. 10A-1–10A-2 and 10B. Sequence of the CD20.4 cDNA (SEQ ID NO:11) FIGS. 10A-1–10A-2. The sites of potential N-linked glycosylation are denoted by the symbol —CHO—; the hydrophobic regions are underscored. See also SEQ ID NO:12 for the CD20.4 amino acid sequence. The site of the poly$(A)^{+}$ tail in clone CD20.6 is denoted by an asterisk.

Figure 10B:
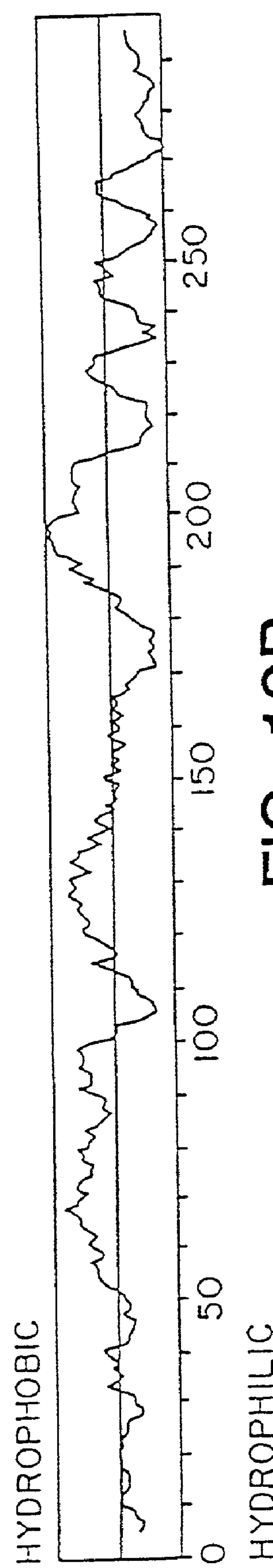

FIG. 10B. Hydrophobicity profile of the amino acid sequence in FIGS. 10A-1–10A-2. See also SEQ ID NO:12.

FIGS. 11A–11C. Sequence of ICAM-1 (SEQ ID NO:13) Complete nucleotide sequence of ICAM-1 cDNA insert and predicted protein sequence (SEQ ID NO:14). Nucleotide numbering is at left, amino acid numbering, center. The RGE motif at position 128 is underlined, the potential N-linked glycosylation sites are indicated by —CHO— and the transmembrane domain by -TM-. The amino acid sequence is numbered from the projected cleavage site of the signal peptide. Sequencing was by dideoxy-chain termination (Sanger, F., et al., Proc. Natl. Acad. Sci. USA 74:5463–5467 (1977)), using a combination of subclones, and specific oligonucleotides.

FIGS. 12A–12B. Nucleotide sequence of CD19 (SEQ ID NO:15)

FIGS. 13A–13B. Nucleotide sequence of CD20 (SEQ ID NO:16)

FIG. 14A–14B. Nucleotide sequence of CDw32a (SEQ ID NO:17)

FIG. 15A–15B. Nucleotide sequence of CDw32b (SEQ ID NO:18)

FIG. 16. Nucleotide sequence of CD40 (SEQ ID NO:19)

DETAILED DESCRIPTION OF THE INVENTION

This invention relates to a novel method for cloning cDNA encoding a cell surface antigen and to a method of constructing cDNA libraries. It also relates to particular cDNA expression vectors and components thereof, nucleotide sequences or genes isolated by the method, substantially pure cell surface antigens encoded by the cDNA segments, and methods of using the isolated nucleotide sequences and encoded products.

In the following description, reference will be made to various methodologies known to those of skill in the art of recombinant genetics. Publications and other materials setting forth such known methodologies to which reference is made are incorporated herein by reference in their entireties. Standard reference works setting forth the general principles of recombinant DNA technology include Darnell, J. E. et al., *Molecular Cell Biology*, Scientific American Books, Inc., publisher, New York, N.Y. (1986); Lewin, B. M., *Genes II*, John Wiley & Sons, publisher, New York, N.Y. (1985); Old, R. W. et al., *Principles of Gene Manipulation: An Introduction to Genetic Engineering,* 2d edition, University of California Press, Berkeley, Calif. (1981); and Maniatis, T. et al., *Molecular Cloning: A Laboratory Manual*, Cold Spring Harbor, N.Y. (1982).

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire genome of an organism. Such a cDNA library may be prepared by art-recognized methods described, for example, in Maniatis et al., *Molecular Cloning: A Laboratory Manual*, supra. Generally, RNA is first isolated from the cells of an organism from whose genome it is desired to clone a particular gene. Preferred for the purposes of the present invention are mammalian, and particularly human, cell lines. More preferred are the human tumor cell line HPB-ALL and the human lymphoblastoid cell line JY. Alternatively, RNA can be isolated from a tumor cell, derived from an animal tumor, and preferably from a human tumor. Thus, a library may be prepared from, for example, a human adrenal tumor, but any tumor may be used.

The immunoselection cloning method of the present invention comprises the preparation of a cDNA library by extracting total RNA including a particular gene from a cell, synthesizing a series of complementary double-stranded cDNA fragments from the RNA and introducing these cDNA fragments into mammalian cells in tissue culture. The mammalian cells are maintained under conditions which allow them to express the protein (i.e. the cell surface antigen). The resulting cells are exposed to a first antibody or pool (group) of antibodies directed against the cell surface antigen. This results in formation of a cell surface antigen-first antibody complex. The complexes are exposed to a substrate to which is coated or bound a second antibody directed against the first antibody. Cells expressing the cell surface antigen adhere to the substrate (because of formation of a cell surface antigen-first antibody-second antibody complex). Adherent cells are separated from non-adherent cells.

Isolation of Total RNA

The guanidium thiocyanate/CsCl method of isolating total RNA is preferred. More preferred is a guanidium thiocyanate/LiCl variant of the GuSCN/CsCl method, which has added capacity and speed. Briefly, for each ml of mix desired, 0.5 g GuSCN are dissolved in 0.58 ml of 25% LiCl (stock filtered through 0.45 micron filter) and 20 l of mercaptoethanol is added. Cells are spun out and the pellet is dispersed on walls by flicking, add 1 ml of solution to up to $5\times10^{7}$ cells. The resulting combination is sheared by polytron until nonviscous. For small scale preps (less than $10^{8}$ cells) layer 2 ml of sheared mix on 1.5 ml of 5.7M CsCl (RNase free; 1.26 g CsCl added to every ml 10 mM EDTA pH 8), overlay with RNase-free water and spin SW55 50k rpm 2 h. For large scale preps, layer 25 ml on 12 ml CsCl in a SW28 tube, overlay, and spin 24 k rpm 8 h. Aspirate contents carefully with a sterile pasteur pipet connected to a vacuum flask. Once past the CsCl interface, scratch a band around the tube with the pipet tip to prevent the layer on the wall of the tube from creeping down. The remaining CsCl solution is aspirated. The pellets are taken up in water (do not try to redissolve). 1/10 vol. NaOAc and 3 vol. EtOH are added and the resulting combination is spun. If necessary, the pellet is resuspended in water (e.g., at 70°). Adjust concentration to 1 mg/ml and freeze. Small RNA (e.g. 5S) does not come down. For small amounts of cells, scale down volumes and overlay GuSCN with RNase-free water on gradient (precipitation is inefficient when RNA is dilute).

Preparation of Poly $A^+$ RNA

Next, poly$A^+$ RNA may be prepared, preferably by the oligo dT selection method. Briefly, a disposable polypropylene column is prepared by washing with 5M NaOH and then rinsing with RNase-free water. For each milligram total RNA about 0.3 ml (final packed bed) oligo dT cellulose is used. Oligo dT cellulose is prepared by resuspending about 0.5 ml of dry powder in 1 ml of 0.1M NaOH and transferring it into the column, or by percolating 0.1 NaOH through a previously used column (columns can be reused many times). This is washed with several column volumes of RNase-free water, until pH is neutral, and rinsed with 2–3 ml of loading buffer. The column bed is then removed into a sterile 15 ml tube using 4–6 ml of loading buffer. The total RNA to 70° C. for 2–3 min., LiCl from RNase-free stock is added (to 0.5M), and combined with oligo dT cellulose in a 15 ml tube. This is followed by vortexing or agitation for 10 min, The result is poured into a column and washed with 3 ml loading buffer and then 3 ml of middle wash buffer. mRNA is eluted directly into an SW55 tube with 1.5 ml of 2 mM EDTA, 0.1% SDS; the first two or three drops are discarded.

Eluted mRNA is precipitated by adding 1/10 vol. 3M NaOAc and filling the tube with EtOH. This is then mixed, chilled for 30 minutes at −20° C., and spun at 50 k rpm at 5° C. for 30 min. The poured off and the tube is air dried. The mRNA pellet is resuspended in 50–100 μl of RNase-free water. Approximately 5 μl is melted at 70° in MOPS/EDTA/formaldehyde and run on an RNase-free 1% agarose gel to check quality.

cDNA Synthesis

From this, cDNA is synthesized. A preferred method of cDNA synthesis is a variant of that described by Gubler and Hoffman (*Gene,* 25:263–269 (1982)). This is carried out as follows:

a. First Strand. 4 μg of mRNA and heated to about 100° C. in a microfuge tube for 30 seconds and quenched on ice. The volume is adjusted to 70 μl with RNase-free water. The following are added: 20 μl of RT1 buffer, 2 μl of RNAse inhibitor (Boehringer 36 μ/μl), 1 μl of 5 μg/μl of oligo dT (Collaborative Research), 2.5 μl of 20 mM dXTP's (ultrapure), 1 μl of 1 M DTT and 4 l of RT-LX (Life Science, 24 U/μl). The resulting combination is incubated at 42° C. for 40 min. It is heated to inactivate (70° C. 10 min).

b. Second Strand. 320 μl of RNAse free water, 80 μl of RT2 buffer, 5 μl of DNA Polymerase I (Boehringer, 5 μ/μl), 2 μl RNAse H (BRL 2 U/μl). Incubate at 15° C. for 1 hr and 22° C. for 1 hr. Add 20 μl of 0.5M EDTA pH 8.0, phenol extract and EtOH precipitate by adding NaCl to 0.5M, linear polyacrylamide (carrier) to 20 μg/ml, and filling tube with EtOH. Spin 2–3 minutes in microfuge, remove, vortex to dislodge precipitate high up on wall of tube, and respin 1 minute.

c. Adaptors. Resuspend precipitated cDNA in 240 μl of TE (10/1). Add 30 μl of 10× low salt buffer, 30 μl of 10× low salt buffer, 30 μl of 10× ligation additions, 3 μl (2.4 μg) of kinased 12-mer adaptor, 2 μl (1.6 μg) of kinased 8-mer adaptor, and 1 μl of T4 DNA ligase (BioLabs, 400 μ/μl, or Boehringer, 1 Weiss unit/ml). Incubate at 15° C. overnight. Phenol extract and EtOH precipitate as above (no extra carrier now needed), and resuspend in 100 μl of TE.

Use of cDNA Fragments in Expression Vectors

For use with the BstXI-based cDNA expression vectors of the invention (see infra), oligonucleotide segments containing terminal sequences corresponding to BstXI sites on the vectors are ligated to the cDNA fragment desired to be inserted. The resulting fragments are pooled by fractionation. A preferred method is as follows:

Prepare a 20% KOA, 2 mM EDTA, 1 μg/ml EthBr solution and a 5% KOAc, 2 mM EDTA, 1 μg/ml EthBr solution. Add 2.6 ml of 20% KOAc solution to back chamber of a small gradient maker. Remove air bubble from tube connecting the two chambers by allowing solution to flow into the front chamber and then tilt back. Close passage between chambers, and add 2.5 ml. of the 5% solution to the front chamber. If there is liquid in the tubing from a previous run, allow the 5 solution to run just to the end of the tubing, and then return to chamber. Place the apparatus on a stirplate, set the stir bar moving as fast as possible, open the stopcock connecting the two chambers and then open the front stopcock. Fill a polyallomer SW55 tube from the bottom with the KOAc solution. Overlay the gradient with 100 μl of cDNA solution. Prepare a balance tube and spin the gradient for 3 hrs at 50k rpm at 22° C. To collect fractions from the gradient, pierce the SW55 tube with a butterfly infusion set (with the luer hub clipped off) close to the bottom of the tube and collect three 0.5 ml fractions and then 6 0.25 ml fractions into microfuge tubes (about 22 and 11 drops respectively). EtOH precipitate the fractions by adding linear polyacrylamide to 20 μg/ml and filling the tube to the top with EtOH. After cooling tubes, spin them in a microfuge for 3 min. Vortex and respin 1 min. Rinse pellets with 70% EtOH (respin). Do not dry to completion. Resuspend each 0.25 ml fraction in 10 μl of TE. Run 1 μl on a 1% agarose minigel. Pool the first three fractions, and those of the last six which contain no material smaller than 1 kb.

Suppressor tRNA plasmids may be propagated by known methods. In a preferred method according to the present invention, supF plasmids can be selected in nonsuppressing hosts containing a second plasmid, p3, which contains amber mutated ampicillin and tetracycline drug resistance elements (Seed, 1983). The p3 plasmid is derived from PR1, is 57 kb in length, and is a stably maintained, single copy episome. The ampicillin resistance of this plasmid reverts at a high rate, so that $amp^r$ plasmids usually cannot be used in p3-containing strains. Selection for tet resistance alone is almost as good as selection for amp+tet resistance. However, spontaneous appearance of chromosomal suppressor tRNA mutations presents an unavoidable background (frequency about $10^{-9}$) in this system. Colonies arising from spontaneous suppressor mutations are usually bigger than colonies arising from plasmid transformation. Suppressor plasmids typically are selected for in LB medium containing amp at 12.5 μg/ml and tet at 7.5 μg/ml. For large plasmid preps, M9 casamino acids medium containing glycerol (0.8%) may be used as a carbon source, and the bacteria grown to saturation.

Vector DNA may be isolated by known methods. The following method is preferred for plasmid from 1 liter of saturated cells:

Spin down cells in 1 liter J6 bottles, 4.2 k rpm, 25 minutes. Resuspend in 40 ml 10 mM EDTA pH 8 (Thump on soft surface). Add 80 ml 0.2M NaOH, 1% SDS, swirl until clearish, viscous. Add 40 ml 5M KOAc, pH 4.7 (2.5M KOAc, 2.5M HOAc) shake semi-vigorously (until lumps are 2–3 mm in size). Spin (same bottle) 4.2K rpm, 5 min. Pour supernatant through cheesecloth into 250 ml bottle. Fill bottle with isopropyl alcohol. Spin J6, 4.2 k rpm, 5 min. Drain bottle, rinse gently with 70% EtOH (avoid fragmenting the pellet). Invert bottle, and remove traces of EtOH with Kimwipe. Resuspend in 3.5 ml Tris base/EDTA 20 mM/10 mM. Add 3.75 ml of resuspended pellet to 4.5 g CsCl. Add 0.75 ml 10 mg/ml ethidium bromide, mix. Fill VTi80 tubes with solution. Run at a speed of 80 rpm for 2.5 hours or longer. Extract bands by visible light with 1 ml syringe and 20 gauge or lower needle. Cut top off tube, insert the needle upwards into the tube at an angle of about 30° with respect to the tube, (i.e., as shallowly possible) at a position about 3 mm beneath the band, with the bevel of the needle up. After the band is removed, pour tube contents into bleach. Deposit extracted bands in 13 ml Sarstedt tube. Fill tube to top with n-butanol saturated with 1M NaCl, extract. If a very large quantity of DNA is obtained, reextract. Aspirate butanol into trap containing 5M NaOH (to destroy ethidium). Add about equal volume 1M ammonium acetate to DNA (squirt bottle). Add about 2 volumes 95% ethanol (squirt bottle). Spin 10K rpm, 5 min. J2-21. Rinse pellet carefully with 70% ethanol. Dry with swab, or lyophilizer.

The vector may be prepared for cloning by known methods. A preferred method begins with cutting 20 μl of vector in a 200 μl reaction with 100 units of BstXI (New York Biolabs), cutting at 50° C. overnight in a well-thermostatted water bath (i.e., circulating water bath). Prepare 2 KOAc 5–20% gradients in SW55 tubes as described above. Add 100 μl of the digested vector to each tube and run for 3 hrs, 50K rpm at 2° C. Examine the tube under 300 nm UV light. The desired band will have migrated ⅔ of the length of the tube. Forward trailing of the band means the gradient is overloaded. Remove the band with a 1 ml syringe and 20 gauge needle. Add linear polyacrylamide and precipitate the plasmid by adding 3 volumes of EtOH. Resuspend in 50 μl of TE. Set up ligations using a constant amount of vector and increasing amounts of cDNAs. On the basis of these trial ligations, set up large scale ligation, which can be accomplished by known methods. Usually the entire cDNA prep requires 1–2 μg of cut vector.

Adaptors may be prepared by known methods, but it is preferred to resuspend crude adaptors at a concentration of 1 μg/μl, add MgSO4 to 10 mM, and precipitate by adding 5 volumes of EtOH. Rinse with 70% EtOH and resuspend in TE at a concentration of 1 μg/μl. To kinase take 25 μl of resuspended adaptors, add 3 μl of 10× kinasing buffer and 20 units of kinase; incubate 37° C. overnight.

Preparation of buffers mentioned in the above description of preferred methods according to the present invention will be evident to those of skill. For convenience, preferred buffer compositions are as follows:

| | |
|---|---|
| Loading Buffer: | 0.5 M LiCl, 10 mM Tris pH 7.5, 1 mM EDTA 0.1% SDS. |
| Middle Wash Buffer: | 0.15 M LiCl, 10 mM Tris pH 7.5, 1 mM EDTA 0.1% SDS. |
| Rt1 Buffer: | 0.25 M Tris pH 8.8 (8.2 at 42°), 0.25 M KCl, 30 mM $MgCl_2$. |
| RT2 Buffer: | 0.1 M Tris pH 7.5, 25 mM $MgCl_2$, 0.5 M KCl, 0.25 mg/ml BSA, 50 mM DTT. |
| 10× Low Salt: | 60 mM Tris pH 7.5, 60 mM $MgCl_2$, 50 mM NaCl, 2.5 mg/ml BSA, 70 mM Me. |
| 10× Ligation Additions: | 1 mM ATP, 20 mM DTT, 1 mg/ml BSA, 10 mM spermidine. |

-continued

| | |
|---|---|
| 10× Kinasing Buffer: | 0.5 M Tris pH 7.5, 10 mM ATP, 20 mM DTT, 10 mM spermidine, 1 mg/ml BSA 100 mM $MgCl_2$. |

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages.

Preferred for the purposes of the present invention, however, are viral vectors, such as those derived from simian virus strain 40 (SV40). SV40 is a papovavirus having a molecular weight of 28 Mdal, and containing a circular double-stranded DNA molecule having a molecular weight of 3 Mdal, which comprises the entire genome of the virus. The entire nucleotide sequence of this single, small, covalently closed circular DNA molecule has been determined. Fiers et al., *Nature* 273:113–120 (1978); Reddy et al., *Science* 200:494–502 (1978). The viral DNA of SV40 may be obtained in large quantities, and the genomic regions responsible for various viral functions have been accurately located with respect to a detailed physical map of the DNA. Fiers et al., supra; Reddy et al., supra. The viral genome of SV40 can multiply vegetatively or as an integral part of cellular chromosomes, and a wealth of information exists on the replication and expression of this genome.

Also preferred for the purposes of the present invention is a single-stranded bacteriophage cloning vehicle, designated M13, having a closed circular DNA genome of approximately 6.5 kb. An advantage of utilizing M13 as a cloning vehicle is that the phage particles released from infected cells contain single-stranded DNA homologous to only one of the two complementary strands of the cloned DNA, which therefore can be used as a template for DNA sequencing analysis.

Even more preferred for the purposes of the present invention are the expression vectors designated piH3, piH3M, and CDM8, deposited at the American Type Culture Collection (ATCC), 10801 University Boulevard, Manassas, Va. 20110-2209. piH3 was deposited at the ATCC on Feb. 24, 1988, and has accession number ATCC 67634. piH3M was deposited at the ATCC on Feb. 24, 1988, and has accession number ATCC 67633. CDM8 was deposited at the ATCC on Feb. 24, 1988, and has accession number ATCC 67635.

By "tissue culture" is meant the maintenance or growth of animal tissue cells in vitro so as to allow further differentiation and preservation of cell architecture or function or both. "Primary tissue cells" are those taken directly from a population consisting of cells of the same kind performing the same function in an organism. Treating such tissue cells with the proteolytic enzyme trypsin, for example, dissociates them into individual primary tissue cells that grow well when seeded onto culture plates at high densities. Cell cultures arising from multiplication of primary cells in tissue culture are called "secondary cell cultures." Most secondary cells divide a finite number of times and then die. A few secondary cells, however, may pass through this "crisis period", after which they are able to multiply indefinitely to form a continuous "cell line." Cell lines often will contain extra chromosomes, and usually are abnormal in other respects as well. The immortality of these cells is a feature shared in common with cancer cells.

Preferred cell lines for use as tissue culture cells according to the present invention include the monkey kidney cell line, designated "COS." COS cells are those that have been transformed by SV40 DNA containing a functional early gene region but a defective origin of viral DNA replication. COS cell clone M6 is particularly preferred for use according to the method of the invention. Also preferred for the purposes of the present invention are murine "WOP" cells, which are NIH 3T3 cells transfected with polyoma origin deletion DNA. cDNA may be introduced into the host tissue culture cells of the present invention by any methods known to those of skill. Transfection may be accomplished by, for example, protoplast fusion, by spheroplast fusion, or by the DEAE dextran method (Sussman et al., *Cell. Biol.* 4:1641–1643 (1984)).

If spheroplast fusion is employed, a preferred method is the following variant based on Sandri-Goldrin et al., *Mol. Cell Bio.* 1:743–752 (1981). Briefly, for example, a set of six fusions requires 100 ml of cells in broth. Grow cells containing amplifiable plasmid to OD 600=0.5 in LB. Add spectinomycin to 100 μg/ml (or chloramphenicol to 150 μg/ml). Continue incubation at 37° C. with shaking for 10–16 hours. (Cells begin to lyse with prolonged incubation in spectinomycin or chloramphenicol medium). Spin down 100 ml of culture (JA14/GSA rotor, 250 ml bottle) 5 min. at 10,000 rpm. Drain well, resuspend pellet in bottle with 5 ml cold 20% sucrose, 50 mM Tris-HCL pH 8.0. Incubate on ice 5 min. Add 2 ml cold 0.25M EDTA pH 8.0, incubate 5 min. at 37° C. (waterbath). Place on ice, check percent conversion to spheroplasts by microscopy. In flow hood, slowly add 20 ml of cold DME/10% sucrose/10 mM $MgC_2$ (dropwise, ca. 2 drops per second). Remove media from cells plated the day before in 6 cm dishes (50% confluent). Add 5 ml of spheroplast suspension to each dish. Place dishes on top of tube carriers in swinging bucket centrifuge. Up to 6 dishes can be comfortably prepared at once. Dishes can be stacked on top of each other, but 3 in a stack is not advisable as the spheroplast layer on the top dish is often torn or detached after centrifugation. Spin at 1000×g 10 mm. Force is calculated on the basis of the radius to the bottom plate. Aspirate fluid from dishes carefully. Pipet 1.5–2 ml 50% (w/w) PEG 1450 (or PEG 1000)/50% DME (no serum) into the center of the dish. If necessary, sweep the pipet tip around to ensure that the PEG spreads evenly and radially across the whole dish. After PEG has been added to the last dish, prop all of the dishes up on their lids so that the PEG solution collects at the bottom. Aspirate the PEG. The thin layer of PEG that remains on the cells is sufficient to promote fusion; the layer remaining is easier to wash off, and better cell viability can be obtained, than if the bulk of the PEG is left behind. After 90 to 120 seconds (PEG 1000) or 120 to 150 seconds (PEG 1450) of contact with the PEG solution, pipet 1.5 ml of DME (no serum) into the center of the dish. The PEG layer will be swept radially by the DME. Tilt the dishes and aspirate. Repeat the DME wash. Add 3 ml of DME/10% serum containing 15 μg/ml gentamicin sulfate. Incubate 4–6 hours in incubator. Remove media and remaining bacterial suspension, add more media and incubate 2–3 days. Extensive washing of the cell layer to remove PEG tends to remove many of the cells without any substantial benefit. If the cells are allowed to sit in the second DME wash for a few minutes, most of the spheroplast layer will come up spontaneously; however it is preferred to wash briefly and allow the layer to come off in the complete medium at 37° C.

The PEG solution can be conveniently prepared by melting a fresh bottle of PEG at 60° C. and pouring approximate 50 ml aliquots by means of a 50 ml centrifuge tube into preweighed bottles. The aliquoted PEG is stored at 5° C. in the dark. To make up a fresh bottle, weigh the aliquot, remelt, and add an equal volume of DME (no serum). Adjust the pH with 7.5% Na bicarbonate solution if necessary, and filter sterilize. The resulting PEG solution may be stored up to 3 months at room temperature without detectable adverse consequence.

Transfected host cells will be cultured according to the invention in order to accomplish expression of the protein encoded by the cDNA clone, and to increase the absolute numbers of cells available for subsequent immunoselection. Those skilled in the art will know of appropriate methods and media for this purpose, taking into account the cell type and other variables routinely considered. COS cells, for example, may be cultured in Dulbecco's modified Eagle's medium (DME) supplemented with 10% calf serum and gentamycin sulfate. Transient expression of transfected cells normally can be expected between 48 and 72 hours post-transfection. However, this time period may vary depending upon the type or strain of host cell used and the cell culture conditions, as will be apparent to those of ordinary skill.

Immunoprecipitation, blotting, and cDNA sequencing of genes cloned according to the methods of the present invention may be carried out by any convenient methods known to those of skill. For example, the immunoprecipitation protocol of Clark et al., *Leukocyte Typing II*, Vol. II, pp. 155–167 (1986), is preferred. Southern, Northern, or other blot analysis methods known to those of skill may be employed, using hybridization probes prepared by known methods, such as that of Hu et al. (*Gene* 18:271–277 (1982)). cDNA sequencing also may be accomplished by known methods, including the dideoxynucleotide method of Sanger et al., *Proc. Natl. Acad. Sci.* (*USA*) 74:5463–5467 (1977).

The antibodies used according to the present invention may be polyclonal or monoclonal. These may be used singly, or in conjunction with other polyclonal or monoclonal antibodies to effect immunoselection of cells expressing the desired antigen or antigens by the methods of the present invention. Methods of preparing antibodies or fragments thereof for use according to the present invention are known to those of skill.

Standard reference works setting forth general principles of immunology include Klein, J., *Immunology: The Science of Self-Nonself Discrimination*, John Wiley & Sons, publisher, New York (1982); Kennett, R., et al., eds., *Monoclonal Antibodies, Hybridoma: A New Dimension in Biological Analyses*, Plenum Press, publisher, New York (1980); Campbell, A., "Monoclonal Antibody Technology" in Burden, R., et al., eds., *Laboratory Techniques in Biochemistry and Molecular Biology*, Vol. 13, Elsevere, publisher, Amsterdam (1984).

The term "antibody" is meant to include the intact molecule as well as fragments thereof, such as, for example, Fab and $F(ab)'_2$ fragments, which also are able to bind to antigen. Polyclonal antibody preparations may be derived directly from the blood of the desired animal species after immunization with the antigen of interest, or a fragment thereof, using any of the standard protocols known to those of ordinary skill. Similarly, monoclonal antibodies may be prepared using known methods (Kohler et al., *Eur. J. Immu-*

*nol.* 6:292 (1976)). Use of monoclonal antibodies is preferred for the purposes of the present invention.

For the purposes of immunoselection according to the present invention, the tissue culture host cells which have been exposed to antibodies directed against the target cell surface antigen are separated from host cells which do not express the target antigen by distributing the cells onto a substrate coated with antibody directed against the antibody for the antigen. This technique, termed "panning," will be known to those of skill, and is described, for example, by Mage et al., *J. Immunol. Meth.* 15:47–56 (1977), and Wysocki and Sato, *Proc. Natl. Acad. Sci.* (*USA*) 75:2844–2848 (1978).

Panning according to the methods of the present invention may be carried out as follows:

a. Antibody-coated dishes. Bacteriological 60 mm plates, Falcon 1007 or equivalent, or 10 cm dishes such as Fisher 8-757-12 may be used. Sheep anti-mouse affinity purified antibody (from, for example, Cooper BioMedical (Cappell)) is diluted to 10 μg/ml in 50 mM Tris HCl, pH9.5. Add 3 ml per 6 cm dish, or 10 ml per 10 cm dish. Let sit ca. 1.5 hrs., remove to next dish 1.5 hrs., then to 3rd dish. Wash plates 3× with 0.15 M NaCl (a wash bottle is convenient for this), incubate with 3 ml 1 mg/ml BSA in PBS overnight, aspirate and freeze.

b. Panning. Cells will be in 60 mm dishes. Aspirate medium from dish, add 2 ml PBS/0.5 mM EDTA/0.02% azide and incubate dishes at 37° C. for 30 min. to detach cells from dish. Triturate cells vigorously with short pasteur pipet, and collect cells from each dish in a centrifuge tube. Spin 4 min. setting 2.5 (200×g) (takes 5 min). Resuspend cells in 0.5–1.0 ml PBS/EDTA/azide/5% FBS and add antibodies. Incubate at least 30 min. on ice. Add an equal volume of PBS/EDTA/azide, layer carefully on 3 ml PBS/EDTA/azide/2% Ficoll, and spin 4 min. at setting 2.5. Aspirate supernatant in one smooth movement. Take up cells in 0.5 ml PBS/EDTA/azide and add aliquots to antibody-coated dishes containing 3 ml PBS/EDTA/azida/5% FBS by pipetting through 100 micron Nylon mesh (Tetko). Add cells from at most two 60 mm dishes to one 60 mm antibody-coated plate. Let sit at room temperature 1–3 hours. Remove excess cells not adhering to dish by gentle washing with PBS/5% serum or with medium. 2 or 3 washes of 3 ml are usually sufficient.

c. Hirt Supernatant. A preferred variant of the method of Hirt, J. Molec. Biol. 26:365–369 (1967), is as follows: Add 0.4 ml 0.6% SDS, 10 mM EDTA to panned plate. Let sit 20 minutes (can be as little as 1 min. if there are practically no cells on the plate). Pipet viscous mixture into microfuge tube. Add 0.1 ml SM NaCl, mix, put on ice at least 5 hrs. Keeping the mixture as cold as possible seems to improve the quality of the Hirt. Spin 4 min., remove supematant carefully, phenol extract (twice if the first interface is not clean), add 10 μg linear polyacrylamide (or other carrier), fill tube to top with EtOH, precipitate, and resuspend in 0.1 ml. Add 3 volumes EtOH/NaOAc, reprecipitate and resuspend in 0.1 ml. Transform into MC106I/p3, preferably using the high efficiency protocol hereinafter described. If the DNA volume exceeds 2% of the competent cell aliquot, the transformation efficiency will suffer. 5% gives the same number of colonies as 2.5% (efficiency is halved).

It is preferred for this aspect of the present invention to use "blockers" in the incubation medium. Blockers assure that non-specific proteins, proteases, or antibodies present do not cross-link with or destroy the antibodies present on the substrate or on the host cell surface, to yield false positive or false negative results. Selection of blockers can substantially improve the specificity of the immunoselection step of the present invention. A number of non-specific monoclonal antibodies, for example, of the same class or subclass (isotype) as those used in the immunoselection step (e.g., $IgG_1$, $IgG_2A$, IgGm, etc.) can be used as blockers. Blocker concentration (normally 1–100 μg/μl) is important to maintain the proper sensitivity yet inhibit unwanted interference. Those of skill also will recognize that the buffer system used for incubation may be selected to optimize blocking action and decrease non-specific binding.

A population of cells to be panned for those expressing the target cell surface antigen is first detached from its cell culture dish (harvested) without trypsin. The cells then are exposed to a first antibody, which may be polyclonal or monoclonal, directed against the antigen of interest or against a family of related antigens. At this initial stage, a single antibody or a group of antibodies may be used, the choice depending upon the nature of the target antigen, its anticipated frequency, and other variables that will be apparent to those of skill. Target antigens expressed on the surfaces of host cells will form an antigen-antibody complex.

The cells subsequently are placed in close apposition to a substrate, such as a culture dish, filter disc, or the like, which previously has been coated with a second antibody or group of antibodies. This second antibody will be directed against the first antibody, and its choice will be a matter of ordinary skill dictated by, for example, the animal in which the first antibody was raised. For example, if the first antibody was raised in mice, the second antibody might be directed against mouse immunoglobulins, raised in goats or sheep. Cells expressing the target antigen will adhere to the substrate via the complex formed between the antigen, the first antibody, and the second antibody. Adherent cells then may be separated from nonadherent cells by washing. DNA encoding the target antigen is prepared from adherent cells by known methods, such as that of Hirt, *J. Molec. Biol.* 26:365–369 (1967). This DNA may be transformed into *E. coli* or other suitable host cells for further rounds of fusion and selection, to achieve the desired degree of enrichment.

In the usual case, the initial rounds of immunoselection will employ a panel of first antibodies directed against an epitope or group of epitopes common to the family of antigens to which the target antigen belongs. This will be sufficient to narrow the number of clones for future rounds quite significantly. Two such rounds usually will be found adequate, but the number of rounds may vary as mentioned above. Thereafter, a single round of selection may be performed employing a single first antibody or a group of first antibodies recognizing only the target antigen.

By "substrate" is meant a solid surface to which antibodies may be bound for immunoselection according to the present invention. Known suitable substrates include glass, polystyrene, polypropylene, dextran, nylon, and other materials. Tubes, beads, microtiter plates, bacteriological culture dishes, and the like formed from or coated with such materials may be used. Antibodies may be covalently or physically bound to the substrate by known techniques, such as covalent bonding via an amide or ester linkage, or by absorption. Those skilled in the art will know many other suitable substrates and methods for immobilizing antibodies thereupon, or will be able to ascertain such substrates and methods using no more than routine experimentation.

The choice of host tissue culture cells for use according to the present invention preferably should be such as to avoid the situation in which the antibodies used for panning recognize determinants on untransfected cells. Thus, while COS cells are preferred for transient expression of certain surface antigens, more preferred are murine WOP cells. Of the latter, WOP 3027 cells are even more preferred. WOP cells allow virtually all antibodies to be used, since cross-reactions between murine antibodies and murine cell surface determinants are rare.

The insert size of the recombinant DNA molecule should be chosen to maximize the likelihood of obtaining an entire coding sequence. Those of skill will know various methods by which a preliminary determination of optimal insert size for a given gene may be determined.

Vector Construction and cDNA Insertion

Vectors suitable for expression of cDNA in mammalian tissue culture cells may be constructed by known methods. Preferred for the purposes of the present invention is an expression vector containing the SV40 origin. The vector may contain a naturally derived or synthetic transcription origin, and the SV40 early region promoter. Even more preferred is a chimeric promoter composed of human cytomegalovirus immediate early enhancer sequences. Various "enhancer sequences" also may be used with SV40 vectors. These are described, for example, by Banerji et al., *Cell* 27:299–308 (1981); Levinson et al., *Nature* 295:568–572 (1982); and Conrad et al., *Mol. Cell. Biol.* 2:949–965 (1982).

Insertion of cDNA into the vectors of the present invention can occur, for example, by homopolymeric tailing with terminal transferase. However, homopolymeric tracts located 5' to cDNA inserts may inhibit in vitro and in vivo expression. Thus, preferred for purposes of the present invention is the use of inverted identical cleavage sites separated by a short replaceable DNA segment. Such inverted identical cleavage sites, preferably employing the BstXI restriction endonuclease, may be used in parallel with cDNA synthetic oligonucleotides, giving the same termini as the replaceable segment of the vector. In this manner, the cDNA cannot ligate to itself, but can ligate to the vector. This allows the most efficient use of both cDNA and vector.

Another embodiment of the present invention is the above-described efficient oligonucleotide-based strategy to promote cDNA insertion into the vecctor. The piH3M vector of the present invention is preferred, and employs the inverted endonuclease sites. This vector may contain an SV40 origin of replication, but a more preferred form contains an M13 origin. This vector, containing the M13 origin, allows high level expression in COS cells of coding sequences placed under its control. Also, the small size and particular arrangement of sequences in the plasmid permit high level replication in COS cells.

By "cell surface antigen" is meant any protein that is transported through the intracellular membrane system to the cell surface. Such antigens normally are anchored to the cell surface membrane through a carboxyl terminal domain containing hydrophobic amino acids that lie in the lipid bilayer of the membrane, and there exert their biological and antigenic effects. Antigens such as those of T-lymphocytes are particularly suited for gene cloning by the method of the present invention. However, cell surface antigens of any cells may be cloned according to the present method. Moreover, proteins not normally expressed on the cell surface may admit of cloning according to the present method by, for example, using fluorescence activated cell sorting (FACS) to enrich for fixed cells expressing intracellular antigens.

By "substantially pure" is meant any antigen of the present invention, or any gene encoding any such antigen, which is essentially free of other antigens or genes, respectively, or of other contaminants with which it might normally be found in nature, and as such exists in a form not found in nature.

By "functional derivative" is meant the "fragments," "variants," "analogs," or "chemical derivatives" of a molecule. A "fragment" of a molecule, such as any of the antigens of the present invention, is meant to refer to any polypeptide subset of the molecule containing a functional domain such as an epitope, a ligand binding site, an extracellular domain or an immunoglobulin domain, which comprises at least about 6 amino acids. A "variant" of such molecules is meant to refer to a naturally occurring molecule substantially similar to either the entire molecule, or a fragment thereof. An "analog" of a molecule is meant to refer to a non-natural molecule substantially similar to either the entire molecule or a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th ed., Mack Publishing Co., Easton, Pa. (1980).

A fragment, variant, analog and/or chemical derivative of a subject antigen is said to be a "functional derivative" of the antigen if the amino acid of the former has at least about 80% identity to the sequence of the latter, and if the former has at least about 30% of a biological activity or function of the latter. Increasingly preferred are amino acid identities that increase integrally, i.e., at least about 81%, 82%, etc. identity. Also, increasely preferred biological activities are those of at least about 40%, 50%, 60%, 70%, 80%, and 90%.

A nucleotide sequence is said to be a "functional derivative" of a disclosed nucleotide sequence encoding an antigen if the former encodes a disclosed antigen or a functional derivative thereof.

Biological activities are those operations, functions or processes which are characteristic of living organisms. Biological activities can also include the reproduction, extension or adaptation of living processes to in vitro or non-natural systems, such as the biological activity exhibited when an antigen or its functional derivative is artificially introduced into a test animal to induce the production of antibodies. An antigen can have one or more biological activities. Biological activities can be detected or measured by methods or assays that are characteristic for that activity. For a functional derivative to have a biological activity substantially the same as that of an antigen, it must have a biological activity of at least about 30% of that of antigen as measured by an assay characteristic for that activity and known to those of skill in the art.

The substantially pure antigens that have been expressed by methods of the present invention may be used in immunodiagnostic assay methods well known to those of skill, including radio-immunoassays (RIAs), enzyme immunoassays (EIAs) and enzyme-linked immunosorbent assays (ELISAs). The substantially pure proteins of the present invention, in soluble form, may be administered alone or in combination with other antigens of the present invention, or with other agents, including lymphokines and monokines or drugs, for the treatment of immune-related diseases and disorders in animals, including humans. As examples of such disorders that may benefit from treatment with the substantially pure proteins of the present invention may be mentioned immune deficiency diseases, diseases of immediate type hypersensitivity, asthma, hypersensitivity pneumonitis, immune-complex disease, vasculitis, systemic lupus erythematosus, rheumatoid arthritis, immunopathogenic renal injury, acute and chronic inflammation, hemolytic anemias, platelet disorders, plasma and other cell neoplasms, amyloidosis, parasitic diseases, multiple sclerosis, Guillain-Barre syndrome, acute and subacute myopathic paralysis, myasthenia gravis, immune endocrinopathies, and tissue and organ transplant rejection, all as described in Petersdorf et al., eds., *Harrison's Principles of Internal Medicine*, supra. See also Weir, ed., supra; Boguslaski et al., eds., supra; and Holborow et al., eds., supra.

When used for immunotherapy, the antigens of the present invention may be unlabeled or labeled with a therapeutic agent. Examples of therapeutic agents which can be coupled to the antigens of the invention for immunotherapy are drugs, radioisotopes, lectins, and toxins.

The dose ranges for the administration of the antigens of the present invention are those large enough to produce the desired immunotherapeutic effect, but not so large as to cause adverse side effects, such as unwanted cross-reactions, anaphylactic reactions, and the like. Generally, the dosage employed will vary with the age, condition, sex, and extent of the disease in the patient. Counterindications (if any), immune tolerance and other variables also will affect the proper dosage. Administration may be parenteral, by injection or by gradual perfusion over time. Administration also may be intravenous, intraparenteral, intramuscular, subcutaneous, or intradermal.

Preparations for parenteral administration include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic and aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives also may be present, such as, for example, antimicrobials, antioxidants, chelating agents, inert gases and the like. Such preparations, and the manner and method of making them, are known and described, for example, in *Remington's Pharmaceutical Science,* 16th ed., supra.

The antigens of the present invention also may be prepared as medicaments or pharmaceutical compositions comprising the antigens, either alone or in combination with other antigens or other agents such as lymphokines, monokines, and drugs, the medicaments being used for therapy of animal, including human, immune-related indications.

Although the antigens of the present invention may be administered alone, it is preferred that they be administered as a pharmaceutical composition. The compositions of the present invention comprise at least one antigen or its pharmaceutically acceptable salt, together with one or more acceptable carriers and optionally other therapeutic agents. By "acceptable" is meant that the agent or carrier be compatible with other ingredients of the composition and not injurious to the patient. Compositions include those suitable for oral, rectal, nasal, topical (including buccal and sublingual), vaginal, or parenteral administration. The compositions conveniently may be presented in unit dosage form, and may be prepared by methods well known in the pharmaceutical arts. Such methods include bringing into association the active ingredient with the carrier which constitutes one or more accessory ingredients. In general, compositions are prepared by uniformly and intimately bringing into association the active ingredient with liquid carriers or finely divided solid carriers, or both, and shaping the product formed thereby, if required.

Orally administered pharmaceutical compositions according to the present invention may be in any convenient form, including capsules, cachets, or tablets, each containing a predetermined amount of the active ingredient. Powders or granules also are possible, as well as solution or suspension in aqueous or nonaqueous liquids, or oil-in-water liquid emulsions, or water-in-oil liquid emulsions. The active ingredient also may be presented as a bolus, electuary or paste.

Having now described the invention, the same will be more fully understood by reference to the following examples, which are not intended in any way to limit the scope of the invention.

EXAMPLE I

Isolation, Molecular Cloning, and Structure of the Human CD2 Antigen

A COS cell expression vector was constructed from piSV (Little et al., *Mol. Biol. Med.* 1:473–488 (1983)) by inserting a synthetic transcription unit between the suppressor tRNA gene and the SV40 origin. The transcription unit consisted of a chimeric promoter composed of human cytomegalovirus AD169 immediately early enhancer sequences fused to the HIV LTR −67 to +80 sequences. Immediately downstream from the LTR +80 sequence was inserted a polylinker containing two BstXI sites separated by a 350 bp stuffer; the BstXI sites were flanked by Xbal sites, which could also be used to excise the insert. Downstream from the polylinker were placed the SV40 small t antigen splice and early region polyadenylation signals derived from pSV2. The nucleotide sequence of the vector is shown in FIGS. 1A–1B.

cDNA Library Construction

RNA was prepared from HPB-ALL cells by the guanidinium thiocyanate/CsCl method, as described above. Poly$A^+$ RNA was prepared from total RNA by oligo dT selection. Maniatis et al, *Molecular Cloning: A Laboratory Manual,* supra. cDNA was synthesized by the method of Gubler and Hoffman (*Gene* 25:263–269 (1982)). BstXI adaptors were ligated to the cDNA, and the reaction products fractionated by centrifugation through a 5 ml—20% potassium acetate gradient containing 1 mM EDTA for 3 hours at 50k rpm in a SW55 rotor. 0.5 ml fractions were collected manually through a syringe needle or butterfly inserted just above the curve of the tube. Individual fractions were ethanol-precipitated after addition of linear polyacrylamide (Strauss and Varshavsky, *Cell* 37:889–901 (1984)) t0 20 μg/ml. Fractions containing cDNA larger than 700 bp were pooled and ligated to gradient purified BstXI digested piH3 vector.

The ligated DNA was transformed into *E. coli* MC1061/p3 made competent by the following protocol: The desired strain was streaked out on an LB plate. The next day a single colony was inoculated into 20 ml TYM broth (recipes below) in a 250 ml flask. The cells were grown to midlog phase ($OD_{600}$ about 0.2–0.8), poured into a 2 L flask containing 100 ml TYM, and vigorously agitated until cells grew to 0.5–0.9 OD, then diluted again to 500 ml in the same vessel. When the cells grew to $OD_{600}$ 0.6, the flask was placed in ice-water, and shaken gently to assure rapid cooling. When the culture was cool, it was spun at 4.2 k rpm for 15 minutes (J6). The supernatant was poured off and the pellet resuspended in about 100 ml cold TfB I (below) by gentle shaking on ice. Thereafter, it was respun in the same bottle at 4.2 k rpm for 8 minutes (J6). The supernatant was poured off and the pellet resuspended in 20 ml cold TfB II by gentle shaking on ice. 0.1 to 0.5 ml aliquots were placed in prechilled microfuge tubes, frozen in liquid nitrogen, and stored at −70° C. For transformation, an aliquot was removed, thawed at room temperature until just melting, and placed on ice. DNA was added, let sit on ice 15–30 minutes, and incubated at 37° C. for 5 minutes (6 minutes for 0.5 ml aliquots). Thereafter the DNA-containing suspensions were diluted 1:10 in LB and grown for 90 minutes before plating or applying antibiotic selection. Alternatively, the heat-pulsed transformation mix was plated directly on antibiotic plates onto which a thin (4–5 ml) layer of antibiotic-free LB agar was poured just before plating.

Media and Buffers: TYM: 2% Bacto-Tryptone, 0.5% Yeast Extract, 0.1M NaCl, 10 mM $MgSO_4$ (can be added before autoclaving). TfB I: 30 mM KOAc, 50 mM $MnCl_2$, 100 mM KCL, 10 mM $CaCl_2$, 15% (v/v) glycerol. TfB II: 10 mM Na-MOPS, pH 7.0, 75 MM $CaCl_2$, 10 mM KCl, 15% glycerol.

Recovery of cDNA Clones by Panning

Bacteriological culture dishes (Falcon 1007) were prepared for panning by coating with an affinity purified sheep anti-mouse IgG antibody as described by Wysocki and Sato (*Proc. Natl. Acad. Sci. USA* 75:2844–2848 (1978)), except that dishes were washed with 0.15M NaCl from a wash bottle instead of PBS, and unreacted sites were blocked by overnight incubation in PBS containing 1 mg/ml BSA. Dishes were typically prepared in large batches and stored frozen, after aspiration of the PBS/BSA. In the first round of screening, 24 6 cm dishes of 50% confluent COS cells were transfected by protoplast fusion according to the method of Sandri-Goldrin et al., *Mol. Cell Biol.* 1:743–752 (1981). 72 hours post fusion the cells were detached by incubation in PBS/1 mM EDTA/0.028 sodium azide at 37° C. for 30 minutes. The detached cells were pooled, centrifuged, and resuspended in cold PBS/EDTA/5% Fetal Bovine Serum containing monoclonal antibodies, usually as ascites at 1:1000 dilution, but also as commercial reagents at the concentrations suggested by the manufactures. After 1 hour on ice, the cells were diluted with 1:1 with PBS/EDTA/azide and layered on 10 ml of PBS/EDTA/azide containing 2% Ficoll 400. After centrifugation (400×g, 5 minutes), the supernatant was carefully aspirated, the pellet resuspended in a small amount of PBS/EDTA/5% FBS, and the cells distributed into panning plates containing 3 ml of PBS/EDTA/5% FBS. The plates were then treated essentially as described by Wysocki and Sato, *Proc. Natl. Acad. Sci. USA* 75:2844–2848 (1978). Episomal DNA was recovered from the adherent cells by the Hirt (*J. Mol. Biol.* 26:365–269 (1967)) procedure and transformed into MC1061/p3.

Cell lines and cell culture

COS cell clone M6 cells were propagated in Dulbecco's modified Eagle's medium supplemented with 10% calf serum and gentamycin sulfate at 15 μg/ml (DME/10% calf serum). Cells were split the day before transfection in 6 cm dishes at approximately 1:8 ratio from stock plates kept as dense as possible without overtly affronting the cells. T cell lines were grown in Iscove's modification of Dulbecco's medium (IMDM) containing gentamycin as above, and either NuSerum (Collaborative Research) or fetal bovine serum at 10%.

COS Cell Transfection for Immunofluorescence Studies

COS cells at 50% confluence in 6 cm dishes were transfected in a volume of 1.5 ml with a cocktail consisting of DME or IMDM medium containing 10% NuSerum (Collaborative Research), 400 μg/ml DEAE Dextran, 10 μM chloroquine diphosphate, and 1 μg/ml DNA. After 4 hours at 37° C. (or earlier if the cells appeared ill), the transfection mix was removed and the cells were treated with 10% DMSO in PBS for 2 minutes. Sussman and Milman, *Cell Biol.* 4:1641–1643 (1984). Cells were then returned to DME/10% calf serum for 48 to 72 hours to allow expression.

Immunoprecipitations, Northerns and Southerns

T cells were labeled by lactoperoxidase treatment, lysed, and immunoprecipitated by the procedure of Clark and Einfeld (*Leukocyte Typing II*, Vol. II, pp. 155–167 (1986)), using commercially available goat anti-mouse IgG agarose beads (Cooper Biomedical). COS cells were transfected by DEAE Dextran method and trypsinized and passed without dilution into new plates 24 hours after transfection. 36 hours later, cells were detached by exposure to PBS/EDTA as above, centrifuged, and labeled by the lactoperoxidate method. A cleared lysate was prepared as for the T cell immunoprecipitations, except that the lysis buffer contained 1 mM PMSF, and incubation with the primary antibody was carried out for only 2 hours at 4° C. Eluted samples were fractionated on discontinuous 11.25% polyacrylamide gels using the buffer system of Laemmli (*Nature* 227:680–685 (1970)).

Northern blot analysis was carried out essentially as described (Maniatis et al., *Molecular Cloning, a Laboratory Manual* (1982)), except that DMSO was omitted from the loading buffer, denaturation was at 70° C. for 5 minutes, and the gel contained 0.6% formaldehyde rather than 6%. The gel was stained in two volumes of water containing 1 μg/ml ethidium bromide, photographed, and transferred to nylon (GeneScreen, DuPont) in the staining liquor. The transferred RNA was irradiated by exposure to a germicidal lamp through Saran Wrap (Church and Gilbert, *Proc. Natl. Acad. Sci. USA* 8:1991–1995 (1984)) for 5 minutes at a flux (measured at 254 nm) of 0.22 $mW/cm^2$. Southern blot analysis was carried out by alkaline transfer to nylon (GeneScreen, DuPont) as described by Reed and Mann (*Nucl. Acids Res.* 13:7207–7221 (1986)). Hybridization probes were prepared by the method of Hu and Messing (*Gene* 18:271–277 (1982)), and blots were prehybridized in SDS/phosphate buffer (Church and Gilbert, *Proc. Natl. Acad. Sci. USA* 8:1991–1995 (1984)) containing 10 DNA microgram equivalents of M13 mp19 phage.

Erythrocyte Rosetting

Erythrocytes were prepared from whole blood by three centrifugations in PBS. COS cells were transfected in 6 cm dishes with CD2 or other surface antigen expression clones by the DEAE method. 48 to 72 hours posttransfection, the medium was aspirated and 2 ml of PBS/5% FDS/azide was added to each plate, followed by 0.4 ml of the appropriate erythrocyte samples as 20% suspensions in PBS. After 1 hour at room temperature, the nonadherent erythrocytes were gently washed off, and the plates were examined.

A cDNA encoding CD2 antigen determinants was isolated in the following manner: cDNA was prepared from RNA extracted from the human T Cell tumor line HPB-ALL and inserted into the SV40 origin-based expression vector piH3 as described above. A cDNA library of approximately $3\times10^5$ recombinants was constructed, and the library was introduced into COS cells by protoplast fusion. Three days later the cells were detached by exposure to EDTA and treated with a pool of monoclonal antibodies, including three (OKT11, Leu5b, and Coulter T11) directed against CD2 determinants. The antibody-treated cells were distributed into dishes coated with an affinity purified sheep anti-mouse IgG antibody, allowed to attach, and separated from the nonadherent cells by gentle washing. This method of enrichment is known in the immunological literature (Mage et al. *J. Immunol. Methods* 15:47–56 (1977).

The resulting colonies were pooled, fused into COS cells, and subjected to a second round of panning as before. In the third round, a portion of the detached cells was treated with a mixture of three monoclonal antibodies specific for CD2, and a Hirt supernatant was again generated and transformed into *E. coli*. DNA was prepared from eight of the resulting colonies and transfected into COS cells. After three days, surface expression of the CD2 antigen was detected by indirect immunofluorescence in six of eight transfected dishes. Restriction enzyme digestion of the corresponding plasmid DNAs revealed a 1.5 kb insert in all six isolates.

One of the six clones was prepared in larger quantities for further analysis. Following transfection into COS cells, indirect immunofluorescence analysis with a partial panel of antibodies provided by the Third International Workshop on Leukocyte Differentiation Antigens showed that all of the antibodies provided gave positive reactions with the exception of one sample which also failed to react with phytohemagglutinin-activated T lymphocytes. Among the 17 antibodies tested were at least eight distinguishable groups defined by their differing patterns of reactivity with lymphocytes of various primate species. Jonker and Nooij, *Leukocyte Typing II, Vol. I, pp.* 373–387 (1986).

cDNA Sequence Analysis

The CD2 cDNA insert was subcloned into M13 mp19 (Vieira and Messing, *Gene* 19:259–268 (1982)) in both orientations, and the sequence determined by the dideoxynucleotide method (FIGS. 2A and 2B). Sanger et al., *Proc. Natl. Acad. Sci. USA* 74:5463–5467 (1977). An open reading frame was observed to extend 360 residues from an ATG triplet satisfying the consensus criteria of Kozak (*Microbiol. Rev.:* 1–47:45 (1983)) for translational initiation codons (FIGS. 1A and 1B). The predicted amino acid sequence evokes an integral membrane protein with a single membrane spanning hydrophobic anchor terminating in a rather large intracytoplasmic domain. Comparison of the N-terminal amino sequence with the matrix of signal sequence residue frequencies constructed by von Heijne (*Nucl. Acids Res.* 14:4683–4690 (1986)) suggests that mature CD2 peptide is formed by cleavage of a precursor peptide between the 19th (Ser) and 20th (Lys) residues.

A surprising and unexpected feature of this sequence is the presence of a potential N-linked glycosylation site just proximal to the proposed cleavage site. The resulting polypeptide backbone has a predicted molecular weight of 38.9 kd divided into an external domain of mass 21.9 kb and a cytoplasmic domain of mass 14.6 kd. Three N-linked glycosylation sites are present in the extracellular domain.

The membrane spanning domain comprises 26 unchanged residues of predominantly hydrophobic character. In the nine residues immediately following are seven basic residues, either lysines or arginines. The appearance of predominantly hydrophobic residues followed by basic residues is a common organizational feature of transmembrane proteins bearing carboxyl-terminal anchors.

Another surprising feature of the transmembrane domain is the appearance of a cys-gly-gly-gly, a beta turn motif (Chou and Fasman, *Annual Review of Biochemistry* 47:251–276 (1978)), flanked by hydrophobic residues (which are frequently found flanking beta turns). Because only 20 residues arrayed in an alpha helix are theoretically needed to traverse the 3 nm membrane bilayer (Tanford, *Science* 200:1012–1018 (1978)), and as few as 14 hydrophobic residues can allow insertion and export of an integral membrane protein (Adams and Rose, *Cell* 41:1007–1015 (1985)), the transmembrane segment of the CD2 antigen may contain a bend or kink.

The rather large size of the cytoplasmic domain leaves open the possibility that CD2 possesses an intrinsic enzymatic activity. The cytoplasmic domain is very rich in prolines and contains three sites with high turn probability.

Comparison of the amino acid sequence with the NBRF database revealed no substantive homologies with other proteins. In particular, no homology with the T cell receptor alpha or beta chains was observed, ruling out the suggestion that CD2 is a primordial T cell receptor. Milanese et al., *Science* 231:1118–1122 (1986).

Just inside the cytoplasmic face of the protein is a run of basic proteins followed by a serine residue, a pattern found at the same location in both the EGF receptor and the class I histocompatibility genes, and in each case a known site for either in vivo (EGF) and in vitro (HLA) phosphorylation by protein kinase C or cyclic AMP-dependent protein kinase, respectively. Hunter et al., *Nature* 311:480–482 (1984); Davis and Czech, *Proc. Natl. Acad. Sci.* 82:1974–1978 (1985); Guild and Strominger, *J. Biol. Chem.* 259:9235–9240 and 13504–13510 (1984). A similar site is found in the intracytoplasmic domain of the interleukin 2 receptor, and is phosphorylated in vivo by protein kinase C. Leonard et al., *Nature* 311:626–631 (1984); Nikaido et al., *Nature* 311:631–635 (1984); Shackelford and Trowbridge, (1984) *J. Biol. Chem.* 259:11706.

Immunoprecipitation of CD2 Antigen Expressed by Transfected Cells

COS cells were transfected with the CD2 expression plasmid and surface labeled with $125_I$ by the lactoperoxidase method 60 hours post-transfection. A cell lysate was prepared, and portions were incubated either with monoclonal anti-CD2 antibody (OKT11) or with an extraneous (OKT4; anti-CD4) antibody for 2 hours at 4° C. Sepharose-bound anti-mouse antibody was added, and after several washing steps, the adsorbed proteins were eluted and electrophoresed through a 11.25% acrylamide gel together with similarly prepared immunoprecipitates from phytohemagglutinin-activated T lymphocytes, the cDNA donor line HPB-ALL, or a long-term T cell line generated in this laboratory. Autoradiography demonstrated a prominent band of immunoreactive material precipitated from transfected COS cells by the anti-CD2 antibody, but not by the control. The calculated mean molecular weight of the COS cell material was 51 kd, compared to a mean molecular weight of 54 kd for the T blast and T cell line material; the antigen from HPB-ALL cells was found to have a molecular weight of approximately 61 kd. The observed differences in size were attributed to different patterns of glycosylation in the different cell types. A minor band of apparent molecular weight 38 kd was present in material immunoprecipitated from COS cells but not from T cells or HPB-ALL cells. The size of this species agrees within experimental error with the predicted molecular weight of mature unglycosylated peptide, 39 kd.

COS Cells Expressing CD2 Form Rosettes with Sheep Erythrocytes

COS cells transfected with the CD2 expression clone were treated for 1 hour with purified MT910 (IgG, kappa) anti-CD2 antibody (Rieber et al., *Leukocyte Typing II*, Vol. I, pp. 233–242 (1986)) at a concentration of 1 μg/ml, or with purified MB40.5 (IgG1, kappa; Kawata et al., *J. Exp. Med.* 160:633–651 (1984)) antibody at the same concentration. MB40.5 recognizes a monomorphic HLA-ABC determinant and cross-reacts with African Green Monkey histocompatibility antigens; it was chosen because it represents an isotype-matched antibody recognizing a surface antigen of approximately the same abundance as the CD2 antigen expressed by transfected cells. Sheep erythrocyte rosettes were observed in the presence of MB40.5, but not of MT910. Rosette inhibition was also observed with OKT11 antibody, and not with various other control antibodies.

Transfected COS Cells Form Rosettes with other Animal Erythrocytes

In addition to sheep erythrocytes, human T cells are known to form rosettes with horse, pig, dog, goat, and rabbit, but not mouse or rat erythrocytes. Johansen et al., *J. Allergy Clin. Immunol.* 54:86–94 (1974); Amiot et al., in, A. Bernard et al., eds., *Leucocyte Typing*, Springer, publisher, New York, N.Y., pp. 281–293 (1984); Nalet and Fournier, *Cell. Immunol.* 96:126–136 (1985). Autorosettes between human erythrocytes and human thymocytes (Baxley et al., *Clin. Exp. Immunol.* 15:385–393 (1973)) have also been reported. COS cells transfected with the CD2 expression clone were treated with either MT910 or with the control antibody, MB40.5, and exposed to erythrocytes from the species above. Rosettes were observed with horse, pig, dog, goat, sheep, rabbit, and human erythrocytes, but not with mouse or rat erythrocytes. Rosette formation was blocked by pretreatment of transfected COS cells with MT910, but not with MB40.5. In these experiments, it was noticed that horse erythrocytes formed unusually dense rosettes, and that goat erythrocytes formed rather sparse rosettes, possibly because their small size made them more susceptible to washing. Mouse erythrocytes showed weak spontaneous binding to the culture dish as well as to MT910 and MB40.5 pretreated cells, while rat erythrocytes showed no detectable binding of any sort.

Binding of Human Erythrocytes is Blocked by LFA3 Antibody

Because it has been suggested on the basis of antibody blocking studies that LFA3 is the target structure for the CD2 antigen (Shaw et al., *Nature* 323:262–264 (1986)), the ability of anti-LFA3 antibody to prevent rosette formation was investigated. Transfected cells were exposed to human erythrocytes pretreated for 2 hours with either anti-LFA3 (IgG1, kappa) as ascites at 1:1000 dilution, or with a 10 μg/ml concentration of each of four isotype-matched nonagglutinating antibodies directed against human erythrocyte antigens as prevalent or more prevalent than LFA3:G10/B11 and D10, anti-K14 antigen, D6, anti-Wr$^b$ antigen; and F7/B9, anti-k antigen. Nichols et al., *Vox Sang*, in press. The erythrocytes were washed free of excess LFA3 antibody, but were allowed to form rosettes in the presence of the control antibodies to guard against possible loss of antibody blocking power by desorption. Rosette formation was observed in the presence of all four control antibodies, but not with erythrocytes pretreated with anti-LFA3.

COS Cells Expressing other T Cell Antigens do not Form Rosettes

A number of clones were isolated by the same expression technique used to clone CD2 and characterized to varying degrees by antibody reactivity, nucleic acid restriction and sequence analysis, and immunoprecipitation. Representative clones were transfected into COS cells and analyzed for ability to sustain rosette formation. The CD1a, CD1b, CD1c, CD4, CD5, CD6, CD6, CD8, and CD28 (Tp44) clones did not form rosettes with human erythrocytes.

RNA Blot Analysis

Equal amounts of total RNA prepared from cell types expressing or lacking CD2 antigen were electrophoresed through denaturing agarose gels and transferred to nylon. Hybridization of the transferred RNA with a strand selective probe (Hu and Messing, *Gene* 17:271–277 (1982)) prepared from an M13 clone containing a CD2 cDNA insert revealed the presence of prominent 1.65 and 1.3 kb transcripts present in RNA derived from thymocyte, activated T cell, and senescent T cell populations. Lesser amounts were found in RNA extracted from the cDNA donor line, HPB-ALL and less still from MOLT4; barely detectable levels were recorded in RNA from the HSB-2 line. No reactivity was observed with RNA from Namalwa (Burkitt lymphoma), U937 (histiocytic leukemia), HuT-78 (Adult T cell leukemia), PEER (T cell leukemia), or Jurkat clone J3R7 (T cell leukemia) lines. The pattern of reactivity conformed well with the known or measured pattern of expression of CD2 antigen, which was absent or indetectable on the Namalwa, *937, HuT-78, J3R7, PEER, and HSB-2 cell lines, weakly present on MOLT4, more strongly present on EPB-ALL, and most strongly present on activated T cells. Thymocytes are also known to express high levels of CD2 antigen.

Examination of the sequence of the cDNA clone suggested that the 1.3 kb RNA might arise by formation of an alternate 3' end distal to the canonical polyadenylation signal AATAAA at position 1085 in the cDNA sequence. To test this notion, RNA from HPB-ALL and activated T cells was subjected to Northern blot analysis and hybridized either with a complete cDNA probe, or with a probe derived from the 3' portion of the cDNA distal to nucleotide 1131. The latter probe reacted only with the 1.65 kb species, while the former showed the same reactivity pattern observed in FIG. 5. This result is consistent with the suggested origin of the 1.3 kb transcript.

In both activated and senescent T cell RNA preparations, a weakly hybridizing transcript of approximately 0.75 kb was detected. At present the origin of this RNA is unknown.

Genomic Organization of the CD2 Gene

Southern blot analysis of, genomic DNA from placenta, peripheral blood lymphocytes, T cells, HeLa cells, or the tumor lines used in the RNA analysis above showed identical BamHI digest patterns, indicating that rearrangement is not involved in the normal expression of the CD2 gene during development. Similarly, no gross genomic alteration underlies the failure of the examined T cell tumor lines to express CD2 antigen. Restriction analysis of total genomic DNA with a number of other enzymes, as well as preliminary results with an incomplete collection of 1 phage recombinants bearing the CD2 sequence, shows that the gene is divided into at least four exons.

EXAMPLE II

Isolation and Molecular Cloning of Human LFA-3 Antigen

The previous example shows that cDNAs encoding surface antigens, such as the CD2 antigen, can be isolated by the transient expression system of the present invention, in which COS cells transfected with cDNA libraries are allowed to attach to ("panned" on) antibody-coated plates. Plasmid DNA is recovered from cells adhering to the plates, transformed into *E. coli*, and the process is repeated, usually twice, to isolate the desired clone. Although powerful, this approach cannot be used when the monoclonal antibodies used for panning recognize determinants on the untransfected cells. This appears to be the case for anti-LFA3 monoclonal TS2/9. However, a similar transient expression system based on polyoma virus replication-competent cells should allow almost all monoclonals to be used, since the probability of cross reaction between murine antibodies and murine cell surface determinants should usually be small.

A new expression vector, CDM8 (FIG. 3) was created from the COS cell vector piH3M described previously. The new vector differs by the inclusion of a deleted version of a mutant polyoma virus early region selected for high efficiency expression in both murine and monkey cells, by the replacement of substantially all of the human immunodeficiency promoter region with the cognate sequences of the human cytomegalovirus immediate early promoter, and by inclusion of a bacteriophage T7 promoter between the eukaryotic promoter and the site of cDNA insertion. Expression in COS cells of chloramphenicol acetyltransferase by all of the vectors was equivalent.

A library of $1.9\times10^6$ recombinants having inserts greater than 0.8 kb in size was prepared in the CDM8 vector from a microgram of poly $A^+$ RNA isolated from the human lymphoblastoid cell line JY. The library was introduced into WOP cells (NIH 3T3 war cells transfected with polyoma origin deletion DNA) by spheroplast fusion, and subjected to three rounds of panning and reintroduction into *E. coli* as described in Example I.

A clone encoding the LFA-3 antigen was identified by indirect immunofluorescence of transfected WOP cells, amplified and sequenced (FIG. 4A). Within the 874 bp insert, an open reading frame of 237 residues originates at a methionine codon closely corresponding to the consensus sequence suggested by Kozak, *Microbiol. Rev.* 47:1–45 (1983). The reading frame terminates in a series of hydrophobic residues lacking the characteristic basic anchoring residues of internal membrane proteins, but sharing features with known phosphatidylinositol-linked superficial membrane proteins. The features include clustered serine or threonine residues in a hydrophilic region immediately preceding the hydrophobic domain, and the presence of syrines and threonines in the hydrophobic portion.

The amino acid sequence predicted from the nucleotide sequence of the LFA-3 clone was compared to the NBRF database, and no significant homologies were uncovered; the most significant scores were to the HIV envelope protein. Within the 200 residues comprising the presumed mature protein are 6 N-linked glycosylation sites, and 5 tandem serine or tandem threonine residues that frequently appear in O-linked glycosylated proteins. Ten cysteine residues appear in the complete sequence, 6 of which are distributed in the latter half of the mature protein, and one of which falls in the carboxy-terminal hydrophobic domain. Although esterification of cysteine thiols to fatty acids is a common occurrence in integral membrane proteins, and may play an alternate role in membrane anchoring of LFA-3, two examples are known of cysteine residues within or at the margin of the hydrophobic region of phosphatidylinositol linked proteins.

The predicted sequence suggests that the known manipulations for increasing erythrocyte adhesion to T cells may find direct physical explanation in the structure of the LFA-3 molecule. Aminoethylisothiouronium bromide, the thiourea adduct of bromoethylamine, undergoes spontaneous rearrangement to mercaptoethylguanidine at alkaline pH. The latter likely gains access to disulfide bonds inaccessible to less chaotropic reducing agents and may thereby reduce and promote the unfolding of the LFA-3 molecule. Similarly, neuraminidase may decrease steric interference by the many carbohydrate chains on the molecule.

RNA and DNA blot hybridization analysis showed that the LFA-3 gene shares no closely related sequences in the genome, and encodes a single RNA species of about 1 kb in length. Cell lines that express large amounts of surface LFA-3 have greater amounts of LFA-3 RNA than those that express small or nondetectable amounts.

Radioimmunoprecipitation of the antigen expressed in transfected COS and murine cells shows a broad band of approximately 50 kd mean molecular mass, similar to that found in JY cells.

EXAMPLE III

Isolation and Molecular Cloning of the Human CD28 cDNA Antigen

The previous examples illustrate the monoclonal antibody-based technique of the present invention for enrichment of cDNAs encoding surface antigens. In the present example, a method of constructing plasmid expression libraries is described which allows the enrichment technique to be fully exploited. The method of the present invention for making plasmid expression libraries is of general use for expression cloning.

The antibody selection technique of the present invention has also been applied to isolate a cDNA clone encoding the CD28 antigen. The antigen shares substantial homology with members of the immunoglobulin superfamily and forms a dimer structure on the surface of transfected COS cells similar to the dimer structure found on T lymphocytes.

Preparation of cDNA Libraries

Poly(A)+ RNA was prepared from the human T-cell tumor line HPB-ALL by oligo(dT) cellulose chromatography of total RNA isolated by the guanidinium thiocyanate method (Chirgwin, J. M. et al., *Biochemistry* 18:5294–5299 (1979)). cDNA was prepared by a protocol based on the method of Gubler and Hoffman (Gubler, U. et al., *Gene* 25:263–269 (1982)). 4 μg of mRNA was heated to approximately 100° C. in a 1.5 ml centrifuge tube for 30 seconds, quenched on ice, and the volume adjusted to 70 μl with RNAse-free water. To this were added 20 μl of buffer (0.25 M Tris pH 8.8 (8.2 at 42° C.), 0.25 M KCl, 30 mM $MgCl_2$), 2 μl of RNAse inhibitor (Boehringer 36 μ/μl), 1 μl of 1M DTT, 1 μl of 5 μg/μl of oligo dT (Collaborative Research), 2 μl of 25 mM each deoxynucleoside triphosphate (US Biochemicals), and 4 μl of reverse transcriptase (Life Sciences, 24 μ/μl). After 40 minutes at 42° C., the reaction was terminated by heating to 70° C. for 10 minutes. To the reaction mix was then added 320 μl of RNAse free water, 80 μl of buffer (0.1 M Tris pH 7.5, 25 mM $MgCl_2$, 0.5 M KCl, 0.25 mg/ml BSA, and 50 mM DTT), 25 units of DNA Polymerase I (Boehringer), and 4 units of RNAse H (BRL). After 1 hour at 15° C. and 1 hour at 22° C., 20 μl of 0.5M EDTA pH 8.0 were added, the reaction mixture was extracted with phenol, NaCl was added to 0.5 M, linear polyacrylamide (carrier; Strauss, F. et al., *Cell* 37:889–901 (1984)) was added to 20 μg/ml, and the tube was filled with ethanol. After centrifugation for 2–3 minutes at 12,000×g, the tube was removed, vortexed to dislodge precipitate spread on the wall of the tube, and respun for 1 minute.

Unpurified oligonucleotides having the sequence CTCTAAAG and CTTTAGAGCACA (SEQ ID NO:37) were dissolved at a concentration of 1 mg/ml, $MgSO_4$ was added to 10 mM, and the DNA precipitated by adding 5 volumes of EtOH. The pellet was rinsed with 70% ETOH and resuspended in TE at a concentration of 1 mg/ml. 25 μl of the resuspended oligonucleotides were phosphorylated by the addition of 3 μl of buffer (0.5 M Tris pH 7.5, 10 mM ATP, 20 mM DTT, mM spermidine, 1 mg/ml BSA, and 10 mM $MgCl_2$) and 20 units of polynucleotide kinase followed by incubation at 37° C. overnight.

3 μl of the 12-mer and 2 μl of the 8-mer phosphorylated oligonucleotides were added to the cDNA prepared as above in a 300 μl reaction mixture containing 6 mM Tris pH 7.5, 6 mM $MgCl_2$, 5 mM NaCl, 0.35 mg/ml BSA, 7 mM mercaptoethanol, 0.1 mM ATP, 2 mM DTT, 1 mM spermidine and 400 units T4 DNA ligase (New England BioLabs) at 15° overnight. 10 μl of 0.5 M EDTA were added, the reaction was phenol extracted, ethanol precipitated, resuspended in a volume of 100 μl and layered on a 5 ml gradient of 5–20% potassium acetate in 1 mM EDTA, 1 μg/ml ethidium bromide. The gradient was spun 3 hours at 50,000 rpm (SW55 rotor) and fractionated manually, collecting three approximately 0.5 ml fractions followed by six approximately 0.25 ml fractions in microcentrifuge tubes by means of a butterfly infusion set inserted just above the curve of the tube. Linear polyacrylamide was added to 20 μg/ml, the tubes were filled with ethanol, chilled, spun, vortexed and respun as above. The precipitate was washed with 70% ethanol, dried, and resuspended in 10 μl. 1 μl of the last 6 fractions was run on a gel to determine which fractions to pool, and material less than 1 kb in size was typically discarded. Remaining fractions were pooled and ligated to the vector.

The complete sequence and derivation of the vector is shown in FIG. 5. The vector was prepared for cloning by digestion with BstXI and fractionation on 5–20% potassium acetate gradients as described for the cDNA. The appropriate band was collected by syringe under 300 nm UV light and ethanol precipitated as above. cDNA and vector were titrated in test ligations. Usually 1–2 μg of purified vector were used for the cDNA from 4 μg of poly A+ RNA. The ligation reactions were composed as described for the adaptor addition above. The ligation reactions were transformed into MC1061/p3 cells made competent as described above. The transformation efficiency for supercoiled vector was $3–5\times10^8$ colonies/μg.

Recovery and Characterization of the CD28 Clone

Panning of the library was carried out as described herein above, using purified antibody 9.3 (DuPont) at a concentration of 1 μg/ml in the antibody cocktail. The methods used for COS cell transfection, radioimmunoprecipitation, RNA and DNA blot hybridization, and DNA sequencing were all as described herein above.

To isolate the CD28 cDNA, a large plasmid cDNA library was constructed in a high efficiency expression vector containing an SV40 origin of replication. A preferred version of the vector, containing an M13 origin, is shown in FIGS. 6A–6D. Three features of the vector make it particularly suitable for this use: (i) the eukaryotic transcription unit allows high level expression in COS cells of coding sequences placed under its control; (ii) The small size and particular arrangement of sequences in the plasmid permit high level replication in COS cells; and (iii) the presence of two identical BstXI sites in inverted orientation and separated by a short replaceable fragment allows the use of an efficient oligonucleotide-based strategy to promote cDNA insertion in the vector.

The BstXI cleavage site, CCAN'$_5$NTGG, creates a four base 3' extension which varies from site to site. A vector was created in which two identical sites were placed in inverted orientation with respect to each other, and separated by a short replaceable segment of DNA. Digestion with BstXI followed by removal of the replaceable segment yielded a vector molecule capable of ligating to fragments having the same ends as the replaceable segment, but not to itself. In parallel, cDNA synthetic oligonucleotides were employed that give the same termini as the replaceable segment. The cDNA then could not ligate to itself, but could ligate to the vector. In this way, both cDNA and vector were used as efficiently as possible.

Tailing with terminal transferase achieves the same end, but with less convenience and less overall efficiency. Moreover, homopolymer tracts located 5' to cDNA inserts have been reported to inhibit expression in vitro and in vivo (Yokota, T., et al., *Nucl. Acids Res.* 14:1511–1524 (1986); Riedel, H., *EMBO J.* 3:1477–1483 (1985)). Similar approaches based on the use of partially filled restriction sites to favor insertion of genomic DNAs (Zabarovsky, E. R., et al., *Gene* 42:119–123 (1986)) and cDNAs (Yang, Y., et al., *Cell* 47:3–10 (1986)) recently have been reported. These approaches give 2 or 3 base complementary termini, which usually ligate less efficiently than the 4 base extensions reported here.

Although the cloning scheme of the present invention does not result in a directional insertion of the cDNA, the ability to make large libraries easily, coupled with a powerful selection procedure, makes directional insertion unnecessary. The library construction efficiencies observed according to the present invention, between 0.5 and $2\times10^6$ recombinants per g of mRNA, with less than 1% background and an insert size greater than 1 kb, compared favorably with those described for phage vectors lambda gt10 (7.5×105/μg of mRNA) and lambda gt11 ($1.5\times10^6$/μg of mRNA) (Huynh, T., et al., *In: DNA Cloning Vol. I. A Practical Approach*, Glover, D. M. (ed.), IRL Press, Oxford (1985), pp. 49–78); but the resulting clones were more convenient to manipulate.

Surface antigen cDNAs can be isolated from these libraries using the antibody enrichment method of the present invention. In this method, the library is introduced into COS cells (for example, by spheroplast or protoplast fusion), where it replicates and expresses its inserts. The cells are harvested by detaching without trypsin, treated with monoclonal antibodies specific for the surface antigens desired, and distributed in dishes coated with affinity purified antibody to mouse immunoglobulins. Cells expressing surface antigen adhere, and the remaining cells can be washed away. From the adherent cells, a Hirt fraction is prepared (Hirt, B., *J. Molec. Biol.* 26:365–369 (1967)), and the resulting DNA transformed back into *E. coli* for further rounds of fusion and selection. Typically, after two rounds of selection with monoclonal antibodies recognizing different surface antigens, a single round of selection is performed with a single antibody, or pool of antibodies recognizing the same antigen.

Isolation of a CD28 cDNA

The CD28 cDNA was isolated from a library of about $3\times10^5$ recombinants prepared from cDNA from 0.8 μg of poly $A^+$ RNA using an earlier version of the protocol described in the Materials and Methods. The library was screened for CD28 (and other surface antigen) cDNA clones by the method outlined above. After the third transfection, COS cells were panned with the 9.3 antibody alone. A Hirt supernatant was prepared from the adherent cells and transformed into *E. coli*. Plasmid DNA was isolated from eight colonies and transfected individually into COS cell cultures. The presence of the CD28 antigen was detected in three of eight transfected cultures by indirect immunofluorescence. All three plasmid DNAs contained an insert of about 1.5 kb.

cDNA Sequence Analysis

The CD28 cDNA encodes a long open reading frame of 220 residues having the typical features of an integral membrane protein (FIGS. 7A–7B). Removal of a predicted (von Heijne, *Nucl. Acids Res.* 14:4683–4690 (1986)) N-terminal signal sequence gives a mature protein of 202 residues comprising an extracellular domain with five potential N-linked glycosylation sites (Asn-X-Ser/Thr), a 27-amino acid hydrophobic membrane spanning domain, and a 41-amino acid cytoplasmic domain. Comparison of the amino acid sequence of CD28 with the National Biomedical Research Foundation database (Version 10.0) revealed substantial homology with mouse and rabbit immunoglobulin heavy-chain variable regions over a domain spanning almost the entire extracellular portion of CD28. Within this domain two cysteine residues in the homology blocks Leu-(Ser or Thr)-Cys and Tyr-(Tyr or Phe)-Cys are shared by CD28, CD4, CD8, immunoglobulin heavy- and light-chain variable sequences and related molecules with approximately the same spacing (Maddon et al., *Annu. Rev. Biochem.* 48:961–997 (1979)).

CD28 cDNA Directs the Production of a Homodimer in Transfected COS Cells

Immunoprecipitation of CD28 antigen from transfected COS cells was carried out using the monoclonal antibody 9.3 (Hansen, J. A., et al., *Immunogenetics* 10:247–260 (1980)). The material obtained from COS cells migrated with a molecular weight of 74 kd under nonreducing conditions and 39 kd under reducing conditions, a pattern consistent with homodimer formation. Under the same conditions activated T cells give bands with molecular weights of 87 and 44 kd, and HPB-ALL cells give bands of 92 and 50 kd, under nonreducing and reducing conditions respectively. The variation in molecular weight of the material obtained from different cell types arises as a result of differing glycosylation patterns characteristic of each type. Similar results were observed with other leukocyte surface antigens (Seed et al., *Proc. Natl. Acad. Sci USA* 87 (1987)). The nucleotide sequence of the CD28 cDNA predicts a mature protein with molecule weight of 23 kd, much smaller than observed in these experiments, and probably attributable to utilization of the 5 N-linked glycosylation sites predicted by the amino acid sequence.

RNA Blot Analysis

Equal amounts of total RNA prepared from cell types expressing or lacking CD28 were subjected to RNA blot analysis as described hereinabove. Four bands with molecular weights of 3.7, 3.5, 1.5, and 1.3 kb were visible in lanes containing RNA thymocytes, T blasts, senescent T cells, and the T cell leukemia cell lines PEER and HPB-ALL. No bands were detected in lanes containing RNA prepared from the cell lines U937 (histiocytic leukemia), HuT-78 (Adult T cell leukemia), Jurkat (T cell leukemia), Namalwa (Burkitt lymphoma), MOLT4, and HSB-2, all of which do not express CD28. The 1.5 kb transcript presumably corresponds to the isolated cDNA, and the 3.7 and 3.5 kb species reflect incomplete splicing or alternative polyadenylation site utilization. The 1.3 kb transcript may terminate at an unconventional polyadenylation signal, since there is no obvious candidate in the sequence.

The CD28 Gene is not Rearranged

DNA blot analysis (Seed et al., *Proc. Natl. Acad. Sci USA* 87 (1987)) of genomic DNA from placenta, peripheral blood lymphocytes, T cells, HeLa cells, or the tumor lines used in the RNA blot analysis above showed identical Dra 1 digest patterns indicating that rearrangement is not involved in the normal expression of the CD28 gene during development. Similarly, no gross genomic rearrangement underlies the failure of the examined T-cell tumor lines to express CD28 antigen. It may be inferred from the Dra 1 fragment pattern that the CD28 gene contains at least two introns.

EXAMPLE IV

Isolation and Molecular Cloning of Two Human CD7 Antigen cDNAs

The CD7 cluster of antibodies (Palker, et al., *Leukocyte Typing II*, Springer-verlag, New York, 303–313 (1985)) recognized a 40 kd glycoprotein (gp40) on the surface of peripheral blood T cells and thymocytes. Early studies with anti-CD7 antibodies showed that $CD7^+$ T cells enhance immunoglobulin (Ig) synthesis by B cells (Miroshima et al., *J. Immunol.* 129:1091–1098 1982)), suppress B cell Ig synthesis when stimulated with Concanavalin A (Haynes et al., *Proc. Natl. Acad. Sci. U.S.A.* 76:5829–5833 (1979)) and are the precursors of the cytotoxic T cells generated in mixed lymphocytic culture (Morishima et al., *J. Immunol.* 129:1091–1098 (1982)). Furthermore, CD7 has been found to be the most reliable marker for the identification of T cell acute lymphoblastic leukemia (Link et al., *Blood* 62:722–728 (1983)). As such, studies have been carried out, in which cytotoxins coupled to the anti-CD7 antibody 3A1 were used to purge bone marrow prior to reinfusion to avoid early relapse in autologous bone marrow transplants or as prophylaxis against graft vs. host disease in allogenic bone marrow transplants (Ramakrishnan et al., *J. Immuol.* 135:3616–3622 (1985)). Similarly, anti-CD7 antibodies also show promise as immunosuppressive agents in the treatment of allograft rejections (Raftery et al., *Transpl. Proc.* 17:2737–2739 (1985)) which is in accord with the recent observation that the anti-CD7 antibody 7G5 significantly inhibits the primary mixed lymphocyte reaction (Lazarovits et al., *Leukocyte Typing III*. Oxford Univ. Press, Oxford (1987)).

At present the physiological role of CD7 is not understood. It is known that anti-CD7 antibodies are not mitogenic, and do not block the T cells' response to PHA, or tetanus toxoid (Palker et al., *Leukocyte Typing*, Springer-Verlag, New York, 303–313 (1985)). Some have noted that expression of CD7 in thymocytes occurs prior to the onset of T cell receptor beta-chain rearrangement (Pittaluga et al., *Blood* 68:134–139 (1986)) and have pointed to a possible role for CD7 in this rearrangement and subsequent expression of the T cell receptor. It is clear that the cloning of the CD7 antigen would further efforts to understand its role in T cell physiology. Nucleotide sequencing and preliminary characterization of two cDNAs encoding the CD7 antigen was carried out according to the method of the present invention. Prompted by the recent suggestion that CD7 may be, or be part of, the T cell IgM receptor (Sandrin et al., *Leukocyte Typing III. Oxford Univ. Press, Oxford* (1987)), the ability of COS cells expressing CD7 to bind IgM or IgM immune complexes was evaluated. The results do not support the simple notion that CD7 itself is an IgM receptor.

Preparation of cDNA Library and Recovery and Characterization of CD7 Clones

Preparation of an HPB-ALL cDNA library in the expression vector piH3 was carried out as described herein. Panning of the library was carried out according to the method of the present invention, using purified anti-CD7 antibody Leu9 (Becton Dickinson) and antibody 7G5 as ascites fluid was diluted 1:1000. Methods for cell transfection, radioimmunoprecipitation, DNA and RNA blot hybridization and DNA sequencing were all as described herein.

IgM and IgG Binding by COS Cells Transfected with CD7 and CDw32

Human IgM, IgG, and IgA antibodies, affinity purified FITC conjugated goat anti-human immunoglobulins antibodies (anti-Ig(G+M+A)), washed and preserved bovine red blood cells, and IgG and IgM fractions of rabbit anti-bovine red blood cell antibodies were purchased from Cooper Biomedical (Malverne, Pa.). COS cells were transfected by the DEAE Dextran method with cDNAs encoding the CD7, CDw32, and CD28 surface antigens. 48 hours after transfection the cells were washed with PBS/0.5% BSA and incubated with either human IgM, IgG or IgA antibodies at a concentration of 1 μg/ml, at 4° C. for 2 hours. Subsequently the cells were washed with PBS/0.5% BSA and incubated for 30 minutes at 4° C. with FITC conjugated rabbit anti-human immunoglobulins. After washing the cells were examined with a fluorescence microscope. The experiments were also performed in the presence of 0.1% azide with the same results.

Bovine erythrocytes for rosette assays were prepared as described by Ercolani et al., *J. Immunol.* 127:2044–2051 (1981). Briefly, a 2% suspension of bovine erythrocytes was washed with PBS/0.5% BSA and treated with subagglutinating amounts of either IgG or the IgM fraction of rabbit anti-bovine erythrocyte antibodies at 4° C. for 1 hour. Erythrocytes were then washed twice with PBS/0.5% BSA and adjusted to a 2% solution. 2 ml of antibody-coated erythrocytes were layered on 60 mm dishes containing COS cells which had been transfected 48 hours earlier with either CD7, CD32 or CD28 by the DEAE Dextran method. The dishes were then centrifuged at 150×g at 4° C. for 15 minutes. After an additional 45 minute incubation at 4° C., the plates were gently washed 5 times with 5 mls of PBS/0.5% BSA, and the COS cells were examined for rosette formation. These experiments were also performed in the presence of 0.1% sodium azide without alteration of the results.

Formation of T Cell Rosettes with Antibody-Coated Erythrocytes

Peripheral blood lymphocytes were obtained from heparinized blood by centrifugation at 40° C. over a Ficoll-Hypaque gradient at 400×g for 30 minutes. Leukocytes at the interface were washed two times with PBS. The leukocytes were adjusted to $10^7$ cells/ml in IMDM/10% Fetal Bovine Serum (FBS) and incubated in tissue culture dishes at 37° C. for 30 minutes. Nonadherent cells were transferred to new dishes, and PHA was added to stimulate proliferation of T lymphocytes. On the next day the cells were washed with PBS and placed in fresh IMDM/10% FBS.

Rosette assays were performed three days later. Cells were washed with PBS/0.5% BSA, and a 10 μl suspension of 2% Ig-coated erythrocytes prepared as described above was added to 10 μl of PBS/0.5% BSA containing $5\times10^6$ cells/ml. The mixtures were placed in Falcon round bottom 96 well plates and centrifuged at 150×g for 15 min at 4° C. After an additional incubation of 45 min at 4° C. pellets were resuspended with 10 μl of PBS/0.5% BSA, and the rosettes scored by phase contrast microscopy. The experiments were carried out in both the presence and absence of 0.1% sodium azide with no detectable difference.

Isolation of cDNAs Encoding the Human CD7 Antigen

To isolate CD7 cDNAs, a large plasmid library was constructed in the expression vector $_{\pi}$3M as describe hereinabove. The library was introduced into COS cells by spheroplast fusion, and allowed to replicate and express its inserts. The COS cells were harvested by detaching without trypsin 48 to 72 hours after transfection, treated with monoclonal antibodies specific for surface antigens believed to be encoded in the library, and distributed in dishes coated with affinity purified anti-mouse antibody as described herein. Under these conditions, cells expressing surface antigen adhere and the remaining cells can be washed way.

A Hirt (Hirt, *J. Mol. Biol.* 26:365–369 (1967)) fraction was prepared from adherent cells, and the resulting DNA transformed back into *E. coli* for further rounds of fusion and selection. In the third round of selection the detached cells were treated with a mixture of monoclonal antibodies specific for CD7 (765 and Leu9), and a Hirt supernatant was again generated and transformed into *E. coli*. After transformation of the DNA into *E. coli* 8 colonies were picked, and the plasmid DNA prepared from them by an alkaline miniprep procedure (Maniatis, et al., *Molecular Cloning: A Laboratory Manual*, Cold Spring Harbor Press, Cold Spring Harbor, N.Y. (1982)). DNA was prepared from 8 resulting colonies and transfected into COS cells. After 3 days, surface expression of the CD7 antigen was detected by indirect immunofluorescence in 7 of 8 transfected dishes. Restriction enzyme digest of the corresponding plasmid DNAs revealed two species. One contained a 1.2 kb insert, and the other a 1.3 kb insert.

CD7 cDNA Sequence Analysis

Both isolates were sequenced by the dideoxynucleotide method. The 1.2 kb cDNA encodes a long open reading frame of 240 residues having the typical features of an integral membrane protein. The initial assignment of the signal sequence cleavage site by the method of von Heijne (*Nucl. Acids Res.* 14:4683–4690 (1986)) was at the 18th residue. It later was determined, however, that the homology with immunoglobulin variable regions would better predict the mature terminus at residue 26; this assignment would also correlate well with the position of the intron as discussed below and as shown in FIGS. 8A–8B. Removal of the predicted N-terminal signal sequence gives a mature protein of 215 residues with a predicted molecular mass of 23 kd. In the extracellular domain are two N-linked glycosylation sites (Asn-X-Ser Thr), in agreement with the results of Sutherland et al. (*J. Immunol.* 133:327–333 (1984)), who also showed the presence of O-linked glycans and covalently associated palmitic acid on the mature protein. In the 27 amino acid hydrophobic membrane spanning domain is a single cysteine residue which may be the site of fatty acylation (Rose et al., *Proc. Natl. Acad. Sci. USA* 81:2050–2054 (1984); Kaufman etal., *J. Biol. Chem.* 259: 7230–7238 (1984)). The length of the cytoplasmic domain, 39 residues, is in good agreement with the 30–40 amino acids predicted by protease digestion of the CD7 precursor in rough microsomal membrane fractions (Sutherland et al., *J. Immunol.* 133:327–333 (1984)).

Sequence analysis of the 1.7 kb clone (FIGS. 8A–8B) revealed the presence of an intron located 121 bp from the 5' end. The 411 bp intron contains stop codons in all three reading frames and is located just downstream of the secretory signal sequence, as is frequently obseryed for secreted or surface proteins. Both the 5' and 3' ends of the intron conform to the splice donor/acceptor consensus AAG GTRAGA/ . . . /$Y_{6-11}$NYAG A (Mount, *Nucl. Acids Res.* 10:459–472 (1982)). Because both the 1.2 and 1.7 kb clones express CD7 antigen equally well in COS cells, the intron must be excised in COS cells fairly efficiently.

Comparison of the amino acid sequence with the National Biomedical Research Foundation database revealed substantial homology with human and mouse immunoglobulin kappa chain and T-cell receptor gamma chain variable regions over almost the entire extracellular portion of the molecule. Two cysteine residues shared in approximately equal spacing by all three structures fall in the conserved sequences Ile-Thr-Cys and Tyr-X-Cys. In kappa chain variable regions these cysteines form a disulfide bridge. The presence of at least one intrastrand disulfide bond in the CD7 structure has previously been proposed by Sutherland et al. (*J. Immunol.* 133:327–333 (1984)), who noted that immunoprecipitation of CD7 gave rise to a band with an apparent molecular mass of 40 kd under reducing conditions and 38 kd under nonreducing conditions.

Based on the homology with immunoglobulin V-regions, it is predicted that CD7 contains a disulfide bond linking Cys 23 and Cys 89. A second disulfide bond, linking Cys 10 and Cys 117, has been proposed, based on the structural similarity between CD7 and Thy-1. The extracellular domains of both Thy-1 and CD7 have 4 cysteine residues, in roughly homologous positions. The 4 cysteine residues of Thy-1 are joined in two internal disulfide bridges between Cys9-111 and Cys19-85 (Williams et al., *Science* 216:696–703 (1982)). In Thy-1, Cys111 forms an amide bond with the ethanolamine moiety of a substituted phosphatidylinositol, and is thus the last residue of the mature molecule (Tse et al., *Science* 230:1003–1008 (985)). In CD7, Cys117 is followed by four repeats of a sequence whose consensus is Xaa-Pro-Pro-Xaa-Ala-Ser-Ala-Leu-Pro (SEQ ID NO:38), and which, it is proposed, plays the role of a stalk projecting the V-like domain away from the surface of the cell.

In addition to the homologies shown in FIG. 20 and mentioned above, the extracellular domain of CD7 has significant homology with both chains of the rat CD8 heterodimer (Johnson et al., *Nature* 323:74–76 (1986)), and the myelin $P_0$ protein (Lemke et al., *Cell* 40:501–508 (1985)).

CD7 Directs the Production of a 40 kd Protein in Transfected COS Cells

Immunoprecipitation of CD7 antigen from transfected COS cells was carried out as described herein using monoclonal antibody 7G5 (Lazarovits et al., *Leukocyte Typing III*, Oxford Univ. Press, publisher, Oxford, England (1987). The material obtained from COS cells migrated with as a broad band with molecular weight of 40 kd under reducing conditions. Under the same conditions HPB-ALL cells (the cDNA donor line) and activated T cells gave bands with molecular widths of 41 and 39 kd respectively. In both the COS cell and HPB-ALL lane a faint band with molecular weight of 30 kd was also observed, possibly corresponding to a partially glycosylated precursor (Sutherland, D. R., et al., *J. Immunol.* 133:327–333 (1984)).

RNA Blot Analysis

Equal amounts of total RNA prepared from cell types expressing or lacking CD7 were subjected to Northern blot analysis as described herein. A single 1.3 kb species was visible in lanes containing RNA from thymocytes, activated T cells, resting T cells, and the T cell leukemia lines HuT-78, HPB-ALL, Jurkat J3R7, HSB-2 and PEER. With the exception of the PEER cell line, none of the T cell tumors showed significant overexpression of CD7 transcripts. CD7 RNA was detected in all of the thymus-derived cells, but not in RNA from U937 (histiocytic leukemia) and Namalwa (Burkitt Lymphoma) cells. No band corresponding to the 1.7 kb cDNA could be detected, suggesting that this species is artificially enriched during the cloning or library amplification process.

Enrichment during amplification seems unlikely because the 12 kb cDNA clone propagates as well in *E. coli* as the 1.7 kb clone. However, immediately upstream and downstream from the site of insertion of the intron are sequences that could form an interrupted stem and loop structure. Eight of the 10 basepairs of the potential stem are GC pairs, perhaps giving the structure sufficient stability to interfere with elongation of the cDNA first strand. The presence of the intron greatly separates the two halves of the stem, potentially eliminating the structure via unfavorable loop entropy and allowing efficient first strand synthesis.

The CD7 Gene is not Rearranged

Southern blot analysis of genomic DNA from placenta, peripheral blood lymphocytes, T cells, HeLa cells, or the tumor lines used in the RNA blot analysis above showed identical Dra 1 digest patterns. Thus, the CD7 gene is not grossly altered during development, and the high level of expression in the PEER cell line is not the consequence of a substantial genomic rearrangement.

COS Cells Expressing CD7 do not Bind IgM

Human peripheral blood T lymphocytes express receptors for IgM antibodies (FcRu: Moretta et al., *Eur. J. Immunol.* 5:565–569 (1975); McConnell et al., *Immunol.* 30:835–837 (1976)). Recently it has been reported that CD7 might play a role in IgM binding by T cells (Sandrin et al., *Leukocyte Typing III*, Oxford Univ. Press, publisher, Oxford, England (1987)). L cells, normally $CD7^{-}$0 and $FcRu^{-}$, become $CD7^{+}$ and $FcRu^{+}$ when transfected with a 16 kb genomic fragment encoding the CD7 antigen (Sandrin et al., *Leukocyte Typing III*, Oxford Univ. Press, publisher, Oxford, England (1987)). Furthermore, IgM binding to CD7-positive cells can be blocked by the anti-CD7 monoclonal antibody Huly-m2 (Thurlow et al., *Transplantation* 38:143–147 (1984)), and IgM columns bind a 37 kd protein from radiolabeled lysates of peripheral blood T lymphocytes (Sandrin et al., *Leukocyte Typing III*, Oxford Univ. Press, publisher, Oxford, England (1987)).

Accordingly, COS cells expressing CD7 were tested for their ability to bind IgM. IgM receptor activity was assayed either by direct binding (Hardin et al., *Proc. Natl. Acad. Sci. USA* 76:912–914 (1979)) or by a rosette assay with ox erythrocytes coated with an IgM fraction of rabbit anti-bovine red cell serum as described by Ercolani et al., *J. Immunol.* 127:2044–2051 (1981)). Cells expressing CD7 neither bound human IgM nor formed rosettes with IgM-coated erythrocytes. Under the same conditions, COS cells transfected with a cDNA encoding the human IgG receptor CDw32 bound IgG directly and formed rosettes with IgG-coated erythrocytes. Erythrocytes coated with IgM or IgG antibodies also adhered to a fraction of peripheral blood lymphocytes as reported (Moretta et al., *Eur. J. Immunol.* 5:565–569 (1975)).

These results do not support the notion that the CD7 antigen is by itself an IgM receptor, although they do not exclude the possibility that COS cells suppress IgM binding activity in some manner, or that CD7 is part of, or modified to become, an IgM receptor. That CD7 is not by itself an IgM receptor is supported by the observation that a number bf $CD7^+$ T cell lines are FcRu- (Sandrin et al., *Leukocyte Typing III*, Oxford Univ. Press, publisher, Oxford, England (1987)).

EXAMPLE V

Isolation and Molecular Cloning of the Human CDw32 Antigen

A cDNA encoding the human CDw32 antigen, a human receptor for immunoglobulin G constant domains (Fc receptor), was isolated by the method of the present invention, by virtue of its affinity for its ligand, IgG. The sequence of the isolated clone is most closely related to the murine beta 2 Fc receptor, but has diverged completely in the portion encoding the cytoplasmic domain. The receptor expressed in COS cells shows a preference for $IgG_1$ among IgG subtypes, and no affinity for IgM, IgA or IgE.

To isolate the Fc receptor clone, cDNA libraries were prepared from tumor cell lines or from a human tumor and transfected into COS cells. After 48 hours, the cells were treated with mouse or human IgG antibodies, and allowed to settle on dishes coated with affinity-purified sheep anti-mouse IgG or goat anti-human IgG antibodies. After lysis, DNA recovery, and transformation in *E. coli*, the cycle was repeated for two more rounds. Although no positive clones were isolated from the tumor line libraries, a cDNA clone encoding an Fc receptor was isolated from a library prepared from a human adrenal tumor. It has been discovered that many tumors are heavily infiltrated by macrophages and lymphocytes. Thus, tumor RNA may be a productive source in general for transcripts of human macrophages.

By indirect immunofluorescence assay, the human receptor expressed on COS cells bound all mouse and human IgGs with relatively low affinity $-10^{-7}$M), and a clear discrimination was noted among human antibodies for $IgG_1$. Human IgM, $IgA_1$, $IgA_2$, and IgE did not bind, nor did murine IgM or IgA. As expected, human Fc, but not Fab fragments, bound to the transfected cells. Among monoclonal antibodies donated to the Third International Workshop on Leukocyte Differentiation Antigens, three gave strong positive immunofluorescence: two (out of two) recognizing the Fc Receptor CDw32 determinant, and one (out of four) recognizing the CD23 (B cell IgE Fc receptor) determinant. Monoclonals recognizing the T cell/Macrophage Fc receptor antigen CD16 gave only weak immunofluorescence comparable to that shown by control ascites.

Radioimmunoprecipitation of transfected COS cells with CDw32 antibodies showed the presence of a single 40 kd species, comparable in size to the antigen recognized on the surface of the myeloid $CDw32^+$ line HL-60, and to the less abundant antigen present on the histiocytic leukemia line U937. This result reinforces the notion that the isolated receptor is CDw32, as the CD16 receptor is reported to be substantially larger (60–70 kd).

The nucleotide sequence of the isolated receptor (FIGS. 9A–9B) is highly homologous to that of members of the recently isolated murine receptor family, and most closely related to the murine $beta_2$ receptor by nucleic acid homology. Surprisingly, the murine $beta_2$ receptor is found on T and B lymphocytes and macrophages, while the alpha receptor is restricted to macrophages; in the human system, CDw32 (shown here to be $beta_2$-like) is restricted to macrophages while another Fc receptor (CD16) is found on lymphocytes and macrophages. The human sequence appears to have diverged from the mouse sequence by insertion of approximately 1 kb of DNA a few bases 3' to the junction between the transmembrane and cytoplasmic domains. The junctions of the insertion site do not show obvious relationships to splice donor and acceptor sequences. Comparison of the human and murine peptide sequences showed that the peptide sequence diverges at the end of the transmembrane domain, before the nucleotide sequence diverges, suggesting the existence of a selective pressure favoring the creation of a differenct cytoplasmic domain.

RNA blot analysis showed that myeloid but not lymphocytic cell lines expressed RNA homologous to the CDw32 probe. DNA blot analysis showed multiple bands consistent with the existence of a small multigene family.

EXAMPLE VI

Isolation and Molecular Cloning of Two cDNA Clones Encoding the B Lymphocyte-Specific CD20 (B1, Bp35) Antigen Recent studies suggest that the pan B cell antigen CD20 (B1, Bp35) plays an important role in B cell activation. Monoclonal antibodies (mAb) to CD20 induce different cellular responses depending on the antibody used and the stage of differentiation or activation of the target B cells. The monoclonal antibody 1F5 activates resting B cells by initiating the transition from the $G_0$ to the $G_1$ phase of the cell cycle, and induces dense tonsillar B cells to proliferate (Clark et al., *Proc. Natl. Acad. Sci USA* 82:1766 (1985); Clark and Shu, *J. Immunol.* 138:720 (1987)). However, 1F5 does not induce an increase in cytoplasmic free calcium and does not induce circulating B cells to proliferate (Rabinovitch et al, In: *Leukocyte Typing III* (McMichael, Ed.), p. 435, Oxford University Press (1987)). Other anti-CD20 mAbs, such as B1, have been shown to block B cell activation (Tedder et al., *J. Immunol.* 135:973 (1985)) and both 1F5 and B1 can inhibit B cell differentiation (Golay et al., *J. Immunol.* 135:3795 (1985)). Recently it has been suggested that phosphorylation and internalization of CD20 may be necessary steps for B cell entry into the $G_1$ phase of the cell cycle (Valentine et al., In: *Leukocyte Typing III* (McMichael, Ed.), p. 440, Oxford University Press (1987)). In the present example, two CD20 cDNA clones were isolated and expressed using the methods of the present invention.

Preparation of cDNA Library and Recovery of cDNA Clones by Panning

Poly $(A)^+$ RNA was prepared from the human Burkitt cell line Daudi by oligo (dT) cellulose chromatography of total RNA isolated by procedures described herein. cDNA preparation and expression library construction were carried out as described.

Anti CD20 mAbs 1F5, 2H7, B1, L27, G28-2, 93-1B3, B-C1, and NU-B2 were obtained from the International Leukocyte Typing Workshop (Valentine et al., In: *Leukocyte Typing III* (McMichael, Ed.), p. 440, Oxford University Press (1987)). Purified mAbs were used at a concentration of 1 μg/ml and ascites were used at a dilution of 1:1000. Panning was done according to the present method. In the first round of screening, eight 10 cm dishes of 50% confluent COS cells were transfected by the DEAE-Dextran method. Subsequent screening cycles were performed by spheroplast fusion.

Immunoprecipitation, Sequencing, RNA and DNA Blot Hybridization

B cell lines CESS and Daudi were metabolically labeled with $^{35}$S-methionine and $^{35}$S-cysteine for 6 h at 37° C. COS cells transfected by the DEAE-Dextran method were similarly labeled 36 hours post-transfection. The labeled cells were incubated with the B1 mAb (Coulter) at 4° C. for 1 h, washed in PBS, and lysed with 0.5% NP-40, 0.1% SDS, 0.05% deoxycholate and 1 mM PMSF in PBS. After centrifuging (13000×g, 5 min.), the lysate was incubated with fixed *S. aureus* cells (Calbiochem) for 1 hr at 4° C. The *S. aureus* cells were pelleted, washed 5 times with 1% NP-40/PBs, eluted and electrophoresed through 12.5% polyacrylamide gels.

DNA and RNA blot analysis and hybridization probe preparation were carried out as described. Sequencing was done by the method of Sanger et al., *Proc. Natl. Acad. Sci. USA* 74:5463 (1977)). The nucleotide sequence of the CD20.4 cDNA is represented in FIGS. 10A–10B.

Two cDNA clones, bearing inserts of 1.5 (CD20.4) and 1.0 kb (CD20.6), were isolated from a Daudi cell DNA library by panning with a panel of mAbs against CD20. COS cells transfected with either clone reacted with all members of the panel of antibodies. Immunoprecipitation of the cDNA-encloded protein from transfected COS cells showed two bands of 32 and 30 kd reminiscent of the 37 and 35 kd bands observed in different B cell subsets and lines (Valentine et al., "Structure and Function of the B Cell Specific 35–37 kDa CD20 Protein," In: *Leukocyte Typing III*, A. McMichael et al., eds., Oxford University Press, p. 440 (1987)). It has been the experience of the present inventors that the molecular masses of surface antigens expressed in COS cells are consistently smaller than those of their native counterparts. This may be due to differences in glycosylation.

Both cDNA clones have the same coding sequence, and differ only in the 3' untranslated region. The insert in clone CD20.6 has a short polyA tail and lacks a consensus polyadenylation signal, while the insert in CD20.4 lacks a polyA tail and extends 431 bp beyond the 3' terminus in CD20.6 (FIG. 10A).

RNA blot analysis showed that three transcripts of 3.8, 3.0 and 1.5 kb were present in B cells but absent from other cell types, in agreement with the known pattern of antibody reactivity (Clark et al., *Proc. Natl. Acad. Sci. USA* 82:1766 (1985); Clark et al, *J. Immunol.* 138:720 (1987); Tedder et al., *J. Immunol.* 135:973 (1985); Golay et al., *J. Immunol.* 135:3795 (1985)). It appears likely that the CD20.6 clone is derived from the 1.5 kb transcript or possibly from an even shorter, undetectable species. Because the CD20.4 clone lacks a poly(A)$^+$ tail, its source cannot be inferred at present.

DNA blot analysis showed that the CD20 genomic sequences are not rearranged during development and are not amplified in the cell lines examined. A restriction fragment length polymorphism was observed in a DNA sample obtained from placenta.

The amino acid sequence predicted by the cDNA contains 297 residues and has a molecular mass of 33,097 daltons. The sequence contains three major hydrophobic stretches involving residues 51–103, 117–141 and 183–203 (FIGS. 10A–10B). Two other notable characteristics are the absence of an amino-terminal signal peptide and the presence of a highly charged carboxy-terminal domain. A polyclonal anti-CD20 antibody that recognized the last 18 residues of the carboxy-terminus reacts with lysates of cells expressing CD20 but not with intact cells, suggesting that the CD20 carboxy terminus is located within the cytoplasm. Since there is no amino-terminal signal peptide, it is likely that the amino-terminus is also intracellular, and that the first hydrophobic region acts as an internal membrane insertion signal (Zerial et al., *EMBO J.* 5:1543 (1986)). The first hydrophobic region is composed of 53 residues and is therefore long enough to span the membrane twice if organized as an alpha helix. Because there are two remaining hydrophobic regions, the intracellular localization of the carboxy-terminus requires that the first hydrophobic domain exit the membrane on the side. Alternatively, the carboxy-terminal antibody may only recognize epitopes exposed by detergent treatment allowing the carboxy-terminus to be extracellular and forcing the first hydrophobic domain to exit the membrane on the extracellular side. The sequence contains 2 potential N-glycosylation sites (Asn-Xaa-Ser/Thr, where Xaa cannot be Pro (Bause, *Biochem. J.* 209:331 (1983)) at positions 9 and 293, but neither of these is expected to be used if located in intracellular domains of the molecule. The difference in molecular mass between CD20 expressed on COS cells and on B cells is therefore presumably due to 0-linked glycosylation, although other forms of post-translational modification are not excluded. If the carboxy-terminus is intracellular, the only extracellular domain would lie between residues 142 and 182. This region is rich in serine and threonine residues which might support 0-glycosylation.

The observation of two protein species in COS cells cannot be explained by alternate splice formation because the cDNA sequence does not contain any promising splice donor or acceptor sequences (Shapiro et al., *Nucl. Acids Res.* 15:7155 (1987)). A difference in glycosylation or alternate translational initiation site selection may account for the two species observed. Initiation at either the first or the second ATG gives protein molecular masses of 33.1 and 30.8 kd respectively, in good agreement with the sizes observed in COS cells. Neither ATG is embedded in the consensus sequence proposed by Kozak (*Nucl. Acids Res.* 12:857 (1984)). Use of alternate initiation sites has been reported for several proteins (Kozak, *Nucl. Acids Res.* 12:857 (1984)).

Comparison of the peptide sequence with the sequences in the National Biomedical Research Foundation database showed no significant homology by the FASTP rapid sequence alignment algorithm. Because the bulk of the protein appears to be confined to the interior of the membrane and the cell, it seems plausible that it may play a role in transducing signals from other transmembrane proteins to the cell interior. Consistent with this role is the relatively hydrophilic nature of the hydrophobic regions which might allow hydrogen bond interactions with the transmembrane portions of other proteins.

EXAMPLE VII

Isolation and Molecular Cloning of ICAM, An Adhesion Ligand of LFA-1

Antigen-specific cell contacts in the immune system are strengthened by antigen-non-specific interactions mediated in part by lymphocyte function associated or LFA antigens (Springer, T. A., et al., *Annu. Rev. Immunol.* 5:223–252 (1987); Anderson, D. C., et al., *Annu. Rev. Medicine* 5:175–194 (1987)). The LFA-1 antigen, a major receptor of T cells, B cells and granulocytes (Rothlein, R., et al., *Exp. Med.* 163:1132–1149 (1987)), is involved in cytolytic conjugate formation, antibody-dependent killing by NK cells and granulocytes, and helper T cell interactions. LFA-1 has been placed in the integrin family of cell surface receptors by virtue of the high sequence similarity between the LFA-1 and integrin beta chains (Kishimoto, T. K., et al., *Cell* 48:681–690 (1987); Hynes, R. O. *Cell* 48:549–554 (1987)). The adhesion ligands of the integrin family are glycoproteins bearing the Arg-Gly-Asp (RGD) sequence motif, e.g., fibronectin, fibrinogen, vitronectin and von Willebrand factor (Ruoslahti, E., et al., *Cell* 44:517–518 (1987)).

In this example, the Intercellular Adhesion Molecule-1 (ICAM-1), a ligand for LFA-1 (Rothlein, R., et al., *J. Immunol.* 137:1270–1275 (1986); Dustin, M. L., et al., *J. Immunol.* 137:245–254 (1986)), was cloned according to the methods of the present invention. ICAM contains no RGD motifs, and instead is homologous to the neural cell adhesion molecule NCAM (Cunningham, B. A., et al. *Science* 236: 799–806 (1987); Barthels, D., et al., *EMBO J.* 6:907–914 (1987)). COS cells transfected with the ICAM cDNA clone bind myeloid cells by a specific interaction which can be blocked by monoclonal antibodies directed against either LFA-1 or ICAM-1.

A cDNA library was constructed using RNA prepared from HL60 cells induced with phorbol myristyl acetate (PMA). The library was transfected into COS cells and cells expressing surface antigens were recovered according to the methods of the present invention by panning with the anti-ICAM monoclonal antibodies (mAbs) 8F5 and 84H10 (McMichael, A. J., et al., eds., *Leukocyte Typing III. White Cell Differentiation Antigens*, Oxford University Press (1987)). Episomal DNA was recovered from the panned cells and the expression-panning cycle repeated a further 2 times to obtain a cDNA clone designated pICAM-1.

COS cells transfected with pICAM-1 gave positive surface immunofluorescence reactions with three anti-ICAM-1 antibodies: 8F5; 84H10; and RR-1. Immunoprecipitation of pICAM-1-transfected COS cells with the mAb 84H10 gave a band of molecular mass 100 kd. 30). A slightly larger protein of 110 kd was precipitated from HL60 cells induced for 48 hours with either phorbol myristyl acetate (PMA), gamma-interferon (gammaIFN), tumour necrosis factor (TNF), or interleukin-1 beta (IL-1 beta), but was absent from uninduced cells. The smaller molecular mass of ICAM-1 expressed in COS cells is consistent with the lower molecular masses observed for other surface antigens expressed in COS cells.

RNA blot analysis showed 2 species of 3.2 kb and 1.9 kb present in HL60 cells stimulated with either PMA, gamma IFN, TNF or IL-1 gamma, but absent in uninduced cells. Thus, the expression of ICAM-1 is regulated by a number of cytokines, apparently at the level of transcription. Similar species were present in B cells (JY and Raji), T cells (Peer and T blasts) and Lymphokine Activated Killer cells (LAK). The structure of these ICAM-1 transcripts and their relationship to the pICAM-1 cDNA remains to be established. Blot hybridization of genomic DNA from placenta revealed a pattern consistent with a single copy gene.

To investigate whether pICAM-1 encodes a functional cell adhesion molecule, COS cells expressing ICAM-1 were tested for their ability to bind HL60 cells. After 30 minutes at 37° C. in the presence of $Mg^{2+}$, HL60 cells strongly adhered to the ICAM-expressing COS cells, but not to mock transfected cells. The specificity of this adhesion was demonstrated by preincubating the ICAM-1 expressing COS cells with mAb 84H10. All HL60 binding was abolished under these conditions. An isotype matched monoclonal antibody, W6/32, which recognizes a monomorphic HLA-ABC related determinant of approximately equal abundance to ICAM-1 on transfected COS cells, had no effect on the adhesion. Similarly, preincubation of the HL60 cells with either 84H10 or W6/32 did not inhibit binding.

To determine if LFA-1 was acting as the receptor for ICAM-1 in this system, HL60 cells were pretreated with antibodies against the beta chain of LFA-1 (CD18 (McMichael, A. J., et al., eds., *Leukocyte Typing III. White Cell Differentiation Antigens*, Oxford University Press (1987))) and then subjected to the binding assay. All adhesion to ICAM-expressing COS cells was blocked. Pretreatment of COS cells with the CD18 antibodies had no effect on the adhesion. This provides direct evidence that ICAM-1 is indeed acting as an adhesion ligand for LFA-1.

The sequence of the pICAM-1 cDNA insert consists of 1846 nucleotides (FIGS. 11A–11C). The predicted peptide sequence of 532 residues has the typical features of a transmembrane protein including a putative signal sequence, which may be cleaved between glycine-25 and asparagine-26 (von Heijne, G., *Nucl. Acids Res.* 14:4683–4690 (1986)), and a single 25 residue membrane-spanning domain terminating in a short, highly charged cytoplasmic domain. The extracellular domain contains seven potential N-linked glycosylation sites which could adequately explain the difference in size between the deglycosylated precursor (55 kd) and the final product (90–115 kd) (Dustin, M. L., et al., *J. Immunol.* 137:245–254 (1986)). Differential use of these putative glycosylation sites could also explain the heterogeneous molecular mass of ICAM-1 observed in different cell types (Dustin, M. L., et al *J. Immunol.* 137:245–254 (1986)).

LFA-1 is a member of the integrin family of cell surface receptors (Kishimoto, T. K., et al., *Cell* 48:681–690 (1987); Hynes, R. O., *Cell* 48:549–554 (1987)). The tripeptide motif Arg-Gly-Asp (RGD) is a common feature of the ligands for this family, e.g., fibronectin, fibrinogen, vitronectin and von Willebrand factor, and is crucial for ligand-receptor interaction (Ruoslahti, E, et al., *Cell* 44:517–518 (1987)). However, ICAM-1 contains no RGD motifs, bearing instead a single RGE sequence at position 152. A search of the National Biomedical Research Foundation (Dayhoff, M. O., et al., *Methods Enzymol.* 91:524–545 (1983)) (NBRF) database revealed no significant similarities to other proteins. However, a comparison to a laboratory database containing recently published surface proteins did reveal a surprising and significant similarity between ICAM-1 and the neural cell adhesion molecule NCAM-1 (Cunningham, B. A., et al., *Science* 236:799–806 (1987); Barthels, D., et al., *EMBO J.* 6:907–914 (1987)). The optimal alignment score obtained using the NBRF ALIGN program is 8 standard deviations above the mean score obtained from 500 random permutations of the sequences. The probability of the spontaneous occurrence of an equal or higher score is approximately $10^{-9}$.

Using a database of known immunoglobulin related sequences, it has been shown that ICAM-1 may be divided into five Ig domains (28–112, 115–206, 217–310, 312–391, and 399–477) each of which shows significant similarity with other members of the Ig superfamily (Williams, A. F., *Immunol. Today* 8:298-3-3 (1987)). For example, domain I is similar to CD3 while domains IV and V are similar to domains of myelin associated glycoprotein (Arguint, M., et al., *Proc. Natl. Acad. Sci. USA* 84:600–604 (1987)) and carcinoembryonic antigen (Beauchemin, N., et al., *Mol. Cell. Biol.* 7:3221–3230 (1987)). All five Ig domains of NCAM align with the Ig segments in ICAM, and the principal contribution to the similarity comes from domains II and III of ICAM. Finally, the T cell-specific adhesion molecule CD2 shows roughly the same similarity to NCAM as does ICAM, but ICAM and CD2 are only weakly related. Thus, some precursor of NCAM is ancestral to both ICAM and CD2.

Through its cell adhesion to LFA-1, ICAM can mediate migration of lymphocytes into areas of inflammation. Inhibiting such migration by blocking ICAM binding to LFA-1 could reduce or inhibit inflammation. Such inhibition could be affected by small organic molecules, i.e., drugs, identified in an ICAM streaming assay. Fusion proteins composed of the extracellular domain of ICAM and IgG molecules are suitable for identifying such inhibitors. Likewise, compounds that interfere with ICAM binding to Rhinovirus or *Plasmodium falciparium* can be identified by analogous methods.

The Applicants have constructed fusion proteins consisting of the Ig domains of the ICAM-1 extracellular domain, which are useful in streaming assays. The CH2 and CH3 domains of IgG1 were fused to extracellular Ig domain 1, domains 1 and 2, domains 1–3, domains 1–4, and domains 1–5 of ICAM-1. The corresponding clones have been designated ICAM1-Eγ1, ICAM1-Eγ2, ICAM1-Eγ3, ICAM1-Eγ4 and ICAM1-Eγ5. The first two N-terminal domains (amino acids 28–112 and 115–206, respectively) are believed to be most useful in a binding assay to identify compounds that inhibit ICAM binding to another ligand.

Soluble ICAM can also be used directly to interfere with the binding of cellular ICAM to Rhinovirus or Plasmodium, thereby inhibiting the infection. Soluble ICAM includes the extracellular domain of ICAM, or functional derivatives thereof, in truncated form or fused to a soluble protein such as Ig.

For the purpose of the invention as it relates to ICAM-1 protein, the term “functional derivatives” includes polypeptides that have at least about 80% amino acid identity to the entire disclosed ICAM-1 amino acid sequence, its intracellular domain, its extracellular domain (amino acids 1–477) or any of immunoglobulin domains 1–5 therein, or the sequence comprising the LFA-1 binding site, and that have a binding affinity to a ligand of ICAM-1 such as LFA-1 that is at least about 30% as that of the disclosed sequence. Such polypeptides may optionally be included as part of a larger protein. Increasingly preferred are amino acid identities that increase integrally, i.e., at least about 81%, 82%, 83%, etc. Binding affinity of ICAM-1 to a ligand such as LFA-1 can be determined by methods known in the art. Increasingly preferred are binding affinities that increase in increments of 10%, i.e., at least about 40%, 50%, etc., of that of the disclosed sequence.

A nucleotide sequence is a “functional derivative” of ICAM-1 if it encodes the diclosed ICAM-1 amino acid sequence or a functional derivative thereof.

In designing functional derivatives of ICAM-1 protein, amino acids or regions known to be important to the binding of ICAM-1 to a ligand such as LFA-1 should be highly conserved. Publications relating to binding of ICAM-1 to LFA-1 include:

Hedman, H. & Ludman, E. (1991) J. Immunol. 149:2295–9; Dang, L & Rock, K. (1991) J. Immunol. 146:3273–9; Ross, L et al. (1992) J. Biol. Chem. 267:8537–43; Hibbs, M. et al. (1991) Science 251:1611–3; Berendt, A. et al. (1992) Cell 68:71–81; Ockenhouse, C. et al. (1992) Cell 68:63–9; Diamond, M. et al. (1991) Cell 65:961–71; Cabanas, C. & Hogg, N. (1991) FEBS Lett 292:284–8; and Staunton, D. et al. (1990) Cell 61:243–54 (errata at Cell (1990) 61:1157 and Cell (1991) 667:1312).

Additional publications relating to function of ICAM-1 include: Salkind, A. et al. (1991) J. Clin. Invest. 88:505–11; Fischer, H. et al. (1992) J. Immunol. 148:1993–8; Carlow, D. et al. (1992) J. Immunol. 148:1595–606; Rothlein, R. et al. (1991) J. Immunol. 147:3788; Fine, J. & Kruisbeek, A. (1991) J. Immunol. 147:2852–9; Tang, A. & Udey M. (1991) J. Immunol. 146:3347–55; Symington, F. & Santos, E. (1991) J. Immunol. 146:2169–75; Rosenstein, Y. et al. (1991) Nature 354:233–5; Fujiota, H. et al. (1991) Biochem. Biophys. Res. Commun. 177:664–72; Nambu, M. et al. (1992) Cell Immunol. 143:335–47; Sanders, V. & Vitetta, E. (1991) Cell Immunol. 132:45–55; Diamond, M. et al. (1990) J. Cell Biol. 111:3129–39; Maraskovsky, E. et al. (1992) Int. Immunol. 4:475–85; Padros, M. et al. (1992) Clin. Exp. Immunol. 88:329–34; and Van Seventer, G. et al. (1991) Eur. J. Immunol. 21:1711–18.

In particular, Piela-Smith, T. et al. (1992) J. Immunol. 148:1375–81; Staunton, D. et al. (1990) Cell 61:243–54 (errata at Cell (1990) 61:1157 and Cell (1991) 667:1312); Staunton, D. et al. (1989) Cell 56:849–53; Greve, J. et al. (1989) Cell 56:839–47; Staunton, D. et al. (1992) J. Immunol. 148:3271–4; Register, R. et al. (1991) J. Virol. 65:6589–96; Greve, J. et al. (1991) J. Virol. 65:6015–23; and Lineberger, D. et al. (1992) Virus Res. 24:173–186, discuss binding of ICAM-1 to rhinovirus. Oppenheimer-Marks, N. et al. (1991) J. Immunol. 147:2913–21; and Perry, M. et al. (1992) Cell Tissue Res. 268:317–26; describe the role of ICAM-1 in transendothelial migration, and Dustin, M. et al. (1992) J. Immunol. 148:2654–63, describe B cell migration on ICAM-1 coated substrates. Webb, D. et al. (1991) J. Immunol. 146:3682–6, describe the role of ICAM-1 in monocyte invasion of tumors. Berendt, A. et al. (1992) Cell 68:71–81; Ockenhouse, C. et al. (1992) Cell 68:63–9; and Ockenhouse, C. et al. (1991) J. Infect. Dis. 164:163–169, discuss ICAM-1 in its role as a receptor for *Plasmodium falciparum*. Gruber, M. et al. (1991) AIDS Res. Hum. Retroviruses 7:45–53, discuss the role of ICAM-1 in HIV syncytia formation. Dohlsten, M. et al. (1991) Eur. J. Immunol. 21:131–5, discuss the role of ICAM-1 in staphylococcal enterotoxin-mediated cytotoxicity.

EXAMPLE VIII

Isolation and Molecular Cloning of the Human CD19, CD20, CDw32a, CDw32b and CD40 Antigens The rapid immunoselection cloning method of the present invention was applied to isolate and clone the CD19, CD20, CDw32a, CDw32b, and CD40 antigens. The nucleotide sequence of CD19 is shown in FIGS. 12A–12B. The nucleotide sequence of CD20 is shown in FIGS. 13A–13B. The nucleotide sequence of CDw32a is shown in FIGS. 14A–14B. The nucleotide sequence of CDw32b is shown in FIGS. 15A–15B. The nucleotide sequence of CD40 is shown in FIG. 16.

EXAMPLE IX

Cloning, Sequence and Expression of CD36

To isolate a cDNA clone encoding CD36, a human placenta cDNA (Simmons and Seed (1988) Nature 333: 568–570) was transferred into COS cells using DEAE-Dextran as a facilitator (Example I, supra). 48 hours post-transfection the cells were detached from the dishes without trypsin, incubated with monoclonal anti-CD36 antibodies 5F1 (Bernstein et al. (1982) *J. Immunol.* 128:876–881) (Andrews et al. (1984) *J. Immunol.* 128:398–404) and panned on dishes coated with goat anti-mouse immunoglobulin antibodies. Nonadherent cells were removed by gentle washing, the adherent cells were lysed, and episomal plasmids recovered from the cells were purified and transformed into *E. coli*. After two similar rounds of enrichment following spheroplast fusion, plasmid DNAs recovered from 11 out of 12 randomly chosen colonies were found to direct the appearance of CD36 determinants in transfected COS cells.

Two of the clones were chosen at random for further analysis. Both bore inserts of about 1.9 kb, and showed identical restriction enzyme fragment patterns. COS cells transfected with either of these clones reacted with monoclonal antibodies 5F1 and F13, and with OKM5 (Ortho, Raritan, N.J.). Immunoprecipitation of transfected cells with a pool of anti-CD36 antibodies revealed the presence of an 83 kd molecule present on transfected COS cells and C32 melanoma cells, and absent from control (CD25-transfected) COS cells. A high molecular weight species, possibly dimeric CD36, was immunoprecipitated from the transfected COS cell lysate, but not from the C32 cell lysate. The nucleotide sequence is given in Table 1. In Table 1, the nucleotide sequence numbering is shown in the left margin at the beginning of each line. The deduced amino acid sequence is shown as single letter code underneath the beginning of each coding nucleotide triplet, with the initiation methionine indicated by the number 1 above the initiator codon. The potential sites of N-linked glycosylaton in the derived amino acid sequence are underlined by a single dashed line. The putative transmembrane domain is double-underlined. Although two consensus polyadenylation (AATAAA) motifs are found in the cDNA, there is no poly(A) tail, and none of the RNA species observed by blot hybridization are short enough to correspond to polyadenylation at these sites, assuming that the transcripts bear the same approximate 5' end as observed in the clone. The presumed initiation codon is not the first ATG found in the clone, but the previous two are closely followed by in-frame termination codons. The predicted initiator methionine is followed by a short hydrophobic region resembling a secretory signal sequence for which, however, no clear identification of the cleavage site can be made. The recent determination of Table 1 the amino terminal 36 amino acid sequence (Tandon et al. *J. Biol. Chem.* 264:7570–7575 (1989)) indicates that the mature polypeptide begins at the amino acid residue immediately following the initiator methionine. It is not clear whether the single Arg residue preceding the hydrophobic region would be sufficient to allow amino terminal membrane anchoring. The resulting polypeptide possesses 471 residues with a predicted molecular weight of about 53 kd. The proposed extracellular domain is followed by 27 predominantly hydrophobic residues corresponding to a transmembrane domain, and 6 residues (of which 3 are basic) corresponding to an attenuated intracellular domain. The presence of 10 potential N-linked glycosylation sites appears sufficient to account for the discrepancy in molecular mass between the predicted polypeptide and the 83 kd species found by immunoprecipitation. No significant homology was detected following comparison of the entire sequence to various databases of known proteins. However some internal structure was apparent. All of the cysteine residues in the extracellular domain are confined to a domain defined by residues 937 to 1209 of the nucleotide sequence. Taking the cysteine placement as a guide, the extracellular domain could be divided into three segments, in which two domains without cysteine preceded and followed the cysteine rich segment. However sequence comparisons with these segments did not show any significant relatedness to other molecules in existing databases, nor, in particular, to thrombospondin.

The CD36 protein was purified by immunoprecipitation. Since the rapid immunoselection cloning method depended upon expression of transfected COS cells, it follows that the same cell lines from which CD36 cDNA was cloned could also be used as a source of the expressed protein.

C32 melanoma cells, CD36 transfected cells COS cells, and CD25 (control) transfected COS cells were surface labelled with $Na^{125}I$ and lysed in a phosphate buffered saline solution containing 1 mM phenylmethylsulfonyl fluoride, 0.50%. NP-40 and 0.1% sodium dodecyl sulfate. Anti-CD36 monoclonal antibodies were added, and allowed to absorb to the lysate for 12 hours at 4° C., after which goat anti-mouse Immunoglobulin beads (Cappel)

TABLE 1

(SEQ ID NO:20) and (SEQ ID NO:21)

```
               *         *         *         *         *         *         *         *         *
  1   GAAAAATCCTTCTTAGCCATTTTAAAGATAGCTTTCCAATGATTAGACGAATTGATTCTTTCTGTGACTCATCAGTTCCTTTCCTGTAAAATTCAT
                                                                                     *         *
                                                                                  GTCTTGCTGTTGATTTGTGAATAA

               *         *         *         *         *         *         *         *         *1
121   GAACCAGAGCTTGTAGAAACCACTTTAATCATATCCAGGAGTTTGCAAGAAACAGGTGCTTAACACTAATTCACCTCCTGAACAAGAAAAATGGGC
                                                                                                 M  G
                                                                                     *         *         *
                                                                                  TGTGACCGGAACTGTGGGCTCATC
                                                                                  C  D  R  N  C  G  L  I

               *         *         *         *         *         *         *         *         *
241   GCTGGGGCTGTCATTGGTGCTGTCCTGGCTGTGTTTGGAGGTATTCTAATGCCAGTTGGAGACCTGCTTATCCAGAAGACAATTAAAAAGCAAGTT
```

TABLE 1-continued (SEQ ID NO:20) and (SEQ ID NO:21)

```
      A  G  A  V  I  G  A  V  L  A  V  F  G  G  I  L  W  P  V  G  D  L  L  I  Q  K  T  I  K  K  Q  V
                                                                                       *         *         *
                                                                                    GTCCTCGAAGAAGGTACAATTGCT
                                                                                    V  L  E  E  G  T  I  A

               *         *         *         *         *         *         *         *         *
  381 TTTAAAAATTGGGTTAAAACAGGCACAGAAGTTTACAGACAGTTTTGGATCTTTGATGTGCAAAATCCACAGGAAGTGATGATGAACAGCAGCAAC
      F  K  N  W  V  K  T  G  T  E  V  Y  R  Q  F  W  I  F  D  V  Q  N  P  Q  E  V  M  M  N  S  S  N
                                                                                       *         *         *
                                                                                    ATTCAAGTTAAGCAAAGAGGTCCT
                                                                                    I  Q  V  K  Q  R  G  P

               *         *         *         *         *         *         *         *   -------
  481 TATACGTACAGAGTTCGTTTTCTAGCCAAGGAAAATGTAACCCAGGACGCTGAGGACAACACAGTCTCTTTCCTGCAGCCCAATGGTGCCATCTTC
      Y  T  Y  R  V  R  F  L  A  K  E  N  V  T  Q  D  A  E  D  N  T  V  S  F  L  Q  P  N  G  A  I  F
                                                                                       *         *         *
                                                                                    GAACCTTCACTATCAGTTGGAACA
                                                                                    E  P  S  L  S  V  G  T

               *         *         *   -------         *         *         *         *         *
  801 GAGGCTGACAACTTCACAGTTCTCAATCTGGCTGTGGCAGCTGCATCCCATATCTATCAAAATCAATTTGTTCAAATGATCCTCAATTCACTTATT
      E  A  D  N  F  T  V  L  N  L  A  V  A  A  A  S  H  I  Y  Q  N  Q  F  V  Q  M  I  L  N  S  L  I
                                                                                       *         *         *
                                                                                    AACAAGTCAAAATCTTCTATGTTC
                                                                                    N  K  S  K  S  S  M  F

               -------   *         *         *         *         *         *         *         *
  721 CAAGTCAGAACTTTGAGAGAACTGTTATGGGGCTATAGGGATCCATTTTTGAGTTTGGTTCCGTACCCTGTTACTACCACAGTTGGTCTGTTTTAT
      Q  V  R  T  L  R  E  L  L  W  G  Y  R  D  P  F  L  S  L  V  P  Y  P  V  T  T  T  V  G  L  F  Y
                                                                                    -------      *         *
                                                                                    CCTTACAACAATACTGCAGATGGA
                                                                                    P  Y  N  N  T  A  D  G

               *         *         *         *         *         *         *         *         *
  841 GTTTATAAAGTTTTCAATGGAAAAGATAACATAAGTAAAGTTGCCATAATCGACACATATAAAGGTAAAAGGAATCTGTCCTATTGGGAAAGTCAC
      V  Y  K  V  F  N  G  K  D  N  I  S  K  V  A  I  I  D  T  Y  K  G  K  R  N  L  S  Y  W  E  S  H
                                                                                       *  -------*         *
                                                                                    TGCGACATGATTAATGGTACAGAT
                                                                                    C  D  W  I  N  G  T  D

               *         *     -------     *         *         *         *  -------*         *
  981 GCAGCCTCATTTCCACCTTTTGTTGAGAAAAGCCAGGTATTGCAGTTCTTTTCTTCTGATATTTGCAGGTCAATCTATGCTGTATTTGAATCCGAC
      A  A  S  F  P  P  F  V  E  K  S  Q  V  L  Q  F  F  S  S  D  I  C  R  S  I  Y  A  V  F  E  S  D
                                                                                       *        -------    *
                                                                                    GTTAATCTGAAAGGAATCCCTGTG
                                                                                    V  N  L  K  G  I  P  V

               *         *         *         *         *         *         *         *         *
 1081 TATAGATTTGTTCTTCCATCCAAGGCCTTTGCCTCTCCAGTTGAAAACCCAGACAACTATTGTTTCTGCACAGAAAAAATTATCTCAAAAAATTGT
      Y  R  F  V  L  P  S  K  A  F  A  S  P  V  E  N  P  D  N  Y  C  F  C  T  E  K  I  I  S  K  N  C
                                                                                       *         *         *
                                                                                    ACATCATATGGTGTGCTAGACATC
                                                                                    T  S  Y  G  V  L  D  I

               *         *         *         *         *         *         *         *         *------
 1201 AGCAAATGCAAAGAAGGGAGACCTGTGTACATTTCACTTCCTCATTTTCTGTATGCAAGTCCTGATGTTTCAGAACCTATTGATGGATTAAACCCA
      S  K  C  K  E  G  R  P  V  Y  I  S  L  P  H  F  L  Y  A  S  P  D  V  S  E  P  I  D  G  L  N  P
                                                                                    -  *         *         *
                                                                                    AATGAAGAAGAACATAGGACATAC
                                                                                    N  E  E  E  H  R  T  Y

               *         *         *         *         *         *         *         *         *
 1321 TTGGATATTGAACCTATAACTGGATTCACTTTACAATTTGCAAAACGGCTGCAGGTCAACCTATTGGTCAAGCCATCAGAAAAAATTCAAGTATTA
      L  D  I  E  P  I  T  G  F  T  L  Q  F  A  K  R  L  Q  V  N  L  L  V  K  P  S  E  K  I  Q  V  L
                                                                                       *         *         *
                                                                                    AAGAATCTGAAGAGGAACTATATT
                                                                                    K  N  L  K  R  N  Y  I

               *         *         *         *         *         *         *         *         *
 1461 GTGCCTATTCTTTGGCTTAATGAGACTGGGACCATTGGTGATGAGAAGGCAAACATGTTCAGAAGTCAAGTAACTGGAAAAATAAACCTCCTTGGC
      Y  P  I  L  W  L  N  E  T  G  T  I  G  D  E  K  A  N  M  F  R  S  Q  V  T  G  K  I  N  L  L  G
                                                                                       *         *         *
                                                                                    CTGATAGAAATGATCTTACTCAGT
                                                                                    L  I  E  M  I  L  L  S

               *     -------   *         *         *         *         *         *     _________
 1671 GTTGGTGTGGTGATGTTTGTTGCTTTTATGATTTCATATTGTGCATGCAGATCGAAAACAATAAAATAAGTATGTACCAAAAAATATTGCTTCAAT
```

TABLE 1-continued (SEQ ID NO:20) and (SEQ ID NO:21)

```
      Y  G  V  V  M  F  V  A  F  M  I  S  Y  C  A  C  R  S  K  T  I  K  ↑
                                                                             ___________________________
                                                                             AATATTAGCTTATATATTACTTGT

      ==============================================  *          *         *          *          *
1891  TTTCACTTTATCAAAGAGAAGTTACATATTAGGCCATATATATTTCTAGACATGTCTAGCCACTGATCATTTTTAAATATAGGTAAATAAACCTAT
                                                                                *          *          *
                                                                             AAATATTATCACGCAGATCACTAA

                *          *          *          *          *          *          *
1811   AGTATATCTTTAATTCTGGGAGAAATGAGATAAAAGATGTACTTGTGACCATTGTAACAATAGCACAAAT
```

were added, mixed for two hours, and washed as described (Clark and Einfeld *J. Immunol.* 135:155–167 (1986)). Larger amounts of protein can also be obtained in purified form from a transfected COS cell lysate by an immunoaffinity column purification. Other antibodies to CD36 may be obtained, using CD36 protein, expressed and/or purified as described, as immunogen.

CD36 has been identified as a binding site for cytoadherence of *Plasmodum falciparum* parasitized erythrocytes, by the inventors herein and by Ockenhouse, C. D. et al. (1989) Science 243:1469–1741. Cytoadhesion of parasitized erythrocytes has been shown to be blocked by monoclonal antibodies to CD36. Incubation of infected erythrocytes with COS cells transfected with a CD36 cDNA showed pronounced cytoadherence. The ability of *P. falciparum* parasitized erythrocytes to evade splenic clearance by adherence to peripheral vascular beds is thought to play an important role in the pathogenicity of *Falciparum* malaria and to contribute to the lethal syndrome of cerebral malaria by causing occlusion of the small vessels of the brain. Therefore the cDNA and purified protein of the present invention are useful for providing sufficient purified CD36 to make therapeutic monoclonal antibodies.

EXAMPLE X

Isolation and Cloning of Three cDNA Clones Encoding Macrophage-Specific FcRI Three independent cDNA clones (designated p135, p90 and p98/X2) encoding human FcRI were isolated by the rapid immunoselection cloning method of the present invention from a cDNA library expressed in COS cells. (See also Allen, J. M. and Seed B., *Science* 243:378–381 (1989)). The cDNA library was constructed from polyadenylated RNA obtained from cells of a single patient undergoing extracorporeal interleukin-2 induction therapy. Expression of the three cDNAs in COS cells gave rise to IgG binding of the appropriate affinity and subtype specificity. DNA sequence analysis revealed that the cDNAs encode similar type I integral membrane proteins with 3 extracellular immunoglobulin domains. The intracellular domain of p98/X2 diverges from that of the other two cDNAs. A composite sequence of the three cDNAs is shown in Table 2 with the nucleotide differences of the p89/X2 or p90 clones shown respectively below or above the p135 sequence. Dashes denote gaps and no residues are shown above or below where the sequences are identical. The p90 cDNA has the shortest 5' untranslated region, 7 additional residues between the polyadenylation motif and the poly A tract, and 2 polymorphisms in the coding region. The p98/X2 cDNA has the longest 5' untranslated region, 1 polymorphism in the coding sequence, and diverges from the other two cDNAs at residue 1051, becoming a complex pattern of repeats of upstream sequences. The p98/X2 clone lacks a polyadenylation site.

The FcRI protein from each of the three clones was purified from the respective COS cell lines which expressed them, by immuno-adsorption to IgG-agarose. (See Stengelin S. et al., *EMBO J.* 7:1053 (1988)). Gel electrophoresis of purified proteins showed a single species from p135 and p90 COS cells, relative molecular size 70 kd. Cells transfected with p98/X2 expressed a protein of 67 kd. A slightly larger protein of 75 kd was adsorbed from untreated and interferon-gamma-treated U937 promonocyte cells. The smaller mass observed in COS cells is consistent with the reduced masses observed from Table 2 other surface antigens expressed in COS cells, see e.g., Example IX.

The predicted polypeptide sequences show the typical features of a type I integral membrane protein, and include a short hydrophobic signal sequence, a single 21-residue hydrophobic membrane-spanning domain, and a short, highly charged cytoplasmic domain (FIG. 4A). The extracellular portion contains six potential N-linked glycosylation sites and six Cys residues distributed among three C2 set Ig-related domains.

FcRI is a high-affinity receptor for the Fc portion of IgG, normally located on the cell surfaces of macrophages. The ability to interfere with such bonding, or to cause it to occur on surfaces other than macrophages, is useful in therapy. For

TABLE 2

(SEQ ID NO:22) and (SEQ ID NO:23)

```
----------------------------------------------------      *         *         *         *      100
------------------GACAGATTTCACTQCTCCCACCAQCTTQQAQACAACATQTQQTTCTTQACAATCTTGCTCCTTTGQQTTCCAQTTCATQGQCAA
CTTCAATATCTTGCATGTT                                        M  W  F  L  T  T  L  L  L  W  V  P  Y  D  G  Q

      *         *       A *         *         *         *         *         *         *      200
```

TABLE 2-continued (SEQ ID NO:22) and (SEQ ID NO:23)

```
GTCCACACCACAAAGGCAGTCATCTCTTTGCAGCCTCCATGGGTCAGCGTGTTCCAAGAGGAAACCGTAACCTTGCACTQTGAGGTGCTCCATCTGCCTGQGA
Y  D  T  T  K  A  Y  I  S  L  Q  P  P  W  V  S  V  F  Q  E  E  T  V  T  L  H  C  E  V  L  H  L  P  Q  S
                        A

  *         *     G *         *         *         *         *         *         *     300
QCAGCTCTACACAGTGGTTTCTCAATGGCACAGCCACTCACACCTCGACCCCCAGCTACAGAATCACCTCTGCCAGTGTCAATQACAQTGGTGAATACAGQTG
  S  S  T  Q  V  F  L  H  C  T  A  T  C  T  S  T  P  S  Y  R  I  T  S  A  S  V  N  D  S  G  E  Y  R  C

*         *         *         *         *         *         *         *         *     400         *
CCAGACAQQTCTCTCAGGQCQAAQTQACCCCATACAGCTGGAAATCCACAGAGGCTGGCTACTACTGCAGGTCTCCAGCAGAQTCTTCACGGAAGQAGAACCT
 Q  R  G  L  S  Q  R  S  D  P  I  Q  L  E  I  H  R  C  W  L  L  L  Q  V  S  S  R  V  F  T  E  Q  E  P

      *         *         *         *         *         *         *         *     500         *
CTQQCCTTGAGQTQTCATQCGTGGAAQCATAAQCTQQTQTACAATGTGCTTTACTATCGAAATGGCAAAGCCTTTAAGTTTTTCCACTGGAATTCTAACCTCA
L  A  L  R  C  H  A  W  K  D  K  L  V  Y  N  V  L  Y  Y  R  H  C  K  A  F  K  F  F  H  W  N  S  H  L  T

    *         *         *         *         *         *         *         *     600         *
CCATTCTQAAAACCAACATAAQTCACAATGGCACCTACCATTQCTCAGGCATQQQAAAGCATCGCTACACATCAGCAGGAATATCTCTCACTGTCAAAGAGCT
  I  L  K  T  H  I  S  H  H  G  T  Y  H  C  S  Q  N  G  K  H  R  Y  Y  S  A  G  I  S  V  T  V  K  E  L

 *         *         *         *         *         *         *         *     700         *         *
ATTTCCAGCTCCAGTGCTGAATGCATCTQTQACATCCCCACTCCTGGAQQQGAATCTGQTCACCCTQAGCTQTCAAACAAAGTTGCTCTTGCAGAGGCCTGGT
 F  F  A  P  V  L  N  A  S  V  T  S  P  L  L  E  Q  N  L  V  Y  L  S  C  E  T  K  L  L  L  Q  R  P  G

       *         *         *         *         *         *         *     800         *         *
TTGCAGCTTTACTTCTCCTTCTACATGQQCAGCAAGACCCTGCQAGQCAQQAACACATCCTCTQAATACCAAATACTAACTQCTAQAAQAGAAQACTCTGGGT
L  Q  L  Y  F  S  F  Y  H  C  S  K  T  L  R  Q  R  N  T  S  S  E  Y  Q  I  L  T  A  R  R  E  D  S  C  L

     *         *         *         *         *         *         *     900         *         *
TATACTQGTGCQAGGCTCCCACAGAGGATGGAAATGTCCTTAAQCGCAGCCCTGAGTTGGAGCTTCAAQTQCTTQQCCTCCAQTTACCAACTCCTQTCTGGTT
  Y  W  C  E  A  A  T  E  D  G  N  V  L  K  R  S  P  E  L  E  L  Q  V  L  G  L  Q  L  P  Y  P  V  W  F

 *         *         *         *         *         *         *     1000         *         *         *
TCATQTCCTTTTCTATCTGGCAGTGQGAATAATCTTTTTACTGAACACTGTTCTCTGQQTGACAATACQTAAAQAACTQAAAAQAAAQAAAAAGTGQQATTTA
 H  V  L  F  Y  L  A  V  Q  I  N  F  L  V  N  T  V  L  W  V  T  I  R  K  E  L  K  R  K  K  K  W  D  L

        *         *         *         *         *         *     1100         *         *         *
QAAATCTCTTTQGATTCTQQTCATQAQAAQAAQQTAACTTCCAGCCTTCAACAAGACAGACATTTAGAAGAAGACCTQAAATGTCACQAACAAAAAQAAQAAC
E  I  S  L  D  S  G  H  E  K  K  V  T  S  S  L  Q  E  D  R  H  L  E  E  E  L  K  C  Q  E  Q  K  E  E  Q
              98   AGGCCAAQCACTTQAACCTCCAACTCACQGCTGCGCTTAAGGACATTTACATCCTCTGAATACCAAATACTAACTQCTAGAAQ
                     G  Q  A  L  E  A  P  T  Q  O  C  A  *

      *         *         *         *         *         *     1200         *         *         *
AQCTQCAQQAAQQGGTGCACCQGAAGGAQCCCCAQQQGGCCACQTAQCAGCGGCTCAGTGGQTQQCCATGGATCTCCACCQTCCCCTQCCCACTTGCTCCCCQ
  L  Q  E  G  V  H  R  K  E  P  Q  G  A  T  *
AQAAGACTCTGGGTTATACTGGTGCQAGGCTGCCACAGAGTCTTCTCTTCTAGCAGTTAGTATTTGGTACTTCAGACCATCTCTTCCTGCCTCGCAGGGTCTT

  *         *         *         *         *         *     1800         *         *    *     AACTGGG
TQAQCACTQCQTACAAACATCCAAAAQTTCAACAACACCAQAACTGTQTQTCTCATGGTATGTAACTCTTAAAGCAAATAAATGAACTGACTTC-------AA
GCAQCTTTACTTCTCCTTCTACATQQQCAQCAACCTTTAGAG

*
AAAAAAAA
```

example, a fusion protein of FcRI and a receptor ligand will be helpful to increase the potency of antibodies in therapy.

EXAMPLE XI

Isolation and Cloning of cDNA Encoding T-Lymphocyte TLiSA Antigen

A cDNA clone encoding TLiSA1 was obtained from a human T-cell cDNA library transferred into COS cell as described and subjected to the rapid immunoselection cloning method of the invention. A monoclonal antibody ACT-T-SET TLiSA1 (T-Cell Sciences Corp., Cambridge, Mass.) was used to detect transfected COS cells expressing the cloned cDNA, by positive indirect immunofluorescence. The positive plasmid contained in a 1.7 kb insert.

TLiSA protein was isolated by immunoprecipitation, as described supra, Example IX. The protein had a molecular weight of about 50 kd, as measured by gel electrophoresis.

The nucleotide sequence of the cDNA was determined by dideoxynucleotide chain termination as described, supra. The sequence of 1714 residues is given in Table 3, together with the deduced amino acid sequence shown in single letter code under the first nucleotide of each coding triplet. The ATG encoding the presumed initiator methionine is followed by a short hydrophobic region consistent with a secretory signal sequences, the most likely excision site being 19 residues into the open reading frame. The resulting polypeptide, if not further processed, would possess 317 residues with a predicted molecular weight of about 36 kd. The proposed extracellular domain is followed by 25 predominantly hydrophobic residues corresponding to the intracellular domain. (Table 3, double underlined.) The presence of 9 potential N linked glycosylation sites (Table 3, single dashed lines) appears sufficient to account for the discrepancy in molecular mass between the predicted polypeptide and the 50 kd species found by immunoprecipitation.

TLiSA is involved in mediating IL-2 induced differentiation of T-cells into cytolytic forms. Antibodies to TLiSA are useful to prevent IL-2 stimulated T cell differentiation, and to modulate adverse effects of IL-2 in therapy.

EXAMPLE XII

The Isolation and Molecular Cloning of cDNA Encoding for B Lymphocyte-Specific CD22 Antigen To isolate a CD22 cDNA, an expression library was constructed from the Burkitt lymphoma cell line Daudi, introduced into COS cells by the DEAE-Dextran method described supra, and subjected to three rounds of panning and re-introduction into *E. coli* as described in Seed and Aruffo, *Proc. Natl. Acad. Sci. USA* 84:3365–3369 (1987) and Aruffo and Seed, *Proc Natl. Acad. Sci. USA* 84:8573–8577 (1987). Of 16 plasmids picked after the third round, two tested positive for CD22 expression by indirect immunofluorescence in COS cells. Of the five carbohydrate-related epitopes, A, B, C, D and E, recognized by anti-CD22 monoclonal antibodies, only epitopes A and D were expressed in COS cells.

Immunoprecipitation of CD22 from transfected COS cells yielded a single band corresponding to a molecular mass of 110 kd, smaller than the 135 kd species obtained from Burkitt lymphoma Raji cells. The difference in mass may be related to differences in glycosylation. Since the immunogenic epitopes of CD22 are carbohydrate-related, these differences might account for the absence of epitopes B, C and E.

RNA blot hybridization analysis has revealed the presence of a major 3 kb RNA species and 4 minor species of 2.6, 2.3, 2.0 and 1.5 kb in several B cell lines. RNA encoding CD22 has not been found in several T cell lines, including peripheral blood T cells, the T cell leukemia Jurkat, the myeloid leukemia lines HL60 and U937 and the hepatoma HepG2.

TABLE 3

(SEQ ID NO:24) and (SEQ ID NO:25)

```
               *         *         *         *         *         *         *         *         *
    1 GCGGGGAGCTTGCAGTGACCAAGAGGGTGTTGAGGCTAAGAGGCCACGATAAACAGGATACGATAAAAGTCCTTAACCAAGACGCAGATGGAAGA
                                                                                       *         *         *
                                                                                    AGCGTTAGAGCGAGCAGCACTCAC

               *         *         *         *         *         *         *          -3    -1 +1
  121 ATCTCAAGAACCAGCCTTTCAAACAGTTTCCAGAGATGGATTATCCTACTTTACTTTTGGCTCTTCTTCATGTATACAGAGCTCTATGTGAAGAGG
                                          M  D  Y  P  T  L  L  L  A  L  L  H  V  Y  R  A  L  C  E  E  V
                                                                                       *         *         *
                                                                                    TGCTTTGGCATACATCAGTTCCCT
                                                                                     L  W  H  T  S  Y  P  F

               *         *   +19   *         *         *         *         *         *         *
  241 TTGCCGAGAACATGTCTCTAGAATGTGTGTATCCATCAATGGGCATCTTAACACAGGTGGAGTGGTTCAAGATCGGGACCCAGCAGGATTCCATAG
         A  E  N  M  S  L  E  C  V  Y  P  S  M  G  I  L  T  Q  V  E  W  F  K  I  G  T  Q  Q  D  S  I  A
               -------        ◆
                                                                                       *         *         *
                                                                                    CCATTTTCAGCCCTACTCATGGCA
                                                                                     I  F  S  P  T  H  G  M

               *         *         *         *         *         *         *         *         *
  381 TGGTCATAAGGAAGCCCTATGCTGAGAGGGTTTACTTTTTGAATTCAACGATGGCTTCCAATAACATGACTCTTTTCTTTCGGAATGCCTCTGAAG
         V  I  R  K  P  Y  A  E  R  V  Y  F  L  N  S  T  M  A  S  N  N  M  T  L  F  F  R  N  A  S  E  D
                                                -------              -------                 -------
                                                                                       *         *     +90 *
                                                                                    ATGATGTTGGCTACTATTCCTGCT
                                                                                     D  V  G  Y  Y  S  C  S

               *         *         *         *         *         *         *         *         *
  481 CTCTTTACACTTACCCACAGGGAACTTGGCAGAAGGTGATACAGGTGGTTCAGTCAGATAGTTTTGAGGCAGCTGTGCCATCAAATAGCCACATTG
         L  Y  T  Y  P  Q  G  T  W  Q  K  V  I  Q  V  V  Q  S  D  S  F  E  A  A  V  P  S  N  S  H  I  V
                                                                                       *         *         *
                                                                                    TTTCGGAACCTGGAAAGAATGTCA
                                                                                     S  E  P  G  K  N  V  T
                                                                                                    -------

             +134        *         *         *         *         *         *         *         *
  801 CACTCACTTGTCAGCCTCAGATGACGTGGCCTGTGCAGGCAGTCAGGTGGGAAAAGATCCAGCCCCGTCAGATCGACCTCTTAACTTACTGCAACT
         L  T  C  Q  P  Q  M  T  W  P  V  Q  A  V  R  W  E  K  I  Q  P  R  Q  I  D  L  L  T  Y  C  N  L
               ◆                                                                             ◆
                                                                                       *         *         *
                                                                                    TGGTCCATGGCAGAAATTTCACCT
                                                                                     Y  H  G  R  N  F  T  S
                                                                                           -------

               *         *         *         *         *         *         *         *         *
  721 CCAAGTTCCCAAGACAAATAGTGAGCAACTGCAGCCACGGAAGGTGGAGCGTCATCGTCATCCCCGATGTCACAGTCTCAGACTCGGGGCTTTACC
         K  F  P  R  Q  I  V  S  N  C  S  H  G  R  W  S  V  I  V  I  P  D  V  T  V  S  D  S  G  L  Y  R
                                 ---◆---
```

TABLE 3-continued (SEQ ID NO:24) and (SEQ ID NO:25

```
                                                                                    +203      *         *
                                                                                   GCTGCTACTTGCAGGCCAGCGCAG
                                                                                     C  Y  L  Q  A  S  A  G
                                                                                     ◆

          *         *         *         *         *         *         *         *         *
 841 GAGAAAACGAAACCTTCGTGATCAGATTGACTGTAGCCGAGGGTAAAACCGATAACCAATATACCCTCTTTGTGGCTGGAGGGACAGTTTTATTGT
       E  N  E  T  F  V  M  R  L  T  V  A  E  G  K  T  D  N  Q  Y  T  L  F  V  A  G  G  T  V  L  L  L
          -------
                                                                                     *         *         *
                                                                                TGTTCTTTGTTATCTCAATTACCA
                                                                                  L  F  V  I  S  I  T  T

          *         *         *         *         *         *         *         *         *
 981 CCATCATTGTCATTTTCCTTAACAGAAGGAGAAGGAGAGAGAGAAGAGATCTATTTACAGAGTCCTGGGATACACAGAAGGCACCCAATAACTATA
       I  I  V  I  F  L  N  R  R  R  R  R  E  R  R  D  L  F  T  E  S  W  D  T  Q  K  A  P  N  N  Y  R

                                                                                      *         *         *
                                                                                   GAAGTCCCATCTCTACCAGTCAAC
                                                                                     S  P  I  S  T  S  Q  P

          *         *         *         *         *         *         *         *         *
1081 CTACCAATCAATCCATGGATCATACAAGAGAGGATATTTATGTCAACTATCCAACCTTCTCTCGCAGACCAAAGACTAGAGTTTAAGCTTATTCTT
       T  N  Q  S  M  D  D  T  R  E  D  I  Y  V  N  Y  P  T  F  S  R  R  P  K  T  R  V
                                                                                      *         *         *
                                                                                   GACATGAGTGCATTAGTAATGACT

          *         *         *         *         *         *         *         *         *
1201 CTTATGTACTCATGCATGGATCTTTATGCAATTTTTTTCCACTACCCAAGGTCTACCTTAGATACTAGTTGTCTGAATTGAGTTACTTTGATAGGA
                                                                                      *         *         *
                                                                                   AAAATACTTCATTACCTAAAATCA

          *         *         *         *         *         *         *         *         *
1321 TTTTTCATAGAACTGTTTCAGAAAACCTGACTCTAACTGGTTTATATACAAAAGAAAACTTACTGTATCATATAACAGAATGATCCAGGGGAGATT
                                                                                      *         *         *
                                                                                   AAGCTTTGGGCAAGGGCTATTTAC

          *         *         *         *         *         *         *         *         *
1441 CAGGGCTTAAATGTTGTGTCTAGAATTAAGTATGGGCATAAACTGGCTTCTGAATCCCTTTCCAGAGTGTTGGATCCATTTCCCTGGTCTTGGCCT
                                                                                      *         *         *
                                                                                   CACTCTCATGCAGGCTTTCCTCTT

          *         *         *         *         *         *         *         *         *
1681 CTGTTGGCAAGATGGCTGCCAACTCTTGGCAATTCATACATCCTTGTTTCTGTCTGGTAGAGAGTTTGCTTCTCAAATGGAGCAAACAAATTTCAT
                                                                                      *         *         *
                                                                                   TATTTTTTCATTGTTAAATAGGCA

          *         *         *
1881 ACATGACCATAAAGGATGGAATGGCTTAAGTAAA
```

TABLE 4

(SEQ ID NO:26) and (SEQ ID NO:27)

```
  1  ACGCGGAAAC AGGCTTGCAC CCAGACACGA CACCATGCAT CTCCTCGGCC CCTGGCTCCT GCTCCTGGTT CTAGAATACT
                                      M  H   L  L  G  P   W  L  L   L  L  V   L  E  Y  L

 81  TGGCTTTCTC TGACTCAAGT AAATGGGTTT TTGAGCACCC TGAAACCCTC TACGCCTGGG AGGGGGCCTG CGTCTGGATC
       A  F  S   D  S  S   K  W  V  F   E  H  P   E  T  L   Y  A  W  E   G  A  C   V  W  I

161  CCCTGCACCT ACAGAGCCCT AGATGGTGAC CTGGAAAGCT TCATCCTGTT CCACAATCCT GAGTATAACA AGAACACCTC
     P  C  T  Y   R  A  L   D  G  D   L  E  S  F   I  L  F   H  N  P   E  Y  N  K   N  T  S

241  GAAGTTTGAT GGGACAAGAC TCTATGAAAG CACAAAGGAT GGGAAGGTTC CTTCTGAGCA GAAAAGGGTG CAATTCCTGG
      K  F  D   G  T  R  L   Y  E  S   T  K  D   G  K  V  P   S  E  Q   K  R  V   Q  F  L  G

321  GAGACAAGAA TAAGAACTGC ACACTGAGTA TCCACCCGGT GCACCTCAAT GACAGTGGTC AGCTGCGGCT GAGGATGGAG
       D  K  N   K  N  C   T  L  S  I   H  P  V   H  L  N   D  S  G  Q   L  G  L   R  M  E

401  TCCAAGACTG AGAAATGGAT GGAACGAATA CACCTCAATG TCTCTGAAAG GCCTTTTCCA CCTCATATCC AGCTCCCTCC
     S  K  T  E   K  W  M   E  R  I   H  L  N  V   S  E  R   P  F  P   P  H  I  Q   L  P  P
```

TABLE 4-continued (SEQ ID NO:26) and (SEQ ID NO:27)

```
 481 AGAAATTCAA GAGTCCCAGG AAGTCACTCT GACCTGCTTG CTGAATTTCT CCTGCTATGG GTATCCGATC CAATTGCAGT
      E  I  Q   E  S  Q  E   V  T  L   T  C  L   L  N  F  S   C  Y  C   Y  P  I   Q  L  Q  W

 561 GGCTCCTAGA GGGGGTTCCA ATGAGGCAGG CTGCTGTCAC CTCGACCTCC TTGACCATCA AGTCTGTCTT CACCCGGAGC
      L  L  E   G  V  P   M  R  Q  A   A  V  T   S  T  S   L  T  I  K   S  V  F   T  R  S

 641 GAGCTCAAGT TCTCCCCACA GTGGAGTCAC CATGGGAAGA TTGTGACCTG CCAGCTTCAG GATGCAGATG GGAAGTTCCT
     E  L  K  F   S  P  Q   W  S  H   H  G  K  I   V  T  C   Q  L  Q   D  A  D  G   K  F  L

 721 CTCCAATGAC ACGGTGCAGC TGAACGTGAA GCATCCTCCC AAGAAGGTGA CCACAGTGAT TCAAAACCCC ATGCCGATTC
      S  N  D   T  V  Q  L   N  V  K   H  P  P   K  K  V  T   T  V  I   Q  N  P   M  P  I  R

 801 GAGAAGGAGA CACAGTGACC CTTTCCTGTA ACTACAATTC CAGTAACCCC AGTGTTACCC GGTATGAATG GAAACCCCAT
      E  G  D   T  V  T   L  S  C  N   Y  N  S   S  N  P   S  V  T  R   Y  E  W   K  P  H

 881 GGCGCCTGGG AGGAGCCATC GCTTGGGGTG CTGAAGATCC AAAACGTTGG CTGGGACAAC ACAACCATCG CCTGCGCAGC
     G  A  W  E   E  P  S   L  G  V   L  K  I  Q   N  V  G   W  D  N   T  T  I  A   C  A  A

 961 TTGTAATAGT TGGTGCTCGT GGGCCTCCCC TGTCGCCCTG AATGTCCAGT ATGCCCCCCG AGACGTGAGG GTCCGGAAAA
      C  N  S   W  C  S  W   A  S  P   V  A  L   N  V  Q  Y   A  P  R   D  V  R   V  R  K  I

1041 TCAAGCCCCT TTCCGAGATT CACTCTGGAA ACTCGGTCAG CCTCCAATGT GACTTCTCAA GCAGCCACCC CAAAGAAGTC
      K  P  L   S  E  I   H  S  G  N   S  V  S   L  Q  C   D  F  S  S   S  H  P   K  E  V

1121 CAGTTCTTCT GGGAGAAAAA TGGCAGGCTT CTGGGGAAAG AAAGCCAGCT GAATTTTGAC TCCATCTCCC CAGAAGATGC
     Q  F  F  W   E  K  N   G  R  L   L  G  K  E   S  Q  L   N  F  D   S  I  S  P   E  D  A

1201 TGGGAGTTAC AGCTGCTGGG TGAACAACTC CATAGGACAG ACAGCGTCCA AGGCCTGGAC ACTTGAAGTG CTGTATGCAC
      G  S  Y   S  C  W  V   N  N  S   I  G  Q   T  A  S  K   A  W  T   L  E  V   L  Y  A  P

1281 CCAGGAGGCT GCGTGTGTCC ATGAGCCCGG GGGACCAAGT GATGGAGGGG AAGAGTGCAA CCCTGACCTG TGAGAGCGAC
      R  R  L   R  V  S   M  S  P  G   D  Q  V   M  E  G   K  S  A  T   L  T  C   E  S  D

1361 GCCAACCCTC CCGTCTCCCA CTACACCTGG TTTGACTGGA ATAACCAAAG CCTCCCCTAC CACAGCCAGA AGCTGAGATT
     A  N  P  P   V  S  H   Y  T  W   F  D  W  N   N  Q  S   L  P  Y   H  S  Q  K   L  R  L

1441 GGAGCCGGTG AAGGTCCAGC ACTCGGGTGC CTACTGGTGC CAGGGGACCA ACAGTGTGGG CAAGGGCCGT TCGCCTCTCA
      E  P  V   K  V  Q  H   S  G  A   Y  W  C   Q  G  T  N   S  V  G   K  G  R   S  P  L  S

1521 GCACCCTCAC CGTCTACTAT AGCCCGGAGA CCATCGGCAG GCGAGTGGCT GTGGGACTCG GGTCCTGCCT CGCCATCCTC
      T  L  T   V  Y  Y   S  P  E  T   I  G  R   R  V  A   V  G  L  G   S  C  L   A  I  L

1601 ATCCTGGCAA TCTGTGGGCT CAAGCTCCAG CGACGTTGGA AGAGGACACA GAGCCAGCAG GGGCTTCAGG AGAATTCCAG
     I  L  A  I   C  G  L   K  L  Q   R  R  W  K   R  T  Q   S  Q  Q   G  L  Q  E   N  S  S

1681 CGGCCAGAGC TTCTTTGTGA GGAATAAAAA GGTTAGAAGG GCCCCCCTCT CTGAAGGCCC CCACTCCCTG GGATGCTACA
      G  Q  S   F  F  V  R   N  K  K   V  R  R   A  P  L  S   E  G  P   H  S  L   G  C  Y  N

1761 ATCCAATGAT GGAAGATGGC ATTAGCTACA CCACCCTGCG CTTTCCCGAG ATGAACATAC CACGAACTGG AGATGCAGAG
      P  M  M   E  D  G   I  S  Y  T   T  L  R   F  P  E   M  N  I  P   R  T  G   D  A  E

1841 TCCTCAGAGA TGCAGAGACC TCCCCCGGAC TGCGATGACA CGGTCACTTA TTCAGCATTG CACAAGCGCC AAGTGGGCAC
     S  S  E  M   Q  R  P   P  P  D   C  D  D  T   V  T  Y   S  A  L   H  K  R  Q   V  G  T

1921 TATGAGAACG TCATTCCAGA TTTTCCAGAA GATGAGGGGA TTCATTACTC AGAGCTGATC CAGTTTGGGG TCGGGGAGCG
      M  R  T   S  F  Q  I   F  Q  K   M  R  G   F  I  T  Q   S  *

2001 GCCTCAGGCA CAAGAAAATG TGGACTATGT GATCCTCAAA CATTGACACT GGATGGGCTG CAGCAGAGGC ACTGGGGGCA

2081 GCGGGGGCCA GGGAAGTCCC CGAGTTT
```

DNA blot hybridization of placental DNA gave a simple pattern consistent with a single copy gene. DNA sequence analysis by the dideoxy method described supra showed that the 2107 bp insert encoded a polypeptide of 647 amino acids. The nucleotide and amino acid sequences appear in Table 4. The initial methionine is followed by 18 predominantly hydrophobic amino acids resembling a secretory signal sequence. The mature protein, having a relative molecular weight of 71.1 kd consists of an extracellular portion of 491 residues, followed by a 19 residue membrane-spanning domain (doubly underlined), and an intracellular domain of 118 amino acids. Ten potential N-linked glycosylation sites (N-X-S/T, X not equal to P) are found in the predicted extracellular domain, as well as a large number of serine and threonine residues which may be sites of O-linked glycan addition. The abundance of potential glycosylation sites and the difference in mass between the predicted protein backbone and the product precipitated from COS cells and B cell lines suggest that about 50% of the mass of CD22 is contributed by carbohydrate.

The extracellular portion of CD22 consists of five segments having Ig-like domain organization. The short intercysteine spacing (63 and 64 residues in domains 1 and 2, and 42 residues in domains 3–5) suggests that they fold into the 7 strand two layer beta-sheet structure characteristic of immunoglobulin constant regions rather than the 9 strand structure of variable regions.

Because CD22 has been found to be highly homologous to myelin associated glycoprotein (MAG), a neuronal cell surface protein which mediates cell-cell contacts during myelogenesis, it was postulated that CD22 has a role in B cell adhesion. COS cells transfected with CD22 cDNA were contacted with erythrocytes or peripheral blood mononuclear cells and incubated under conditions which minimized nonspecific interaction. Erythrocyte and mononuclear cell resetting was observed with CD22-positive COS cells but not with COS cells transfected with an unrelated cDNA clone.

B cell adhesion studies involving anti-epitope monoclonal antibodies have indicated that different epitopes of CD22 may participate in erythrocyte and monocyte adhesion and that different ligands may be recognized on each cell type. B cell adhesion studies also suggest that CD22, in a manner analogous to T cell CD2, CD4 and CD8 adhesion to target cells, may promote recognition by the B cell antigen receptor by intensifying B cell-presenting cell contacts. CD22 has been previously implicated in the transmission of signals synergizing with the antigen receptor (Pezutto et al., *J. Immunol.* 138:98–103 (1987)) and crosslinking of surface IgM produces an intracellular calcium flux in $IgM^{+}CD22^{+}$ but not in $IgM^{+}CD22^{-}$ cells (Pezzutto et al., *J. Immunol.* 140:1791–1795 (1988)). These results suggest that, like T cell accessory molecules, CD22 may also participate in the regulation of signal transduction.

The ability to interfere with the binding of CD22 positive B cells with accessory cells, or the ability to cause such binding to occur on surfaces other than lymphocyte cells can be useful in diagnostics and therapy. For example, a fusion protein of CD22 and a receptor ligand fixed to a substrate will be useful in detecting the presence of a particular antigen in body fluids. A soluble form of CD22 can have immunomodulatory activity.

EXAMPLE XIII

The Isolation and Molecular Cloning of cDNA Encoding for T Lymphocyte-specific CD27 Antigen A cDNA clone encoding CD27 was obtained from human T lymphocyte cDNA transferred into COS cells and immunoselected by the method of the present invention. RNA was extracted from the mononuclear cells derived from a unit of blood, after four days of culture in medium containing 1 μg/ml phytohemagglutinin (PHA), using guanidium thiocyanate. The total RNA was poly-A selected. cDNA was made and cloned into CDM8, transfected into COS cells and the CD27 cDNA was immunoselected with monoclonal antibodies OKT18a and CLB-9F4 (provided as described in Seed and Aruffo *Proc. Natl. Acad. Sci.* 84:8573–8577 (1987); and Aruffo and Seed *Proc. Natl. Acad. Sci. USA* 84:3365–3369 (1987)). The vector contained a 1.2 kb cDNA insert.

The nucleotide sequence of the eDNA was determined by dideoxynucleotide chain termination as described, supra. The sequence of 1203 residues and the deduced amino acid sequence appear in Table 5. See also SEQ ID NO:28 and 29. The initiation methionine is indicated by the number 1 above the initiator codon. The deduced CD27 polypeptide demonstrates the typical features of a type I integral membrane protein. It begins with a twenty amino acid hydrophobic region consistent with a secretory signal sequence. This hydrophobic region is followed by a 171 residue extracellular domain, a 20 residue hydrophobic membrane spanning domain (doubly underlined) and a 49 amino acid cytoplasmic domain beginning with a positively charged stop transfer sequence. There is no poly (A) tail.

The deduced CD27 amino acid sequence is highly homologous to the B lymphocyte and carcinoma antigen CD40, described supra, over its entire length. CD27 is also highly homologous to the the the receptor for nerve growth factor (NGFR) over the extracellular and transmembrane domains (Stamenkovic et al., *EMBO J.* 8:1403–1410 (1989); Johnson et al., *Cell* 47:545–554 (1989)). The most conserved structural motif found in these three proteins is the abundance of cysteines or histidines in the extracellular region. These are often found in pairs separated by two or four intervening amino acid residues similar to the arrangement seen in proteins which use this structure to bind a zinc ion. The cysteine and histidine rich region is followed by a serine, threonine and proline rich membrane proximal domain which has been suggested to be the region in which biochemically identified O-linked glycans are added to NGFR (Johnson et al. (1986), supra; Grob et al., *J. Biol. Chem.* 260:8044–8049 (1985)).

Immunoprecipitation of transfected COS cells with anti-CD27 antibodies followed by gel electrophoresis revealed the presence

TABLE 5

(SEQ ID NO:28) and (SEQ ID NO:29)

```
  1  GGGGTGCAAA GAAGAGACAG CAGCGCCCAG CTTGGAGGTG CTAACTCCAG AGGCCAGCAT CAGCAACTGG GCACAGAAAG

                         1
 81  GAGCCGCCTG GGCAGGGACC ATGGCACGGC CACATCCCTG GTGGCTGTGC GTTCTGGGGA CCCTGGTGGG GCTCTCAGCT
                         M  A  R  P   H  P  W   W  L  C   V  L  G  T   L  V  G   L  S  A

161  ACTCCAGCCC CCAAGAGCTG CCCAGAGAGG CACTACTGGG CTCAGGGAAA GCTGTGCTGC CAGATGTGTG AGCCAGGAAC
     T  P  A  P   K  S  C   P  E  R   H  Y  W  R   Q  G  K   L  C  C   Q  M  C  E   P  G  T

241  ATTCCTCGTG AAGGACTGTG ACCAGCATAG AAAGGCTGCT CAGTGTGATC CTTGCATACC GGGGGTCTCC TTCTCTCCTG
      F  L  V   K  D  C  D   Q  H  R   K  A  A   Q  C  D  P   C  I  P   G  V  S   F  S  P  D

321  ACCACCACAC CCGGCCCCAC TGTGAGAGCT GTCGGCACTG TAACTCTGGT CTTCTCGTTC GCAACTGCAC CATCACTGCC
        H  H  T   R  P  H   C  E  S  C   R  H  C   N  S  G   L  L  V  R   N  C  T   I  T  A
```

TABLE 5-continued (SEQ ID NO:28) and (SEQ ID NO:29)

```
 401 AATGCTGAGT GTGCCTGTCG CAATGGCTGG CAGTGCAGGG ACAAGGAGTG CACCGAGTGT GATCCTCTTC CAAACCCTTC
     N  A  E  C  A  C  R   N  G  W   Q  C  R  D  K  E  C   T  E  C   D  P  L  P  N  P  S

 481 GCTGACCGCT CGGTCGTCTC AGGCCCTGAG CCCACACCCT CAGCCCACCC ACTTACCTTA TGTCAGTGAG ATGCTGGAGG
      L  T  A  R  S  S  Q   A  L  S   P  H  P   Q  P  T  H  L  P  Y   V  S  E   M  L  E  A

 561 CCAGGACAGC TGGGCACATG CAGACTCTGG CTGACTTCAG GCAGCTGCCT GCCCGGACTC TCTCTACCCA CTGGCCACCC
      R  T  A   G  H  M   Q  T  L  A   D  F  R   Q  L  P   A  R  T  L   S  T  H   W  P  P

 641 CAAAGATCCC TGTGCAGCTC CGATTTTATT CGCATCCTTG TGATCTTCTC TGGAATGTTC CTTGTTTTCA CCCTGGCCGG
     Q  R  S  L   C  S  S   D  F  I   R  I  L  V   I  F  S   G  M  F   L  V  F  T   L  A  G

 721 GGCCCTGTTC CTCCATCAAC GAAGGAAATA TAGATCAAAC AAAGGAGAAA GTCCTGTGGA GCCTGCAGAG CCTTGTCGTT
      A  L  F  L  H  Q  R   R  K  Y   R  S  N   K  G  E  S   P  V  E   P  A  E   P  C  R  Y

 801 ACAGCTGCCC CAGGGAGGAG GAGGGCAGCA CCATCCCCAT CCAGGAGGAT TACCGAAAAC CGGAGCCTGC CTGCTCCCCC
      S  C  P   R  E  E   E  G  S  T   I  P  I   Q  E  D   Y  R  K  P   E  P  A   C  S  P

 881 TGAGCCAGCA CCTGCGGTAG CTGCACTACA GCCCTGGCCT CCACCCCCAC CCCGCCGACC ATCCAAGGGA GAGTGAGACC
     *

 961 TGGCAGCCAC AACTGCAGTC CCATCCTCTT GTCAGGGCCC TTTCCTGTGT ACACGTGACA GAGTGCCTTT TCGAGACTGG

1041 CAGGGACGAG GACAAATATG GATGAGGTGG AGAGTGGGAA GCAGGAGCCC AGCCAGCTGC GCGCGCGTGC AGGAGGGCGG

1121 GGGCTCTGGT TGTAAGGCAC ACTTCCTGCT GCGAAAGACC CACATGCTAC AAGACGGGCA AAATAAAGTG ACAGATGACC
```

of a 110 kd species when not reduced and a single 55 kd band in the presence of reducing agent. This indicates that on transfected COS cells, CD27 is a disulfide linked homodimer comprised of 55 kd monomers, similar to the forms precipitated from T lymphocytes. (Bigler et al., *J. Immunol.* 141:21–28 (1988); Stockinger et al., *Leukocyte Typing II, Vol. I:*513–529 (1986); Van Lier et al., *Eur. J. Immunol.* 18:811–816 (1987)).

CD27 is a T lymphocyte activation antigen. Its structure suggests that it may function as the receptor for a lymphokine or growth factor. The recognition of CD27 causes T cell proliferation and increased expression of certain genes needed for the helper and effector functions of the T cell. The expression of CD27 on T cells increases two to five fold with stimulation by phytohemagglutinin (PHA) or anti-CD3 monoclonal antibodies and the addition of at least one CD27 monoclonal antibody can augment PHA stimulated proliferation of T cells (Bigler and Chiorazzi, *Leukocyte Typing II, Vol. I:*503–512 (1986); Van Lier, (1987)). T cells positive for CD27 have been found to provide help to B cells for IgM synthesis and secrete Il-2 when appropriately stimulated (Van Lier et al., *Eur. J. Immunol.* 18:811–816 (1988)).

The ability to interfere with the binding of CD27 positive T cells with antigen presenting cells, or the ability to cause such binding to occur on surfaces other than lymphocyte cells, can be useful in diagnostics and therapy. For example, a fusion protein of CD27 and a receptor ligand fixed to a substrate will be useful in detecting the presence of a particular antigen in body fluids. A soluble CD27 fusion protein will be useful to prevent undesired T cell proliferation, for example, in certain autoimmune diseases.

EXAMPLE XIV

The Isolation and Molecular Cloning of the Two cDNA Clones Encoding T Lymphocyte-Specific Leu8 Antigens Two cDNA clones encoding Leu8 determinants were isolated from a human T cell library by the method of the present invention.

The nucleotide sequence of the cDNA was determined by dideoxynucleotide chain termination as described, supra. The DNA sequence analyses (Table 6) shows that the longer insert of the two contains 2,350 residues, whereas the shorter lacks 436 internal residues but is otherwise identical. The entire sequence of the longer clone is shown, with the portion deleted from the shorter clone overlined. The predicted amino acid sequence is shown below the nucleotide sequence. Sites of potential N-linked glycosylation are designated —CHO— and the proposed transmembrane region for the longer form is doubly underlined.

DNA blot hybridization of fragmented human T cell genome showed a pattern consistent with a single copy gene. RNA blot hybridization revealed a major transcript of 2.4 kb in peripheral blood mononuclear cells, tonsillar B cells, and several lymphocytic cell lines; and a minor transcript of 2.0 kb, present in peripheral blood mononuclear cells, and the Jurkat and HSB-2 leukaemic T cell lines.

The deduced protein encoded by the larger insert (the conventional form) bears a strongly hydrophobic putative membrane spanning domain near its C terminus, followed by several positively charged residues resembling a cytoplasmic anchor sequence. The protein is closely related to the recently described murine Mel-14 homing receptor (Lasky et al., *Cell* 56:1045–1055 (1989); Siegelman et al., *Science* 243:1165–1172 (1989)).

The protein encoded by the shorter insert (the phospholipid anchored form) bears a weakly hydrophobic C-terminal domain characteristic of surface proteins that are attached to the cell

TABLE 6

(SEQ ID NO:30) and (SEQ ID NO:41)

```
   1 CTCCCTTTGG GCAAGGACCT GAGACCCTTG TGCTAAGTCA AGAGGCTCAA TGGGCTGCAG AAGAACTAGA GAAGGACCAA
                                                           M   G  C  R   R  T  R   E  G  P  S

  81 GCAAAGCCAT GATATTTCCA TGGAAATGTC AGAGCACCCA GAGGGACTTA TGGAACATCT TCAAGTTGTG GGGGTGGACA
       K  A  M   I  F  P   W  K  C  Q   S  T  Q   R  D  L   W  N  I  F   K  L  W   G  W  T

 161 ATGCTCTGTT GTGATTTCCT GGCACATCAT GGAACCGACT GCTGGACTTA CCATTATTCT GAAAAACCCA TGAACTGGCA
     M  L  C  C   D  F  L   A  H  H   G  T  D  C   W  T  Y   H  Y  S   E  K  P  M   N  W  Q

 241 AAGGGCTAGA AGATTCTGCC GAGACAATTA CACAGATTTA GTTGCCATAC AAAACAAGGC GGAAATTGAG TATCTGGAGA
       R  A  R   R  F  C  R   D  N  Y   T  D  L   V  A  I  Q   N  K  A   E  I  E   Y  L  E  K

       (1)                                                                   --CHO --
 321 AGACTCTGCC TTTCAGTCGT TCTTACTACT GGATAGGAAT CCGGAAGATA GGAGGAATAT GGACGTGGGT GGGAACCAAC
       T  L  P   F  S  R   S  Y  Y  W   I  G  I   R  K  I   G  G  I  W   T  W  V   G  T  N

 401 AAATCTCTCA CTGAAGAAGC AGAGAACTGG GGAGATGGTG AGCCCAACAA CAAGAAGAAC AAGGAGGACT GCGTGGAGAT
     K  S  L  T   E  E  A   E  N  W   G  D  G  E   P  N  N   K  K  N   K  E  D  C   V  E  I

                                           --C HO--
 481 CTATATCAAG AGAAACAAAG ATGCAGGCAA ATGGAACGAT GACGCCTGCC ACAAACTAAA GGCAGCCCTC TGTTACACAG
       Y  I  K   R  N  K  D   A  G  K   W  N  D   D  A  C  H   K  L  K   A  A  L   C  Y  T  A

 561 CTTCTTGCCA GCCCTGGTCA TGCAGTGGCC ATGGAGAATG TGTAGAAATC ATCAATAATT ACACCTGCAA CTGTGATGTG
       S  C  Q   P  W  S   C  S  G  H   G  E  C   V  E  I   I  N  N  Y   T  C  N   C  D  V

 641 GGGTACTATG GGCCCCAGTG TCAGTTTGTG ATTCAGTGTG AGCCTTTGGA GGCCCCAGAG CTGGGTACCA TGGACTGTAC
     G  Y  Y  G   P  Q  C   Q  F  V   I  Q  C  E   P  L  E   A  P  E   L  G  T  M   D  C  T

                    --CH O--
 721 TCACTCTTTG GGAAACTTCA GCTTCAGCTC ACAGTGTGCC TTCAGCTGCT CTGAAGGAAC AAACTTAACT GGGATTGAAG
       H  S  L   G  N  F  S   F  S  S   Q  C  A   F  S  C  S   E  G  T   N  L  T   G  I  E  E

                                                              --CHO--
 801 AAACCACCTG TGGACCATTT GGAAACTGGT CATCTCCAGA ACCAACCTGT CAAGTGATTC AGTGTGAGCC TCTATCAGCA
       T  T  C   G  P  F   G  N  W  S   S  P  E   P  T  C   Q  V  I  Q   C  E  P   L  S  A

                               --CHO--                                   --CHO--
 881 CCAGATTTGG GGATCATGAA CTGTAGCCAT CCCCTGGCCA GCTTCAGCTT TACCTCTGCA TGTACCTTCA TCTGCTCAGA
     P  D  L  G   I  M  N   C  S  H   P  L  A  S   F  S  F   T  S  A   C  T  F  I   C  S  E

                                                                     -- CHO--
 961 AGGAACTGAG TTAATTGGGA AGAAGAAAAC CATTTGTGAA TCATCTGGAA TCTGGTCAAA TCCTAGTCCA ATATGTCAAA
       G  T  E   L  I  G  K   K  K  T   I  C  E   S  S  G  I   W  S  N   P  S  P   I  C  Q  K

                                             -- ---------- ---------- ---------- ----------
1041 AATTGGACAA AAGTTTCTCA ATGATTAAGG AGGGTGATTA TAACCCCCTC TTCATTCCAG TGGCAGTCAT GGTTACTGCA
       L  D  K   S  F  S   M  I  K  E   G  D  Y   N  P  L   F  I  P  V   A  V  M   V  T  A

     ---------- ---------- ---------- ---------- ---------- ---------- ---------- ----------
1121 TTCTCTGGGT TGGCATTTAT CATTTGGCTG GCAAGGAGAT TAAAAAAAGG CAAGAAATCC AAGAGAAGTA TGAATGACCC
     F  S  G  L   A  F  I   I  W  L   A  R  R  L   K  K  G   K  K  S   K  R  S  M   N  D  P

     ---------- ---------- ---------- ---------- ---------- ---------- ---------- ----------
1201 ATATTAAATC GCCCTTGGTG AAAGAAAATT CTTGGAATAC TAAAAATCAT GAGATCCTTT AAATCCTTCC ATGAAACGTT
       Y  *

     ---------- ---------- ---------- ---------- ---------- ---------- ---------- ----------
1281 TTGTGTGGTG GCACCTCCTA CGTCAAACAT GAAGTGTGTT TCCTTCAGTG CATCTGGGAA GATTTCTACC TGACCAACAG

     ---------- ---------- ---------- ---------- ---------- ---------- ---------- ----------
1361 TTCCTTCAGC TTCCATTTCG CCCCTCATTT ATCCCTCAAC CCCCAGCCCA CAGGTGTTTA TACAGCTCAG CTTTTTGTCT

     ---------- ---------- ---------- ---------- ---------- ---------- ---------- ----
1441 TTTCTGAGGA GAAACAAATA AGACCATAAA GGGAAAGGAT TCATGTGGAA TATAAAGATG GCTGACTTTG CTCTTTCTTG
                                                                                   F  L
```

TABLE 6-continued (SEQ ID NO:30) and (SEQ ID NO:41)

```
                                                                                    (293)
1521 ACTCTTGTTT TCAGTTTCAA TTCAGTGCTG TACTTGATGA CAGACACTTC TAAATGAAGT GCAAATTTGA TACATATGTG
      T  L  V  F   S  F  N   S  V  L   Y  L  M  T   D  T  S   K  *

1601 AATATGGACT CAGTTTTCTT GCAGATCAAA TTTCACGTCG TCTTCTGTAT ACTGTGGAGG TACACTCTTA TAGAAAGTTC

1681 AAAAAGTCTA CGCTCTCCTT TCTTTCTAAC TCCAGTGAAG TAATGGGGTC CTGCTCAAGT TGAAAGAGTC CTATTTGCAC

1761 TGTAGCCTCG CCGTCTGTGA ATTGGACCAT CCTATTTAAC TGGCTTCAGC CTCCCCACCT TCTTCAGCCA CCTCTCTTTT

1841 TCAGTTGGCT GACTTCCACA CCTAGCATCT CATGAGTGCC AAGCAAAAGG AGAGAAGAGA GAAATAGCCT GCGCTGTTTT

1921 TTAGTTTGGG GGTTTTGCTG TTTCCTTTTA TGAGACCCAT TCCTATTTCT TATAGTCAAT GTTTCTTTTA TCACGATATT

2001 ATTAGTAAGA AAACATCACT GAAATGCTAG CTGCAAGTGA CATCTCTTTG ATGTCATATG GAAGAGTTAA AACAGGTGGA

2081 GAAATTCCTT GATTCACAAT GAAATGCTCT CCTTTCCCCT GCCCCCAGAC CTTTTATCCG ACTTACCTAG ATTCTACATA

2161 TTCTTTAAAT TTCATCTCAG GCCTCCCTCA ACCCCACCAC TTCTTTTATA ACTAGTCCTT TACTAATCCA ACCCATGATG

2241 AGCTCCTCTT CCTGGCTTCT TACTGAAAGG TTACCCTGTA ACATGCAATT TTGCATTTGA ATAAAGCCTG CTTTTTAAGT

2321 GTTAAAAAAA AAAAAAAAAA AAAAAAAAAA
```

membrane by covalent linkage to a phosphatidylinositol-substituted glycan.

Monoclonal antibodies TQ1 (Reinherz et al. (1982) J. Immun. 128:463–468) and Mel-14 (Gallatin et al. (1983) Nature 304:30–34) have been observed to react with COS cells transfected with either Leu8 clone.

The presence or absence of Leu8 on CD4+ T lymphocytes identifies suppressor-inducer and helper-inducer CD4+ T cell subsets. Leu8 is a homing receptor, allowing T cells to adhere to the specialized post-capillary endothelium of peripheral lymph nodes. The presence or absence of Leu8 classifies the T cell in terms of homing potential and tissue distribution. Serological studies have indicated that Leu8 is a marker of resting lymphocytes in peripheral lymph nodes (Poletti et al., *Hum. Pathol.* 19:1001–1007 (1988)). Activation of T cells by phorbol ester plus PHA results in reduced Leu8 expression and transcripts, with the reduction in Leu8 expression being more rapid than the reduction of Leu8 transcripts. It therefore appears that surface Leu8 is lost more rapidly than predicted by RNA turnover, possibly by shedding of the phosphatidylinositol-linked form (Ferguson & Williams, *A. Rev. Biochem.* 57:285–320 (1988)). Among peripheral T cells, the $CD4^+$ $Leu8^-$ subset provides help for B cell IgM and IgG synthesis (Reinherz et al., *J. Immun.* 128:463–468 (1982); Gatenby et al., *J. Immun.* 129:1997–2000), whereas $CD4^+$ $Leu8^-$ cells have been found to directly inhibit pokeweed mitogen-induced IgG synthesis (Kanof et al., *J. Immun.* 139:49–54 (1987)). It therefore appears that $CD4^+$ $Leu8^-$ cells, activated to provide help for B cell Ig synthesis, exit the nodes and circulate peripherally to encounter antigen-presenting cells.

The ability to interfere with the binding of $Leu8^-$ T cells to antigen presenting cells, or the ability to cause such binding to occur on surfaces other than lymphocyte cells, can be useful in diagnostics and therapy. For example, the level of activated $Leu8^-$ T cells relative to resting $Leu8^+$ cells could serve as a measure of immune response to a particular antigen.

The extracellular domain of the Leu8 transmembrane protein, which mediates adhesion to specialized endothelial cells of lymph nodes, has been observed to be quite specific in its recognition of the lectin ligand, sulfated galactosyl ceramide (sulfatide). Modification of the specificity of this binding could serve to regulate the homing potential of resting T cells. Soluble forms of Leu8 can act as anti-inflammatory agents by reducing lymphocyte migration.

EXAMPLE XV

The Isolation and Molecular Cloning of cDNAs Encoding CD44 Antigens

CD44 is a polymorphic integral membrane protein. Immunochemical and RNA blot data have supported the existence of two forms of CD44: a mesenchymal form expressed by hematopoietic cells and an epithelial form weakly expressed by normal epithelium but highly expressed by carcinomas.

To isolate a cDNA clone encoding hematopoietic CD44 (Stamenkovic et al., *Cell* 56:1057–1062 (1989)), libraries prepared from the histiocytic lymphoma cell line U937, the B lymphoblastoid line JY, the Burkitt's lymphoma line Raji, and the myeloid leukemia line KG-1 were transfected separately into COS cells by the DEAE-Dextran method, described supra. The cells were pooled 48 hours after transfection, incubated with anti-CD44 monoclonal antibodies J173 (Pesandro et al., *J. Immunol.* 137:3689–3695 (1986)), and panned on dishes coated with goat antimouse affinity purified antibody. After several washes, the adherent cells were lysed, and episomal DNA was purified and transformed into *E. coli*. After two similar rounds of enrichment following spheroplast fusion, plasmid DNA recovered from three out of eight randomly picked colonies was found to direct the appearance of hematopoietic CD44 determinants on transfected COS cells.

Two of the three clones, CD44.5 and CD44.8, bore inserts of about 1.4 kb, while the third, CD44.4, contained an insert of about 1.7 kb. COS cells transfected with either of these clones reacted with anti-CD44 monoclonal antibodies J173, F-10-44-2 (Dalchau et al., *Eur. J. Immunol.* 10:745–749 (1980)) and the anti-Pgp-1 monoclonal antibody IM7

(Trowbridge et al., *Immunogenetics* 15:299–312 (1982)). Untransfected cells showed weak J173 reactivity.

The nucleotide sequence of the hematopoietic CD44.5 cDNA (Table 7) consists of 1354 residues terminating in a short poly(A) tail 19 base pairs downstream from a CATAAA sequence. The ATG encoding the first methionine is embedded in a consensus initiation sequence and followed by 19 predominantly hydrophobic residues resembling a secretory signal peptide sequence. Cleavage of this peptide would yield a mature protein of 341 residues with a predicted relative molecular mass of 37.2 kd. The extracellular amino terminal domain of 248 residues is followed by 21 predominantly hydrophobic amino acids corresponding to the predicted transmembrane domain (doubly underlined) and a 72 residue hydrophilic (cytoplasmic) domain. The discrepancy between the predicted mass of the protein backbone and the deglycosylated forms observed in immunoprecipitates suggest that, extensive O-linked glycosylation is present. The extracellular domain has six potential N-linked glycosylation sites, indicated in Table 7 by a —CHO— designation, and is rich in serine and threonine residues (22% in aggregate). The dipeptide SG that forms the minimal attachment site of serine-linked chondroitin sulfate in proteoglycan proteins appears at residues 160, 170, 211 and 238 in the predicted extracellular domain; these potential glycosylation sites are underlined.

RNA blot hybridization revealed three major messages of 1.6, 2.2 and 5.0 kb in a variety of hematopoietic cell lines, including the B lymphoblastoid line CESS, the T cell leukemias

TABLE 7

(SEQ ID NO:31) and (SEQ ID NO:32)

```
   1 CCAGCCTCTG CCAGGTTCGG TCCGCCATCC TCGTCCCGTC CTCCGCCGGC CCCTGCCCCG CGCCCAGGGA TCCTCCAGCT

  81 CCTTTCGCCC GCGCCCTCCG TTCGCTCCGG ACACCATGGA CAAGTTTTGG TGGCACGCAG CCTGGGGACT CTGCCTCGTG
                                               M  D   K  F  W   W  H  A  A   W  G  L   C  L  V

 161 CCGCTGAGCC TGGCGCAGAT CGATTTGAAT ATAACCTGCC GCTTTGCAGG TGTATTCCAC GTGGAGAAAA ATGGTCGCTA
     P  L  S  L   A  Q  I   D  L  N   I  T  C  R   F  A  G   V  F  H   V  E  K  N   G  R  Y

                                                                              --C HO--
 241 CAGCATCTCT CGGACGGAGG CCGCTGACCT CTGCAAGGCT TTCAATAGCA CCTTGCCCAC AATGGCCCAG ATGGAGAAAG
      S  I  S   R  T  E  A   A  D  L   C  K  A   F  N  S  T   L  P  T   M  A  Q   M  E  K  A

 321 CTCTGAGCAT CGGATTTGAG ACCTGCAGGT ATGGGTTCAT AGAAGGGCAT GTGGTGATTC CCCGGATCCA CCCCAACTCC
       L  S  I   G  F  E   T  C  R  Y   G  F  I   E  G  H   V  V  I  P   R  I  H   P  N  S

        --CHO--
 401 ATCTGTGCAG CAAACAACAC AGGGGTGTAC ATCCTCACAT ACAACACCTC CCAGTATGAC ACATATTGCT TCAATGCTTC
     I  C  A  A   N  N  T   G  V  Y   I  L  T  Y   N  T  S   Q  Y  D   T  Y  C  F   N  A  S

                                                              --CHO--
 481 AGCTCCACCT GAAGAAGATT GTACATCAGT CACAGACCTG CCCAATGCCT TTGATGGACC AATTACCATA ACTATTGTTA
      A  P  P   E  E  D  C   T  S  V   T  D  L   P  N  A  F   D  G  P   I  T  I   T  I  V  N

       --CHO--                          --CHO--
 561 ACCGTGATGG CACCCGCTAT GTCCAGAAAG GAGAATACAG AACGAATCCT GAAGACATCT ACCCCAGCAA CCCTACTGAT
       R  D  G   T  R  Y   V  Q  K  G   E  Y  R   T  N  P   E  D  I  Y   P  S  N   P  T  D

 641 GATGACGTGA GCAGCGGCTC CTCCAGTGAA AGGAGCAGCA CTTCAGGAGG TTACATCTTT TACACCTTTT CTACTGTACA
     D  D  V  S   S  G  S   S  S  E   R  S  S  T   S  G  G   Y  I  F   Y  T  F  S   T  V  H
                  ----                             ----

 721 CCCCATCCCA GACGAAGACA GTCCCTGGAT CACCGACAGC ACAGACAGAA TCCCTGCTAC CAGAGACCAA GACACATTCC
      P  I  P   D  E  D  S   P  W  I   T  D  S   T  D  R  I   P  A  T   R  D  Q   D  T  F  H

 801 ACCCCAGTGG GGGGTCCCAT ACCACTCATG AATCTGAATC AGATGGACAC TCACATGGGA GTCAAGAAGG TGGAGCAAAC
       P  S  G   G  S  H   T  T  H  E   S  E  S   D  G  H   S  H  G  S   Q  E  G   G  A  N

 881 ACAACCTCTG GTCCTATAAG GACACCCCAA ATTCCAGAAT GGCTGATCAT CTTGGCATCC CTCTTGGCCT TGGCTTTGAT
     T  T  S  G   P  I  R   T  P  Q   I  P  E  W   L  I  I   L  A  S   L  L  A  L   A  L  I
           ----                                = ========== ========== ========== ==========

                                             --C HO--
 961 TCTTGCAGTT TGCATTGCAG TCAACAGTCG AAGAAGGTGT GGGCAGAAGA AAAAGCTAGT GATCAACAGT GGCAATGGAG
      L  A  V   C  I  A  V   N  S  R   R  R  C   G  Q  K  K   K  L  V   I  N  S   G  N  G  A
     ========== ========== ==

1041 CTGTGGAGGA CAGAAAGCCA AGTGGACTCA ACGGAGAGGC CAGCAAGTCT CAGGAAATGG TGCATTTGGT GAACAAGGAG
       V  E  D   R  K  P   S  G  L  N   G  E  A   S  K  S   Q  E  M  V   H  L  V   N  K  E

1121 TCGTCAGAAA CTCCAGACCA GTTTATGACA GCTGATGAGA CAAGGAACCT GCAGAATGTG GACATGAAGA TTGGGGTGTA
     S  S  E  T   P  D  Q   F  M  T   A  D  E  T   R  N  L   Q  N  V   D  M  K  I   G  V  *

1201 ACACCTACAC CATTATCTTG GAAAGAAACA ACCGTTGTAA ACATAACCAT TACAGGGAGC TGGGACACTT AACAGATGCA

1281 ATGTGCTACT GATTGTTTCA TTGCGAATCT TTTTTAGCAT AAAATTTTCT ACTCTTTTTG TTAAAAAAAA AAAA  1354
```

HUT-102 and HPB-ALL, lymphokine activated T cells, tonsillar B cells and the histiocytic lymphoma U937.

Immunoprecipitation of CD44 from transfected COS cells reveals that the mesenchymal or hematopoietic form of CD44 is about 80–90 kd. Hematopoietic CD44 transfected into a B cell line has been observed to result in the binding of the CD44-bearing lymphocytes to rat lymph node stromal cells in primary culture, indicating that hematopoietic CD44 may play a role in lymphocyte homing. It has been shown that hematopoietic CD44 is an extracellular matrix receptor with affinity for collagens type I and VI (Stamenkovic et al., *Cell* 56:1057–1062 (1989)). Hematopoietic CD44 may also have a lymphocyte activation role.

The ability to interfere with the binding of hematopoietic CD44 to lymph node cells, or the ability to cause such binding to occur on other surfaces, can be useful in diagnostics and therapy. For example, modification of this binding can serve to regulate the homing potential of lymphocytes. Soluble forms of CD44 can have immunomodulatory activity.

To isolate a cDNA clone encoding the epithelial form of CD44, a cDNA library prepared from the colon carcinoma line HT29 was transfected into COS cells by the DEAE-Dextran method described supra. The cells were pooled 48 hours after transfection, incubated with anti-CD44 monoclonal antibody F-10-44-2 (Dalchau et al., *Eur. J. Immunol.* 10:745–749 (1980)) and panned on dishes coated with goat-anti-mouse affinity purified antibody. After several washes, the adherent cells were lysed, and episomal DNA purified and transformed into *E. coli*. After two similar rounds of enrichment following spheroplast fusion, as described supra, plasmid DNA recovered from seven out of ten randomly picked colonies was found to direct the appearance of epithelial CD44 determinants on transfected COS cells. All seven of the positive clones bore cDNA inserts of about 2.4 kb.

Restriction enzyme analysis of the clone containing the epithelial cDNA insert showed that the coding sequence (Table 8) was enlarged relative to the hematopoietic CD44 insert by the addition of 496 base pair. DNA sequence analysis showed that the epithelial CD44 cDNA is quite similar to the CD44.5 cDNA, but encoded an additional extracellular domain of 165 amino acids, inserted about 140 residues upstream of the transmembrane section shared by both clones. The mature protein would comprise 493 residues.

RNA blot analysis has revealed that the epithelial CD44 transcripts comprise 2.2, 2.7 and 5.5 kb species. Epithelial CD44 isolated by immunoprecipitation has revealed that the glycoprotein is about 160 kd.

Transfected B cells expressing epithelial CD44 do not adhere to rat lymph node stromal cells in primary culture as do hematopoietic CD44 transfected lymphocytes. The epithelial CD44 is weakly expressed by normal epithelium but highly expressed by carcinomas. It is possible that an extracellular matrix receptor function of epithelial CD44 may promote tumor invasiveness.

The ability to interfere with the binding of epithelial CD44 with extracellular matrices can be useful in therapy or diagnostics. For example, interference of the epithelial CD44 binding to extracellular matrices can diminish the likelihood of metastasis in cancer patients. Soluble forms of CD44 can act to prevent metastatic cells from "homing" to lymph nodes.

EXAMPLE XVI

The Isolation and Molecular Cloning of cDNA Encoding CD53 Antigens

CD53, the antigen recognized by antibodies MEM-53 (Hadam, M. R. (1989) in *Leucocyte Typing IV*, Knapp, B. et al. (eds.) Oxford Univ. Press, p. 674), HD77, HI29 and HI36, and 63-5A3, is a glycoprotein widely distributed among, but strictly restricted to, nucleated cells of the hematopoietic lineages (Stevanova, I., et al., (1989) in *Leucocyte Typing IV*, Knapp, B. et al. (eds.) Oxford Univ. Press, p. 678). CD53 is expressed by monocytes and

TABLE 8

(SEQ ID NO:33) and (SEQ ID NO:34)

```
  1  CCAGCCTCTG CCAGGTTCGG TCCGCCATCC TCGTCCCGTC CTCCGCCGGC CCCTGCCCCG CGCCCAGGGA TCCTCCAGCT

 81  CCTTTCGCCC GCGCCCTCCG TTCGCTCCGG ACACCATGGA CAAGTTTTGG TGGCACGCAG CCTGGGGACT CTGCCTCGTG
                                           M  D   K  F  W   W  H  A  A   W  G  L   C  L  V

161  CCGCTGAGCC TGGCGCAGAT CGATTTGAAT ATAACCTGCC GCTTTGCAGG TGTATTCCAC GTGGAGAAAA ATGGTCGCTA
     P  L  S  L   A  Q  I   D  L  N   I  T  C  R   F  A  G   V  F  H   V  E  K  N   G  R  Y

                                                                              --C HO--
241  CAGCATCTCT CGGACGGAGG CCGCTGACCT CTGCAAGGCT TTCAATAGCA CCTTGCCCAC AATGGCCCAG ATGGAGAAAG
      S  I  S   R  T  E  A   A  D  L   C  K  A   F  N  S  T   L  P  T   M  A  Q   M  E  K  A

321  CTCTGAGCAT CGGATTTGAG ACCTGCAGGT ATGGGTTCAT AGAAGGGCAT GTGGTGATTC CCCGGATCCA CCCCAACTCC
       L  S  I   G  F  E   T  C  R  Y   G  F  I   E  G  H   V  V  I  P   R  I  H   P  N  S

        --CHO--
401  ATCTGTGCAG CAAACAACAC AGGGGTGTAC ATCCTCACAT ACAACACCTC CCAGTATGAC ACATATTGCT TCAATGCTTC
     I  C  A  A   N  N  T   G  V  Y   I  L  T  Y   N  T  S   Q  Y  D   T  Y  C  F   N  A  S

                                                              --CHO--
481  AGCTCCACCT GAAGAAGATT GTACATCAGT CACAGACCTG CCCAATGCCT TTGATGGACC AATTACCATA ACTATTGTTA
      A  P  P   E  E  D  C   T  S  V   T  D  L   P  N  A  F   D  G  P   I  T  I   T  I  V  N

       --CHO--                          --CHO--
561  ACCGTGATGG CACCCGCTAT GTCCAGAAAG GAGAATACAG AACGAATCCT GAAGACATCT ACCCCAGCAA CCCTACTGAT
       R  D  G   T  R  Y   V  Q  K  G   E  Y  R   T  N  P   E  D  I  Y   P  S  N   P  T  D
```

TABLE 8-continued (SEQ ID NO:33) and (SEQ ID NO:34)

```
 641 GATGACGTGA GCAGCGGCTC CTCCAGTGAA AGGAGCAGCA CTTCAGGAGG TTACATCTTT TACACCTTTT CTACTGTACA
     D  D  V  S   S  G  S   S  S  E   R  S  S  T   S  G  G   Y  I  F   Y  T  F  S   T  V  H
              ----                                ----

 721 CCCCATCCCA GACGAAGACA GTCCCTGGAT CACCGACAGC ACAGACAGAA TCCCTCGTAC CAATATGGAC TCCAGTCATA
      P  I  P   D  E  D  S   P  W  I   T  D  S   T  D  R  I   P  R  T   N  M  D   S  S  H  S

 801 GTACAACGCT TCAGCCTACT GCAAATCCAA ACACAGGTTT GGTGGAAGAT TTGGACAGGA CAGGACCTCT TTCAATGACA
       T  T  L   Q  P  T   A  N  P  N   T  G  L   V  E  D   L  D  R  T   G  P  L   S  M  T

 881 ACGCAGCAGA GTAATTCTCA GAGCTTCTCT ACATCACATG AAGGCTTGGA AGAAGATAAA GACCATCCAA CAACTTCTAC
     T  Q  Q  S   N  S  Q   S  F  S   T  S  H  E   G  L  E   E  D  K   D  H  P  T   T  S  T

 961 TCTGACATCA AGCAATAGGA ATGATGTCAC AGGTGGAAGA AGAGACCCAA ATCATTCTGA AGGCTCAACT CATTTACTGG
      L  T  S   S  N  R  N   D  V  T   G  G  R   R  D  P  N   H  S  E   G  S  T   H  L  L  E

1041 AAGGTTATAC CTCTCATTAC CCACACACGA AGGAAAGCAG GACCTTCATC CCAGTGACCT CAGCTAAGAC TGGGTCCTTT
       G  Y  T   S  H  Y   P  H  T  K   E  S  R   T  F  I   P  V  T  S   A  K  T   G  S  F

1121 GGAGTTACTG CAGTTACTGT TGGAGATTCC AACTCTAATG TCAATCGTTC CTTATCAGGA GACCAAGACA CATTCCACCC
     G  V  T  A   V  T  V   G  D  S   N  S  N  V   N  R  S   L  S  G   D  Q  D  T   F  H  P

1201 CAGTGGGGGG TCCCATACCA CTCATGGATC TGAATCAGAT GGACACTCAC ATGGGAGTCA AGAAGGTGGA GCAAACACAA
      S  G  G   S  H  T  T   H  G  S   E  S  D   G  H  S  H   G  S  Q   E  G  G   A  N  T  T

1281 CCTCTGGTCC TATAAGGACA CCCCAAATTC CAGAATGGCT GATCATCTTG GCATCCCTCT TGGCCTTGGC TTTGATTCTT
       S  G  P   I  R  T   P  Q  I  P   E  W  L   I  I  L   A  S  L  L   A  L  A   L  I  L
      ----                                =====  =========  ==========  =========  =========

                                            --CHO--
1361 GCAGTTTGCA TTGCAGTCAA CAGTCGAAGA AGGTGTGGGC AGAAGAAAAA GCTAGTGATC AACAGTGGCA ATGGAGCTGT
     A  V  C  I   A  V  N   S  R  R   R  C  G  Q   K  K  K   L  V  I   N  S  G  N   G  A  V
     __________  _______

1441 GGAGGACAGA AAGCCAAGTG GACTCAACGG AGAGGCCAGC AAGTCTCAGG AAATGGTGCA TTTGGTGAAC AAGGAGTCGT
      E  D  R   K  P  S  G   L  N  G   E  A  S   K  S  Q  E   M  V  H   L  V  N   K  E  S  S

1521 CAGAAACTCC AGACCAGTTT ATGACAGCTC ATGAGACAAG GAACCTGCAG AATGTGGACA TGAAGATTGG GGTGTAACAC
       E  T  P   D  Q  F   M  T  A  D   E  T  R   N  L  Q   N  V  D  M   K  I  G   V  *

1601 CTACACCATT ATCTTGGAAA GAAACAACGT TGGAAACATA ACCATTACAG GGGAGCTGGG ACACTTAACA GATGCAATGT

1681 GCTACTGATT GTTTCATTTC GAATCTATAA TAGCATAAAA TTTTCTACTC TTTTTGTTTT TTGTGTTTTG TTCTTTAAAG

1761 TCAGGTCCAA TTTGTAAAAA CAGCATTGCT TTCTGAAATT AGGGCCCAAT TAATAATCAG CAAGAATTTT GATCGTTTCA

1841 GTTCCCCACT TGGAGGCCTT TCATCCCTCC GGTGTGCTAT GGATGGCTTC TAACAAAAAC CTACCACATA GTTATTCCTG

1921 ATCGCCAACC TTGCCCCCCA CCAGCTAAGG ACATTTCCAG GGTTAATAGG GCCTGGTCCT GGGAGGAAAT TTGAATGGCT

2001 CATTTTCCCC TTCCATTAGC CTAATCCCTG GGCATTGCTT TCCACTGAGG TTGGGGGTTG GGGTGTACTA GTTACACATC

2081 TTCAACAGAC CCCCTCTAGA AATTTTTCAG ATGCTTCTGG GAGACACCCA AAGGGTAAGT CTATTTATCT GTAGTAAACT

2161 ATTTATCTGT GTTTTTGAAA TATTAAACCC TGGATCAGTC CTTTTATTCA GTATAATTTT TTAAAGTTAC TTTGTCAGAG

2241 GCACAAAAAG GGTTTAAACT GATTCATAAT AAATATCTGT ACCTTCTTCG AAAAAAAAAA AAAAAAAA
```

macrophages, by granulocytes, dendritic cells, osteoclasts and osteoblasts, and by T and B cells from every stage of differentiation.

To obtain a cDNA clone encoding CD53, cDNA libraries constructed from peripheral blood lymphocytes and the promyelocytic tumor cell line HL60 were transfected into COS cells by the DEAE-Dextran method, described supra. The cells were pooled 48 hours after transfection, incubated with monoclonal antibodies MEM-53, and panned as described in Seed and Aruffo, *Proc. Natl. Acad. Sci. USA* 84:3365–3369 (1987) and Aruffo and Seed, *Proc. Natl. Acad. Sci. USA* 84:8573–8577 (1987). After two subsequent rounds of enrichment following spheroplast fusion, plasmid DNA recovered from single colony isolates was transfected into COS cells, and scored for CD53 expression by immunofluorescence.

Two of eight transfectants were positive, each bearing an insert of about 1.5 kb. COS cells transfected with either clone reacted with each of the antibodies MEM-53, HI29, HI36 and 63-5A3.

To isolate CD53 from peripheral blood lymphocytes and transfected COS cells for purposes of comparison, the lymphocytes and transfected COS cells were surface labeled with $^{125}I$ using lactoperoxidase and $H_2O_2$, and then lysed in a lysis buffer of 50 mM Tris-HCl pH 8.0 containing 1% NP40, 150 mM NaCl, 5 mM $MgCl_2$, 5 mM KCl, 20 mM iodoacetamide and 1 mM phenylmethylsulfonyl-fluoride.

Cells were solubilized at a concentration of $2.5\times10^7$ cells/ml in lysis buffer for 45 minutes then centrifuged at 12,000 g. After preclearing with goat anti-mouse immunoglobulin beads (Cappel, Malvern, Pa.), immunoprecipitations were performed with monoclonal antibodies MEM53 or 63-5A3 and protein A-Sepharose CL-4B (Sigma, St. Louis, Mo.) as described by Schneider et al. (*J. Biol. Chem.* 257:10766 (1982)). Immunoprecipitates were eluted in SDS-sample buffer and analyzed on 12.5% acrylamide gels containing sodium dodecyl sulfate.

A broad band of radioiodinated protein ranging in mass from 34 kd to 42 kd was obtained from peripheral blood lymphocytes either with MEM-53 or 63-5A3 monoclonal antibodies, comparable to the band obtained from CD53-transfected COS cells, which extended from 36 kd to 46 kd. The higher molecular mass in COS cells is a typical, as cell surface proteins recovered from transfected COS cells usually display unchanged or lower molecular mass than those found on the cell from which the cDNA clone originated (Aruffo and Seed, *Proc. Natl. Acad. Sci. USA* 84:3365–3369 (1987)). Approximately 15 kd of mass are liberated from the glycoprotein by digestion with endoglycosidase F (N-glycanase), whereas treatment with neuraminidase and O-glycanase has no effect on the apparent molecular mass (Hadam, M. R. (1989) in *Leucocyte Typing IV*, Knapp, B. et al. (eds.) Oxford Univ. Press, p. 674; Stevanova et al., in *Leucocyte Typing IV*, Knapp, B. et al. (eds.) Oxford Univ. Press, p. 678). An additional faint band of 20 kd, possibly unglycosylated precursor, was detected in immunoprecipitates of transfected COS cells, but was absent from immunoprecipitates of peripheral blood lymphocytes.

Blot hybridization of genomic DNA from the T cell line PEER digested with several enzymes revealed a pattern consistent with a single copy gene. RNA blot analysis revealed a single 1.8 kb mRNA derived from B, T, and myeloid cell lines and from peripheral blood lymphocytes. The level of expression was comparable in the different cell lines except in THP1 cell line, which had little CD53 mRNA. CD53 transcripts are more abundant in peripheral blood lymphocytes than in cultivated cell lines, consistent with the higher surface expression of CD53 among these cells.

The nucleotide sequence of CD53 cDNA was determined by dideoxynucleotide chain termination as described, supra, using synthetic oligonucleotide primers. The sequence of the CD53 insert consists of 1452 nucleotides (Table 9), and terminates close to two overlapping AATAAA motifs (singly underlined). The 3' noncoding sequence contains three examples of the ATTTA sequence (indicated by quotation marks), which has been shown to mediate mRNA instability (Shaw and Kamen, *Cell* 46:659 (1986)). An open reading frame beginning at residue 74 encodes a protein of 219 amino acids with a predicted molecular weight of 24,340 kd.

The predicted polypeptide is unusual in that it bears four major hydrophobic segments (doubly underlined), three of which fall in close proximity near the amino terminus of the molecule. The first hydrophobic segment is a typically long for either a signal sequence or a simple transmembrane alpha helix, and contains three cysteine residues and a glycine located in the middle. Both cysteine and glycine have been found to immediately precede the signal cleavage site (von Heijne, *Nucleic Acids Res.* 14:4683 (1986)), suggesting that the amino terminus of the mature protein begins in the middle of the first hydrophobic domain. Some support for this view is afforded by the finding that the size of the polypeptide backbone of ME491, a related type III integral membrane protein, discussed infra, is smaller than the size predicted from the cDNA sequence, possibly as a consequence of signal peptide excision. Because there are only two potential sites for N-linked glycan addition (indicated in Table 9 by —CHO— designations), located between the third and fourth hydrophobic segments, the carboxyl terminus must lie inside the cell, as well as the short hydrophilic portion between the second and third hydrophobic segments. If the amino terminus is not processed, it must likewise remain intracellular.

CD53 is a Type III integral membrane protein related to three other membrane proteins: ME491 antigen, a melanoma protein whose increased expression correlates well with tumor progression (Hotta et al., *Cancer Res.* 48:2955 (1988)); CD37, an extensively glycosylated antigen predominantly expressed on B cells, but not B cell lineage specific (Schwartz et al., *J. Immun.* 140:905 (1988); and S5.7, an unglycosylated antigen broadly expressed on cells of hematopoietic lineage (Pressano et al., *Cancer Res.* 43:4812 (1983)). In addition, CD53 is distantly related to *E. coli* lac Y permease, a type III integral membrane protein which ferries lactose into the bacterial cell. CD53 transcripts in peripheral blood lymphocytes increase in prevalence following mitogenic stimulation by PHA, suggesting that the protein may be involved in the transport of factors essential for cell proliferation.

Among the molecules with broad reactivity in the hemopoietic system, CD53 presently holds the widest reactivity as well as the strictest restriction to hematopoietic cells. Anti-CD53 antibodies are a useful tool for the identification of hematopoietic neoplasms, and may prove helpful for identifying morphologically poorly defined cells, for example in spleen or bone marrow primary cultures.

Equivalents

Those skilled in the art will recognize or be able to ascertain, using no more than routine experimentation, many equivalents to the specific embodiments of the invention described herein. Such equivalents are intended to be encompassed within the scope of this invention.

TABLE 9

(SEQ ID NO:35) and (SEQ ID NO:36)

```
    1  CTCAAGGATA ATCACTAAAT TCTGCCGAAA GGACTGAGGA ACGGTGCCTG GAAAAGGGCA AGAATATCAC GGCATGGGCA
                                                                                  M  G  M

   81  TGAGTAGCTT GAAACTGCTG AAGTATGTCC TGTTTTTCTT CAACTTGCTC TTTTGGATCT GTGGCTGCTG CATTTTGGGC
         S  S  L   K  L  L  K  Y  V  L   F  F  F   N  L  L   F  W  I  C   G  C  C   I  L  G
                       ------ ---------- ---------- ---------- ---------- ---------- ----------

  161  TTTGGGATCT ACCTGCTGAT CCACAACAAC TTCGGAGTGC TCTTCCATAA CCTCCCCTCC CTCACGCTGG GCAATGTGTT
       F  G  I  Y   L  L  I   H  N  N   F  G  V  L   F  H  N   L  P  S   L  T  L  G   N  V  F
       ========== ==========                                                               =====
```

TABLE 9-continued (SEQ ID NO:35) and (SEQ ID NO:36)

```
 241 TGTCATCGTG GGCTCTATTA TCATGGTAGT TGCCTTCCTG GGCTGCATGG GCTCTATCAA GGAAAACAAG TGTCTGCTTA
      V  I  V   G  S  I  I   M  V  V   A  F  L   G  C  M  G   S  I  K   E  N  K   C  L  L  M
     ———————— ———————— ———————— ———————— ———————— ——————                 —————

 321 TGTCGTTCTT CATCCTGCTG CTGATTATCC TCCTTGCTGA GGTGACCTTG GCCATCCTGC TCTTTGTATA TGAACAGAAG
      S  F  F   I  L  L   L  I  I  L   L  A  E   V  T  L   A  I  L  L   F  V  Y   E  Q  K
     ———————— ———————— ———————— ———————— ———————— ———————— ————————

 401 CTGAATGAGT ATGTGGCTAA GGGTCTGACC GACAGCATCC ACCGTTACCA CTCAGACAAT AGCACCAAGG CAGCGTGGGA
     L  N  E  Y   V  A  K   G  L  T   D  S  I  H   R  Y  H   S  D  N   S  T  K  A   A  W  D

                                                 --C HO--
 481 CTCCATCCAG TCATTTCTGC AGTGTTGTGG TATAAATGGC ACGAGTGATT GGACCAGTGG CCCACCAGCA TCTTGCCCCT
      S  I  Q   S  F  L  Q   C  C  G   I  N  G   T  S  D  W   T  S  G   P  P  A   S  C  P  S

                    --CHO-
 561 CAGATCGAAA AGTGGAGGGT TGCTATGCGA AAGCAAGACT GTGGTTTCAT TCCAATTTCC TGTATATCGG AATCATCACC
      D  R  K   V  E  G   C  Y  A  K   A  R  L   W  F  H   S  N  F  L   Y  I  G   I  I  T
                                                                ———  ———————— ————————

 641 ATCTGTGTAT GTGTGATTGA GGTGTTGGGG ATGTCCTTTG CACTGACCCT GAACTGCCAG ATTGACAAAA CCAGCCAGAC
     I  C  V  C   V  I  E   V  L  G   M  S  F  A   L  T  L   N  C  Q   I  D  K  T   S  Q  T
     ———————— ———————— ———————— ———————— ————————

 721 CATAGGGCTA TGATCTGCAG TAGTTCTGTG GTGAAGAGAC TTGTTTCATC TCCGGAAATG CAAAACCATT TATAGCATGA
      I  G  L   *                                                              """ ""

 801 AGCCCTACAT GATCACTGCA GGATGATCCT CCTCCCATCC TTTCCCTTTT TAGGTCCCTG TCTTATACAA CCAGAGAAGT

 881 GGGTGTTGGC CAGGCACATC CCATCTCAGG CAGCAAGACA ATCTTTCACT CACTGACGGC AGCAGCCATG TCTCTCAAAG

 961 TGGTGAAACT AATATCTGAG CATCTTTTAG ACAAGAGAGG CAAAGACAAA CTGGATTTAA TGGCCCAACA TCAAAGGGTG
                                                          """""

1041 AACCCAGGAT ATGAATTTTT GCATCTTCCC ATTGTCGAAT TAGTCTCCAG CCTCTAAATA ATGCCCAGTC TTCTCCCCAA

1121 AGTCAAGCAA GAGACTAGTT GAAGGGAGTT CTGGGGCCAG GCTCACTGGA CCATTGTCAC AACCCTCTGT TTCTCTTTGA

1201 CTAAGTGCCC TGGCTACAGG AATTACACAG TTCTCTTTCT CCAAAGGGCA AGATCTCATT TCAATTTCTT TATTAGAGGG

1281 CCTTATTGAT GTGTTCTAAG TCTTTCCAGA AAAAAACTAT CCAGTGATTT ATATCCTGAT TTCAACCAGT CACTTAGCTG
                                                """" "

1361 ATAATCACAG TAAGAAGACT TCTGGTATTA TCTCTCTATC AGATAAGATT TTGTTAATGT ACTATTTTAC TCTTCAATAA
                                                                                     -----

1441 ATAAAACAGT TT  1452
     -----
```

The invention claimed is:

1. An isolated cDNA comprising SEQ ID NO:28.

* * * * *

SEQUENCE LISTING

<160> NUMBER OF SEQ ID NOS: 41

<210> SEQ ID NO 1
<211> LENGTH: 2932
<212> TYPE: DNA
<213> ORGANISM: artificial
<220> FEATURE:
<223> OTHER INFORMATION: Nucleotide sequence of piH3 vector

<400> SEQUENCE: 1

```
ggcgtaatct gctgcttgca aacaaaaaaa ccaccgctac cagcggtggt ttgtttgccg     60

gatcaagagc taccaactct ttttccgaag gaactggctt cagcagagcg cagataccaa    120

atactgtcct tctagtgtag ccgtagttag gccaccactt caagaactct gtagcaccgc    180

ctacatacct cgctctgcta atcctgttac cagtggctgc tgccagtggc gataagtcgt    240
```

-continued

```
gtcttaccgg gttggactca agacgatagt taccggataa ggcgcagcgg tcgggctgaa    300
cgggggggttc gtgcacacag cccagcttgg agcgaacgac ctacaccgaa ctgagatacc    360
tacagcgtga gctatgagaa agcgccacgc ttcccgaagg gagaaaggcg gacaggtatc    420
cggtaagcgg cagggtcgga acaggagagc gcacgaggga gcttccaggg ggaaacgcct    480
ggtatcttta tagtcctgtc gggtttcgcc acctctgact tgagcgtcga tttttgtgat    540
gctcgtcagg ggggcggagc ctatggaaaa acgccagcaa cgccgaatta ccgcggtgtt    600
tctcaacgta acactttaca gcggcgcgtc atttgatatg atgcgccccg cttcccgata    660
agggagcagg ccagtaaaag cattacccgt ggtggggttc ccgagcggcc aaagggagca    720
gactctaaat ctgccgtcat cgacttcgaa ggttcgaatc cttcccccac caccatcact    780
ttcaaaagtc cgaaagaatc tgctccctgc ttgtgtgttg gaggtcgctg agtagtgcgc    840
gagtaaaatt taagctacaa caaggcaagg cttgaccgac aattgcatga agaatctgct    900
tagggttagg cgttttgcgc tgcttcgcga tgtacgggcc agatatacgc gttgacattg    960
attattgact agttattaat agtaatcaat tacggggtca ttagttcata gcccatatat   1020
ggagttccgc gttacataac ttacggtaaa tggcccgcct ggctgaccgc ccaacgaccc   1080
ccgcccattg acgtcaataa tgacgtatgt tcccatagta acgccaatag ggactttcca   1140
ttgacgtcaa tgggtggact atttacggta aactgcccac ttggcagtac atcaagtgta   1200
tcatatgcca agtacgcccc ctattgacgt caatgacggt aaatggcccg cctggcatta   1260
tgcccagtac atgaccttat gggactttcc tacttggcag tacatctacg tattagtcat   1320
cgctattacc atggtgatgc ggttttggca gtacatcaat gggcgtggat agcggtttga   1380
ctcacgggga tttccaagtc tccaccccat tgacgtcaat gggagtttgt tttggcacca   1440
aaatcaacgg gactttccaa aatgtcgtaa caactccgcc ccattgacgc aaatgggcgg   1500
aattcctggg cgggactggg gagtggcgag ccctcagatg ctgcatataa gcagctgctt   1560
tttgcctgta ctgggtctct ctggttagac cagatctgag cctgggagct ctctggctaa   1620
ctagagaacc cactgcttaa gcctcaataa agcttctaga gatccctcga cctcgaggga   1680
tcttccatac ctaccagttc tgcgcctgca ggtcgcggcc gcgactctag aggatctttg   1740
tgaaggaacc ttacttctgt ggtgtgacat aattggacaa actacctaca gagatttaaa   1800
gctctaaggt aaatataaaa tttttaagtg tataatgtgt taaactactg attctaattg   1860
tttgtgtatt ttagattcca acctatggaa ctgatgaatg ggagcagtgg tggaatgcct   1920
ttaatgagga aaacctgttt tgctcagaag aaatgccatc tagtgatgat gaggctactg   1980
ctgactctca acattctact cctccaaaaa agaagagaaa ggtagaagac cccaaggact   2040
ttccttcaga attgctaagt tttttgagtc atgctgtgtt tagtaataga actcttgctt   2100
gctttgctat ttacaccaca aaggaaaaag ctgcactgct atacaagaaa attatggaaa   2160
aatattctgt aacctttata agtaggcata acagttataa tcataacata ctgttttttc   2220
ttactccaca caggcataga gtgtctgcta ttaataacta tgctcaaaaa ttgtgtacct   2280
ttagcttttt aatttgtaaa ggggttaata aggaatattt gatgtatagt gccttgacta   2340
gagatcataa tcagccatac cacatttgta gaggttttac ttgctttaaa aaacctccca   2400
cacctccccc tgaacctgaa acataaaatg aatgcaattg ttgttgttaa cttgtttatt   2460
gcagcttata atggttacaa ataaagcaat agcatcacaa atttcacaaa taaagcattt   2520
ttttcactgc attctagttg tggtttgtcc aaactcatca atgtatctta tcatgtctgg   2580
atcctgtgga atgtgtgtca gttagggtgt ggaaagtccc caggctcccc agcaggcaga   2640
```

```
agtatgcaaa gcatgcatct caattagtca gcaaccaggt gtggaaagtc cccaggctcc   2700

ccagcaggca gaagtatgca aagcatgcat ctcaattagt cagcaaccat agtcccgccc   2760

ctaactccgc ccatcccgcc cctaactccg cccagttccg cccattctcc gccccatggc   2820

tgactaattt tttttattta tgcagaggcc gaggccgcct cggcctctga gctattccag   2880

aagtagtgag gaggcttttt tggaggccta ggcttttgca aaaagctaat tc           2932


<210> SEQ ID NO 2
<211> LENGTH: 1504
<212> TYPE: DNA
<213> ORGANISM: Homo sapiens
<220> FEATURE:
<221> NAME/KEY: CDS
<222> LOCATION: (7)..(1059)

<400> SEQUENCE: 2

cctaag atg agc ttt cca tgt aaa ttt gta gcc agc ttc ctt ctg att        48
       Met Ser Phe Pro Cys Lys Phe Val Ala Ser Phe Leu Leu Ile
       1               5                   10

ttc aat gtt tct tcc aaa ggt gca gtc tcc aaa gag att acg aat gcc        96
Phe Asn Val Ser Ser Lys Gly Ala Val Ser Lys Glu Ile Thr Asn Ala
15                  20                  25                  30

ttg gaa acc tgg ggt gcc ttg ggt cag gac atc aac ttg gac att cct       144
Leu Glu Thr Trp Gly Ala Leu Gly Gln Asp Ile Asn Leu Asp Ile Pro
                35                  40                  45

agt ttt caa atg agt gat gat att gac gat ata aaa tgg gaa aaa act       192
Ser Phe Gln Met Ser Asp Asp Ile Asp Asp Ile Lys Trp Glu Lys Thr
            50                  55                  60

tca gac aag aaa aag att gca caa ttc aga aaa gag aaa gag act ttc       240
Ser Asp Lys Lys Lys Ile Ala Gln Phe Arg Lys Glu Lys Glu Thr Phe
        65                  70                  75

aag gaa aaa gat aca tat aag cta ttt aaa aat gga act ctg aaa att       288
Lys Glu Lys Asp Thr Tyr Lys Leu Phe Lys Asn Gly Thr Leu Lys Ile
    80                  85                  90

aag cat ctg aag acc gat gat cag gat atc tac aag gta tca ata tat       336
Lys His Leu Lys Thr Asp Asp Gln Asp Ile Tyr Lys Val Ser Ile Tyr
95                  100                 105                 110

gat aca aaa gga aaa aat gtg ttg gaa aaa ata ttt gat ttg aag att       384
Asp Thr Lys Gly Lys Asn Val Leu Glu Lys Ile Phe Asp Leu Lys Ile
                115                 120                 125

caa gag agg gtc tca aaa cca aag atc tcc tgg act tgt atc aac aca       432
Gln Glu Arg Val Ser Lys Pro Lys Ile Ser Trp Thr Cys Ile Asn Thr
            130                 135                 140

acc ctg acc tgt gag gta atg aat gga act gac ccc gaa tta aac ctg       480
Thr Leu Thr Cys Glu Val Met Asn Gly Thr Asp Pro Glu Leu Asn Leu
        145                 150                 155

tat caa gat ggg aaa cat cta aaa ctt tct cag agg gtc atc aca cac       528
Tyr Gln Asp Gly Lys His Leu Lys Leu Ser Gln Arg Val Ile Thr His
    160                 165                 170

aag tgg acc acc agc ctg agt gca aaa ttc aag tgc aca gca ggg aac       576
Lys Trp Thr Thr Ser Leu Ser Ala Lys Phe Lys Cys Thr Ala Gly Asn
175                 180                 185                 190

aaa gtc agc aag gaa tcc agt gtc gag cct gtc agc tgt cca gag aaa       624
Lys Val Ser Lys Glu Ser Ser Val Glu Pro Val Ser Cys Pro Glu Lys
                195                 200                 205

ggt ctg gac atc tat ctc atc att ggc ata tgt gga gga ggc agc ctc       672
Gly Leu Asp Ile Tyr Leu Ile Ile Gly Ile Cys Gly Gly Gly Ser Leu
            210                 215                 220

ttg atg gtc ttt gtg gca ctg ctc gtt ttc tat atc acc aaa agg aaa       720
```

-continued

```
Leu Met Val Phe Val Ala Leu Leu Val Phe Tyr Ile Thr Lys Arg Lys
        225                 230                 235

aaa cag agg agt cgg aga aat gat gag gag ctg gag aca aga gcc cac      768
Lys Gln Arg Ser Arg Arg Asn Asp Glu Glu Leu Glu Thr Arg Ala His
    240                 245                 250

aga gta gct act gaa gaa agg ggc cgg aag ccc cac caa att cca gct      816
Arg Val Ala Thr Glu Glu Arg Gly Arg Lys Pro His Gln Ile Pro Ala
255                 260                 265                 270

tca acc cct cag aat cca gca act tcc caa cat cct cct cca cca cct      864
Ser Thr Pro Gln Asn Pro Ala Thr Ser Gln His Pro Pro Pro Pro Pro
                275                 280                 285

ggt cat cgt tcc cag gca cct agt cat cgt ccc ccg cct cct gga cac      912
Gly His Arg Ser Gln Ala Pro Ser His Arg Pro Pro Pro Pro Gly His
            290                 295                 300

cgt gtt cag cac cag cct cag aag agg cct cct gct ccg tcg ggc aca      960
Arg Val Gln His Gln Pro Gln Lys Arg Pro Pro Ala Pro Ser Gly Thr
        305                 310                 315

caa gtt cac cag cag aaa ggc ccg ccc ctc ccc aga cct cga gtt cag     1008
Gln Val His Gln Gln Lys Gly Pro Pro Leu Pro Arg Pro Arg Val Gln
    320                 325                 330

cca aaa cct ccc cat ggg gca gca gaa aac tca ttg tcc cct tcc tct     1056
Pro Lys Pro Pro His Gly Ala Ala Glu Asn Ser Leu Ser Pro Ser Ser
335                 340                 345                 350

aat taaaaaagat agaaactgtc tttttcaata aaaagcactg tggatttctg          1109
Asn

ccctcctgat gtgcatatcc gtacttccat gaggtgtttt ctgtgtgcag aacattgtca   1169

cctcctgagg ctgtgggcca cagccacctc tgcatcttcg aactcagcca tgtggtcaac   1229

atctggagtt tttggtctcc tcagagagct ccatcacacc agtaaggaga agcaatataa   1289

gtgtgattgc aagaatggta gaggaccgag cacagaaatc ttagagattt cttgtcccct   1349

ctcaggtcat gtgtagatgc gataaatcaa gtgattggtg tgcctgggtc tcactacaag   1409

cagcctatct gcttaagaga ctctggagtt tcttatgtgc cctggtggac acttgcccac   1469

catcctgtga gtaaaagtga aataaaagct ttgac                              1504


<210> SEQ ID NO 3
<211> LENGTH: 351
<212> TYPE: PRT
<213> ORGANISM: Homo sapiens

<400> SEQUENCE: 3

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125
```

-continued

```
Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
            340                 345                 350


<210> SEQ ID NO 4
<211> LENGTH: 874
<212> TYPE: DNA
<213> ORGANISM: Homo sapiens
<220> FEATURE:
<221> NAME/KEY: CDS
<222> LOCATION: (13)..(723)

<400> SEQUENCE: 4

gcccgacgag cc atg gtt gct ggg agc gac gcg ggg cgg gcc ctg ggg gtc      51
              Met Val Ala Gly Ser Asp Ala Gly Arg Ala Leu Gly Val
              1               5                   10

ctc agc gtg gtc tgc ctg ctg cac tgc ttt ggt ttc atc agc tgt ttt       99
Leu Ser Val Val Cys Leu Leu His Cys Phe Gly Phe Ile Ser Cys Phe
    15                  20                  25

tcc caa caa ata tat ggt gtt gtg tat ggg aat gta act ttc cat gta      147
Ser Gln Gln Ile Tyr Gly Val Val Tyr Gly Asn Val Thr Phe His Val
30                  35                  40                  45

cca agc aat gtg cct tta aaa gag gtc cta tgg aaa aaa caa aag gat      195
Pro Ser Asn Val Pro Leu Lys Glu Val Leu Trp Lys Lys Gln Lys Asp
                50                  55                  60

aaa gtt gca gaa ctg gaa aat tct gaa ttc aga gct ttc tca tct ttt      243
Lys Val Ala Glu Leu Glu Asn Ser Glu Phe Arg Ala Phe Ser Ser Phe
            65                  70                  75

aaa aat agg gtt tat tta gac act gtg tca ggt agc ctc act atc tac      291
Lys Asn Arg Val Tyr Leu Asp Thr Val Ser Gly Ser Leu Thr Ile Tyr
        80                  85                  90

aac tta aca tca tca gat gaa gat gag tat gaa atg gaa tcg cca aat      339
```

```
Asn Leu Thr Ser Ser Asp Glu Asp Glu Tyr Glu Met Glu Ser Pro Asn
    95                  100                 105

att act gat acc atg aag ttc ttt ctt tat gtg ctt gag tct ctt cca      387
Ile Thr Asp Thr Met Lys Phe Phe Leu Tyr Val Leu Glu Ser Leu Pro
110                 115                 120                 125

tct ccc aca cta act tgt gca ttg act aat gga agc att gaa gtc caa      435
Ser Pro Thr Leu Thr Cys Ala Leu Thr Asn Gly Ser Ile Glu Val Gln
                130                 135                 140

tgc atg ata cca gag cat tac aac agc cat cga gga ctt ata atg tac      483
Cys Met Ile Pro Glu His Tyr Asn Ser His Arg Gly Leu Ile Met Tyr
            145                 150                 155

tca tgg gat tgt cct atg gag caa tgt aaa cgt aac tca acc agt ata      531
Ser Trp Asp Cys Pro Met Glu Gln Cys Lys Arg Asn Ser Thr Ser Ile
        160                 165                 170

tat ttt aag atg gaa aat gat ctt cca caa aaa ata cag tgt act ctt      579
Tyr Phe Lys Met Glu Asn Asp Leu Pro Gln Lys Ile Gln Cys Thr Leu
    175                 180                 185

agc aat cca tta ttt aat aca aca tca tca atc att ttg aca acc tgt      627
Ser Asn Pro Leu Phe Asn Thr Thr Ser Ser Ile Ile Leu Thr Thr Cys
190                 195                 200                 205

atc cca agc agc ggt cat tca aga cac aga tat gca ctt ata ccc ata      675
Ile Pro Ser Ser Gly His Ser Arg His Arg Tyr Ala Leu Ile Pro Ile
                210                 215                 220

cca tta gca gta att aca aca tgt att gtg ctg tat atg aat gtt ctt      723
Pro Leu Ala Val Ile Thr Thr Cys Ile Val Leu Tyr Met Asn Val Leu
            225                 230                 235

taattgagaa gacaatttct tcatttttag gtattctgaa atgtgacaga aaaccagaca    783

gaaccaactc caattgattg gtaacagaag atgaagacaa cagcataact aaattatttt    843

aaaaactaaa aagccatctg atttctcatt t                                   874


<210> SEQ ID NO 5
<211> LENGTH: 237
<212> TYPE: PRT
<213> ORGANISM: Homo sapiens

<400> SEQUENCE: 5

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160
```

```
Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Val Leu
225                 230                 235
```

<210> SEQ ID NO 6
<211> LENGTH: 3900
<212> TYPE: DNA
<213> ORGANISM: Artificial
<220> FEATURE:
<223> OTHER INFORMATION: Nucleotide sequence of the piH3M vector.

<400> SEQUENCE: 6

```
ggcgtaatct gctgcttgca aacaaaaaaa ccaccgctac cagcggtggt ttgtttgccg     60

gatcaagagc taccaactct ttttccgaag gtaactggct tcagcagagc gcagatacca    120

aatactgtcc ttctagtgta gccgtagtta ggccaccact tcaagaactc tgtagcaccg    180

cctacatacc tcgctctgct aatcctgtta ccagtggctg ctgccagtgg cgataagtcg    240

tgtcttaccg ggttggactc aagacgatag ttaccggata aggcgcagcg gtcgggctga    300

acggggggtt cgtgcacaca gcccagcttg gagcgaacga cctacaccga actgagatac    360

ctacagcgtg agcattgaga aagcgccacg cttcccgaag ggagaaaggc ggacaggtat    420

ccggtaagcg gcagggtcgg aacaggagag cgcacgaggg agcttccagg gggaaacgcc    480

tggtatcttt atagtcctgt cgggtttcgc cacctctgac ttgagcgtcg atttttgtga    540

tgctcgtcag gggggcggag cctatggaaa aacgccagca acgcaagcta gcttctagct    600

agaaattgta aacgttaata ttttgttaaa attcgcgtta aatttttgtt aaatcagctc    660

atttttaac caataggccg aaatcggcaa aatcccttat aaatcaaaag aatagcccga    720

gatagggttg agtgttgttc cagtttggaa caagagtcca ctattaaaga acgtggactc    780

caacgtcaaa gggcgaaaaa ccgtctatca gggcgatggc cgcccactac gtgaaccatc    840

acccaaatca agttttttgg ggtcgaggtg ccgtaaagca ctaaatcgga accctaaagg    900

gagcccccga tttagagctt gacggggaaa gccggcgaac gtggcgagaa aggaagggaa    960

gaaagcgaaa ggagcgggcg ctagggcgct ggcaagtgta gcggtcacgc tgcgcgtaac   1020

caccacaccc gccgcgctta atgcgccgct acagggcgcg tactatggtt gctttgacga   1080

gcacgtataa cgtgctttcc tcgttggaat cagagcggga gctaaacagg aggccgatta   1140

aagggatttt agacaggaac ggtacgccag ctggatcacc gcggtctttc tcaacgtaac   1200

actttacagc ggcgcgtcat ttgatatgat gcgccccgct tcccgataag ggagcaggcc   1260

agtaaaagca ttacccgtgg tggggttccc gagcggccaa agggagcaga ctctaaatct   1320

gccgtcatcg acttcgaagg ttcgaatcct tcccccacca ccatcacttt caaaagtccg   1380

aaagaatctg ctccctgctt gtgtgttgga ggtcgctgag tagtgcgcga gtaaaattta   1440

agctacaaca aggcaaggct tgaccgacaa ttgcatgaag aatctgctta gggttaggcg   1500

ttttgcgctg cttcgcgatg tacgggccag atatacgcgt tgacattgat tattgactag   1560

ttattaatag taatcaatta cggggtcatt agttcatagc ccatatatgg agttccgcgt   1620
```

-continued

```
tacataactt acggtaaatg gcccgcctgg ctgaccgccc aacgaccccc gcccattgac   1680

gtcaataatg acgtatgttc ccatagtaac gccaataggg actttccatt gacgtcaatg   1740

ggtggactat ttacggtaaa ctgcccactt ggcagtacat caagtgtatc atatgccaag   1800

tacgccccct attgacgtca atgacggtaa atggcccgcc tggcattatg cccagtacat   1860

gaccttatgg gactttccta cttggcagta catctacgta ttagtcatcg ctattaccat   1920

ggtgatgcgg ttttggcagt acatcaatgg gcgtggatag cggtttgact cacggggatt   1980

tccaagtctc caccccattg acgtcaatgg gagtttgttt tggcaccaaa atcaacggga   2040

ctttccaaaa tgtcgtaaca actccgcccc attgacgcaa atgggcggaa ttcctgggcg   2100

ggactgggga gtggcgagcc ctcagatgct gcatataagc agctgctttt tgcctgtact   2160

gggtctctct ggttagacca gatctgagcc tgggagctct ctggctaact agagaaccca   2220

ctgcttaagc ctcaataaag cttctagaga tccctcgacc tcgagatcca ttgtgctggc   2280

gcggattctt tatcactgat aagttggtgg acatattatg tttatcagtg ataaagtgtc   2340

aagcatgaca aagttgcagc cgaatacagt gatccgtgcc gccctagacc tgttgaacga   2400

ggtcggcgta gacggtctga cgacacgcaa actggcggaa cggttggggg ttcagcagcc   2460

ggcgctttac tggcacttca ggaacaagcg ggcgctgctc gacgcactgg ccgaagccat   2520

gctggcggag aatcatagca cttcggtgcc gagagccgac gacgactggc gctcatttct   2580

gactgggaat gcccgcagct tcaggcaggc gctgctcgcc taccgccagc acaatggatc   2640

tcgagggatc ttccatacct accagttctg cgcctgcagg tcgcggccgc gactctagag   2700

gatctttgtg aaggaacctt acttctgtgg tgtgacataa ttggacaaac tacctacaga   2760

gatttaaagc tctaaggtaa atataaaatt tttaagtgta taatgtgtta aactactgat   2820

tctaattgtt tgtgtatttt agattccaac ctatggaact gatgaatggg agcagtggtg   2880

gaatgccttt aatgaggaaa acctgttttg ctcagaagaa atgccatcta gtgatgatga   2940

ggctactgct gactctcaac attctactcc tccaaaaaag aagagaaagg tagaagaccc   3000

caaggacttt ccttcagaat tgctaagttt tttgagtcat gctgtgttta gtaatagaac   3060

tcttgcttgc tttgctattt acaccacaaa ggaaaaagct gcactgctat acaagaaaat   3120

tatggaaaaa tattctgtaa cctttataag taggcataac agttataatc ataacatact   3180

gtttttcctt actccacaca ggcatagagt gtctgctatt aataactatg ctcaaaaatt   3240

gtgtaccttt agctttttaa tttgtaaagg ggttaataag gaatatttga tgtatagtgc   3300

cttgactaga gatcataatc agccatacca catttgtaga ggttttactt gctttaaaaa   3360

acctcccaca cctccccctg aacctgaaac ataaaatgaa tgcaattgtt gttgttaact   3420

tgtttattgc agcttataat ggttacaaat aaagcaatag catcacaaat ttcacaaata   3480

aagcattttt ttcactgcat tctagttgtg gtttgtccaa actcatcaat gtatcttatc   3540

atgtctggat cctgtggaat gtgtgtcagt tagggtgtgg aaagtcccca ggctccccag   3600

caggcagaag tatgcaaagc atgcatctca attagtcagc aaccaggtgt ggaaagtccc   3660

caggctcccc agcaggcaga agtatgcaaa gcatgcatct caattagtca gcaaccatag   3720

tcccgcccct aactccgccc atcccgcccc taactccgcc cagttccgcc cattctccgc   3780

cccatggctg actaattttt tttatttatg cagaggccga ggccgcctcg gcctctgagc   3840

tattccagaa gtagtgagga ggcttttttg gaggcctagg cttttgcaaa aagctaattc   3900
```

<210> SEQ ID NO 7
<211> LENGTH: 1514

-continued

```
<212> TYPE: DNA
<213> ORGANISM: Homo sapiens
<220> FEATURE:
<221> NAME/KEY: CDS
<222> LOCATION: (100)..(759)

<400> SEQUENCE: 7

agactctcag gccttggcag gtgcgtcttt cagttcccct cacacttcgg gttcctcggg      60

gaggaggggc tggaacccta gcccatcgtc aggacaaag atg ctc agg ctg ctc       114
                                           Met Leu Arg Leu Leu
                                           1               5

ttg gct ctc aac tta ttc cct tca att caa gta aca gga aac aag att      162
Leu Ala Leu Asn Leu Phe Pro Ser Ile Gln Val Thr Gly Asn Lys Ile
                10                  15                  20

ttg gtg aag cag tcg ccc atg ctt gta gcg tac gac aat gcg gtc aac      210
Leu Val Lys Gln Ser Pro Met Leu Val Ala Tyr Asp Asn Ala Val Asn
            25                  30                  35

ctt agc tgc aag tat tcc tac aat ctc ttc tca agg gag ttc cgg gca      258
Leu Ser Cys Lys Tyr Ser Tyr Asn Leu Phe Ser Arg Glu Phe Arg Ala
        40                  45                  50

tcc ctt cac aaa gga ctg gat agt gct gtg gaa gtc tgt gtt gta tat      306
Ser Leu His Lys Gly Leu Asp Ser Ala Val Glu Val Cys Val Val Tyr
    55                  60                  65

ggg aat tac tcc cag cag ctt cag gtt tac tca aaa acg ggg ttc aac      354
Gly Asn Tyr Ser Gln Gln Leu Gln Val Tyr Ser Lys Thr Gly Phe Asn
70                  75                  80                  85

tgt gat ggg aaa ttg ggc aat gaa tca gtg aca ttc tac ctc cag aat      402
Cys Asp Gly Lys Leu Gly Asn Glu Ser Val Thr Phe Tyr Leu Gln Asn
                90                  95                  100

ttg tat gtt aac caa aca gat att tac ttc tgc aaa att gaa gtt atg      450
Leu Tyr Val Asn Gln Thr Asp Ile Tyr Phe Cys Lys Ile Glu Val Met
            105                 110                 115

tat cct cct cct tac cta gac aat gag aag agc aat gga acc att atc      498
Tyr Pro Pro Pro Tyr Leu Asp Asn Glu Lys Ser Asn Gly Thr Ile Ile
        120                 125                 130

cat gtg aaa ggg aaa cac ctt tgt cca agt ccc cta ttt ccc gga cct      546
His Val Lys Gly Lys His Leu Cys Pro Ser Pro Leu Phe Pro Gly Pro
    135                 140                 145

tct aag ccc ttt tgg gtg ctg gtg gtg gtt ggt gga gtc ctg gct tgc      594
Ser Lys Pro Phe Trp Val Leu Val Val Val Gly Gly Val Leu Ala Cys
150                 155                 160                 165

tat agc ttg cta gta aca gtg gcc ttt att att ttc tgg gtg agg agt      642
Tyr Ser Leu Leu Val Thr Val Ala Phe Ile Ile Phe Trp Val Arg Ser
                170                 175                 180

aag agg agc agg ctc ctg cac agt gac tac atg aac atg act ccc cgc      690
Lys Arg Ser Arg Leu Leu His Ser Asp Tyr Met Asn Met Thr Pro Arg
            185                 190                 195

cgc ccc ggg ccc acc cgc aag cat tac cag ccc tat gcc cca cca cgc      738
Arg Pro Gly Pro Thr Arg Lys His Tyr Gln Pro Tyr Ala Pro Pro Arg
        200                 205                 210

gac ttc gca gcc tat cgc tcc tgacacggac gcctatccag aagccagccg         789
Asp Phe Ala Ala Tyr Arg Ser
    215                 220

gctggcagcc cccatctgct caatatcact gctctggata ggaaatgacc gccatctcca     849

gccggccacc tcagcccctg ttgggccacc aatgccaatt tttctcgagt gactagacca     909

aatatcaaga tcattttgag actctgaaat gaagtaaaag agatttcctg tgacaggcca     969

agtcttacag tgccatggcc cacattccaa cttaccatgt acttagtgac ttgactgaga    1029

agttagggta gaaaacaaaa agggagtgga ttctgggagc ctcttccctt tctcactcac    1089
```

```
ctgcacatct cagtcaagca aagtgtggta tccacagaca ttttagttgc agaagaaagg   1149

ctaggaaatc attccttttg gttaaatggg tgtttaatct tttggttagt gggttaaacg   1209

gggtaagtta gagtaggggg agggatagga agacatattt aaaaaccatt aaaacactgt   1269

ctcccactca tgaaatgagc cacgtagttc ctatttaatg ctgttttcct ttagtttaga   1329

aatacataga cattgtcttt tatgaattct gatcatattt agtcattttg accaaatgag   1389

ggatttggtc aaatgaggga ttccctcaaa gcaatatcag gtaaaccaag ttgctttcct   1449

cactccctgt catgagactt cagtgttaat gttcacaata tactttcgaa agaataaaat   1509

agttc                                                                1514
```

```
<210> SEQ ID NO 8
<211> LENGTH: 220
<212> TYPE: PRT
<213> ORGANISM: Homo sapiens

<400> SEQUENCE: 8

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

```
<210> SEQ ID NO 9
<211> LENGTH: 1665
<212> TYPE: DNA
<213> ORGANISM: Homo sapiens

<400> SEQUENCE: 9

tagacccaga gaggctcagc tgcactcgcc cggctgggag agctgggtgt ggggaacatg     60

gccgggcctc cgaggctcct gctgctgccc ctgcttctgg cgctggctcg cggcctgcct    120
```

-continued

```
gggggccctgg ctgcccaagg taagagcttc ccaggctctc catggccaca gctccggagc    180

tctccctgcc ccatgagctc agagccccca gtctgagcca cagcacagcc cccaggaagc    240

gggtggggtg ctgagcggcc tccagtgtct gaggactcat ttaagagaag gaaaaagggt    300

ggacccggtg gggagtggcc ggggctgtcc aggcagggcc gctgctttgg gaggaagaag    360

cccacagtct cggaacacga ggacagcacc tcccccaaca ccacagccgg tgcccagatc    420

tgctccatgc cccgtaaggc accgtgtctt tggcgacatg tcagccctgg gctgtctcag    480

ggccccacca tccccaccac tgtcccctgc agggaggaca ttctctgtcc ttctggccag    540

actgatggtg acagcccagg tcctcccaga ggtgcagcag tctccccact gcacgactgt    600

ccccgtggga gcctccgtca acatcacctg ctccaccagc gggggcctgc gtgggatcta    660

cctgaggcag ctcgggccac agccccaaga catcatttac tacgaggacg gggtggtgcc    720

cactacggac agacggttcc ggggccgcat cgacttctca gggtcccagg acaacctgac    780

tatcaccatg caccgcctgc agctgtcgga cactggcacc tacacctgcc aggccatcac    840

ggaggtcaat gtctacggct ccggcaccct ggtcctggtg acagaggaac agtcccaagg    900

atggcacaga tgctcggacg ccccaccaag ggcctctgcc ctccctgccc caccgacagg    960

ctccgccctc cctgacccgc agacagcctc tgccctccct gacccgccag cagcctctgc   1020

cctccctgcg gccctggcgg tgatctcctt cctcctcggg ctgggcctgg gggtggcgtg   1080

tgtgctggcg aggacacaga taaagaaact gtgctcgtgg cgggataaga attcggcggc   1140

atgtgtggtg tacgaggaca tgtcgcacag ccgctgcaac acgctgtcct cccccaacca   1200

gtaccagtga cccagtgggc ccctgcacgt cccgcctgtg gtccccccag caccttccct   1260

gccccaccat gccccccacc ctgccacacc cctcaccctg ctgtcctccc acggctgcag   1320

cagagtttga agggcccagc cgtgcccagc tccaagcaga cacacaggca gtggccaggc   1380

cccacggtgc ttctcagtgg acaatgatgc ctcctccggg aagccttccc tgcccagccc   1440

acgccgccac cgggaggaag cctgactgtc ctttggctgc atctcccgac catggccaag   1500

gagggctttt ctgtgggatg ggcctggcac gcggccctct cctgtcagtg ccggcccacc   1560

caccagcagg cccccaaccc ccaggcagcc cggcagagga cgggaggaga ccagtccccc   1620

acccagccgt accagaaata aaggcttctg tgcttcaaaa aaaaa                   1665
```

```
<210> SEQ ID NO 10
<211> LENGTH: 2290
<212> TYPE: DNA
<213> ORGANISM: Homo sapiens

<400> SEQUENCE: 10

cccaaatgtc tcagaatgta tgtcccagaa acctgtggct gcttcaacca ttgacagttt     60

tgctgctgct ggcttctgca gacagtcaag ctgcagctcc cccaaaggct gtgctgaaac    120

ttgagccccc gtggatcaac gtgctccagg aggactctgt gactctgaca tgccaggggg    180

ctcgcagccc tgagagcgac tccattcagt ggttccacaa tgggaatctc attcccaccc    240

acacgcagcc cagctacagg ttcaaggcca acaacaatga cagcggggag tacacgtgcc    300

agactggcca gaccagcctc agcgaccctg tgcatctgac tgtgctttcc gaatggctgg    360

tgctccagac ccctcacctg gagttccagg agggagaaac catcatgctg aggtgccaca    420

gctggaagga caagcctctg gtcaaggtca cattcttcca gaatggaaaa tcccagaaat    480

tctcccgttt ggatcccacc ttctccatcc cacaagcaaa ccacagtcac agtggtgatt    540

accactgcac aggaaacata ggctacacgc tgttctcatc caagcctgtg accatcactg    600
```

-continued

```
tccaagtgcc cagcatgggc agctcttcac caatggggat cattgtggct gtggtcattg     660

cgactgctgt agcagccatt gttgctgctg tagtggcctt gatctactgc aggaaaaagc     720

ggatttcagc caattccact gatcctgtga aggctgccca atttgagcca cctggacgtc     780

aaatgattgc catcagaaag agacaacttg aagaaaccaa caatgactat gaaacagctg     840

acggcggcta catgactctg aaccccaggg cacctactga cgatgataaa aacatctacc     900

tgactcttcc tcccaacgac catgtcaaca gtaataacta aagagtaacg ttatgccatg     960

tggtcatact ctcagcttgc tgagtggatg acaaaaagag ggaattgtt aaaggaaaat     1020

ttaaatggag actggaaaaa tcctgagcaa acaaaaccac ctggccctta gaaatagctt    1080

taactttgct taaactacaa acacaagcaa aacttcacgg ggtcatacta catacaagca    1140

taagcaaaac ttaacttgga tcatttctgg taaatgctta tgttagaaat aagacaaccc    1200

cagccaatca caagcagcct actaacatat aattaggtga ctagggactt tctaagaaga    1260

tacctacccc caaaaaacaa ttatgtaatt gaaaaccaac cgattgcctt tattttgctt    1320

ccacattttc ccaataaata cttgcctgtg acattttgcc actggaacac taaacttcat    1380

gaattgcgcc tcagattttt cctttaacat cttttttttt tttgacagag tctcaatctg    1440

ttacccaggc tggagtgcag tggtgctatc ttggctcact gcaaacccgc ctcccaggtt    1500

taagcgattc tcatgcctca gcctcccagt agctgggatt agaggcatgt gccatcatac    1560

ccagctaatt tttgtatttt ttattttttt tttttagtag agacagggtt tcgcaatgtt    1620

ggccaggccg atctcgaact tctggcctct agcgatctgc ccgcctcggc ctcccaaagt    1680

gctgggatga ccagcatcag ccccaatgtc cagcctcttt aacatcttct ttcctatgcc    1740

ctctctgtgg atccctactg ctggtttctg ccttctccat gctgagaaca aaatcaccta    1800

ttcactgctt atgcagtcgg aagctccaga agaacaaaga gcccaattac cagaaccaca    1860

ttaagtctcc attgttttgc cttgggattt gagaagagaa ttagagaggt gaggatctgg    1920

tatttcctgg actaaattcc ccttggggaa gacgaaggga tgctgcagtt ccaaaagaga    1980

aggactcttc cagagtcatc tacctgagtc ccaaagctcc ctgtcctgaa agccacagac    2040

aatatggtcc caaatgactg actgcacctt ctgtgcctca gccgttcttg acatcaagaa    2100

tcttctgttc cacatccaca cagccaatac aattagtcaa accactgtta ttaacagatg    2160

tagcaacatg agaaacgctt atgttacagg ttacatgaga gcaatcatgt aagtctatat    2220

gacttcagaa atgttaaaat agactaacct ctaacaacaa attaaaagtg attgtttcaa    2280

ggtgaaaaaa                                                            2290


<210> SEQ ID NO 11
<211> LENGTH: 1474
<212> TYPE: DNA
<213> ORGANISM: Homo sapiens
<220> FEATURE:
<221> NAME/KEY: CDS
<222> LOCATION: (94)..(984)

<400> SEQUENCE: 11

aaagacaaac tgcacccact gaactccgca gctagcatcc aaatcagccc ttgagatttg      60

aggccttgga gactcaggag ttttgagagc aaa atg aca aca ccc aga aat tca      114
                                     Met Thr Thr Pro Arg Asn Ser
                                     1               5

gta aat ggg act ttc ccg gca gag cca atg aaa ggc cct att gct atg      162
Val Asn Gly Thr Phe Pro Ala Glu Pro Met Lys Gly Pro Ile Ala Met
        10                  15                  20
```

-continued

```
caa tct ggt cca aaa cca ctc ttc agg agg atg tct tca ctg gtg ggc      210
Gln Ser Gly Pro Lys Pro Leu Phe Arg Arg Met Ser Ser Leu Val Gly
    25                  30                  35

ccc acg caa agc ttc ttc atg agg gaa tct aag act ttg ggg gct gtc      258
Pro Thr Gln Ser Phe Phe Met Arg Glu Ser Lys Thr Leu Gly Ala Val
40                  45                  50                  55

cag att atg aat ggg ctc ttc cac att gcc ctg ggg ggt ctt ctg atg      306
Gln Ile Met Asn Gly Leu Phe His Ile Ala Leu Gly Gly Leu Leu Met
                60                  65                  70

atc cca gca ggg atc tat gca ccc atc tgt gtg act gtg tgg tac cct      354
Ile Pro Ala Gly Ile Tyr Ala Pro Ile Cys Val Thr Val Trp Tyr Pro
            75                  80                  85

ctc tgg gga ggc att atg tat att att tcc gga tca ctc ctg gca gca      402
Leu Trp Gly Gly Ile Met Tyr Ile Ile Ser Gly Ser Leu Leu Ala Ala
        90                  95                  100

acg gag aaa aac tcc agg aag tgt ttg gtc aaa gga aaa atg ata atg      450
Thr Glu Lys Asn Ser Arg Lys Cys Leu Val Lys Gly Lys Met Ile Met
    105                 110                 115

aat tca ttg agc ctc ttt gct gcc att tct gga atg att ctt tca atc      498
Asn Ser Leu Ser Leu Phe Ala Ala Ile Ser Gly Met Ile Leu Ser Ile
120                 125                 130                 135

atg gac ata ctt aat att aaa att tcc cat ttt tta aaa atg gag agt      546
Met Asp Ile Leu Asn Ile Lys Ile Ser His Phe Leu Lys Met Glu Ser
                140                 145                 150

ctg aat ttt att aga gct cac aca cca tat att aac ata tac aac tgt      594
Leu Asn Phe Ile Arg Ala His Thr Pro Tyr Ile Asn Ile Tyr Asn Cys
            155                 160                 165

gaa cca gct aat ccc tct gag aaa aac tcc cca tct acc caa tac tgt      642
Glu Pro Ala Asn Pro Ser Glu Lys Asn Ser Pro Ser Thr Gln Tyr Cys
        170                 175                 180

tac agc ata caa tct ctg ttc ttg ggc att ttg tca gtg atg ctg atc      690
Tyr Ser Ile Gln Ser Leu Phe Leu Gly Ile Leu Ser Val Met Leu Ile
    185                 190                 195

ttt gcc ttc ttc cag gaa ctt gta ata gct ggc atc gtt gag aat gaa      738
Phe Ala Phe Phe Gln Glu Leu Val Ile Ala Gly Ile Val Glu Asn Glu
200                 205                 210                 215

tgg aaa aga acg tgc tcc aga ccc aaa tct aac ata gtt ctc ctg tca      786
Trp Lys Arg Thr Cys Ser Arg Pro Lys Ser Asn Ile Val Leu Leu Ser
                220                 225                 230

gca gaa gaa aaa aaa gaa cag act att gaa ata aaa gaa gaa gtg gtt      834
Ala Glu Glu Lys Lys Glu Gln Thr Ile Glu Ile Lys Glu Glu Val Val
            235                 240                 245

ggg cta act gaa aca tct tcc caa cca aag aat gaa gaa gac att gaa      882
Gly Leu Thr Glu Thr Ser Ser Gln Pro Lys Asn Glu Glu Asp Ile Glu
        250                 255                 260

att att cca atc caa gaa gag gaa gaa gaa gaa aca gag acg aac ttt      930
Ile Ile Pro Ile Gln Glu Glu Glu Glu Glu Glu Thr Glu Thr Asn Phe
    265                 270                 275

cca gaa cct ccc caa gat cag gaa tcc tca cca ata gaa aat gac agc      978
Pro Glu Pro Pro Gln Asp Gln Glu Ser Ser Pro Ile Glu Asn Asp Ser
280                 285                 290                 295

tct cct taagtgattt cttctgtttt ctgtttcctt ttttaaacat tagtgttcat      1034
Ser Pro
agcttccaag agacatgctg actttcattt cttgaggtac tctgcacata cgcaccacat    1094

ctctatctgg cctttgcatg gagtgaccat agctccttct ctcttacatt gaatgtagag    1154

aatgtagcca ttgtagcagc ttgtgttgtc acgcttcttc ttttgagcaa ctttcttaca    1214

ctgaagaaag gcagaatgag tgcttcagaa tgtgatttcc tactaacctg ttccttggat    1274
```

-continued

```
aggcttttta gtatagtatt ttttttgtc attttctcca tcagcaacca gggagactgc    1334

acctgatgga aaagatatat gactgcttca tgacattcct aaactatctt ttttttattc    1394

cacatctacg tttttggtgg agtccctttt tatcatcctt aaaacaatga tgcaaaaggg    1454

ctttagagca caatggatct                                               1474
```

<210> SEQ ID NO 12
<211> LENGTH: 297
<212> TYPE: PRT
<213> ORGANISM: Homo sapiens

<400> SEQUENCE: 12

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 13
<211> LENGTH: 1888
<212> TYPE: DNA
<213> ORGANISM: Homo sapiens
<220> FEATURE:

```
<221> NAME/KEY: CDS
<222> LOCATION: (13)..(1608)

<400> SEQUENCE: 13

ctcagcctcg ct atg gct ccc agc agc ccc cgg ccc gcg ctg ccc gca ctc      51
              Met Ala Pro Ser Ser Pro Arg Pro Ala Leu Pro Ala Leu
              1               5                   10

ctg gtc ctg ctc ggg gct ctg ttc cca gga cct ggc aat gcc cag aca        99
Leu Val Leu Leu Gly Ala Leu Phe Pro Gly Pro Gly Asn Ala Gln Thr
    15                  20                  25

tct gtg tcc ccc tca aaa gtc atc ctg ccc cgg gga ggc tcc gtg ctg       147
Ser Val Ser Pro Ser Lys Val Ile Leu Pro Arg Gly Gly Ser Val Leu
30                  35                  40                  45

gtg aca tgc agc acc tcc tgt gac cag ccc aag ttg ttg ggc ata gag       195
Val Thr Cys Ser Thr Ser Cys Asp Gln Pro Lys Leu Leu Gly Ile Glu
                50                  55                  60

acc ccg ttg cct aaa aag gag ttg ctc ctg cct ggg aac aac cgg aag       243
Thr Pro Leu Pro Lys Lys Glu Leu Leu Leu Pro Gly Asn Asn Arg Lys
            65                  70                  75

gtg tat gaa ctg agc aat gtg caa gaa gat agc caa cca atg tgc tat       291
Val Tyr Glu Leu Ser Asn Val Gln Glu Asp Ser Gln Pro Met Cys Tyr
        80                  85                  90

tca aac tgc cct gat ggg cag tca aca gct aaa acc ttc ctc acc gtg       339
Ser Asn Cys Pro Asp Gly Gln Ser Thr Ala Lys Thr Phe Leu Thr Val
    95                  100                 105

tac tgg act cca gaa cgg gtg gaa ctg gca ccc ctc ccc tct tgg cag       387
Tyr Trp Thr Pro Glu Arg Val Glu Leu Ala Pro Leu Pro Ser Trp Gln
110                 115                 120                 125

cca gtg ggc aag aac ctt acc cta cgc tgc cag gtg gag ggt ggg gca       435
Pro Val Gly Lys Asn Leu Thr Leu Arg Cys Gln Val Glu Gly Gly Ala
                130                 135                 140

ccc cgg gcc aac ctc acc gtg gtg ctg ctc cgt ggg gag aag gag ctg       483
Pro Arg Ala Asn Leu Thr Val Val Leu Leu Arg Gly Glu Lys Glu Leu
            145                 150                 155

aaa cgg gag cca gct gtg ggg gag ccc gct gag gtc acg acc acg gtg       531
Lys Arg Glu Pro Ala Val Gly Glu Pro Ala Glu Val Thr Thr Thr Val
        160                 165                 170

ctg gtg agg aga gat cac cat gga gcc aat ttc tcg tgc cgc act gaa       579
Leu Val Arg Arg Asp His His Gly Ala Asn Phe Ser Cys Arg Thr Glu
    175                 180                 185

ctg gac ctg cgg ccc caa ggg ctg gag ctg ttt gag aac acc tcg gcc       627
Leu Asp Leu Arg Pro Gln Gly Leu Glu Leu Phe Glu Asn Thr Ser Ala
190                 195                 200                 205

ccc tac cag ctc cag acc ttt gtc ctg cca gcg act ccc cca caa ctt       675
Pro Tyr Gln Leu Gln Thr Phe Val Leu Pro Ala Thr Pro Pro Gln Leu
                210                 215                 220

gtc agc ccc cgg gtc cta gag gtg gac acg cag ggg acc gtg gtc tgt       723
Val Ser Pro Arg Val Leu Glu Val Asp Thr Gln Gly Thr Val Val Cys
            225                 230                 235

tcc ctg gac ggg ctg ttc cca gtc tcg gag gcc cag gtc cac ctg gca       771
Ser Leu Asp Gly Leu Phe Pro Val Ser Glu Ala Gln Val His Leu Ala
        240                 245                 250

ctg ggg gac cag agg ttg aac ccc aca gtc acc tat ggc aac gac tcc       819
Leu Gly Asp Gln Arg Leu Asn Pro Thr Val Thr Tyr Gly Asn Asp Ser
    255                 260                 265

ttc tcg gcc aag gcc tca gtc agt gtg acc gca gag gac gag ggc acc       867
Phe Ser Ala Lys Ala Ser Val Ser Val Thr Ala Glu Asp Glu Gly Thr
270                 275                 280                 285

cag cgg ctg acg tgt gca gta ata ctg ggg aac cag agc cag gag aca       915
Gln Arg Leu Thr Cys Ala Val Ile Leu Gly Asn Gln Ser Gln Glu Thr
```

-continued

```
                290                 295                 300

ctg cag aca gtg acc atc tac agc ttt ccg gcg ccc aac gtg att ctg      963
Leu Gln Thr Val Thr Ile Tyr Ser Phe Pro Ala Pro Asn Val Ile Leu
            305                 310                 315

acg aag cca gag gtc tca gaa ggg acc gag gtg aca gtg aag tgt gag     1011
Thr Lys Pro Glu Val Ser Glu Gly Thr Glu Val Thr Val Lys Cys Glu
        320                 325                 330

gcc cac cct aga gcc aag gtg acg ctg aat ggg gtt cca gcc cag cca     1059
Ala His Pro Arg Ala Lys Val Thr Leu Asn Gly Val Pro Ala Gln Pro
    335                 340                 345

ctg ggc ccg agg gcc cag ctc ctg ctg aag gcc acc cca gag gac aac     1107
Leu Gly Pro Arg Ala Gln Leu Leu Leu Lys Ala Thr Pro Glu Asp Asn
350                 355                 360                 365

ggg cgc agc ttc tcc tgc tct gca acc ctg gag gtg gcc ggc cag ctt     1155
Gly Arg Ser Phe Ser Cys Ser Ala Thr Leu Glu Val Ala Gly Gln Leu
                370                 375                 380

ata cac aag aac cag acc cgg gag ctt cgt gtc ctg tat ggc ccc cga     1203
Ile His Lys Asn Gln Thr Arg Glu Leu Arg Val Leu Tyr Gly Pro Arg
            385                 390                 395

ctg gac gag agg gat tgt ccg gga aac tgg acg tgg cca gaa aat tcc     1251
Leu Asp Glu Arg Asp Cys Pro Gly Asn Trp Thr Trp Pro Glu Asn Ser
        400                 405                 410

cag cag act cca atg tgc cag gct tgg ggg aac cca ttg ccc gag ctc     1299
Gln Gln Thr Pro Met Cys Gln Ala Trp Gly Asn Pro Leu Pro Glu Leu
    415                 420                 425

aag tgt cta aag gat ggc act ttc cca ctg ccc atc ggg gaa tca gtg     1347
Lys Cys Leu Lys Asp Gly Thr Phe Pro Leu Pro Ile Gly Glu Ser Val
430                 435                 440                 445

act gtc act cga gat ctt gag ggc acc tac ctc tgt cgg gcc agg agc     1395
Thr Val Thr Arg Asp Leu Glu Gly Thr Tyr Leu Cys Arg Ala Arg Ser
                450                 455                 460

act caa ggg gag gtc acc cgc gag gtg acc gtg aat gtg ctc tcc ccc     1443
Thr Gln Gly Glu Val Thr Arg Glu Val Thr Val Asn Val Leu Ser Pro
            465                 470                 475

cgg tat gag att gtc atc atc act gtg gta gca gcc gca gtc ata atg     1491
Arg Tyr Glu Ile Val Ile Ile Thr Val Val Ala Ala Ala Val Ile Met
        480                 485                 490

ggc act gca ggc ctc agc acg tac ctc tat aac cgc cag cgg aag atc     1539
Gly Thr Ala Gly Leu Ser Thr Tyr Leu Tyr Asn Arg Gln Arg Lys Ile
    495                 500                 505

aag aaa tac aga cta caa cag gcc caa aaa ggg acc ccc atg aaa ccg     1587
Lys Lys Tyr Arg Leu Gln Gln Ala Gln Lys Gly Thr Pro Met Lys Pro
510                 515                 520                 525

aac aca caa gcc acg cct ccc tgaacctatc ccgggacagg gcctcttcct        1638
Asn Thr Gln Ala Thr Pro Pro
                530

cggccttccc atattggtgg cagtggtgcc acactgaaca gagtggaaga catatgccat   1698

gcagctacac ctaccggccc tgggacgccg gaggacaggg cattgtcctc agtcagatac   1758

aacagcattt ggggccatgg tacctgcaca cctaaaacac taggccacgc atctgatctg   1818

tagtcacatg actaagccaa gaggaaggaa cagcatttgg ggccatggta cctgcacacc   1878

taaaacacta                                                          1888
```

<210> SEQ ID NO 14
<211> LENGTH: 532
<212> TYPE: PRT
<213> ORGANISM: Homo sapiens

<400> SEQUENCE: 14

-continued

```
Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415
```

```
Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Glu Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530
```

<210> SEQ ID NO 15
<211> LENGTH: 1921
<212> TYPE: DNA
<213> ORGANISM: Homo sapiens

<400> SEQUENCE: 15

```
ggagagtctg accaccatgc cacctcctcg cctcctcttc ttcctcctct tcctcacccc     60

catggaagtc aggcccgagg aacctctatg gtcaaggtgg aagagggaga taacgctgtg    120

ctgcagtgcc tcaaggggac ctcagatggc cccactcagc agctgacctg gtctcgggag    180

tccccgctta aacccttctt aaaactcagc ctggggctgc caggcctggg aatccacatg    240

aggcccctgg ccatctggct tttcatcttc aacgtgtctc aacagatggg gggcttctac    300

ctgtgccagc cggggccccc ctctgagaag gcctggcagc ctggctggac agtcaatgtg    360

gagggcagcg gggagctgtt ccggtggaat gtttcggacc taggtggcct gggctgtggc    420

ctgaagaaca ggtggtcaga gggccccagc tccccttccg ggaagctcat gagccccaag    480

ctgtatgtgt gggccaaaga ccgccctgag atctgggagg gagagcctcc gtgtgtccca    540

ccgagggaca gcctgaacca gagcctcagc caggacctca ccatggcccc tggctccaca    600

ctctggctgt cctgtggggt acccccctgac tctgtgtcca ggggccccct ctcctggacc    660

catgtgcacc ccaaggggcc taagtcattg ctgagcctag agctgaagga cgatcgcccg    720

gccagagata tgtgggtaat ggagacgggt ctgttgttgc cccgggccac agctcaagac    780

gctggaaagt attattgtca ccgtggcaac ctgaccatgt cattccacct ggagatcact    840

gctcggccag tactatggca ctggctgctg aggactggtg gctggaaggt ctcagctgtg    900

actttggctt atctgatctt ctgcctgtgt tcccttgtgg gcattcttca tcttcaaaga    960

gccctggtcc tgaggaggaa aagaaagcga atgactgacc ccaccaggag attcttcaaa   1020

gtgacgcctc ccccaggaag cgggccccag aaccagtacg ggaacgtgct gtctctcccc   1080

acacccacct caggcctcgg acgcgcccag cgttgggccg caggcctggg gggcactgcc   1140

ccgtcttatg gaaacccgag cagcgacgtc caggcggatg gagccttggg gtcccggagc   1200

cgccgggagt gggcccagaa gaagaggaag gggagggcta tgaggaacct gacagtgagg   1260

aggactccga gttctatgag aacgactcca accttgggca ggaccagctc tcccaggatg   1320

gcagcggcta cgagaaccct gaggatgagc ccctgggtcc tgaggatgaa gactccttct   1380

ccaacgctga gtcttatgag aacgaggatg aagagctgac ccagccggtc gccaggacaa   1440
```

```
tggacttcct gagccctcat gggtcagcct gggaccccag ccgggaagca acctccctgg   1500
ggtcccagtc ctatgaggat atgagaggaa tcctgtatgc agccccccag ctccgctcca   1560
ttcggggcca gcctggaccc aatcatgagg aagatgcaga ctcttatgag aacatggata   1620
atcccgatgg gccagaccca gcctggggag gaggggggcg catgggcacc tggagcacca   1680
ggtgatcctc aggtggccag cctggatctc ctcaagtccc caagattcac acctgactct   1740
gaaatctgaa gacctcgagc agatgatgcc aacctctgga gcaatgttgc ttaggatgtg   1800
tgcatgtgtg taagtgtgtg tgtgtgtgtg tgtgtgtgtg tgtgtgtata catgccagtg   1860
acacttccag tcccctttgt attccttaaa taaactcaat gagctcttcc aaaaaaaaaa   1920
a                                                                   1921
```

```
<210> SEQ ID NO 16
<211> LENGTH: 1476
<212> TYPE: DNA
<213> ORGANISM: Homo sapiens

<400> SEQUENCE: 16

acaaagacaa actgcaccca ctgaactccg cagctagcat ccaaatcagc ccttgagatt     60
tgaggccttg gagactcagg agttttgaga gcaaaatgac aacacccaga aattcagtaa    120
atgggacttt cccggcagag ccaatgaaag gccctattgc tatgcaatct ggtccaaaac    180
cactcttcag gaggatgtct tcactggtgg gccccacgca aagcttcttc atgagggaat    240
ctaagacttt gggggctgtc cagattatga atgggctctt ccacattgcc ctgggggggtc   300
ttctgatgat cccagcaggg atctatgcac ccatctgtgt gactgtgtgg taccctctct    360
ggggaggcat tatgtatatt atttccggat cactcctggc agcaacggag aaaaactcca    420
ggaagtgttt ggtcaaagga aaaatgataa tgaattcatt gagcctcttt gctgccattt    480
ctggaatgat tctttcaatc atggacatac ttaatattaa aatttcccat tttttaaaaa    540
tggagagtct gaattttatt agagctcaca caccatatat taacatatac aactgtgaac    600
cagctaatcc ctctgagaaa aactccccat ctacccaata ctgttacagc atacaatctc    660
tgttcttggg cattttgtca gtgatgctga tctttgcctt cttccaggaa cttgtaatag    720
ctggcatcgt tgagaatgaa tggaaaagaa cgtgctccag acccaaatct aacatagttc    780
tcctgtcagc agaagaaaaa aaagaacaga ctattgaaat aaaagaagaa gtggttgggc    840
taactgaaac atcttcccaa ccaaagaatg aagaagacat tgaaattatt ccaatccaag    900
aagaggaaga agaagaaaca gagacgaact ttccagaacc tccccaagat caggaatcct    960
caccaataga aaatgacagc tctccttaag tgatttcttc tgttttctgt ttcctttttt   1020
aaacattagt gttcatagct tccaagagac atgctgactt tcatttcttg aggtactctg   1080
cacatacgca ccacatctct atctggcctt tgcatggagt gaccatagct ccttctctct   1140
tacattgaat gtagagaatg tagccattgt agcagcttgt gttgtcacgc ttcttctttt   1200
gagcaacttt cttacactga agaaaggcag aatgagtgct tcagaatgtg atttcctact   1260
aacctgttcc ttggataggc tttttagtat agtatttttt tttgtcattt tctccatcag   1320
caaccaggga gactgcacct gatggaaaag atatatgact gcttcatgac attcctaaac   1380
tatctttttt ttattccaca tctacgtttt tggtggagtc ccttttttatc atccttaaaa  1440
caatgatgca aaagggcttt agagcacaat ggatct                             1476

<210> SEQ ID NO 17
```

<211> LENGTH: 2290
<212> TYPE: DNA
<213> ORGANISM: Homo sapiens

<400> SEQUENCE: 17

```
cccaaatgtc tcagaatgta tgtcccagaa acctgtggct gcttcaacca ttgacagttt     60

tgctgctgct ggcttctgca gacagtcaag ctgcagctcc cccaaaggct gtgctgaaac    120

ttgagccccc gtggatcaac gtgctccagg aggactctgt gactctgaca tgccaggggg    180

ctcgcagccc tgagagcgac tccattcagt ggttccacaa tgggaatctc attcccaccc    240

acacgcagcc cagctacagg ttcaaggcca acaacaatga cagcggggag tacacgtgcc    300

agactggcca gaccagcctc agcgaccctg tgcatctgac tgtgctttcc gaatggctgg    360

tgctccagac ccctcacctg gagttccagg agggagaaac catcatgctg aggtgccaca    420

gctggaagga caagcctctg gtcaaggtca cattcttcca gaatggaaaa tcccagaaat    480

tctcccgttt ggatcccacc ttctccatcc cacaagcaaa ccacagtcac agtggtgatt    540

accactgcac aggaaacata ggctacacgc tgttctcatc caagcctgtg accatcactg    600

tccaagtgcc cagcatgggc agctcttcac caatggggat cattgtggct gtggtcattg    660

cgactgctgt agcagccatt gttgctgctg tagtggcctt gatctactgc aggaaaaagc    720

ggatttcagc caattccact gatcctgtga aggctgccca atttgagcca cctggacgtc    780

aaatgattgc catcagaaag agacaacttg aagaaaccaa caatgactat gaaacagctg    840

acggcggcta catgactctg aaccccaggg cacctactga cgatgataaa aacatctacc    900

tgactcttcc tcccaacgac catgtcaaca gtaataacta aagagtaacg ttatgccatg    960

tggtcatact ctcagcttgc tgagtggatg acaaaaagag gggaattgtt aaaggaaaat   1020

ttaaatggag actggaaaaa tcctgagcaa acaaaaccac ctggccctta gaaatagctt   1080

taactttgct taaactacaa acacaagcaa aacttcacgg ggtcatacta catacaagca   1140

taagcaaaac ttaacttgga tcatttctgg taaatgctta tgttagaaat aagacaaccc   1200

cagccaatca caagcagcct actaacatat aattaggtga ctagggactt tctaagaaga   1260

tacctacccc caaaaaacaa ttatgtaatt gaaaaccaac cgattgcctt tattttgctt   1320

ccacatttc ccaataaata cttgcctgtg acattttgcc actggaacac taaacttcat   1380

gaattgcgcc tcagattttt cctttaacat cttttttttt tttgacagag tctcaatctg   1440

ttacccaggc tggagtgcag tggtgctatc ttggctcact gcaaacccgc ctcccaggtt   1500

taagcgattc tcatgcctca gcctcccagt agctgggatt agaggcatgt gccatcatac   1560

ccagctaatt tttgtatttt ttattttttt tttttagtag agacagggtt tcgcaatgtt   1620

ggccaggccg atctcgaact tctggcctct agcgatctgc ccgcctcggc ctcccaaagt   1680

gctgggatga ccagcatcag ccccaatgtc cagcctcttt aacatcttct ttcctatgcc   1740

ctctctgtgg atccctactg ctggtttctg ccttctccat gctgagaaca aaatcaccta   1800

ttcactgctt atgcagtcgg aagctccaga agaacaaaga gcccaattac cagaaccaca   1860

ttaagtctcc attgttttgc cttgggattt gagaagagaa ttagagaggt gaggatctgg   1920

tatttcctgg actaaattcc ccttggggaa gacgaaggga tgctgcagtt ccaaaagaga   1980

aggactcttc cagagtcatc tacctgagtc ccaaagctcc ctgtcctgaa agccacagac   2040

aatatggtcc caaatgactg actgcacctt ctgtgcctca gccgttcttg acatcaagaa   2100

tcttctgttc cacatccaca cagccaatac aattagtcaa accactgtta ttaacagatg   2160

tagcaacatg agaaacgctt atgttacagg ttacatgaga gcaatcatgt aagtctatat   2220
```

```
gacttcagaa atgttaaaat agactaacct ctaacaacaa attaaaagtg attgtttcaa   2280

ggtgaaaaaa                                                           2290


<210> SEQ ID NO 18
<211> LENGTH: 2171
<212> TYPE: DNA
<213> ORGANISM: Homo sapiens

<400> SEQUENCE: 18

gctgtgactg ctgtgctctg ggcgccactc gctccaggga gtgatgggaa tcctgtcatt     60

cttacctgtc cttgccactg agagtgactg ggctgactgc aagtcccccc agccttgggg    120

tcatatgctt ctgtggacag ctgtgctatc cctggctcct gttgctggga cacctgcagc    180

tcccccaaag gctgtgctga aactcgagcc ccagtggatc aacgtgctcc aggaggactc    240

tgtgactctg acatgccggg ggactcacag ccctgagagc gactccattc agtggttcca    300

caatgggaat ctcattccca cccacacgca gcccagctac aggttcaagg ccaacaacaa    360

tgacagcggg gagtacacgt gccagactgg ccagaccagc ctcagcgacc ctgtgcatct    420

gactgtgctt tctggtcagt ggaggaaggc cccagggtgg acctgggagg gccaggacgg    480

atgaaatctg ctttcaggca gaggtttgca ggaaaggggg gtggcctgct tactgggaag    540

tatcgctgtg agttgcctca gcacatatca gtggttgttt ttgcctcagt tctgattgaa    600

cagaagaagg tttcaaggcc aaaaacaggc agccaagtgt gagagaagca gaaggaaatc    660

cctactgcat aaaacccatt tccattttaa tggcagaatt gaaaagcaca gaccacaact    720

gaatcctagc cctggaaatg actcactata caacatgatg aattcattta acccttgagt    780

ttccatttct tcacctgctc cgtggggcac taacgcctcc ctcagaggct tctggtgaga    840

atcagtgttt ccctgccccc gccccgccct ccatgcccct tctccacgtt ctcactgtgc    900

taggtgctct tctctgtctt tctcttccac cagcctgtgg gaaacctgag atgaaagtcg    960

tgtcttaccc atctttgtat ttccagcatc tgaaactggg cagagcttaa taaatatttt   1020

gctggagagg ttgatgatct tacaaagctc ccattgaaag gtggctctct gtaaagcaaa   1080

gttacaatga gattgtgatg aacattgtcc ttgtggcttt tcacttagtc cctcccttc    1140

acctgaagag caaattttcc tcaaaagtac acagcaaacg aatgacccac tggtgacact   1200

gttgccttta gaccctgctg gaaagaagct ccacatttat taacattccc gaagtaaatt   1260

tatcaggtag cattcatcag gtaacatttg ttgcacattc atgacttttc tactgtccac   1320

aaaggcatat gtccttatca tatgcggact cctcggtcac actggattct tccttccctc   1380

ctcgacatgg aagagatggc atcttagggt ctcttgtgtt cttcctgcag aggcctgtcg   1440

ggcaggaaaa ggctgcagct gccttcctgg gagaaggagg agatgagtgt atcctgaaca   1500

cctattatgt gctaggggct attgtagata catgacacta tcatgctcat tttcacgaat   1560

gaggaaactg aggctcagaa gacttaaatt atttgcccaa gagttataaa tgacagagcc   1620

agcattagag tccaggactg tctgatttca gacctaagct gttccctctg cacatcgtgt   1680

cccaccagta aggaagatct gggtctcaga gctgagccaa gacctcccgg gtcctctgcg   1740

gttttttgtg tctttcagag tggctggtgc tccagacccc tcacctggag ttccaggagg   1800

gagaaaccat cgtgctgagg tgccacagct ggaaggacaa gcctctggtc aaggtcacat   1860

tcttccagaa tggaaaatcc aagaaatttt cccgttcgga tcccaacttc tccatcccac   1920

aagcaaacca cagtcacagt ggtgattacc actgcacagg aaacataggc tacacgctgt   1980
```

-continued

```
actcatccaa gcctgtgacc atcactgtcc aagctcccag ctcttcaccg atggggatca   2040

ttgtggctgt ggtcactggg attgctgtag cggccattgt tgctgctgta gtggccttga   2100

tctactgcag gaaaaagcgg atttcaggtt tgtagctcct cccggtccct tttgttatca   2160

gtttccactt t                                                         2171
```

<210> SEQ ID NO 19
<211> LENGTH: 1004
<212> TYPE: DNA
<213> ORGANISM: Homo sapiens

<400> SEQUENCE: 19

```
gcctcgctcg ggcgcccagt ggtcctgccg cctggtctca cctcgccatg gttcgtctgc     60

ctctgcagtg cgtcctctgg ggctgcttgc tgaccgctgt ccatccagaa ccacccactg    120

catgcagaga aaaacagtac ctaataaaca gtcagtgctg ttctttgtgc cagccaggac    180

agaaactggt gagtgactgc acagagttca ctgaaacgga atgccttcct tgcggtgaaa    240

gcgaattcct agacacctgg aacagagaga cacactgcca ccagcacaaa tactgcgacc    300

ccaacctagg gcttcgggtc cagcagaagg gcacctcaga aacagacacc atctgcacct    360

gtgaagaagg ctggcactgt acgagtgagg cctgtgagag ctgtgtcctg caccgctcat    420

gctcgcccgg ctttggggtc aagcagattg ctacaggggt ttctgatacc atctgcgagc    480

cctgcccagt cggcttcttc tccaatgtgt catctgcttt cgaaaaatgt cacccttgga    540

caagctgtga gaccaaagac ctggttgtgc aacaggcagg cacaaacaag actgatgttg    600

tctgtggtcc ccaggatcgg ctgagagccc tggtggtgat ccccatcatc ttcgggatcc    660

tgtttgccat cctcttggtg ctggtcttta tcaaaaaggt ggccaagaag ccaaccaata    720

aggcccccca ccccaagcag gaaccccagg agatcaattt tcccgacgat cttcctggct    780

ccaacactgc tgctccagtg caggagactt tacatggatg ccaaccggtc acccaggagg    840

atggcaaaga gagtcgcatc tcagtgcagg agagacagtg aggctgcacc cacccaggag    900

tgtggccacg tgggcaaaca ggcagttggc cagagagcct ggtgctgctg ctgcaggggt    960

gcaggcagaa gcggggagct atgcccagtc agtgccagcc cctc                    1004
```

<210> SEQ ID NO 20
<211> LENGTH: 1870
<212> TYPE: DNA
<213> ORGANISM: Homo sapiens
<220> FEATURE:
<221> NAME/KEY: CDS
<222> LOCATION: (211)..(1626)

<400> SEQUENCE: 20

```
gaaaaatcct tcttagccat tttaaagata gctttccaat gattagacga attgattctt     60

tctgtgactc atcagttcct ttcctgtaaa attcatgtct tgctgttgat ttgtgaataa    120

gaaccagagc ttgtagaaac cactttaatc atatccagga gtttgcaaga aacaggtgct    180

taacactaat tcacctcctg aacaagaaaa atg ggc tgt gac cgg aac tgt ggg     234
                                 Met Gly Cys Asp Arg Asn Cys Gly
                                 1               5

ctc atc gct ggg gct gtc att ggt gct gtc ctg gct gtg ttt gga ggt      282
Leu Ile Ala Gly Ala Val Ile Gly Ala Val Leu Ala Val Phe Gly Gly
    10                  15                  20

att cta atg cca gtt gga gac ctg ctt atc cag aag aca att aaa aag      330
Ile Leu Met Pro Val Gly Asp Leu Leu Ile Gln Lys Thr Ile Lys Lys
25                  30                  35                  40
```

-continued

```
caa gtt gtc ctc gaa gaa ggt aca att gct ttt aaa aat tgg gtt aaa      378
Gln Val Val Leu Glu Glu Gly Thr Ile Ala Phe Lys Asn Trp Val Lys
                45                  50                  55

aca ggc aca gaa gtt tac aga cag ttt tgg atc ttt gat gtg caa aat      426
Thr Gly Thr Glu Val Tyr Arg Gln Phe Trp Ile Phe Asp Val Gln Asn
            60                  65                  70

cca cag gaa gtg atg atg aac agc agc aac att caa gtt aag caa aga      474
Pro Gln Glu Val Met Met Asn Ser Ser Asn Ile Gln Val Lys Gln Arg
        75                  80                  85

ggt cct tat acg tac aga gtt cgt ttt cta gcc aag gaa aat gta acc      522
Gly Pro Tyr Thr Tyr Arg Val Arg Phe Leu Ala Lys Glu Asn Val Thr
    90                  95                  100

cag gac gct gag gac aac aca gtc tct ttc ctg cag ccc aat ggt gcc      570
Gln Asp Ala Glu Asp Asn Thr Val Ser Phe Leu Gln Pro Asn Gly Ala
105                 110                 115                 120

atc ttc gaa cct tca cta tca gtt gga aca gag gct gac aac ttc aca      618
Ile Phe Glu Pro Ser Leu Ser Val Gly Thr Glu Ala Asp Asn Phe Thr
                125                 130                 135

gtt ctc aat ctg gct gtg gca gct gca tcc cat atc tat caa aat caa      666
Val Leu Asn Leu Ala Val Ala Ala Ala Ser His Ile Tyr Gln Asn Gln
            140                 145                 150

ttt gtt caa atg atc ctc aat tca ctt att aac aag tca aaa tct tct      714
Phe Val Gln Met Ile Leu Asn Ser Leu Ile Asn Lys Ser Lys Ser Ser
        155                 160                 165

atg ttc caa gtc aga act ttg aga gaa ctg tta tgg ggc tat agg gat      762
Met Phe Gln Val Arg Thr Leu Arg Glu Leu Leu Trp Gly Tyr Arg Asp
    170                 175                 180

cca ttt ttg agt ttg gtt ccg tac cct gtt act acc aca gtt ggt ctg      810
Pro Phe Leu Ser Leu Val Pro Tyr Pro Val Thr Thr Thr Val Gly Leu
185                 190                 195                 200

ttt tat cct tac aac aat act gca gat gga gtt tat aaa gtt ttc aat      858
Phe Tyr Pro Tyr Asn Asn Thr Ala Asp Gly Val Tyr Lys Val Phe Asn
                205                 210                 215

gga aaa gat aac ata agt aaa gtt gcc ata atc gac aca tat aaa ggt      906
Gly Lys Asp Asn Ile Ser Lys Val Ala Ile Ile Asp Thr Tyr Lys Gly
            220                 225                 230

aaa agg aat ctg tcc tat tgg gaa agt cac tgc gac atg att aat ggt      954
Lys Arg Asn Leu Ser Tyr Trp Glu Ser His Cys Asp Met Ile Asn Gly
        235                 240                 245

aca gat gca gcc tca ttt cca cct ttt gtt gag aaa agc cag gta ttg     1002
Thr Asp Ala Ala Ser Phe Pro Pro Phe Val Glu Lys Ser Gln Val Leu
    250                 255                 260

cag ttc ttt tct tct gat att tgc agg tca atc tat gct gta ttt gaa     1050
Gln Phe Phe Ser Ser Asp Ile Cys Arg Ser Ile Tyr Ala Val Phe Glu
265                 270                 275                 280

tcc gac gtt aat ctg aaa gga atc cct gtg tat aga ttt gtt ctt cca     1098
Ser Asp Val Asn Leu Lys Gly Ile Pro Val Tyr Arg Phe Val Leu Pro
                285                 290                 295

tcc aag gcc ttt gcc tct cca gtt gaa aac cca gac aac tat tgt ttc     1146
Ser Lys Ala Phe Ala Ser Pro Val Glu Asn Pro Asp Asn Tyr Cys Phe
            300                 305                 310

tgc aca gaa aaa att atc tca aaa aat tgt aca tca tat ggt gtg cta     1194
Cys Thr Glu Lys Ile Ile Ser Lys Asn Cys Thr Ser Tyr Gly Val Leu
        315                 320                 325

gac atc agc aaa tgc aaa gaa ggg aga cct gtg tac att tca ctt cct     1242
Asp Ile Ser Lys Cys Lys Glu Gly Arg Pro Val Tyr Ile Ser Leu Pro
    330                 335                 340

cat ttt ctg tat gca agt cct gat gtt tca gaa cct att gat gga tta     1290
His Phe Leu Tyr Ala Ser Pro Asp Val Ser Glu Pro Ile Asp Gly Leu
345                 350                 355                 360
```

-continued

```
aac cca aat gaa gaa gaa cat agg aca tac ttg gat att gaa cct ata      1338
Asn Pro Asn Glu Glu Glu His Arg Thr Tyr Leu Asp Ile Glu Pro Ile
                365                 370                 375

act gga ttc act tta caa ttt gca aaa cgg ctg cag gtc aac cta ttg      1386
Thr Gly Phe Thr Leu Gln Phe Ala Lys Arg Leu Gln Val Asn Leu Leu
            380                 385                 390

gtc aag cca tca gaa aaa att caa gta tta aag aat ctg aag agg aac      1434
Val Lys Pro Ser Glu Lys Ile Gln Val Leu Lys Asn Leu Lys Arg Asn
        395                 400                 405

tat att gtg cct att ctt tgg ctt aat gag act ggg acc att ggt gat      1482
Tyr Ile Val Pro Ile Leu Trp Leu Asn Glu Thr Gly Thr Ile Gly Asp
    410                 415                 420

gag aag gca aac atg ttc aga agt caa gta act gga aaa ata aac ctc      1530
Glu Lys Ala Asn Met Phe Arg Ser Gln Val Thr Gly Lys Ile Asn Leu
425                 430                 435                 440

ctt ggc ctg ata gaa atg atc tta ctc agt gtt ggt gtg gtg atg ttt      1578
Leu Gly Leu Ile Glu Met Ile Leu Leu Ser Val Gly Val Val Met Phe
                445                 450                 455

gtt gct ttt atg att tca tat tgt gca tgc aga tcg aaa aca ata aaa      1626
Val Ala Phe Met Ile Ser Tyr Cys Ala Cys Arg Ser Lys Thr Ile Lys
            460                 465                 470

taagtatgta ccaaaaaata ttgcttcaat aatattagct tatatattac ttgttttcac   1686

tttatcaaag agaagttaca tattaggcca tatatatttc tagacatgtc tagccactga   1746

tcatttttaa atataggtaa ataaacctat aaatattatc acgcagatca ctaaagtata   1806

tctttaattc tgggagaaat gagataaaag atgtacttgt gaccattgta acaatagcac   1866

aaat                                                                 1870


<210> SEQ ID NO 21
<211> LENGTH: 472
<212> TYPE: PRT
<213> ORGANISM: Homo sapiens

<400> SEQUENCE: 21

Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
    130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175
```

```
Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
    290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu Glu His Arg
        355                 360                 365

Thr Tyr Leu Asp Ile Glu Pro Ile Thr Gly Phe Thr Leu Gln Phe Ala
    370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
        435                 440                 445

Leu Ser Val Gly Val Val Met Phe Val Ala Phe Met Ile Ser Tyr Cys
    450                 455                 460

Ala Cys Arg Ser Lys Thr Ile Lys
465                 470


<210> SEQ ID NO 22
<211> LENGTH: 1321
<212> TYPE: DNA
<213> ORGANISM: Homo sapiens
<220> FEATURE:
<221> NAME/KEY: CDS
<222> LOCATION: (37)..(1158)

<400> SEQUENCE: 22

gacagatttc actgctccca ccagcttgga gacaac atg tgg ttc ttg aca act       54
                                        Met Trp Phe Leu Thr Thr
                                        1               5

ctg ctc ctt tgg gtt cca gtt gat ggg caa gtg gac acc aca aag gca      102
Leu Leu Leu Trp Val Pro Val Asp Gly Gln Val Asp Thr Thr Lys Ala
            10                  15                  20

gtg atc tct ttg cag cct cca tgg gtc agc gtg ttc caa gag gaa acc      150
Val Ile Ser Leu Gln Pro Pro Trp Val Ser Val Phe Gln Glu Glu Thr
```

-continued

```
        25                  30                  35

gta acc ttg cac tgt gag gtg ctc cat ctg cct ggg agc agc tct aca      198
Val Thr Leu His Cys Glu Val Leu His Leu Pro Gly Ser Ser Ser Thr
    40                  45                  50

cag tgg ttt ctc aat ggc aca gcc act cag acc tcg acc ccc agc tac      246
Gln Trp Phe Leu Asn Gly Thr Ala Thr Gln Thr Ser Thr Pro Ser Tyr
55                  60                  65                  70

aga atc acc tct gcc agt gtc aat gac agt ggt gaa tac agg tgc cag      294
Arg Ile Thr Ser Ala Ser Val Asn Asp Ser Gly Glu Tyr Arg Cys Gln
                75                  80                  85

aga ggt ctc tca ggg cga agt gac ccc ata cag ctg gaa atc cac aga      342
Arg Gly Leu Ser Gly Arg Ser Asp Pro Ile Gln Leu Glu Ile His Arg
            90                  95                  100

ggc tgg cta cta ctg cag gtc tcc agc aga gtc ttc acg gaa gga gaa      390
Gly Trp Leu Leu Leu Gln Val Ser Ser Arg Val Phe Thr Glu Gly Glu
        105                 110                 115

cct ctg gcc ttg agg tgt cat gcg tgg aag gat aag ctg gtg tac aat      438
Pro Leu Ala Leu Arg Cys His Ala Trp Lys Asp Lys Leu Val Tyr Asn
    120                 125                 130

gtg ctt tac tat cga aat ggc aaa gcc ttt aag ttt ttc cac tgg aat      486
Val Leu Tyr Tyr Arg Asn Gly Lys Ala Phe Lys Phe Phe His Trp Asn
135                 140                 145                 150

tct aac ctc acc att ctg aaa acc aac ata agt cac aat ggc acc tac      534
Ser Asn Leu Thr Ile Leu Lys Thr Asn Ile Ser His Asn Gly Thr Tyr
                155                 160                 165

cat tgc tca ggc atg gga aag cat cgc tac aca tca gca gga ata tct      582
His Cys Ser Gly Met Gly Lys His Arg Tyr Thr Ser Ala Gly Ile Ser
            170                 175                 180

gtc act gtg aaa gag cta ttt cca gct cca gtg ctg aat gca tct gtg      630
Val Thr Val Lys Glu Leu Phe Pro Ala Pro Val Leu Asn Ala Ser Val
        185                 190                 195

aca tcc cca ctc ctg gag ggg aat ctg gtc acc ctg agc tgt gaa aca      678
Thr Ser Pro Leu Leu Glu Gly Asn Leu Val Thr Leu Ser Cys Glu Thr
    200                 205                 210

aag ttg ctc ttg cag agg cct ggt ttg cag ctt tac ttc tcc ttc tac      726
Lys Leu Leu Leu Gln Arg Pro Gly Leu Gln Leu Tyr Phe Ser Phe Tyr
215                 220                 225                 230

atg ggc agc aag acc ctg cga ggc agg aac aca tcc tct gaa tac caa      774
Met Gly Ser Lys Thr Leu Arg Gly Arg Asn Thr Ser Ser Glu Tyr Gln
                235                 240                 245

ata cta act gct aga aga gaa gac tct ggg tta tac tgg tgc gag gct      822
Ile Leu Thr Ala Arg Arg Glu Asp Ser Gly Leu Tyr Trp Cys Glu Ala
            250                 255                 260

gcc aca gag gat gga aat gtc ctt aag cgc agc cct gag ttg gag ctt      870
Ala Thr Glu Asp Gly Asn Val Leu Lys Arg Ser Pro Glu Leu Glu Leu
        265                 270                 275

caa gtg ctt ggc ctc cag tta cca act cct gtc tgg ttt cat gtc ctt      918
Gln Val Leu Gly Leu Gln Leu Pro Thr Pro Val Trp Phe His Val Leu
    280                 285                 290

ttc tat ctg gca gtg gga ata atg ttt tta gtg aac act gtt ctc tgg      966
Phe Tyr Leu Ala Val Gly Ile Met Phe Leu Val Asn Thr Val Leu Trp
295                 300                 305                 310

gtg aca ata cgt aaa gaa ctg aaa aga aag aaa aag tgg gat tta gaa     1014
Val Thr Ile Arg Lys Glu Leu Lys Arg Lys Lys Lys Trp Asp Leu Glu
                315                 320                 325

atc tct ttg gat tct ggt cat gag aag aag gta act tcc agc ctt caa     1062
Ile Ser Leu Asp Ser Gly His Glu Lys Lys Val Thr Ser Ser Leu Gln
            330                 335                 340

gaa gac aga cat tta gaa gaa gag ctg aaa tgt cag gaa caa aaa gaa     1110
```

-continued

```
Glu Asp Arg His Leu Glu Glu Glu Leu Lys Cys Gln Glu Gln Lys Glu
        345                 350                 355

gaa cag ctg cag gaa ggg gtg cac cgg aag gag ccc cag ggg gcc acg      1158
Glu Gln Leu Gln Glu Gly Val His Arg Lys Glu Pro Gln Gly Ala Thr
    360                 365                 370

tagcagcggc tcagtgggtg gccatcgatc tggaccgtcc cctgcccact tgctccccgt   1218

gagcactgcg tacaaacatc caaaagttca acaacaccag aactgtgtgt ctcatggtat   1278

gtaactctta aagcaaataa atgaactgac ttcaaaaaaa aaa                     1321


<210> SEQ ID NO 23
<211> LENGTH: 374
<212> TYPE: PRT
<213> ORGANISM: Homo sapiens

<400> SEQUENCE: 23

Met Trp Phe Leu Thr Thr Leu Leu Leu Trp Val Pro Val Asp Gly Gln
1               5                   10                  15

Val Asp Thr Thr Lys Ala Val Ile Ser Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
```

```
305                 310                 315                 320

Lys Lys Trp Asp Leu Glu Ile Ser Leu Asp Ser Gly His Glu Lys Lys
                325                 330                 335

Val Thr Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370


<210> SEQ ID NO 24
<211> LENGTH: 1714
<212> TYPE: DNA
<213> ORGANISM: Homo sapiens
<220> FEATURE:
<221> NAME/KEY: CDS
<222> LOCATION: (156)..(1163)

<400> SEQUENCE: 24

gcggggagct tgcagtgacc aagagggtgt tgaggctagg aggccacgat aaacaggata      60

cgataaaagt ccttaaccaa gacgcagatg ggaagaagcg ttagagcgag cagcactcac     120

atctcaagaa ccagcctttc aaacagtttc cagag atg gat tat cct act tta        173
                                       Met Asp Tyr Pro Thr Leu
                                       1               5

ctt ttg gct ctt ctt cat gta tac aga gct cta tgt gaa gag gtg ctt       221
Leu Leu Ala Leu Leu His Val Tyr Arg Ala Leu Cys Glu Glu Val Leu
            10                  15                  20

tgg cat aca tca gtt ccc ttt gcc gag aac atg tct cta gaa tgt gtg       269
Trp His Thr Ser Val Pro Phe Ala Glu Asn Met Ser Leu Glu Cys Val
        25                  30                  35

tat cca tca atg ggc atc tta aca cag gtg gag tgg ttc aag atc ggg       317
Tyr Pro Ser Met Gly Ile Leu Thr Gln Val Glu Trp Phe Lys Ile Gly
    40                  45                  50

acc cag cag gat tcc ata gcc att ttc agc cct act cat ggc atg gtc       365
Thr Gln Gln Asp Ser Ile Ala Ile Phe Ser Pro Thr His Gly Met Val
55                  60                  65                  70

ata agg aag ccc tat gct gag agg gtt tac ttt ttg aat tca acg atg       413
Ile Arg Lys Pro Tyr Ala Glu Arg Val Tyr Phe Leu Asn Ser Thr Met
                75                  80                  85

gct tcc aat aac atg act ctt ttc ttt cgg aat gcc tct gaa gat gat       461
Ala Ser Asn Asn Met Thr Leu Phe Phe Arg Asn Ala Ser Glu Asp Asp
            90                  95                  100

gtt ggc tac tat tcc tgc tct ctt tac act tac cca cag gga act tgg       509
Val Gly Tyr Tyr Ser Cys Ser Leu Tyr Thr Tyr Pro Gln Gly Thr Trp
        105                 110                 115

cag aag gtg ata cag gtg gtt cag tca gat agt ttt gag gca gct gtg       557
Gln Lys Val Ile Gln Val Val Gln Ser Asp Ser Phe Glu Ala Ala Val
    120                 125                 130

cca tca aat agc cac att gtt tcg gaa cct gga aag aat gtc aca ctc       605
Pro Ser Asn Ser His Ile Val Ser Glu Pro Gly Lys Asn Val Thr Leu
135                 140                 145                 150

act tgt cag cct cag atg acg tgg cct gtg cag gca gtg agg tgg gaa       653
Thr Cys Gln Pro Gln Met Thr Trp Pro Val Gln Ala Val Arg Trp Glu
                155                 160                 165

aag atc cag ccc cgt cag atc gac ctc tta act tac tgc aac ttg gtc       701
Lys Ile Gln Pro Arg Gln Ile Asp Leu Leu Thr Tyr Cys Asn Leu Val
            170                 175                 180

cat ggc aga aat ttc acc tcc aag ttc cca aga caa ata gtg agc aac       749
His Gly Arg Asn Phe Thr Ser Lys Phe Pro Arg Gln Ile Val Ser Asn
```

```
        185                 190                 195

tgc agc cac gga agg tgg agc gtc atc gtc atc ccc gat gtc aca gtc      797
Cys Ser His Gly Arg Trp Ser Val Ile Val Ile Pro Asp Val Thr Val
    200                 205                 210

tca gac tcg ggg ctt tac cgc tgc tac ttg cag gcc agc gca gga gaa      845
Ser Asp Ser Gly Leu Tyr Arg Cys Tyr Leu Gln Ala Ser Ala Gly Glu
215                 220                 225                 230

aac gaa acc ttc gtg atg aga ttg act gta gcc gag ggt aaa acc gat      893
Asn Glu Thr Phe Val Met Arg Leu Thr Val Ala Glu Gly Lys Thr Asp
                235                 240                 245

aac caa tat acc ctc ttt gtg gct gga ggg aca gtt tta ttg ttg ttg      941
Asn Gln Tyr Thr Leu Phe Val Ala Gly Gly Thr Val Leu Leu Leu Leu
            250                 255                 260

ttt gtt atc tca att acc acc atc att gtc att ttc ctt aac aga agg      989
Phe Val Ile Ser Ile Thr Thr Ile Ile Val Ile Phe Leu Asn Arg Arg
        265                 270                 275

aga agg aga gag aga aga gat cta ttt aca gag tcc tgg gat aca cag     1037
Arg Arg Arg Glu Arg Arg Asp Leu Phe Thr Glu Ser Trp Asp Thr Gln
    280                 285                 290

aag gca ccc aat aac tat aga agt ccc atc tct acc ggt caa cct acc     1085
Lys Ala Pro Asn Asn Tyr Arg Ser Pro Ile Ser Thr Gly Gln Pro Thr
295                 300                 305                 310

aat caa tcc atg gat gat aca aga gag gat att tat gtc aac tat cca     1133
Asn Gln Ser Met Asp Asp Thr Arg Glu Asp Ile Tyr Val Asn Tyr Pro
                315                 320                 325

acc ttc tct cgc aga cca aag act aga gtt taagcttatt cttgacatga       1183
Thr Phe Ser Arg Arg Pro Lys Thr Arg Val
            330                 335

gtgcattagt aatgactctt atgtactcat gcatggatct ttatgcaatt tttttccact   1243

acccaaggtc taccttagat actagttgtc tgaattgagt tactttgata ggaaaaatac   1303

ttcattacct aaaatcattt ttcatagaac tgtttcagaa aacctgactc taactggttt   1363

atatacaaaa gaaaacttac tgtatcatat aacagaatga tccaggggag attaagcttt   1423

gggcaagggc tatttaccag ggcttaaatg ttgtgtctag aattaagtat gggcataaac   1483

tggcttctga atccctttcc agagtgttgg atccatttcc ctggtcttgg cctcactctc   1543

atgcaggctt tcctcttgtg ttggcaagat ggctgccaac tcttggcaat tcatacatcc   1603

ttgtttctgt ctggtagaga gtttgcttct caaatggagc aaacaaattt gattattttt   1663

tcattgttaa ataggcaaca tgaccataaa ggatggaatg gcttaagtaa a            1714


<210> SEQ ID NO 25
<211> LENGTH: 336
<212> TYPE: PRT
<213> ORGANISM: Homo sapiens

<400> SEQUENCE: 25

Met Asp Tyr Pro Thr Leu Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Met Gly Ile Leu Thr Gln Val
        35                  40                  45

Glu Trp Phe Lys Ile Gly Thr Gln Gln Asp Ser Ile Ala Ile Phe Ser
    50                  55                  60

Pro Thr His Gly Met Val Ile Arg Lys Pro Tyr Ala Glu Arg Val Tyr
65                  70                  75                  80
```

-continued

```
Phe Leu Asn Ser Thr Met Ala Ser Asn Asn Met Thr Leu Phe Phe Arg
                85                  90                  95

Asn Ala Ser Glu Asp Asp Val Gly Tyr Tyr Ser Cys Ser Leu Tyr Thr
            100                 105                 110

Tyr Pro Gln Gly Thr Trp Gln Lys Val Ile Gln Val Val Gln Ser Asp
        115                 120                 125

Ser Phe Glu Ala Ala Val Pro Ser Asn Ser His Ile Val Ser Glu Pro
    130                 135                 140

Gly Lys Asn Val Thr Leu Thr Cys Gln Pro Gln Met Thr Trp Pro Val
145                 150                 155                 160

Gln Ala Val Arg Trp Glu Lys Ile Gln Pro Arg Gln Ile Asp Leu Leu
                165                 170                 175

Thr Tyr Cys Asn Leu Val His Gly Arg Asn Phe Thr Ser Lys Phe Pro
            180                 185                 190

Arg Gln Ile Val Ser Asn Cys Ser His Gly Arg Trp Ser Val Ile Val
        195                 200                 205

Ile Pro Asp Val Thr Val Ser Asp Ser Gly Leu Tyr Arg Cys Tyr Leu
    210                 215                 220

Gln Ala Ser Ala Gly Glu Asn Glu Thr Phe Val Met Arg Leu Thr Val
225                 230                 235                 240

Ala Glu Gly Lys Thr Asp Asn Gln Tyr Thr Leu Phe Val Ala Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Arg Glu Arg Arg Asp Leu Phe Thr
        275                 280                 285

Glu Ser Trp Asp Thr Gln Lys Ala Pro Asn Asn Tyr Arg Ser Pro Ile
    290                 295                 300

Ser Thr Gly Gln Pro Thr Asn Gln Ser Met Asp Asp Thr Arg Glu Asp
305                 310                 315                 320

Ile Tyr Val Asn Tyr Pro Thr Phe Ser Arg Arg Pro Lys Thr Arg Val
                325                 330                 335


<210> SEQ ID NO 26
<211> LENGTH: 2107
<212> TYPE: DNA
<213> ORGANISM: Homo sapiens
<220> FEATURE:
<221> NAME/KEY: CDS
<222> LOCATION: (35)..(1975)

<400> SEQUENCE: 26

acgcggaaac aggcttgcac ccagacacga cacc atg cat ctc ctc ggc ccc tgg      55
                                      Met His Leu Leu Gly Pro Trp
                                      1               5

ctc ctg ctc ctg gtt cta gaa tac ttg gct ttc tct gac tca agt aaa       103
Leu Leu Leu Leu Val Leu Glu Tyr Leu Ala Phe Ser Asp Ser Ser Lys
        10                  15                  20

tgg gtt ttt gag cac cct gaa acc ctc tac gcc tgg gag ggg gcc tgc       151
Trp Val Phe Glu His Pro Glu Thr Leu Tyr Ala Trp Glu Gly Ala Cys
    25                  30                  35

gtc tgg atc ccc tgc acc tac aga gcc cta gat ggt gac ctg gaa agc       199
Val Trp Ile Pro Cys Thr Tyr Arg Ala Leu Asp Gly Asp Leu Glu Ser
40                  45                  50                  55

ttc atc ctg ttc cac aat cct gag tat aac aag aac acc tcg aag ttt       247
Phe Ile Leu Phe His Asn Pro Glu Tyr Asn Lys Asn Thr Ser Lys Phe
                60                  65                  70
```

-continued

```
gat ggg aca aga ctc tat gaa agc aca aag gat ggg aag gtt cct tct      295
Asp Gly Thr Arg Leu Tyr Glu Ser Thr Lys Asp Gly Lys Val Pro Ser
            75                  80                  85

gag cag aaa agg gtg caa ttc ctg gga gac aag aat aag aac tgc aca      343
Glu Gln Lys Arg Val Gln Phe Leu Gly Asp Lys Asn Lys Asn Cys Thr
        90                  95                  100

ctg agt atc cac ccg gtg cac ctc aat gac agt ggt cag ctg ggg ctg      391
Leu Ser Ile His Pro Val His Leu Asn Asp Ser Gly Gln Leu Gly Leu
    105                 110                 115

agg atg gag tcc aag act gag aaa tgg atg gaa cga ata cac ctc aat      439
Arg Met Glu Ser Lys Thr Glu Lys Trp Met Glu Arg Ile His Leu Asn
120                 125                 130                 135

gtc tct gaa agg cct ttt cca cct cat atc cag ctc cct cca gaa att      487
Val Ser Glu Arg Pro Phe Pro Pro His Ile Gln Leu Pro Pro Glu Ile
                140                 145                 150

caa gag tcc cag gaa gtc act ctg acc tgc ttg ctg aat ttc tcc tgc      535
Gln Glu Ser Gln Glu Val Thr Leu Thr Cys Leu Leu Asn Phe Ser Cys
            155                 160                 165

tat ggg tat ccg atc caa ttg cag tgg ctc cta gag ggg gtt cca atg      583
Tyr Gly Tyr Pro Ile Gln Leu Gln Trp Leu Leu Glu Gly Val Pro Met
        170                 175                 180

agg cag gct gct gtc acc tcg acc tcc ttg acc atc aag tct gtc ttc      631
Arg Gln Ala Ala Val Thr Ser Thr Ser Leu Thr Ile Lys Ser Val Phe
    185                 190                 195

acc cgg agc gag ctc aag ttc tcc cca cag tgg agt cac cat ggg aag      679
Thr Arg Ser Glu Leu Lys Phe Ser Pro Gln Trp Ser His His Gly Lys
200                 205                 210                 215

att gtg acc tgc cag ctt cag gat gca gat ggg aag ttc ctc tcc aat      727
Ile Val Thr Cys Gln Leu Gln Asp Ala Asp Gly Lys Phe Leu Ser Asn
                220                 225                 230

gac acg gtg cag ctg aac gtg aag cat cct ccc aag aag gtg acc aca      775
Asp Thr Val Gln Leu Asn Val Lys His Pro Pro Lys Lys Val Thr Thr
            235                 240                 245

gtg att caa aac ccc atg ccg att cga gaa gga gac aca gtg acc ctt      823
Val Ile Gln Asn Pro Met Pro Ile Arg Glu Gly Asp Thr Val Thr Leu
        250                 255                 260

tcc tgt aac tac aat tcc agt aac ccc agt gtt acc cgg tat gaa tgg      871
Ser Cys Asn Tyr Asn Ser Ser Asn Pro Ser Val Thr Arg Tyr Glu Trp
    265                 270                 275

aaa ccc cat ggc gcc tgg gag gag cca tcg ctt ggg gtg ctg aag atc      919
Lys Pro His Gly Ala Trp Glu Glu Pro Ser Leu Gly Val Leu Lys Ile
280                 285                 290                 295

caa aac gtt ggc tgg gac aac aca acc atc gcc tgc gca gct tgt aat      967
Gln Asn Val Gly Trp Asp Asn Thr Thr Ile Ala Cys Ala Ala Cys Asn
                300                 305                 310

agt tgg tgc tcg tgg gcc tcc cct gtc gcc ctg aat gtc cag tat gcc     1015
Ser Trp Cys Ser Trp Ala Ser Pro Val Ala Leu Asn Val Gln Tyr Ala
            315                 320                 325

ccc cga gac gtg agg gtc cgg aaa atc aag ccc ctt tcc gag att cac     1063
Pro Arg Asp Val Arg Val Arg Lys Ile Lys Pro Leu Ser Glu Ile His
        330                 335                 340

tct gga aac tcg gtc agc ctc caa tgt gac ttc tca agc agc cac ccc     1111
Ser Gly Asn Ser Val Ser Leu Gln Cys Asp Phe Ser Ser Ser His Pro
    345                 350                 355

aaa gaa gtc cag ttc ttc tgg gag aaa aat ggc agg ctt ctg ggg aaa     1159
Lys Glu Val Gln Phe Phe Trp Glu Lys Asn Gly Arg Leu Leu Gly Lys
360                 365                 370                 375

gaa agc cag ctg aat ttt gac tcc atc tcc cca gaa gat gct ggg agt     1207
Glu Ser Gln Leu Asn Phe Asp Ser Ile Ser Pro Glu Asp Ala Gly Ser
                380                 385                 390
```

```
tac agc tgc tgg gtg aac aac tcc ata gga cag aca gcg tcc aag gcc     1255
Tyr Ser Cys Trp Val Asn Asn Ser Ile Gly Gln Thr Ala Ser Lys Ala
            395                 400                 405

tgg aca ctt gaa gtg ctg tat gca ccc agg agg ctg cgt gtg tcc atg     1303
Trp Thr Leu Glu Val Leu Tyr Ala Pro Arg Arg Leu Arg Val Ser Met
        410                 415                 420

agc ccg ggg gac caa gtg atg gag ggg aag agt gca acc ctg acc tgt     1351
Ser Pro Gly Asp Gln Val Met Glu Gly Lys Ser Ala Thr Leu Thr Cys
    425                 430                 435

gag agc gac gcc aac cct ccc gtc tcc cac tac acc tgg ttt gac tgg     1399
Glu Ser Asp Ala Asn Pro Pro Val Ser His Tyr Thr Trp Phe Asp Trp
440                 445                 450                 455

aat aac caa agc ctc ccc tac cac agc cag aag ctg aga ttg gag ccg     1447
Asn Asn Gln Ser Leu Pro Tyr His Ser Gln Lys Leu Arg Leu Glu Pro
                460                 465                 470

gtg aag gtc cag cac tcg ggt gcc tac tgg tgc cag ggg acc aac agt     1495
Val Lys Val Gln His Ser Gly Ala Tyr Trp Cys Gln Gly Thr Asn Ser
            475                 480                 485

gtg ggc aag ggc cgt tcg cct ctc agc acc ctc acc gtc tac tat agc     1543
Val Gly Lys Gly Arg Ser Pro Leu Ser Thr Leu Thr Val Tyr Tyr Ser
        490                 495                 500

ccg gag acc atc ggc agg cga gtg gct gtg gga ctc ggg tcc tgc ctc     1591
Pro Glu Thr Ile Gly Arg Arg Val Ala Val Gly Leu Gly Ser Cys Leu
    505                 510                 515

gcc atc ctc atc ctg gca atc tgt ggg ctc aag ctc cag cga cgt tgg     1639
Ala Ile Leu Ile Leu Ala Ile Cys Gly Leu Lys Leu Gln Arg Arg Trp
520                 525                 530                 535

aag agg aca cag agc cag cag ggg ctt cag gag aat tcc agc ggc cag     1687
Lys Arg Thr Gln Ser Gln Gln Gly Leu Gln Glu Asn Ser Ser Gly Gln
                540                 545                 550

agc ttc ttt gtg agg aat aaa aag gtt aga agg gcc ccc ctc tct gaa     1735
Ser Phe Phe Val Arg Asn Lys Lys Val Arg Arg Ala Pro Leu Ser Glu
            555                 560                 565

ggc ccc cac tcc ctg gga tgc tac aat cca atg atg gaa gat ggc att     1783
Gly Pro His Ser Leu Gly Cys Tyr Asn Pro Met Met Glu Asp Gly Ile
        570                 575                 580

agc tac acc acc ctg cgc ttt ccc gag atg aac ata cca cga act gga     1831
Ser Tyr Thr Thr Leu Arg Phe Pro Glu Met Asn Ile Pro Arg Thr Gly
    585                 590                 595

gat gca gag tcc tca gag atg cag aga cct ccc ccg gac tgc gat gac     1879
Asp Ala Glu Ser Ser Glu Met Gln Arg Pro Pro Pro Asp Cys Asp Asp
600                 605                 610                 615

acg gtc act tat tca gca ttg cac aag cgc caa gtg ggc act atg aga     1927
Thr Val Thr Tyr Ser Ala Leu His Lys Arg Gln Val Gly Thr Met Arg
                620                 625                 630

acg tca ttc cag att ttc cag aag atg agg gga ttc att act cag agc     1975
Thr Ser Phe Gln Ile Phe Gln Lys Met Arg Gly Phe Ile Thr Gln Ser
            635                 640                 645

tgatccagtt tggggtcggg gagcggcctc aggcacaaga aaatgtggac tatgtgatcc   2035

tcaaacattg acactggatg ggctgcagca gaggcactgg gggcagcggg ggccagggaa   2095

gtccccgagt tt                                                       2107
```

<210> SEQ ID NO 27
<211> LENGTH: 647
<212> TYPE: PRT
<213> ORGANISM: Homo sapiens

<400> SEQUENCE: 27

-continued

```
Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Pro Pro Lys Lys Val Thr Thr Val Ile Gln Asn Pro Met Pro Ile Arg
                245                 250                 255

Glu Gly Asp Thr Val Thr Leu Ser Cys Asn Tyr Asn Ser Ser Asn Pro
            260                 265                 270

Ser Val Thr Arg Tyr Glu Trp Lys Pro His Gly Ala Trp Glu Glu Pro
        275                 280                 285

Ser Leu Gly Val Leu Lys Ile Gln Asn Val Gly Trp Asp Asn Thr Thr
    290                 295                 300

Ile Ala Cys Ala Ala Cys Asn Ser Trp Cys Ser Trp Ala Ser Pro Val
305                 310                 315                 320

Ala Leu Asn Val Gln Tyr Ala Pro Arg Asp Val Arg Val Arg Lys Ile
                325                 330                 335

Lys Pro Leu Ser Glu Ile His Ser Gly Asn Ser Val Ser Leu Gln Cys
            340                 345                 350

Asp Phe Ser Ser Ser His Pro Lys Glu Val Gln Phe Phe Trp Glu Lys
        355                 360                 365

Asn Gly Arg Leu Leu Gly Lys Glu Ser Gln Leu Asn Phe Asp Ser Ile
    370                 375                 380

Ser Pro Glu Asp Ala Gly Ser Tyr Ser Cys Trp Val Asn Asn Ser Ile
385                 390                 395                 400

Gly Gln Thr Ala Ser Lys Ala Trp Thr Leu Glu Val Leu Tyr Ala Pro
                405                 410                 415

Arg Arg Leu Arg Val Ser Met Ser Pro Gly Asp Gln Val Met Glu Gly
```

```
            420                 425                 430

Lys Ser Ala Thr Leu Thr Cys Glu Ser Asp Ala Asn Pro Pro Val Ser
        435                 440                 445

His Tyr Thr Trp Phe Asp Trp Asn Asn Gln Ser Leu Pro Tyr His Ser
    450                 455                 460

Gln Lys Leu Arg Leu Glu Pro Val Lys Val Gln His Ser Gly Ala Tyr
465                 470                 475                 480

Trp Cys Gln Gly Thr Asn Ser Val Gly Lys Gly Arg Ser Pro Leu Ser
                485                 490                 495

Thr Leu Thr Val Tyr Tyr Ser Pro Glu Thr Ile Gly Arg Arg Val Ala
            500                 505                 510

Val Gly Leu Gly Ser Cys Leu Ala Ile Leu Ile Leu Ala Ile Cys Gly
        515                 520                 525

Leu Lys Leu Gln Arg Arg Trp Lys Arg Thr Gln Ser Gln Gln Gly Leu
    530                 535                 540

Gln Glu Asn Ser Ser Gly Gln Ser Phe Phe Val Arg Asn Lys Lys Val
545                 550                 555                 560

Arg Arg Ala Pro Leu Ser Glu Gly Pro His Ser Leu Gly Cys Tyr Asn
                565                 570                 575

Pro Met Met Glu Asp Gly Ile Ser Tyr Thr Thr Leu Arg Phe Pro Glu
            580                 585                 590

Met Asn Ile Pro Arg Thr Gly Asp Ala Glu Ser Ser Glu Met Gln Arg
        595                 600                 605

Pro Pro Pro Asp Cys Asp Asp Thr Val Thr Tyr Ser Ala Leu His Lys
    610                 615                 620

Arg Gln Val Gly Thr Met Arg Thr Ser Phe Gln Ile Phe Gln Lys Met
625                 630                 635                 640

Arg Gly Phe Ile Thr Gln Ser
                645


<210> SEQ ID NO 28
<211> LENGTH: 1200
<212> TYPE: DNA
<213> ORGANISM: Homo sapiens
<220> FEATURE:
<221> NAME/KEY: CDS
<222> LOCATION: (101)..(880)

<400> SEQUENCE: 28

ggggtgcaaa gaagagacag cagcgcccag cttggaggtg ctaactccag aggccagcat      60

cagcaactgg gcacagaaag gagccgcctg ggcagggacc atg gca cgg cca cat       115
                                            Met Ala Arg Pro His
                                            1               5

ccc tgg tgg ctg tgc gtt ctg ggg acc ctg gtg ggg ctc tca gct act       163
Pro Trp Trp Leu Cys Val Leu Gly Thr Leu Val Gly Leu Ser Ala Thr
                10                  15                  20

cca gcc ccc aag agc tgc cca gag agg cac tac tgg gct cag gga aag       211
Pro Ala Pro Lys Ser Cys Pro Glu Arg His Tyr Trp Ala Gln Gly Lys
            25                  30                  35

ctg tgc tgc cag atg tgt gag cca gga aca ttc ctc gtg aag gac tgt       259
Leu Cys Cys Gln Met Cys Glu Pro Gly Thr Phe Leu Val Lys Asp Cys
        40                  45                  50

gac cag cat aga aag gct gct cag tgt gat cct tgc ata ccg ggg gtc       307
Asp Gln His Arg Lys Ala Ala Gln Cys Asp Pro Cys Ile Pro Gly Val
    55                  60                  65

tcc ttc tct cct gac cac cac acc cgg ccc cac tgt gag agc tgt cgg       355
Ser Phe Ser Pro Asp His His Thr Arg Pro His Cys Glu Ser Cys Arg
```

-continued

```
70                  75                  80                  85

cac tgt aac tct ggt ctt ctc gtt cgc aac tgc acc atc act gcc aat      403
His Cys Asn Ser Gly Leu Leu Val Arg Asn Cys Thr Ile Thr Ala Asn
                90                  95                  100

gct gag tgt gcc tgt cgc aat ggc tgg cag tgc agg gac aag gag tgc      451
Ala Glu Cys Ala Cys Arg Asn Gly Trp Gln Cys Arg Asp Lys Glu Cys
            105                 110                 115

acc gag tgt gat cct ctt cca aac cct tcg ctg acc gct cgg tcg tct      499
Thr Glu Cys Asp Pro Leu Pro Asn Pro Ser Leu Thr Ala Arg Ser Ser
        120                 125                 130

cag gcc ctg agc cca cac cct cag ccc acc cac tta cct tat gtc agt      547
Gln Ala Leu Ser Pro His Pro Gln Pro Thr His Leu Pro Tyr Val Ser
    135                 140                 145

gag atg ctg gag gcc agg aca gct ggg cac atg cag act ctg gct gac      595
Glu Met Leu Glu Ala Arg Thr Ala Gly His Met Gln Thr Leu Ala Asp
150                 155                 160                 165

ttc agg cag ctg cct gcc cgg act ctc tct acc cac tgg cca ccc caa      643
Phe Arg Gln Leu Pro Ala Arg Thr Leu Ser Thr His Trp Pro Pro Gln
                170                 175                 180

aga tcc ctg tgc agc tcc gat ttt att cgc atc ctt gtg atc ttc tct      691
Arg Ser Leu Cys Ser Ser Asp Phe Ile Arg Ile Leu Val Ile Phe Ser
            185                 190                 195

gga atg ttc ctt gtt ttc acc ctg gcc ggg gcc ctg ttc ctc cat caa      739
Gly Met Phe Leu Val Phe Thr Leu Ala Gly Ala Leu Phe Leu His Gln
        200                 205                 210

cga agg aaa tat aga tca aac aaa gga gaa agt cct gtg gag cct gca      787
Arg Arg Lys Tyr Arg Ser Asn Lys Gly Glu Ser Pro Val Glu Pro Ala
    215                 220                 225

gag cct tgt cgt tac agc tgc ccc agg gag gag gag ggc agc acc atc      835
Glu Pro Cys Arg Tyr Ser Cys Pro Arg Glu Glu Glu Gly Ser Thr Ile
230                 235                 240                 245

ccc atc cag gag gat tac cga aaa ccg gag cct gcc tgc tcc ccc          880
Pro Ile Gln Glu Asp Tyr Arg Lys Pro Glu Pro Ala Cys Ser Pro
                250                 255                 260

tgagccagca cctgcggtag ctgcactaca gccctggcct ccacccccac cccgccgacc    940

atccaaggga gagtgagacc tggcagccac aactgcagtc ccatcctctt gtcagggccc   1000

tttcctgtgt acacgtgaca gagtgccttt tcgagactgg cagggacgag gacaaatatg   1060

gatgaggtgg agagtgggaa gcaggagccc agccagctgc gcgcgcgtgc aggagggcgg   1120

gggctctggt tgtaaggcac acttcctgct gcgaaagacc cacatgctac aagacgggca   1180

aaataaagtg acagatgacc                                               1200


<210> SEQ ID NO 29
<211> LENGTH: 260
<212> TYPE: PRT
<213> ORGANISM: Homo sapiens

<400> SEQUENCE: 29

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
```

-continued

```
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260
```

<210> SEQ ID NO 30
<211> LENGTH: 2350
<212> TYPE: DNA
<213> ORGANISM: Homo sapiens

<400> SEQUENCE: 30

```
ctccctttgg gcaaggacct gagacccttg tgctaagtca agaggctcaa tgggctgcag     60

aagaactaga gaaggaccaa gcaaagccat gatatttcca tggaaatgtc agagcaccca    120

gagggactta tggaacatct tcaagttgtg ggggtggaca atgctctgtt gtgatttcct    180

ggcacatcat ggaaccgact gctggactta ccattattct gaaaaaccca tgaactggca    240

aagggctaga agattctgcc gagacaatta cacagattta gttgccatac aaaacaaggc    300

ggaaattgag tatctggaga agactctgcc tttcagtcgt tcttactact ggataggaat    360

ccggaagata ggaggaatat ggacgtgggt gggaaccaac aaatctctca ctgaagaagc    420

agagaactgg ggagatggtg agcccaacaa caagaagaac aaggaggact gcgtggagat    480

ctatatcaag agaaacaaag atgcaggcaa atggaacgat gacgcctgcc acaaactaaa    540

ggcagccctc tgttacacag cttcttgcca gccctggtca tgcagtggcc atggagaatg    600

tgtagaaatc atcaataatt acacctgcaa ctgtgatgtg gggtactatg ggccccagtg    660

tcagtttgtg attcagtgtg agcctttgga ggccccagag ctgggtacca tggactgtac    720

tcactctttg ggaaacttca gcttcagctc acagtgtgcc ttcagctgct ctgaaggaac    780

aaacttaact gggattgaag aaaccacctg tggaccattt ggaaactggt catctccaga    840

accaacctgt caagtgattc agtgtgagcc tctatcagca ccagatttgg ggatcatgaa    900

ctgtagccat cccctggcca gcttcagctt tacctctgca tgtaccttca tctgctcaga    960

aggaactgag ttaattggga agaagaaaac catttgtgaa tcatctggaa tctggtcaaa   1020
```

```
tcctagtcca atatgtcaaa aattggacaa aagtttctca atgattaagg agggtgatta   1080

taaccccctc ttcattccag tggcagtcat ggttactgca ttctctgggt tggcatttat   1140

catttggctg gcaaggagat taaaaaaagg caagaaatcc aagagaagta tgaatgaccc   1200

atattaaatc gcccttggtg aaagaaaatt cttggaatac taaaaatcat gagatccttt   1260

aaatccttcc atgaaacgtt ttgtgtggtg gcacctccta cgtcaaacat gaagtgtgtt   1320

tccttcagtg catctgggaa gatttctacc tgaccaacag ttccttcagc ttccatttcg   1380

cccctcattt atccctcaac cccagcccca caggtgttta tacagctcag ctttttgtct   1440

tttctgagga gaaacaaata agaccataaa gggaaaggat tcatgtggaa tataaagatg   1500

gctgactttg ctctttcttg actcttgttt tcagtttcaa ttcagtgctg tacttgatga   1560

cagacacttc taaatgaagt gcaaatttga tacatatgtg aatatggact cagttttctt   1620

gcagatcaaa tttcacgtcg tcttctgtat actgtggagg tacactctta tagaaagttc   1680

aaaaagtcta cgctctcctt tctttctaac tccagtgaag taatggggtc ctgctcaagt   1740

tgaaagagtc ctatttgcac tgtagcctcg ccgtctgtga attggaccat cctatttaac   1800

tggcttcagc ctccccacct tcttcagcca cctctctttt tcagttggct gacttccaca   1860

cctagcatct catgagtgcc aagcaaaagg agagaagaga gaaatagcct gcgctgtttt   1920

ttagtttggg ggttttgctg tttcctttta tgagacccat tcctatttct tatagtcaat   1980

gtttctttta tcacgatatt attagtaaga aaacatcact gaaatgctag ctgcaagtga   2040

catctctttg atgtcatatg gaagagttaa aacaggtgga gaaattcctt gattcacaat   2100

gaaatgctct cctttcccct gcccccagac cttttatccg acttacctag attctacata   2160

ttctttaaat ttcatctcag gcctccctca accccaccac ttcttttata actagtcctt   2220

tactaatcca acccatgatg agctcctctt cctggcttct tactgaaagg ttaccctgta   2280

acatgcaatt ttgcatttga ataaagcctg ctttttaagt gttaaaaaaa aaaaaaaaaa   2340

aaaaaaaaaa                                                          2350


<210> SEQ ID NO 31
<211> LENGTH: 1354
<212> TYPE: DNA
<213> ORGANISM: Homo sapiens
<220> FEATURE:
<221> NAME/KEY: CDS
<222> LOCATION: (116)..(1198)

<400> SEQUENCE: 31

ccagcctctg ccaggttcgg tccgccatcc tcgtcccgtc ctccgccggc ccctgccccg     60

cgcccaggga tcctccagct cctttcgccc gcgccctccg ttcgctccgg acacc atg     118
                                                             Met
                                                             1

gac aag ttt tgg tgg cac gca gcc tgg gga ctc tgc ctc gtg ccg ctg      166
Asp Lys Phe Trp Trp His Ala Ala Trp Gly Leu Cys Leu Val Pro Leu
            5                   10                  15

agc ctg gcg cag atc gat ttg aat ata acc tgc cgc ttt gca ggt gta      214
Ser Leu Ala Gln Ile Asp Leu Asn Ile Thr Cys Arg Phe Ala Gly Val
        20                  25                  30

ttc cac gtg gag aaa aat ggt cgc tac agc atc tct cgg acg gag gcc      262
Phe His Val Glu Lys Asn Gly Arg Tyr Ser Ile Ser Arg Thr Glu Ala
    35                  40                  45

gct gac ctc tgc aag gct ttc aat agc acc ttg ccc aca atg gcc cag      310
Ala Asp Leu Cys Lys Ala Phe Asn Ser Thr Leu Pro Thr Met Ala Gln
50                  55                  60                  65
```

-continued

```
atg gag aaa gct ctg agc atc gga ttt gag acc tgc agg tat ggg ttc      358
Met Glu Lys Ala Leu Ser Ile Gly Phe Glu Thr Cys Arg Tyr Gly Phe
                70                  75                  80

ata gaa ggg cat gtg gtg att ccc cgg atc cac ccc aac tcc atc tgt      406
Ile Glu Gly His Val Val Ile Pro Arg Ile His Pro Asn Ser Ile Cys
            85                  90                  95

gca gca aac aac aca ggg gtg tac atc ctc aca tac aac acc tcc cag      454
Ala Ala Asn Asn Thr Gly Val Tyr Ile Leu Thr Tyr Asn Thr Ser Gln
        100                 105                 110

tat gac aca tat tgc ttc aat gct tca gct cca cct gaa gaa gat tgt      502
Tyr Asp Thr Tyr Cys Phe Asn Ala Ser Ala Pro Pro Glu Glu Asp Cys
    115                 120                 125

aca tca gtc aca gac ctg ccc aat gcc ttt gat gga cca att acc ata      550
Thr Ser Val Thr Asp Leu Pro Asn Ala Phe Asp Gly Pro Ile Thr Ile
130                 135                 140                 145

act att gtt aac cgt gat ggc acc cgc tat gtc cag aaa gga gaa tac      598
Thr Ile Val Asn Arg Asp Gly Thr Arg Tyr Val Gln Lys Gly Glu Tyr
                150                 155                 160

aga acg aat cct gaa gac atc tac ccc agc aac cct act gat gat gac      646
Arg Thr Asn Pro Glu Asp Ile Tyr Pro Ser Asn Pro Thr Asp Asp Asp
            165                 170                 175

gtg agc agc ggc tcc tcc agt gaa agg agc agc act tca gga ggt tac      694
Val Ser Ser Gly Ser Ser Ser Glu Arg Ser Ser Thr Ser Gly Gly Tyr
        180                 185                 190

atc ttt tac acc ttt tct act gta cac ccc atc cca gac gaa gac agt      742
Ile Phe Tyr Thr Phe Ser Thr Val His Pro Ile Pro Asp Glu Asp Ser
    195                 200                 205

ccc tgg atc acc gac agc aca gac aga atc cct gct acc aga gac caa      790
Pro Trp Ile Thr Asp Ser Thr Asp Arg Ile Pro Ala Thr Arg Asp Gln
210                 215                 220                 225

gac aca ttc cac ccc agt ggg ggg tcc cat acc act cat gaa tct gaa      838
Asp Thr Phe His Pro Ser Gly Gly Ser His Thr Thr His Glu Ser Glu
                230                 235                 240

tca gat gga cac tca cat ggg agt caa gaa ggt gga gca aac aca acc      886
Ser Asp Gly His Ser His Gly Ser Gln Glu Gly Gly Ala Asn Thr Thr
            245                 250                 255

tct ggt cct ata agg aca ccc caa att cca gaa tgg ctg atc atc ttg      934
Ser Gly Pro Ile Arg Thr Pro Gln Ile Pro Glu Trp Leu Ile Ile Leu
        260                 265                 270

gca tcc ctc ttg gcc ttg gct ttg att ctt gca gtt tgc att gca gtc      982
Ala Ser Leu Leu Ala Leu Ala Leu Ile Leu Ala Val Cys Ile Ala Val
    275                 280                 285

aac agt cga aga agg tgt ggg cag aag aaa aag cta gtg atc aac agt     1030
Asn Ser Arg Arg Arg Cys Gly Gln Lys Lys Lys Leu Val Ile Asn Ser
290                 295                 300                 305

ggc aat gga gct gtg gag gac aga aag cca agt gga ctc aac gga gag     1078
Gly Asn Gly Ala Val Glu Asp Arg Lys Pro Ser Gly Leu Asn Gly Glu
                310                 315                 320

gcc agc aag tct cag gaa atg gtg cat ttg gtg aac aag gag tcg tca     1126
Ala Ser Lys Ser Gln Glu Met Val His Leu Val Asn Lys Glu Ser Ser
            325                 330                 335

gaa act cca gac cag ttt atg aca gct gat gag aca agg aac ctg cag     1174
Glu Thr Pro Asp Gln Phe Met Thr Ala Asp Glu Thr Arg Asn Leu Gln
        340                 345                 350

aat gtg gac atg aag att ggg gtg taacacctac accattatct tggaaagaaa    1228
Asn Val Asp Met Lys Ile Gly Val
    355                 360

caaccgttgt aaacataacc attacaggga gctgggacac ttaacagatg caatgtgcta   1288
```

```
ctgattgttt cattgcgaat cttttttagc ataaaatttt ctactctttt tgttaaaaaa   1348

aaaaaa                                                               1354


<210> SEQ ID NO 32
<211> LENGTH: 361
<212> TYPE: PRT
<213> ORGANISM: Homo sapiens

<400> SEQUENCE: 32

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Tyr Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Arg Asp
    210                 215                 220

Gln Asp Thr Phe His Pro Ser Gly Gly Ser His Thr Thr His Glu Ser
225                 230                 235                 240

Glu Ser Asp Gly His Ser His Gly Ser Gln Glu Gly Gly Ala Asn Thr
                245                 250                 255

Thr Ser Gly Pro Ile Arg Thr Pro Gln Ile Pro Glu Trp Leu Ile Ile
            260                 265                 270

Leu Ala Ser Leu Leu Ala Leu Ala Leu Ile Leu Ala Val Cys Ile Ala
        275                 280                 285

Val Asn Ser Arg Arg Arg Cys Gly Gln Lys Lys Lys Leu Val Ile Asn
    290                 295                 300

Ser Gly Asn Gly Ala Val Glu Asp Arg Lys Pro Ser Gly Leu Asn Gly
305                 310                 315                 320

Glu Ala Ser Lys Ser Gln Glu Met Val His Leu Val Asn Lys Glu Ser
                325                 330                 335

Ser Glu Thr Pro Asp Gln Phe Met Thr Ala Asp Glu Thr Arg Asn Leu
            340                 345                 350

Gln Asn Val Asp Met Lys Ile Gly Val
```

```
        355                 360


<210> SEQ ID NO 33
<211> LENGTH: 2308
<212> TYPE: DNA
<213> ORGANISM: Homo sapiens
<220> FEATURE:
<221> NAME/KEY: CDS
<222> LOCATION: (116)..(1594)

<400> SEQUENCE: 33

ccagcctctg ccaggttcgg tccgccatcc tcgtcccgtc ctccgccggc ccctgccccg      60

cgcccaggga tcctccagct cctttcgccc gcgccctccg ttcgctccgg acacc atg      118
                                                             Met
                                                             1

gac aag ttt tgg tgg cac gca gcc tgg gga ctc tgc ctc gtg ccg ctg      166
Asp Lys Phe Trp Trp His Ala Ala Trp Gly Leu Cys Leu Val Pro Leu
            5                   10                  15

agc ctg gcg cag atc gat ttg aat ata acc tgc cgc ttt gca ggt gta      214
Ser Leu Ala Gln Ile Asp Leu Asn Ile Thr Cys Arg Phe Ala Gly Val
        20                  25                  30

ttc cac gtg gag aaa aat ggt cgc tac agc atc tct cgg acg gag gcc      262
Phe His Val Glu Lys Asn Gly Arg Tyr Ser Ile Ser Arg Thr Glu Ala
    35                  40                  45

gct gac ctc tgc aag gct ttc aat agc acc ttg ccc aca atg gcc cag      310
Ala Asp Leu Cys Lys Ala Phe Asn Ser Thr Leu Pro Thr Met Ala Gln
50                  55                  60                  65

atg gag aaa gct ctg agc atc gga ttt gag acc tgc agg tat ggg ttc      358
Met Glu Lys Ala Leu Ser Ile Gly Phe Glu Thr Cys Arg Tyr Gly Phe
                70                  75                  80

ata gaa ggg cat gtg gtg att ccc cgg atc cac ccc aac tcc atc tgt      406
Ile Glu Gly His Val Val Ile Pro Arg Ile His Pro Asn Ser Ile Cys
            85                  90                  95

gca gca aac aac aca ggg gtg tac atc ctc aca tac aac acc tcc cag      454
Ala Ala Asn Asn Thr Gly Val Tyr Ile Leu Thr Tyr Asn Thr Ser Gln
        100                 105                 110

tat gac aca tat tgc ttc aat gct tca gct cca cct gaa gaa gat tgt      502
Tyr Asp Thr Tyr Cys Phe Asn Ala Ser Ala Pro Pro Glu Glu Asp Cys
    115                 120                 125

aca tca gtc aca gac ctg ccc aat gcc ttt gat gga cca att acc ata      550
Thr Ser Val Thr Asp Leu Pro Asn Ala Phe Asp Gly Pro Ile Thr Ile
130                 135                 140                 145

act att gtt aac cgt gat ggc acc cgc tat gtc cag aaa gga gaa tac      598
Thr Ile Val Asn Arg Asp Gly Thr Arg Tyr Val Gln Lys Gly Glu Tyr
                150                 155                 160

aga acg aat cct gaa gac atc tac ccc agc aac cct act gat gat gac      646
Arg Thr Asn Pro Glu Asp Ile Tyr Pro Ser Asn Pro Thr Asp Asp Asp
            165                 170                 175

gtg agc agc ggc tcc tcc agt gaa agg agc agc act tca gga ggt tac      694
Val Ser Ser Gly Ser Ser Ser Glu Arg Ser Ser Thr Ser Gly Gly Tyr
        180                 185                 190

atc ttt tac acc ttt tct act gta cac ccc atc cca gac gaa gac agt      742
Ile Phe Tyr Thr Phe Ser Thr Val His Pro Ile Pro Asp Glu Asp Ser
    195                 200                 205

ccc tgg atc acc gac agc aca gac aga atc cct cgt acc aat atg gac      790
Pro Trp Ile Thr Asp Ser Thr Asp Arg Ile Pro Arg Thr Asn Met Asp
210                 215                 220                 225

tcc agt cat agt aca acg ctt cag cct act gca aat cca aac aca ggt      838
Ser Ser His Ser Thr Thr Leu Gln Pro Thr Ala Asn Pro Asn Thr Gly
                230                 235                 240
```

-continued

```
ttg gtg gaa gat ttg gac agg aca gga cct ctt tca atg aca acg cag      886
Leu Val Glu Asp Leu Asp Arg Thr Gly Pro Leu Ser Met Thr Thr Gln
            245                 250                 255

cag agt aat tct cag agc ttc tct aca tca cat gaa ggc ttg gaa gaa      934
Gln Ser Asn Ser Gln Ser Phe Ser Thr Ser His Glu Gly Leu Glu Glu
        260                 265                 270

gat aaa gac cat cca aca act tct act ctg aca tca agc aat agg aat      982
Asp Lys Asp His Pro Thr Thr Ser Thr Leu Thr Ser Ser Asn Arg Asn
    275                 280                 285

gat gtc aca ggt gga aga aga gac cca aat cat tct gaa ggc tca act     1030
Asp Val Thr Gly Gly Arg Arg Asp Pro Asn His Ser Glu Gly Ser Thr
290                 295                 300                 305

cat tta ctg gaa ggt tat acc tct cat tac cca cac acg aag gaa agc     1078
His Leu Leu Glu Gly Tyr Thr Ser His Tyr Pro His Thr Lys Glu Ser
                310                 315                 320

agg acc ttc atc cca gtg acc tca gct aag act ggg tcc ttt gga gtt     1126
Arg Thr Phe Ile Pro Val Thr Ser Ala Lys Thr Gly Ser Phe Gly Val
            325                 330                 335

act gca gtt act gtt gga gat tcc aac tct aat gtc aat cgt tcc tta     1174
Thr Ala Val Thr Val Gly Asp Ser Asn Ser Asn Val Asn Arg Ser Leu
        340                 345                 350

tca gga gac caa gac aca ttc cac ccc agt ggg ggg tcc cat acc act     1222
Ser Gly Asp Gln Asp Thr Phe His Pro Ser Gly Gly Ser His Thr Thr
    355                 360                 365

cat gga tct gaa tca gat gga cac tca cat ggg agt caa gaa ggt gga     1270
His Gly Ser Glu Ser Asp Gly His Ser His Gly Ser Gln Glu Gly Gly
370                 375                 380                 385

gca aac aca acc tct ggt cct ata agg aca ccc caa att cca gaa tgg     1318
Ala Asn Thr Thr Ser Gly Pro Ile Arg Thr Pro Gln Ile Pro Glu Trp
                390                 395                 400

ctg atc atc ttg gca tcc ctc ttg gcc ttg gct ttg att ctt gca gtt     1366
Leu Ile Ile Leu Ala Ser Leu Leu Ala Leu Ala Leu Ile Leu Ala Val
            405                 410                 415

tgc att gca gtc aac agt cga aga agg tgt ggg cag aag aaa aag cta     1414
Cys Ile Ala Val Asn Ser Arg Arg Arg Cys Gly Gln Lys Lys Lys Leu
        420                 425                 430

gtg atc aac agt ggc aat gga gct gtg gag gac aga aag cca agt gga     1462
Val Ile Asn Ser Gly Asn Gly Ala Val Glu Asp Arg Lys Pro Ser Gly
    435                 440                 445

ctc aac gga gag gcc agc aag tct cag gaa atg gtg cat ttg gtg aac     1510
Leu Asn Gly Glu Ala Ser Lys Ser Gln Glu Met Val His Leu Val Asn
450                 455                 460                 465

aag gag tcg tca gaa act cca gac cag ttt atg aca gct gat gag aca     1558
Lys Glu Ser Ser Glu Thr Pro Asp Gln Phe Met Thr Ala Asp Glu Thr
                470                 475                 480

agg aac ctg cag aat gtg gac atg aag att ggg gtg taacacctac          1604
Arg Asn Leu Gln Asn Val Asp Met Lys Ile Gly Val
            485                 490

accattatct tggaaagaaa caacgttgga aacataacca ttacagggga gctgggacac   1664

ttaacagatg caatgtgcta ctgattgttt catttcgaat ctataatagc ataaaatttt   1724

ctactctttt tgttttttgt gttttgttct ttaaagtcag gtccaatttg taaaaacagc   1784

attgctttct gaaattaggg cccaattaat aatcagcaag aattttgatc gtttcagttc   1844

cccacttgga ggcctttcat ccctcgggtg tgctatggat ggcttctaac aaaaacctac   1904

cacatagtta ttcctgatcg ccaaccttgc cccccaccag ctaaggacat ttccagggtt   1964

aatagggcct ggtcctggga ggaaatttga atgggtcatt ttgcccttcc attagcctaa   2024

tccctgggca ttgctttcca ctgaggttgg gggttggggt gtactagtta cacatcttca   2084
```

```
acagaccccc tctagaaatt tttcagatgc ttctgggaga cacccaaagg gtaagtctat   2144

ttatctgtag taaactattt atctgtgttt ttgaaatatt aaaccctgga tcagtccttt   2204

tattcagtat aattttttaa agttactttg tcagaggcac aaaaagggtt taaactgatt   2264

cataataaat atctgtacct tcttcgaaaa aaaaaaaaaa aaaa                    2308


<210> SEQ ID NO 34
<211> LENGTH: 493
<212> TYPE: PRT
<213> ORGANISM: Homo sapiens

<400> SEQUENCE: 34

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Tyr Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Arg Thr Asn Met
    210                 215                 220

Asp Ser Ser His Ser Thr Thr Leu Gln Pro Thr Ala Asn Pro Asn Thr
225                 230                 235                 240

Gly Leu Val Glu Asp Leu Asp Arg Thr Gly Pro Leu Ser Met Thr Thr
                245                 250                 255

Gln Gln Ser Asn Ser Gln Ser Phe Ser Thr Ser His Glu Gly Leu Glu
            260                 265                 270

Glu Asp Lys Asp His Pro Thr Thr Ser Thr Leu Thr Ser Ser Asn Arg
        275                 280                 285

Asn Asp Val Thr Gly Gly Arg Arg Asp Pro Asn His Ser Glu Gly Ser
    290                 295                 300

Thr His Leu Leu Glu Gly Tyr Thr Ser His Tyr Pro His Thr Lys Glu
305                 310                 315                 320

Ser Arg Thr Phe Ile Pro Val Thr Ser Ala Lys Thr Gly Ser Phe Gly
                325                 330                 335
```

```
Val Thr Ala Val Thr Val Gly Asp Ser Asn Ser Asn Val Asn Arg Ser
            340                 345                 350

Leu Ser Gly Asp Gln Asp Thr Phe His Pro Ser Gly Gly Ser His Thr
        355                 360                 365

Thr His Gly Ser Glu Ser Asp Gly His Ser His Gly Ser Gln Glu Gly
    370                 375                 380

Gly Ala Asn Thr Thr Ser Gly Pro Ile Arg Thr Pro Gln Ile Pro Glu
385                 390                 395                 400

Trp Leu Ile Ile Leu Ala Ser Leu Leu Ala Leu Ala Leu Ile Leu Ala
                405                 410                 415

Val Cys Ile Ala Val Asn Ser Arg Arg Arg Cys Gly Gln Lys Lys Lys
            420                 425                 430

Leu Val Ile Asn Ser Gly Asn Gly Ala Val Glu Asp Arg Lys Pro Ser
        435                 440                 445

Gly Leu Asn Gly Glu Ala Ser Lys Ser Gln Glu Met Val His Leu Val
    450                 455                 460

Asn Lys Glu Ser Ser Glu Thr Pro Asp Gln Phe Met Thr Ala Asp Glu
465                 470                 475                 480

Thr Arg Asn Leu Gln Asn Val Asp Met Lys Ile Gly Val
                485                 490


<210> SEQ ID NO 35
<211> LENGTH: 1452
<212> TYPE: DNA
<213> ORGANISM: Homo sapiens
<220> FEATURE:
<221> NAME/KEY: CDS
<222> LOCATION: (74)..(730)

<400> SEQUENCE: 35

ctcaaggata atcactaaat tctgccgaaa ggactgagga acggtgcctg gaaaagggca      60

agaatatcac ggc atg ggc atg agt agc ttg aaa ctg ctg aag tat gtc        109
               Met Gly Met Ser Ser Leu Lys Leu Leu Lys Tyr Val
               1               5                   10

ctg ttt ttc ttc aac ttg ctc ttt tgg atc tgt ggc tgc tgc att ttg       157
Leu Phe Phe Phe Asn Leu Leu Phe Trp Ile Cys Gly Cys Cys Ile Leu
        15                  20                  25

ggc ttt ggg atc tac ctg ctg atc cac aac aac ttc gga gtg ctc ttc       205
Gly Phe Gly Ile Tyr Leu Leu Ile His Asn Asn Phe Gly Val Leu Phe
    30                  35                  40

cat aac ctc ccc tcc ctc acg ctg ggc aat gtg ttt gtc atc gtg ggc       253
His Asn Leu Pro Ser Leu Thr Leu Gly Asn Val Phe Val Ile Val Gly
45                  50                  55                  60

tct att atc atg gta gtt gcc ttc ctg ggc tgc atg ggc tct atc aag       301
Ser Ile Ile Met Val Val Ala Phe Leu Gly Cys Met Gly Ser Ile Lys
                65                  70                  75

gaa aac aag tgt ctg ctt atg tcg ttc ttc atc ctg ctg ctg att atc       349
Glu Asn Lys Cys Leu Leu Met Ser Phe Phe Ile Leu Leu Leu Ile Ile
            80                  85                  90

ctc ctt gct gag gtg acc ttg gcc atc ctg ctc ttt gta tat gaa cag       397
Leu Leu Ala Glu Val Thr Leu Ala Ile Leu Leu Phe Val Tyr Glu Gln
        95                  100                 105

aag ctg aat gag tat gtg gct aag ggt ctg acc gac agc atc cac cgt       445
Lys Leu Asn Glu Tyr Val Ala Lys Gly Leu Thr Asp Ser Ile His Arg
    110                 115                 120

tac cac tca gac aat agc acc aag gca gcg tgg gac tcc atc cag tca       493
Tyr His Ser Asp Asn Ser Thr Lys Ala Ala Trp Asp Ser Ile Gln Ser
125                 130                 135                 140
```

```
ttt ctg cag tgt tgt ggt ata aat ggc acg agt gat tgg acc agt ggc      541
Phe Leu Gln Cys Cys Gly Ile Asn Gly Thr Ser Asp Trp Thr Ser Gly
            145                 150                 155

cca cca gca tct tgc ccc tca gat cga aaa gtg gag ggt tgc tat gcg      589
Pro Pro Ala Ser Cys Pro Ser Asp Arg Lys Val Glu Gly Cys Tyr Ala
        160                 165                 170

aaa gca aga ctg tgg ttt cat tcc aat ttc ctg tat atc gga atc atc      637
Lys Ala Arg Leu Trp Phe His Ser Asn Phe Leu Tyr Ile Gly Ile Ile
    175                 180                 185

acc atc tgt gta tgt gtg att gag gtg ttg ggg atg tcc ttt gca ctg      685
Thr Ile Cys Val Cys Val Ile Glu Val Leu Gly Met Ser Phe Ala Leu
    190                 195                 200

acc ctg aac tgc cag att gac aaa acc agc cag acc ata ggg cta          730
Thr Leu Asn Cys Gln Ile Asp Lys Thr Ser Gln Thr Ile Gly Leu
205                 210                 215

tgatctgcag tagttctgtg gtgaagagac ttgtttcatc tccggaaatg caaaaccatt    790

tatagcatga agccctacat gatcactgca ggatgatcct cctcccatcc tttccctttt    850

taggtccctg tcttatacaa ccagagaagt gggtgttggc caggcacatc ccatctcagg    910

cagcaagaca atctttcact cactgacggc agcagccatg tctctcaaag tggtgaaact    970

aatatctgag catcttttag acaagagagg caaagacaaa ctggatttaa tggcccaaca   1030

tcaaagggtg aacccaggat atgaattttt gcatcttccc attgtcgaat tagtctccag   1090

cctctaaata atgcccagtc ttctccccaa agtcaagcaa gagactagtt gaagggagtt   1150

ctggggccag gctcactgga ccattgtcac aaccctctgt ttctctttga ctaagtgccc   1210

tggctacagg aattacacag ttctctttct ccaaagggca agatctcatt tcaatttctt   1270

tattagaggg ccttattgat gtgttctaag tctttccaga aaaaaactat ccagtgattt   1330

atatcctgat ttcaaccagt cacttagctg ataatcacag taagaagact tctggtatta   1390

tctctctatc agataagatt ttgttaatgt actattttac tcttcaataa ataaaacagt   1450

tt                                                                  1452


<210> SEQ ID NO 36
<211> LENGTH: 219
<212> TYPE: PRT
<213> ORGANISM: Homo sapiens

<400> SEQUENCE: 36

Met Gly Met Ser Ser Leu Lys Leu Leu Lys Tyr Val Leu Phe Phe Phe
1               5                   10                  15

Asn Leu Leu Phe Trp Ile Cys Gly Cys Cys Ile Leu Gly Phe Gly Ile
            20                  25                  30

Tyr Leu Leu Ile His Asn Asn Phe Gly Val Leu Phe His Asn Leu Pro
        35                  40                  45

Ser Leu Thr Leu Gly Asn Val Phe Val Ile Val Gly Ser Ile Ile Met
    50                  55                  60

Val Val Ala Phe Leu Gly Cys Met Gly Ser Ile Lys Glu Asn Lys Cys
65                  70                  75                  80

Leu Leu Met Ser Phe Phe Ile Leu Leu Leu Ile Ile Leu Leu Ala Glu
                85                  90                  95

Val Thr Leu Ala Ile Leu Leu Phe Val Tyr Glu Gln Lys Leu Asn Glu
            100                 105                 110

Tyr Val Ala Lys Gly Leu Thr Asp Ser Ile His Arg Tyr His Ser Asp
        115                 120                 125
```

-continued

```
Asn Ser Thr Lys Ala Ala Trp Asp Ser Ile Gln Ser Phe Leu Gln Cys
    130                 135                 140

Cys Gly Ile Asn Gly Thr Ser Asp Trp Thr Ser Gly Pro Pro Ala Ser
145                 150                 155                 160

Cys Pro Ser Asp Arg Lys Val Glu Gly Cys Tyr Ala Lys Ala Arg Leu
                165                 170                 175

Trp Phe His Ser Asn Phe Leu Tyr Ile Gly Ile Ile Thr Ile Cys Val
            180                 185                 190

Cys Val Ile Glu Val Leu Gly Met Ser Phe Ala Leu Thr Leu Asn Cys
        195                 200                 205

Gln Ile Asp Lys Thr Ser Gln Thr Ile Gly Leu
    210                 215


<210> SEQ ID NO 37
<211> LENGTH: 12
<212> TYPE: DNA
<213> ORGANISM: Artificial
<220> FEATURE:
<223> OTHER INFORMATION: Oligonucleotide primer

<400> SEQUENCE: 37

ctttagagca ca                                                           12


<210> SEQ ID NO 38
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(9)
<223> OTHER INFORMATION: Xaa at positions 1 and 4 can be any amino acid

<400> SEQUENCE: 38

Xaa Pro Pro Xaa Ala Ser Ala Leu Pro
1               5


<210> SEQ ID NO 39
<211> LENGTH: 240
<212> TYPE: PRT
<213> ORGANISM: Homo sapiens

<400> SEQUENCE: 39

Met Ala Gly Pro Pro Arg Leu Leu Leu Leu Pro Leu Leu Leu Ala Leu
1               5                   10                  15

Ala Arg Gly Leu Pro Gly Ala Leu Ala Ala Gln Glu Val Gln Gln Ser
            20                  25                  30

Pro His Cys Thr Thr Val Pro Val Gly Ala Ser Val Asn Ile Thr Cys
        35                  40                  45

Ser Thr Ser Gly Gly Leu Arg Gly Ile Tyr Leu Arg Gln Leu Gly Pro
    50                  55                  60

Gln Pro Gln Asp Ile Ile Tyr Tyr Glu Asp Gly Val Val Pro Thr Thr
65                  70                  75                  80

Asp Arg Arg Phe Glu Gly Arg Ile Asp Phe Ser Gly Ser Gln Asp Asn
                85                  90                  95

Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
        115                 120                 125
```

-continued

```
Val Leu Val Thr Glu Glu Gln Ser Gln Gly Trp His Arg Cys Ser Asp
    130                 135                 140

Ala Pro Pro Arg Ala Ser Ala Leu Pro Ala Pro Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
        195                 200                 205

Cys Ser Trp Arg Asp Lys Asn Ser Ala Ala Cys Val Val Tyr Glu Asp
    210                 215                 220

Met Ser His Ser Arg Cys Asn Thr Leu Ser Ser Pro Asn Gln Tyr Gln
225                 230                 235                 240


<210> SEQ ID NO 40
<211> LENGTH: 311
<212> TYPE: PRT
<213> ORGANISM: Homo sapiens

<400> SEQUENCE: 40

Met Ser Gln Asn Val Cys Pro Arg Asn Leu Trp Leu Leu Gln Pro Leu
1               5                   10                  15

Thr Val Leu Leu Leu Leu Ala Ser Ala Asp Ser Gln Ala Ala Ala Pro
            20                  25                  30

Pro Lys Ala Val Leu Lys Leu Glu Pro Pro Trp Ile Asn Val Leu Gln
        35                  40                  45

Glu Asp Ser Val Thr Leu Thr Cys Gln Gly Ala Arg Ser Pro Glu Ser
    50                  55                  60

Asp Ser Ile Gln Trp Phe His Asn Gly Asn Leu Ile Pro Thr His Thr
65                  70                  75                  80

Gln Pro Ser Tyr Arg Phe Lys Ala Asn Asn Asn Asp Ser Gly Glu Tyr
                85                  90                  95

Thr Cys Gln Thr Gly Gln Thr Ser Leu Ser Asp Pro Val His Leu Thr
            100                 105                 110

Val Leu Ser Glu Trp Leu Val Leu Gln Thr Pro His Leu Glu Phe Gln
        115                 120                 125

Glu Gly Glu Thr Ile Met Leu Arg Cys His Ser Trp Lys Asp Lys Pro
    130                 135                 140

Leu Val Lys Val Thr Phe Phe Gln Asn Gly Lys Ser Gln Lys Phe Ser
145                 150                 155                 160

Arg Leu Asp Pro Thr Phe Ser Ile Pro Gln Ala Asn His Ser His Ser
                165                 170                 175

Gly Asp Tyr His Cys Thr Gly Asn Ile Gly Tyr Thr Leu Phe Ser Ser
            180                 185                 190

Lys Pro Val Thr Ile Thr Val Gln Val Pro Ser Met Gly Ser Ser Ser
        195                 200                 205

Pro Met Gly Ile Ile Val Ala Val Val Ile Ala Thr Ala Val Ala Ala
    210                 215                 220

Ile Val Ala Ala Val Val Ala Leu Ile Tyr Cys Arg Lys Lys Arg Ile
225                 230                 235                 240

Ser Ala Asn Ser Thr Asp Pro Val Lys Ala Ala Gln Phe Glu Pro Pro
                245                 250                 255

Gly Arg Gln Met Ile Ala Ile Arg Lys Arg Gln Leu Glu Glu Thr Asn
            260                 265                 270
```

```
Asn Asp Tyr Glu Thr Ala Asp Gly Gly Tyr Met Thr Leu Asn Pro Arg
        275                 280                 285

Ala Pro Thr Asp Asp Asp Lys Asn Ile Tyr Leu Thr Leu Pro Pro Asn
    290                 295                 300

Asp His Val Asn Ser Asn Asn
305                 310


<210> SEQ ID NO 41
<211> LENGTH: 385
<212> TYPE: PRT
<213> ORGANISM: Homo sapiens

<400> SEQUENCE: 41

Met Gly Cys Arg Arg Thr Arg Glu Gly Pro Ser Lys Ala Met Ile Phe
1               5                   10                  15

Pro Trp Lys Cys Gln Ser Thr Gln Arg Asp Leu Trp Asn Ile Phe Lys
            20                  25                  30

Leu Trp Gly Trp Thr Met Leu Cys Cys Asp Phe Leu Ala His His Gly
        35                  40                  45

Thr Asp Cys Trp Thr Tyr His Tyr Ser Glu Lys Pro Met Asn Trp Gln
    50                  55                  60

Arg Ala Arg Arg Phe Cys Arg Asp Asn Tyr Thr Asp Leu Val Ala Ile
65                  70                  75                  80

Gln Asn Lys Ala Glu Ile Glu Tyr Leu Glu Lys Thr Leu Pro Phe Ser
                85                  90                  95

Arg Ser Tyr Tyr Trp Ile Gly Ile Arg Lys Ile Gly Gly Ile Trp Thr
            100                 105                 110

Trp Val Gly Thr Asn Lys Ser Leu Thr Glu Glu Ala Glu Asn Trp Gly
        115                 120                 125

Asp Gly Glu Pro Asn Asn Lys Lys Asn Lys Glu Asp Cys Val Glu Ile
    130                 135                 140

Tyr Ile Lys Arg Asn Lys Asp Ala Gly Lys Trp Asn Asp Asp Ala Cys
145                 150                 155                 160

His Lys Leu Lys Ala Ala Leu Cys Tyr Thr Ala Ser Cys Gln Pro Trp
                165                 170                 175

Ser Cys Ser Gly His Gly Glu Cys Val Glu Ile Ile Asn Asn Tyr Thr
            180                 185                 190

Cys Asn Cys Asp Val Gly Tyr Tyr Gly Pro Gln Cys Gln Phe Val Ile
        195                 200                 205

Gln Cys Glu Pro Leu Glu Ala Pro Glu Leu Gly Thr Met Asp Cys Thr
    210                 215                 220

His Ser Leu Gly Asn Phe Ser Phe Ser Ser Gln Cys Ala Phe Ser Cys
225                 230                 235                 240

Ser Glu Gly Thr Asn Leu Thr Gly Ile Glu Glu Thr Thr Cys Gly Pro
                245                 250                 255

Phe Gly Asn Trp Ser Ser Pro Glu Pro Thr Cys Gln Val Ile Gln Cys
            260                 265                 270

Glu Pro Leu Ser Ala Pro Asp Leu Gly Ile Met Asn Cys Ser His Pro
        275                 280                 285

Leu Ala Ser Phe Ser Phe Thr Ser Ala Cys Thr Phe Ile Cys Ser Glu
    290                 295                 300

Gly Thr Glu Leu Ile Gly Lys Lys Lys Thr Ile Cys Glu Ser Ser Gly
305                 310                 315                 320

Ile Trp Ser Asn Pro Ser Pro Ile Cys Gln Lys Leu Asp Lys Ser Phe
```

-continued

```
                325                 330                 335

Ser Met Ile Lys Glu Gly Asp Tyr Asn Pro Leu Phe Ile Pro Val Ala
            340                 345                 350

Val Met Val Thr Ala Phe Ser Gly Leu Ala Phe Ile Ile Trp Leu Ala
        355                 360                 365

Arg Arg Leu Lys Lys Gly Lys Lys Ser Lys Arg Ser Met Asn Asp Pro
    370                 375                 380

Tyr
385
```